(12) United States Patent
Bauer et al.

(10) Patent No.: US 11,944,611 B2
(45) Date of Patent: Apr. 2, 2024

(54) CAPSID INHIBITORS FOR THE TREATMENT OF HIV

(71) Applicant: Gilead Sciences, Inc., Foster City, CA (US)

(72) Inventors: Laura Elizabeth Bauer, Santa Clara, CA (US); Anna Chiu, Burlingame, CA (US); Eric M. Gorman, Hayward, CA (US); Andrew Stephen Mulato, Dublin, CA (US); Martin Sunkwang Rhee, Foster City, CA (US); Charles William Rowe, San Bruno, CA (US); Scott P. Sellers, Hillsborough, CA (US); Dimitrios Stefanidis, Saratoga, CA (US); Winston C. Tse, Redwood City, CA (US); Stephen R. Yant, Boulder Creek, CA (US); Dana J. Levine, San Leandro, CA (US)

(73) Assignee: Gilead Sciences, Inc., Foster City, CA (US)

( * ) Notice: Subject to any disclaimer, the term of this patent is extended or adjusted under 35 U.S.C. 154(b) by 690 days.

(21) Appl. No.: 16/512,166

(22) Filed: Jul. 15, 2019

(65) Prior Publication Data
US 2020/0038389 A1 Feb. 6, 2020

Related U.S. Application Data

(60) Provisional application No. 62/698,611, filed on Jul. 16, 2018.

(51) Int. Cl.
*A61K 31/4439* (2006.01)
*A61K 9/00* (2006.01)
(Continued)

(52) U.S. Cl.
CPC ........ *A61K 31/4439* (2013.01); *A61K 9/0019* (2013.01); *A61K 9/0053* (2013.01);
(Continued)

(58) Field of Classification Search
CPC ............ A61K 2300/00; A61K 31/4439; A61K 31/4427; A61K 31/34; A61K 31/4418;
(Continued)

(56) References Cited

U.S. PATENT DOCUMENTS 3,845,770 A 11/1974 Theeuwes et al.
4,326,525 A 4/1982 Swanson et al.
(Continued)

FOREIGN PATENT DOCUMENTS

CN 101910133 A 12/2010
CN 107207498 9/2017
(Continued)

OTHER PUBLICATIONS

Plosker GL.( Emtricitabine/tenofovir disoproxil fumarate: a review of its use in HIV-1 pre-exposure prophylaxis. Drugs. Mar. 2013;73(3):279-91. doi: 10.1007/s40265-013-0024-4. PMID: 23444256. P).*

(Continued)

*Primary Examiner* — Jean P Cornet
(74) *Attorney, Agent, or Firm* — Fish & Richardson P.C.

(57) ABSTRACT

The present disclosure relates to compounds of Formula (Ia) and (Ib):

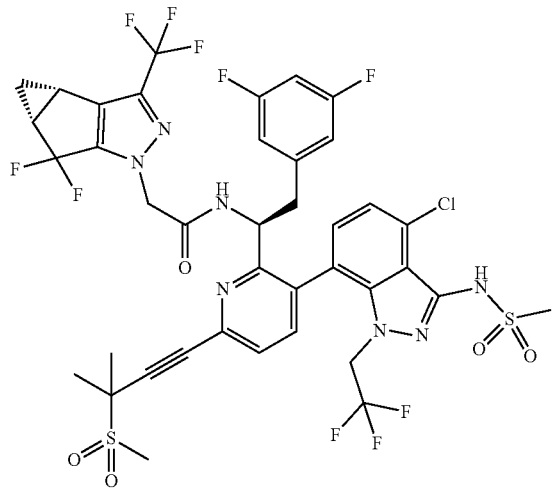

(Ia)

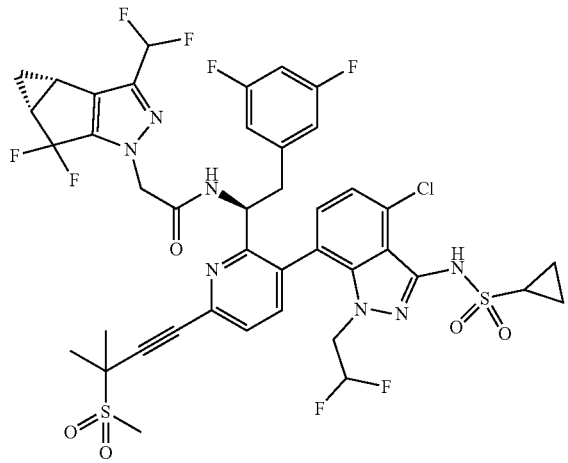

(Ib)

or a pharmaceutically acceptable salt thereof, which are useful in the treatment of an HIV infection in heavily treatment-experienced patients with multidrug resistant HIV infection.

34 Claims, 16 Drawing Sheets

(51) Int. Cl.
- *A61K 9/48* (2006.01)
- *A61K 31/34* (2006.01)
- *A61K 31/4418* (2006.01)
- *A61K 31/536* (2006.01)
- *A61K 31/5365* (2006.01)
- *A61K 31/685* (2006.01)
- *A61P 31/18* (2006.01)

(52) U.S. Cl.
CPC ............ *A61K 9/4825* (2013.01); *A61K 31/34* (2013.01); *A61K 31/4418* (2013.01); *A61K 31/536* (2013.01); *A61K 31/5365* (2013.01); *A61K 31/685* (2013.01); *A61P 31/18* (2018.01)

(58) Field of Classification Search
CPC .............. A61K 31/536; A61K 31/5365; A61K 31/685; A61K 45/06; A61K 47/10; A61K 9/0019; A61K 9/0053; A61K 9/0095; A61K 9/08; A61K 9/2018; A61K 9/4825; A61K 9/4858; A61P 31/18
USPC ........................................................ 514/338
See application file for complete search history.

(56) References Cited

U.S. PATENT DOCUMENTS

| | | | |
|---|---|---|---|
| 4,816,570 | A | 3/1989 | Farquhar |
| 4,902,514 | A | 2/1990 | Barclay et al. |
| 4,968,788 | A | 11/1990 | Farquhar |
| 4,992,445 | A | 2/1991 | Lawter et al. |
| 5,001,139 | A | 3/1991 | Lawter et al. |
| 5,023,252 | A | 6/1991 | Hseih |
| 5,616,345 | A | 4/1997 | Geoghegan et al. |
| 5,663,159 | A | 9/1997 | Starrett, Jr. et al. |
| 5,792,756 | A | 8/1998 | Starrett, Jr. et al. |
| 5,922,695 | A | 7/1999 | Arimilli et al. |
| 5,935,946 | A | 8/1999 | Munger, Jr. et al. |
| 5,977,089 | A | 11/1999 | Arimilli et al. |
| 7,390,791 | B2 | 6/2008 | Becker et al. |
| 7,803,788 | B2 | 9/2010 | Becker et al. |
| 8,193,225 | B2 | 6/2012 | Schneider et al. |
| 8,263,627 | B2 | 9/2012 | Barrow et al. |
| 8,435,968 | B2 | 5/2013 | Greig et al. |
| 8,748,412 | B2 | 6/2014 | Liao et al. |
| 8,754,065 | B2 | 6/2014 | Liu et al. |
| 8,835,488 | B2 | 9/2014 | Yamashita et al. |
| 9,012,441 | B2 | 4/2015 | Bondy et al. |
| 9,050,344 | B2 | 6/2015 | Brizgys et al. |
| 9,220,710 | B2 | 12/2015 | Bondy et al. |
| 9,540,343 | B2 | 1/2017 | Bondy et al. |
| 9,670,205 | B2 | 6/2017 | Aktoudianakis et al. |
| 9,789,089 | B2 | 10/2017 | Bondy et al. |
| 9,873,680 | B2 | 1/2018 | Brizgys et al. |
| 9,944,619 | B2 | 4/2018 | Bondy et al. |
| 9,951,043 | B2 | 4/2018 | Brizgys et al. |
| 10,071,885 | B2* | 9/2018 | O'Brien ................ B66C 1/0256 |
| 10,071,985 | B2 | 9/2018 | Graupe et al. |
| 10,294,234 | B2* | 5/2019 | Bacon .................. C07D 487/08 |
| 10,370,342 | B2 | 8/2019 | Chin et al. |
| 10,370,358 | B2 | 8/2019 | Benson et al. |
| 10,640,499 | B2 | 5/2020 | Chin et al. |
| 10,654,827 | B2* | 5/2020 | Graupe ................. C07C 317/08 |
| 10,696,657 | B2* | 6/2020 | Vandehey ............ C07D 339/06 |
| 10,836,746 | B2 | 11/2020 | Brizgys et al. |
| 10,849,892 | B2 | 12/2020 | Houston et al. |
| 11,078,208 | B1* | 8/2021 | Bacon .................. C07D 487/10 |
| 11,084,832 | B2* | 8/2021 | Chu ..................... C07D 471/04 |
| 11,117,886 | B2* | 9/2021 | Vandehey ............ C07D 231/54 |
| 11,680,064 | B2 | 6/2023 | Chou et al. |
| 11,753,399 | B2 | 9/2023 | Brizgy et al. |
| 11,757,825 | B2 | 9/2023 | Farand et al. |
| 2005/0282805 | A1 | 12/2005 | Hangeland et al. |
| 2007/0032469 | A1 | 2/2007 | Isaac et al. |
| 2007/0032649 | A1 | 2/2007 | Isaac et al. |
| 2007/0083045 | A1 | 4/2007 | Di Francesco et al. |
| 2008/0234251 | A1 | 9/2008 | Doherty et al. |
| 2008/0306050 | A1 | 12/2008 | Doherty et al. |
| 2010/0029585 | A1 | 2/2010 | Dietsch et al. |
| 2010/0129306 | A1 | 5/2010 | Julien et al. |
| 2010/0143301 | A1 | 6/2010 | Desai et al. |
| 2010/0249176 | A1 | 9/2010 | Barrow et al. |
| 2011/0092485 | A1 | 4/2011 | Burgess et al. |
| 2011/0118235 | A1 | 5/2011 | Burgess et al. |
| 2012/0045761 | A1 | 2/2012 | Jagannath et al. |
| 2012/0082658 | A1 | 4/2012 | Hershberg |
| 2012/0219615 | A1 | 8/2012 | Coukos et al. |
| 2013/0091096 | A1 | 4/2013 | Weaver |
| 2013/0165489 | A1 | 6/2013 | Cocklin et al. |
| 2013/0251673 | A1 | 9/2013 | Flores et al. |
| 2014/0045849 | A1 | 2/2014 | McGowan et al. |
| 2014/0066432 | A1 | 3/2014 | Burgess et al. |
| 2014/0073642 | A1 | 3/2014 | Embrechts et al. |
| 2014/0088085 | A1 | 3/2014 | Burgess et al. |
| 2014/0142085 | A1 | 5/2014 | Bondy et al. |
| 2014/0221346 | A1 | 8/2014 | Halcomb et al. |
| 2014/0221347 | A1 | 8/2014 | Brizgys et al. |
| 2014/0221356 | A1 | 8/2014 | Jin et al. |
| 2014/0221378 | A1 | 8/2014 | Miyazaki et al. |
| 2014/0221380 | A1 | 8/2014 | Miyazaki et al. |
| 2014/0221417 | A1 | 8/2014 | Halcomb et al. |
| 2014/0221421 | A1 | 8/2014 | Bondy et al. |
| 2014/0275167 | A1 | 9/2014 | Hartman |
| 2014/0296266 | A1 | 10/2014 | Hu et al. |
| 2014/0303164 | A1 | 10/2014 | Brizgys et al. |
| 2014/0350031 | A1 | 11/2014 | McGowan et al. |
| 2015/0104511 | A1 | 4/2015 | Malhotra et al. |
| 2016/0067224 | A1 | 3/2016 | Bondy et al. |
| 2016/0083368 | A1 | 3/2016 | Brizgys et al. |
| 2016/0108030 | A1 | 4/2016 | Brizgys et al. |
| 2016/0250215 | A1 | 9/2016 | Baszcynski et al. |
| 2016/0289229 | A1 | 10/2016 | Aktoudianakis et al. |
| 2016/0368881 | A1 | 12/2016 | Bondy et al. |
| 2017/0137405 | A1 | 5/2017 | Bondy et al. |
| 2018/0051005 | A1* | 2/2018 | Graupe ................ C07D 231/54 |
| 2018/0194746 | A1 | 7/2018 | Bondy et al. |
| 2018/0273508 | A1 | 9/2018 | Brizgys et al. |
| 2018/0370950 | A1* | 12/2018 | Graupe ................ A61K 31/537 |
| 2019/0083478 | A1 | 3/2019 | Houston et al. |
| 2019/0084963 | A1 | 3/2019 | Shi |
| 2019/0300505 | A1 | 10/2019 | Allan et al. |
| 2019/0345136 | A1 | 11/2019 | Brizgys et al. |
| 2019/0375726 | A1 | 12/2019 | Bondy et al. |
| 2020/0038389 | A1 | 2/2020 | Bauer |
| 2020/0262815 | A1 | 8/2020 | Graupe et al. |
| 2020/0369647 | A1 | 11/2020 | Allan et al. |
| 2020/0397772 | A1 | 12/2020 | Houston et al. |
| 2021/0009555 | A1 | 1/2021 | Brizgys et al. |
| 2021/0188815 | A1 | 6/2021 | Bekerman et al. |
| 2022/0009904 | A1 | 1/2022 | Allan et al. |
| 2022/0249460 | A1 | 8/2022 | Houston et al. |
| 2022/0251069 | A1 | 8/2022 | Shi |
| 2022/0267302 | A1 | 8/2022 | Brizgys et al. |
| 2023/0012449 | A1 | 1/2023 | Bondy et al. |
| 2023/0038823 | A1 | 2/2023 | Chon et al. |
| 2023/0203069 | A1 | 6/2023 | Nair et al. |
| 2023/0312567 | A1 | 10/2023 | Chou et al. |

FOREIGN PATENT DOCUMENTS

| | | |
|---|---|---|
| WO | WO 1991/19721 | 12/1991 |
| WO | WO 2003/002530 | 1/2003 |
| WO | WO 2003/002553 | 1/2003 |
| WO | WO 2004/050643 | 6/2004 |
| WO | WO 2004/071448 | 8/2004 |
| WO | WO 2004/096286 | 11/2004 |
| WO | WO 2005/087725 | 9/2005 |
| WO | WO 2005/123680 | 12/2005 |
| WO | WO 2006/015261 | 2/2006 |
| WO | WO 2006/110157 | 10/2006 |
| WO | WO 2007/070826 | 8/2007 |
| WO | WO 2008/013622 | 1/2008 |
| WO | WO 2008118849 | 10/2008 |

(56) References Cited

FOREIGN PATENT DOCUMENTS

| WO | WO 2009/005677 | 1/2009 |
|---|---|---|
| WO | WO 2009/010804 | 1/2009 |
| WO | WO 2009/062285 | 5/2009 |
| WO | WO 2009/114677 | 9/2009 |
| WO | WO 2010/130034 | 11/2010 |
| WO | WO 2011/059887 | 5/2011 |
| WO | WO 2011/143772 | 11/2011 |
| WO | WO 2012/003497 | 1/2012 |
| WO | WO 2012/003498 | 1/2012 |
| WO | WO 2012/065062 | 5/2012 |
| WO | WO 2012/145728 | 10/2012 |
| WO | WO 2013/006738 | 1/2013 |
| WO | WO 2013/006792 | 1/2013 |
| WO | WO 2013/091096 | 6/2013 |
| WO | WO 2013/159064 | 10/2013 |
| WO | WO 2014/016358 | 1/2014 |
| WO | WO 2014/023813 | 2/2014 |
| WO | WO 2014/028931 | 2/2014 |
| WO | WO 2014/056953 | 4/2014 |
| WO | WO 2014/076221 | 5/2014 |
| WO | WO 2014/100323 | 6/2014 |
| WO | WO 2014/110297 | 7/2014 |
| WO | WO 2014/110298 | 7/2014 |
| WO | WO 2014/110323 | 7/2014 |
| WO | WO 2014/128189 | 8/2014 |
| WO | WO 2014128213 | 8/2014 |
| WO | WO 2014/134566 | 9/2014 |
| WO | WO 2015/008097 | 1/2015 |
| WO | WO 2015/061518 | 4/2015 |
| WO | WO 2015/130966 | 9/2015 |
| WO | WO 2016/033243 | 3/2016 |
| WO | WO 2016/040084 | 3/2016 |
| WO | WO 2016/172424 | 10/2016 |
| WO | WO 2016/172425 | 10/2016 |
| WO | WO 2017/007689 | 1/2017 |
| WO | WO 2018/035359 | 2/2018 |
| WO | WO 2018/145021 | 8/2018 |
| WO | WO 2018/203235 | 11/2018 |
| WO | WO 2019/035904 | 2/2019 |
| WO | WO 2019/035973 | 2/2019 |

OTHER PUBLICATIONS

Benzaria, S. et al. (Dec. 6, 1996). "Synthesis, In Vitro Antiviral Evaluation, and Stability Studies of Bis( S-Acyl-2-Thioethyl) Ester Derivatives of 9-[2-(Phosphonomethoxy)Ethyl]adenine (PMEA) as Potential PMEA Prodrugs with Improved Oral Bioavailability," J. Med. Chem. 39(25):4958-4965.

Berge et al., "Pharmaceutical Salts," J. Pharma. Sci., Jan. 1977, 66(1): 1-19.

Bhattacharya et al. (2014) Structural Basis of HIV-1 Capsid Recognition by PF74 and CPSF6, PNAS; 111 (52):18625-18630.

Blair et al., (2010) "HIV Capsid is a Tractable Target for Small Molecule Therapeutic Intervention," PLoS Pathog. 6(12): e1001220.

Briggs et al., (2003) "Structural Organization of Authentic, Mature HIV-1 Virions and Cores," The EMBO Journal; vol. 22 No. 7 pp. 1707-1715.

Brown, M.K. et al. (2005) "Highly Enantioselective Cu-Catalyzed Conjugate Additions of Dialkylzinc Reagents to Unsaturated Furanones and Pyranones: Preparation of Air-Stable and Catalytically Active Cu-Peptide," Angew Chem. Int. Ed. Engl. 44(33):5306-5310.

Bundgaard, H. (1991). "Design and Application of Prodrugs," Chapter 5 in a Textbook of Drug Design and Development, Krogsgaard-Larsen, P. et al. eds., Harwood Academic Publishers, Chur, Switzerland, pp. 113-191.

Campbell et al., (2015) "HIV-1 Capsid: The Multifaceted Key Player in HIV-1 Infection," Nat Rev Microbial.; 13(8): 471-483.

Chin et al. (2015) "Direct Visualization of HIV-1 Replication Intermediates Shows That Capsid and CPSF6 Modulate HIV-1 Intra-Nuclear Invasion and Integration", Cell Repotis 13:1717-1731.

Cos, P. et al. (1998) "Structure-Activity Relationship and Classification of Flavonoids as Inhibitors of Xanthine Oxidase and Su peroxide Scavengers, " J. Natl. Prod. 61 :71-76.

Cossy, J. et al. (Oct. 23, 1995). "Ring Opening of Cyclopropylketones Induced by Photochemical Electron Transfer," Tetrahedron 51 (43):11751-11764.

Curreli et al., (2011) "Virtual Screening Based Identification of Novel Small-molecule Inhibitors Targeted to the HIV-1 Capsid," Bioorganic & Medicinal Chemistry 19:77-90.

De Lombaert, S. et al. (Feb. 18, 1994). "N-Phosphonomethyl Dipeptides and Their Phosphonate Prodrugs, A New Generation of Neutral Endopeptidase (NEP, EC 3.4.24.11) Inhibitors," J. Med. Chem. 37(4):498-511.

Fader et al., (2013) Optimization of a 1,5 dihydrobenzo[b][1,4]diazepine-2,4-dione Series of HIV Capsid Assembly Inhibitors 2: Structure-Activity Relationships (SAR) of the C3-Phenyl Moiety, Bioorganic & Medicinal Chemistry Letters, doi: httQ://dx.doi.org/10.1016/j.bmcl.2013.03.074>.

Farquhar, D. et al. (Mar. 1983). "Biologically Reversible Phosphate-Protective Groups," J. Pharm. Sci. 72(3):324-325.

Fields, "Methods for Removing the Fmoc Group," Methods in Molecular Biology, 1994, 35: 17-27.

Forshey et al., (2002) "Formation of a Human Immunodeficiency Virus Type 1 Core of Optimal Stability is Crucial for Viral Replication," J. Virology, 76(11) p. 5667-5677.

Foster, "Deuterium Isotope Effects in Studies of Drug Metabolism," Trends Pharmacol. Sci., 1984, 5(12):524-527.

Ganser et al., (1999) "Assembly and Analysis of Conical Models for the HIV-1 Core," Science 283, 80-82.

Ganser-Pornillos et al., (2007) "Structure of Full-Length HIV-1 CA: A Model for the Mature Capsid Lattice," Cell .; 131(1):70-9, 29 pages.

Hagmann et al., "The many roles of fluorine in medicinal chemistry," J. Med. Chem., 2008, 51(15):4359-4396.

Hammer, S. et al. (Aug. 6, 2008). "Antiretroviral Treatment of Adult HIV Infection. 2008 Recommendations of the International AIDS Society: USA Panel," JAMA 300(5):555-570.

Hanack et al., "cis- und trans bicyclo [3.1.0] hexano-(2)," Chemische Berichte, 1964, 97(6): 1669-1672, XP055573746 (with English translation).

Hodgson, D.M. et al. (2007) "Intramolecular Cyclopropanation of Unsaturated Terminal Epoxides and Chlorohydrins," JAGS 129(14):4456-4462.

Hodgson, D.M. et al. (Jul. 21, 2004, e-pub. Jun. 24, 2004). "Intramolecular Cyclopropanation of Unsaturated Terminal Epoxides," J. Am. Chem. Soc. 126(28):8664-8665.

Hung et al. (2013) "Large-Scale Functional Purification of Recombinant HIV-1 Capsid" PLoS One, vol. 8, Issue 3, e58035, 11 pages.

Ishiyama et al., "Palladium(0)-Catalyzed Cross-Coupling Reaction of Alkoxydiboron with Haloarenes: A Direct Procedure for Arylboronic Esters," J. Org. Chem. 1995, 60(23):7508-7510.

Jeong, .J.U. (2010) "Synthesis of Tetrasubstituted Pyrazones and Pyrazone N-Oxides," Tetrahedron Letters 51 (6):974-976.

Jin et al., (2010) "SAR and Molecular Mechanism Study of Novel Acylhydrazone Compounds Targeting HIV-1 CA," Bioorganic & Medicinal Chemistry; 18: 2135-2140.

Jouvenet et al., (2006) "Plasma Membrane is the Site of Productive HIV-1 Particle Assembly," PLoS Biol.;4(12):e435, 15 pages.

Kashima, C. et al. (Aug.-Sep. 1991). "New Peptide Synthesis Using the Ozonolysate of 2-(1-Phthalimido)alkyl-5-Phenyloxazoles," J. Heterocyclic Chem. 28: 1241-1244 (abstract only).

Kelly, et al., (2007) "Structure of the Antiviral Assembly Inhibitor CAP-1 Bound to the HIV-1 CA Protein," Journal of Molecular Biology, doi: 10.1016/j.jmb.2007.07.070, 40 pages.

Khamnei, S. et al. (Sep. 27, 1996). "Neighboring Group Catalysis in the Design of Nucleotide Prodrugs," J. Med. Chem. 39(20):4109-4115.

Kim et al., (2013) "Discovery of a New HIV-1 Inhibitor Scaffold and Synthesis of Potential Prodrugs of Indazoles," Bioorganic & Medicinal Chemistry Letters, doi: <http://dx.doi.org/10.1016/j.bmcl.2013.03.075> 8 pages.

(56) References Cited

OTHER PUBLICATIONS

Kocienski, P.J. (May 1994). "Carbonyl Protecting Groups," Chapter 5 in Protecting Groups, Thieme Publishing Group: New York, NY, pp. 155-184.
Kocienski, P.J. (May 1994). "Carboxyl Protecting Groups," Chapter 4 in Protecting Groups, Thieme Publishing Group: New York, NY, pp. 118-154.
Kocienski, P.J. (May 1994). "Diol Protecting Groups," Chapter 3 in Protecting Groups, Thieme Publishing Group: New York, NY, pp. 95-117.
Kocienski, P.J. (May 1994). "Hydroxyl Protecting Groups," Chapter 2 in Protecting Groups, Thieme Publishing Group: New York, NY, pp. 21-94.
Kocienski, P.J. (May 1994). "Protecting Groups: An Overview," Chapter 1 in Protecting Groups, Thieme Publishing Group: New York, NY, pp. 1-20.
Lad et al., (2015) "Functional Label-Free Assays for Characterizing the in Vitro Mechanism of Action of Small Molecule Modulators of Capsid Assembly" Biochemistry, 54, 2240-2248.
Lamorte et al. (2015) "Discovery of Novel Small-Molecule HIV-1 Replication Inhibitors That Stabilize Capsid Complexes" Antimicrobial Agents and Chemotherapy, 57(10): 4622-4631.
Lazerwith et al., (2017) "New Antiretrovirals for HIV and Antivirals for HBV," in Comprehensive Medicinal Chemistry, 3rd Edition, 1-36.
Lee et al., (2010) "Flexible Use of Nuclear Import Pathways by HIV-1," Cell Host & Microbe; 7, 221-233.
Lemke, C.T. et al. (Jun. 2012). "Distinct Effects of Two HIV-1 Capsid Assembly Inhibitor Families That Bind the Same Site Within the N-Terminal Domain of the Viral CA Protein," J. Viral. 86(12):6643-6655.
MacMillan et al., "Evaluation of alternative solvent in common amide coupling reactions: replacement of dicloromethane and N,N-dimethlformamide," Green Chem, 2013, 15: 596-600.
Matreyek et al., (2013) "Nucleoporin NUP153 Phenylalanine-Glycine Motifs Engage a Common Binding Pocket within the HIV-1 Capsid Protein to Mediate Lentiviral Infectivity" PLOS Pathogens vol. 9, Issue 10, e1003693.
Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," J. Chem. Soc. Perkin Trans. 1, pp. 2345-2353.
Miyaura and Suzuki, "Palladium-Catalyzed Cross-Coupling Reactions of Oganoboron Compounds," Chem Rev, 1995, 95: 2457-2483.
Montalbetti and Falque, "Amide bond formation and peptide coupling," Tetrahedon, 2005, 61: 10827-10852.
Nicolaou et al., "Palladium-Catalyzed Cross-Coupling Reactions in Total Synthesis," Angew Chem Int, 2005, 44:4442-4489.
Ovais et al., "Synthesis, antiproliferative and anti-inflammatory activities of some novel 6-aryl-2-(p-(methanesulfonyl)phenyl)-4,5-dihydropyridazi-3(2H)-ones," European Journal of Medicinal Chemistry, 2013, 67:352-358.
Owen et al., "Strengths, weaknesses, opportunities and challenges for long acting injectable therapies: Insights for applications in HIV therapy," Advances Drug Delivery Reviews 103 (2016) 144-156.
Paella et al., "Declining morbidity and mortality among patients with advanced human immunodeficiency virus infection. HIV Outpatient Study Investigators," N Engl. J Med. 1998, 338:853-860.
Patel et al., "Poloxamers: a pharmaceutical excipients with therapeutic behaviors," International Journal of PharmTech Research, Apr.-Jun. 2009, 1(2):299-303.
Pornillos et al., (2009) "X-ray Structures of the Hexameric Building Block of the HIV Capsid" Cell.; 137(7): 1282-92.
Pornillos et al., (2009) Supplemental Data for "X-ray Structures of the Hexameric Building Block of the HIV Capsid" Cell. Jun. 26, 2009;137(7): 1282-92.
Powers et al., (2009)Synthesis of Methyl-, Fluoro-, and Chloro-substituted 6-Hydroxyisoindolin-1-1-Ones, Tetrahedron Letters 50 (12):1267-1269.

Price et al. (2012) "CPSF6 Defines a Conserved Capsid Interface That Modulates HIV-1 Replication" PLOS Pathogens, 8(8):e1002896, 14 pages.
Puech, F. et al. (Oct. 1993). "Intracellular Delivery of Nucleoside Monophosphates Through a Reductase-Mediated Activation Process," Antiviral Res. 22(2-3):155-174.
Registry (STN) [online], Mar. 22, 2010 [date of retrieval: Nov. 12, 2018], CAS registry No. 1213065-84-9.
Registry (STN) [online], Mar. 23, 2010 [date of retrieval: Nov. 12, 2018], CAS registry No. 1213495-28-3.
Rihn et al., (2013) "Extreme Genetic Fragility of the HIV-1 Capsid" PLOS One, vol. 9 Issue 6 e1003461, 25 pages.
Shi et al. (2011) "Small-Molecule Inhibition of Human Immunodeficiency Virus Type 1 Caps id Destabilization" Journal of Virology 85(1) 542-549.
Siddiqui, A. et al. (1999) "The Presence of Substituents on the Aryl Moiety of the Aryl Phosphoramidate Derivative of d4T Enhances Anti-HIV Efficacy in Cell Culture: A Structure-Activity Relationship" J. Med. Chem. 42:393-399.
Smith, R.J. et al. (2010) "Evolutionary Dynamics of Complex Networks of HIV Drug-Resistant Strains: The Case of San Francisco," Science 327(5966):697-701.
Sticht et al., (2005) "A peptide inhibitor of HIV-1 assembly in vitro" Nature Structural & Molecular Biology, vol. 12 No. 8 671-677.
STN Registry No. 137349-29-2, Nov. 15, 1991, 1 page.
SUBLOCADE Product Label, issued: Nov. 2017, 43 pages.
Taiwo, B. (Sep. 2009; e-pub. Jan. 10, 2009). "Understanding Transmitted HIV Resistance Through the Experience in the USA," Int'/ J. of Infectious Diseases 13(5):552-559.
Tanaka, R. et al. (2005) "One-Pot Synthesis of Metalated Pyridines from Two Acetylenes, a Nitrile, and a Titanium(II) Alkoxide," J. Am. Chem. Soc. 127(21):7774-7780.
Tang et al., (2003) "Antiviral Inhibition of the HIV-1 Capsid Protein," J. Mol. Biol., 327, 1013-1020.
Tse et al., (2017) "Discovery of Novel Potent HIV Capsid Inhibitors with Long-Acting Potential," Abstract for Oral Presentation at the Conference on Retroviruses and Opportunistic Infections (CROI), Seattle, WA, 18 pages.
Tsiang et al., (2012) "A Trimer of Dimers is the Basic Building Block for Human Immunodeficiency Virus-1 Caosid Assembly" Biochemistry, 51, 4416-4428.
Wong et al., (2014) "SPR Assay Development to Characterize Caps id Inhibitors Binding & MOA," Poster Presented at the Developments in Protein Interaction (DiPIA), La Jolla, CA, 1 page.
Yale et al., "The trifluoromethyl group in medical chemistry," J. Med. Chem., 1958, 1(2):121-133.
Yant et al., (2014) "An Improved PF74 Analog Inhibits Multiple HIV Capsid Functions Independently of Host Cyclophilin A and CPSF6" Poster Presented at the Conference on Retroviruses and Opportunistic Infections (CROI), Boston, Massachusetts, 1 page.
Yant et al., (2014) "PF74 Inhibits Multiple HIV Capsid Functions Independently of Host Cyclophilin A and CPSF6" Abstract for Poster Presented at the Conference on Retroviruses and Opportunistic Infections (CROI), Boston, Massachusetts.
Zhou et al. (2015) "HIV-1 Resistance to the Capsid-Targeting Inhibitor PF74 Results in Altered Dependence on Host Factors Required for Virus Neclear Entry" Journal of Virology, doi 10.1128/JVI.00340-15. Published online Jun. 24, 2015, 37 pages.
[No Author Listed], "2-[9-(Difluoromethyl)-5,5-difluoro-7,8-diazatricylo[4.4.0.02,4]nona-1(6),8-dien-7-yl]acetic acid," PubChem CID 71186949, Mar. 21, 2013, 18 pages.
[No Author Listed], "3-Methyl-3-methylsulfonylbut-1-yne," PubChem CID 14241469, Feb. 9, 2002, 16 pages.
[No Author Listed], CAS registry No. 1620056-83-8, Aug. 6, 2014, 1 page.
Carnes et al., "Inhibitors of the HIV-1 Capsid, A Target of Opportunity," Curr. Opin. HIV AIDS, 2018, 13(4):359-365.
PCT International Search Report and Written Opinion in International Appln. No. PCT/US2019/041880, dated Oct. 17, 2019, 11 pages.
Talele, "The 'Cyclopropyl Fragment' is a Versatile Player that Frequently Appears in Preclinical/Clinical Drug Molecules," Journal of Medicinal Chemistry, 2016, 59(19):8712-8756.

(56) References Cited

OTHER PUBLICATIONS

Thenin-Houssier et al., "HIV-1 capsid inhibitors as antiretroviral agents," Curr. HIV Res., 2016, 14(3):270-282.
Tse et al., "Discovery of Novel Potent HIV Capsid Inhibitors with Long-Acting Potential," Presentation at the Conference on Retroviruses and Opportunistic Infections (CROI), Seattle, WA, Feb. 14, 2017, 18 pages.
Wu et al., "Selective Inhibitors of Tumor Progression Loci-2(Tp12) Kinase with Potent Inhibition of TNF-Alpha Production in Human Whole Blood," Biorg. Med. Chem. Lett., 2009, 19(13):3485-3488.
Xiangbui et al., "In Silico Virtual Screening," Biotechnology in the Post-Genome Era, 2003, 16 pages.
Yadav et al., "Co-crystals: a novel approach to modify physicochemical properties of active pharmaceutical ingredients" Indian J. Pharm. Sci., 2009, 71(4):359-370.
Brittain, "Polymorphism in pharmaceutical solids," Marcel Dekker, Inc., 1999, 235-238.
Jarvis et al., "Conquering HIV's capsid", C&EN Chicago, Jul. 2017, 95(31): 23-25.
Molina et al., "On-Demand Preexposure Prophylaxis in Men at High Risk for HIV-1 Infection," N Engl. J Med. 2015, 353:2237-2246.
Taiwanese Office Action in Patent Application No. 108124960, dated Apr. 6, 2021, 14 pages (with English translation).
Japanese Office Action in JP Appln. No. 2021-502563, dated Mar. 17, 2022, 9 pages (with English translation).
Australian Office Action in AU Appln. No. 2019307500, dated May 25, 2022, 3 pages.
Bastin et al., "Salt Selection and Optimisation Procedures for Pharmaceutical New Chemical Entities," Organic Process Research & Development, Jul. 2000, 4(5): 427-435.
Fontes Ferreira da Cunha et al., "4D-QSAR Models of HOE/BAY-793 Analogues as HIV-1 Protease Inhibitors," QSAR & Combinatorial Science, 2005, 24(2): 240-253.
Morissette et al., "High-throughput crystallization: polymorphs, salts, co-crystals and solvates of pharmaceutical solids," Advanced Drug Delivery Reviews, Feb. 2004, 56(3):275-300.
Pornillos et al., "Atomic level modeling of the HIV capsid," Nature, Jan. 2011, 469(7330):424-427.
Pungpo et al., "Computer-aided molecular design of highly potent HIV-1 RT inhibitors: 3D QSAR and molecular docking studies of efavirenz derivatives," SAR and QSAR in Environmental Research, 2006, 17(4):353-370.
Silverman, "The Organic Chemistry of Drug Design and Drug Action," Elsevier, 2004, pp. 121-169.
Silvestri et al., "Novel Indolyl Aryl Sulfones Active against HIV-1 Carrying NNRTI Resistance Mutations: Synthesis and SAR Studies," Journal of Medical Chemistry, 2003, 46(12): 2482-2493.
Yang et al., "Design, synthesis and anti-HIV-1 evaluation of hydrazide-based peptidomimetics as selective gelatinase inhibitors," Bioorganic & Medicinal Chemistry, May 2016, 24(9):2125-2136.
Zheng et al. "GS-6207: A Novel, Potent and Selective First-In-Class Inhibitor of HIV-1 Capsid Function Displays Nonclinical Pharmacokinetics Supporting Long-Acting Potential," Poster Presented at ID Week 2018, San Francisco, CA, 1 page.
Australian Examination Report in AU Appln. No. 2019307500, dated Sep. 23, 2021, 3 pages.
Canadian Office Action in CA Patent Application No. 3,103,522, dated Feb. 15, 2022, 5 pages.
PCT International Preliminary Report on Patentability in International Application No. PCT/US2019/041880, dated Jan. 19, 2021, 7 pages.
Taiwanese Office Action in TW Appln. No. 108124960, dated Feb. 21, 2022, 7 pages (with English translation).
AU Office Action in Australian Application No. 2019307500, dated Sep. 29, 2022, 3 pages.
Canadian Office Action issued in CA Appln. No. 3,103,522, dated Sep. 29, 2022, 4 pages.
Choy et al., "Synthesis of irreversible HIV-1 protease inhibitors containing sulfonamide and sulfone as amide bond isosteres," Bioorganic & Medicinal Chemistry Letters, Oct. 1997, 7(20):2635-38.
Japanese Office Action in JP Appln. No. 2021-502563, dated Oct. 27, 2022, 8 pages (with English translation).
Korean Office Action in KR Appln. No. 10-2021-7004348, dated Dec. 13, 2022, 17 pages (with English translation).
Taiwanese Office Action in TW Appln. No. 111115021, dated Oct. 4, 2022, 8 pages (with English translation).
Chinese Office Action in CN Appln. No. 201980047511.X, dated Aug. 10, 2023, 20 pages (with English translation).
Chinese Office Action in CN Appln. No. 201980047511.X, dated Feb. 11, 2023, 25 pages (with English translation).
Japanese Pre-Appeal Examination Report in JP Appln No. 2021-502563, dated May 11, 2023, 11 pages (with English translation).
Jindal et al., "Nevirapine loaded Poloxamer 407/Pluronic P123 mixed micelles: Optimization of formulation and in vitro evaluation," Colloids and Surfaces B: Biointerfaces, May 2015, 129:100-106.
Klooster et al., "Pharmacokinetics and Disposition of Rilpivirine (TMC278) Nanosuspension as a Long-Acting Injectable Antiretroviral Formulation," Antimicrobial Agents and Chemotherapy, May 2010, 54(5):2042-2050.
Korean Office Action in KR Appln. No. 10-2021-7004348, dated Jun. 19, 2023, 8 pages (with English translation).
Landovitz et al., "The promise and pitfalls of long acting injectable agents for HIV prevention," Current Opinion in HIV and AIDS, Jan. 2016, (1):122-128.
Magiorakos et al., "Multidrug-resistant, extensively drug-resistant and pandrug-resistant bacteria: an international expert proposal for interim standard definitions for acquired resistance," Clinical Microbiology and Infection, Mar. 2012, 18(3): 268-281.
Palombo et al., "Prodrug and conjugate drug delivery strategies for improving HIV/ADS therapy," Journal of drug delivery science and technology, Jan. 2009, 19(1):3-14.
Seremeta et al., "Poly(ε-caprolactone), Eudragit® RS 100 and poly(ε-caprolactone)/Eudragit® RS 100 blend submicron particles for the sustained release of the antiretroviral efavirenz," Colloids and Surfaces B: Biointerfaces, Feb. 2013, 102: 441-449.
Spreen et al., "Long-acting injectable antiretrovirals for HIV treatment and prevention," Current Opinion in HIV and AIDS, Nov. 8, 2013, 8(6):565-571.
Taiwanese Office Action in TW Appln. No. 108124960, dated Jul. 10, 2023, 4 pages (with English translation).
Office Action in Chinese Appln. No. 201980047511.X, dated Nov. 1, 2023, 22 pages (with English translation).
Office Action in Japanese Appln. No. 2023-028566, dated Dec. 12, 2023, 3 pages (with English translation).

\* cited by examiner

CAPSID INHIBITORS FOR THE TREATMENT OF HIV

CROSS REFERENCE TO RELATED APPLICATIONS

This application claims the benefit of U.S. Provisional Application No. 62/698,611, filed on Jul. 16, 2018, the entire content of which is hereby incorporated by reference in its entirety.

FIELD

The present disclosure relates to methods for the treatment of a human immunodeficiency virus (HIV) infection in heavily treatment-experienced patients (e.g., patients with multidrug resistant HIV infection).

BACKGROUND

The viral capsid protein (CA) is essential for multiple stages of the HIV life cycle. During viral maturation following the processing of Gag polyprotein by the HIV protease, CA self-assembles into the conical shaped core characteristic of mature HIV-1 virions. Contained within this capsid core are the viral RNA, nucleocapsid, reverse transcriptase, and integrase. Failure to generate a suitable core precludes infectivity. In addition, CA contributes to multiple essential processes during the early stages of HIV replication, including important roles in regulating proper capsid core disassembly (uncoating) kinetics to ensure efficient and productive viral DNA synthesis via coupled reverse transcription, and contributes to the active transport of pre-integration complexes into the nuclear compartment to support viral DNA integration into transcriptionally active loci. Defects in the proper function of capsid ultimately inhibit efficient nuclear uptake and integration of viral DNA into the host genome.

There are currently a number of antiretroviral drugs available to combat HIV infection. These drugs can be divided into classes based on the viral protein they target or their mode of action. Used alone, these drugs are effective in reducing viral replication. However, the effect is only temporary as the virus readily develops resistance to all known agents used as monotherapy. Combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D.; N. Engl. J. Med. 1998, 338:853-860).

Despite the success of combination antiretroviral therapy, a significant proportion of patients experience a loss of virologic, immunologic, or clinical benefit from their current regimens, leading to treatment failure and a rebound of the amount of HIV that can be measured in the blood. Initial studies suggest that approximately 30-50% of patients ultimately fail at least one drug in the suppressive combination. Treatment failure can be caused by the emergence of viral resistance. Viral resistance in turn can be caused by the replication rate of HIV-1 during the course of infection combined with the relatively high viral mutation rate associated with the viral polymerase and the lack of adherence of HIV-infected individuals in taking their prescribed medications. Because of structural similarities of the drugs within an antiretroviral class, cross resistance is commonly seen to the other members of that class (for example, virologic failure on a regimen containing a non-nucleoside reverse transcriptase inhibitor (NNRTI) will lead to cross resistance to the other first generation NNRTI agents). As patients experience repeated virologic failure on antiretroviral combination therapy, their viruses develop broad multi-class antiretroviral drug resistance which limits the effectiveness of the next round of antiretroviral therapy. Many heavily treatment-experienced patients have viral resistance to several classes of antiretroviral drugs and there are often not even two drugs that remain fully active to form the core of a new, effective antiretroviral drug regimen. Frequently, these patients have limited options for alternative treatment regimens and are at risk of significant morbidity and mortality.

Thus, there is a need for safe and effective therapies for heavily treatment-experienced patients who have limited treatment options due to antiretroviral drug resistance.

SUMMARY

The present disclosure relates to methods of treating human immunodeficiency virus (HIV) infection in a heavily treatment-experienced patient. The method includes administering to the patient a therapeutically effective amount of a compound of Formula (Ia) or Formula (Ib):

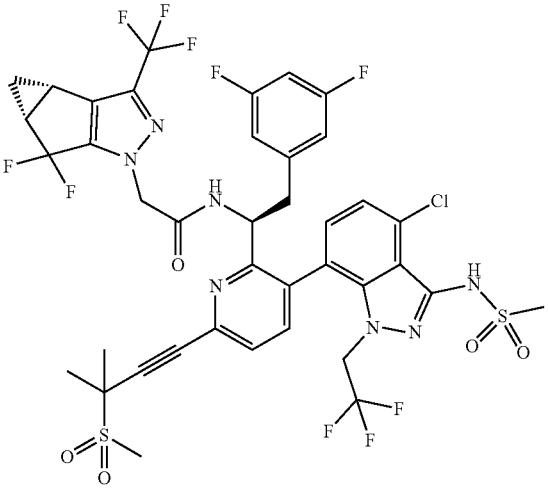

(Ia)

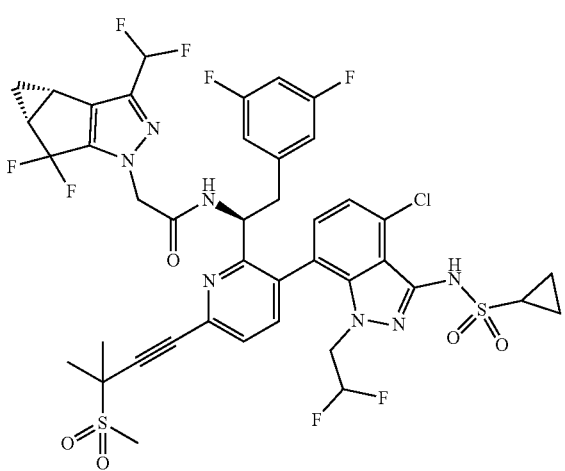

(Ib)

or a pharmaceutically acceptable salt thereof.

In some embodiments, the HIV infection is an HIV-1 infection characterized by HIV-1 mutant resistance to one or more antiretroviral medications. In some embodiments, the HIV infection is an HIV-1 infection characterized by HIV-1 mutant resistance to two or more antiretroviral medications. In some embodiments, the HIV infection is an HIV-1 infection characterized by HIV-1 mutant resistance to three or more antiretroviral medications.

In some embodiments, the HIV-1 mutant is resistant to a protease inhibitor (PI), a nucleoside or nucleotide reverse transcriptase inhibitor (NRTI), a non-nucleoside or non-nucleotide reverse transcriptase inhibitor (NNRTI), or an integrase strand transfer inhibitor (INSTI). In certain embodiments, the HIV-1 mutant resistant to a protease inhibitor is selected from I50V, I84V/L90M, G48V/V82A/L90M, and G48V/V82S. In certain embodiments, the HIV-1 mutant resistant to a nucleoside or nucleotide reverse transcriptase inhibitor is selected from K65R, M184V, and 6TAMs. In certain embodiments, the HIV-1 mutant resistant to a non-nucleoside or non-nucleotide reverse transcriptase inhibitor is selected from K103N, Y181C, Y188L, L100I/K103N, and K103N/Y181C. In certain embodiments, the HIV-1 mutant resistant to a integrase strand transfer inhibitor is selected from Y143R, E138K/Q148K, G140S/Q148R, E92Q/N155H, N155H/Q148R, and R263K/M50I.

In some embodiments, the patient is infected with HIV-1 resistant to at least one antiretroviral medication. In some embodiments, the patient is infected with multidrug resistant HIV-1 which is resistant to at least one antiretroviral medication from each of two different classes of antiretroviral medications. In some embodiments, the patient is infected with multidrug resistant HIV-1 which is resistant to at least one antiretroviral medication from each of three different classes of antiretroviral medications. In some embodiments, the different classes of antiretroviral medications are selected from a nucleoside or nucleotide reverse transcriptase inhibitor (NRTI), a non-nucleoside or non-nucleotide reverse transcriptase inhibitor (NNRTI), a protease inhibitor (PI), and an integrase strand transfer inhibitor (INSTI).

In some embodiments, the NRTI is selected from emtricitabine, lamivudine (3TC), zidovudine (azidothymidine (AZT)), didanosine (ddI), dideoxyinosine, tenofovir, tenofovir alafenamide, tenofovir disoproxil fumarate, stavudine (d4T), zalcitabine (dideoxycytidine, ddC), and abacavir.

In some embodiments, the NNRTI is selected from efavirenz, etravirine, rilpivirine, nevirapine, and delavirdine.

In some embodiments, the PI is selected from amprenavir, atazanavir, darunavir, fosamprenavir, indinavir, lopinavir, nelfinavir, ritonavir, saquinavir, and tipranavir.

In some embodiments, the INSTI is selected from raltegravir, elvitegravir, dolutegravir, and bictegravir.

In some embodiments of the method, the patient had been previously treated with at least one antiretroviral medication for at least 3 months, at least 6 months, at least 9 months, or at least 12 months.

In some embodiments, the patient failed a prior HIV treatment regimen including administration of at least one antiretroviral medication. In certain embodiments, the prior treatment regimen included administration of at least one antiretroviral medication from each of two different classes of antiretroviral medications. In certain embodiments, the prior treatment regimen included administration of at least one antiretroviral medication from each of three different classes of antiretroviral medications. In some embodiments, the different classes of antiretroviral medications are selected from a nucleoside reverse transcriptase inhibitor (NRTI), a non-nucleoside reverse transcriptase inhibitor (NNRTI), a protease inhibitor (PI), and an integrase strand transfer inhibitor (INSTI).

In certain embodiments of the method, the compound of Formula (Ia) or Formula (Ib), or a pharmaceutically acceptable salt thereof, is administered orally, subcutaneously, intramuscularly, or intravenously.

In some embodiments, the compound of Formula (Ia) or Formula (Ib), or a pharmaceutically acceptable salt thereof, is administered orally at a concentration of about 20 mg/mL to about 100 mg/mL. In some embodiments, the compound of Formula (Ia) or Formula (Ib) is formulated as a hard gelatin capsule. In some embodiments, the compound of Formula (Ia) or Formula (Ib) is formulated as a soft gelatin capsule. In some embodiments, the compound of Formula (Ia) or Formula (Ib) is formulated as a tablet.

In some embodiments, the compound of Formula (Ia) or Formula (Ib), or a pharmaceutically acceptable salt thereof, is administered subcutaneously. In some embodiments, the compound of Formula (Ia) or Formula (Ib), or a pharmaceutically acceptable salt thereof, is administered subcutaneously at a concentration of about 50 mg/mL to about 500 mg/mL. In some embodiments, the compound of Formula (Ia) or Formula (Ib), or a pharmaceutically acceptable salt thereof, is formulated as a solution formulation. In some embodiments, the compound of Formula (Ia) or Formula (Ib), or a pharmaceutically acceptable salt thereof, is formulated as an aqueous suspension. In some embodiments, the compound of Formula (Ia) is a sodium salt. In some embodiments, the compound of Formula (Ib) is a trifluoroacetic acid salt.

In some embodiments of the method, the compound of Formula (Ia) or Formula (Ib) is formulated with one or more other compounds selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV nucleoside reverse transcriptase translocation inhibitors, and pharmacokinetic enhancers. In some embodiments, the HIV nucleoside reverse transcriptase translocation inhibitor is 4'-ethynyl-2-fluoro-2'-deoxyadenosine triphosphate (MK-8591).

In some embodiments, the compound of Formula (Ia) or Formula (Ib), or a pharmaceutically acceptable salt thereof, is administered once daily. In some embodiments, the compound of Formula (Ia) or Formula (Ib), or a pharmaceutically acceptable salt thereof, is administered once every 1 week, 2 weeks, 4 weeks, 8 weeks, 12 weeks, 16 weeks, 20 weeks, 24 weeks, or 48 weeks.

In some embodiments of the method, the patient has a viral load of greater than about 200 copies of HIV-1 RNA/mL, greater than about 500 copies of HIV-1 RNA/mL, greater than about 750 copies of HIV-1 RNA/mL, greater than about 1000 copies of HIV-1 RNA/mL, or greater than about 2000 copies of HIV-1 RNA/mL at the time of beginning administration of the compound of Formula (Ia) or Formula (Ib), or a pharmaceutically acceptable salt thereof.

In some embodiments, the patient is failing an HIV treatment regimen including administration of at least one antiretroviral medication at the time of beginning administration of the compound of Formula (Ia) or Formula (Ib), or a pharmaceutically acceptable salt thereof.

In some embodiments of the method, administration of the compound of Formula (Ia) or Formula (Ib), or a pharmaceutically acceptable salt thereof, results in a decrease in the viral load in the patient. In some embodiments, the viral load is decreased by about 0.5 $\log_{10}$ to about 2.5 $\log_{10}$ after administration of the compound of Formula (Ia) or Formula (Ib), or a pharmaceutically acceptable salt thereof, for about 24 weeks as compared to the viral load at the time of beginning administration of the compound of Formula (Ia) or Formula (Ib), or a pharmaceutically acceptable salt thereof. In some embodiments, the viral load is decreased by about 0.5 $\log_{10}$, about 1 $\log_{10}$, about 1.5 $\log_{10}$, about 2 $\log_{10}$, or about 2.5 $\log_{10}$ after administration of the compound of Formula (Ia) or Formula (Ib), or a pharmaceutically acceptable salt thereof, for about 24 weeks as compared to the viral load at the time of beginning administration of the compound of Formula (Ia) or Formula (Ib), or a pharmaceutically acceptable salt thereof.

In some embodiments, the viral load in the patient is about 200 copies of HIV-1 RNA/mL or less after administration of the compound of Formula (Ia) or Formula (Ib), or a pharmaceutically acceptable salt thereof, for about 24 weeks. In some embodiments, the viral load in the patient is about 50 copies of HIV-1 RNA/mL or less after administration of the compound of Formula (Ia) or Formula (Ib), or a pharmaceutically acceptable salt thereof, for about 24 weeks.

In some embodiments, the patient is concurrently treated with at least one additional antiretroviral medication. In some embodiments, the additional antiretroviral medication is selected from a nucleoside reverse transcriptase inhibitor (NRTI), a non-nucleoside reverse transcriptase inhibitor (NNRTI), a protease inhibitor (PI), an integrase strand transfer inhibitor (INSTI), a gp41 fusion inhibitor, a CCR5 co-receptor antagonist, and combinations thereof.

In some embodiments, the NRTI is selected from emtricitabine, lamivudine (3TC), zidovudine (azidothymidine (AZT)), didanosine (ddI), dideoxyinosine, tenofovir, tenofovir alafenamide, tenofovir disoproxil fumarate, stavudine (d4T), zalcitabine (dideoxycytidine, ddC), and abacavir.

In some embodiments, the NNRTI is selected from efavirenz, etravirine, rilpivirine, nevirapine, and delavirdine.

In some embodiments, the PI is selected from amprenavir, atazanavir, darunavir, fosamprenavir, indinavir, lopinavir, nelfinavir, ritonavir, saquinavir, and tipranavir.

In some embodiments, the INSTI is selected from raltegravir, elvitegravir, dolutegravir, and bictegravir.

In some embodiments, the gp41 fusion inhibitor is selected from albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer, and sifuvirtide.

In some embodiments, the CCR5 co-receptor antagonist is selected from aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Also included in the present disclosure is a method of treating human immunodeficiency virus-1 (HIV-1) infection in a heavily treatment-experienced patient with multidrug resistant HIV-1, the method including administering to the patient a therapeutically effective amount of a compound of Formula (Ia) or Formula (Ib):

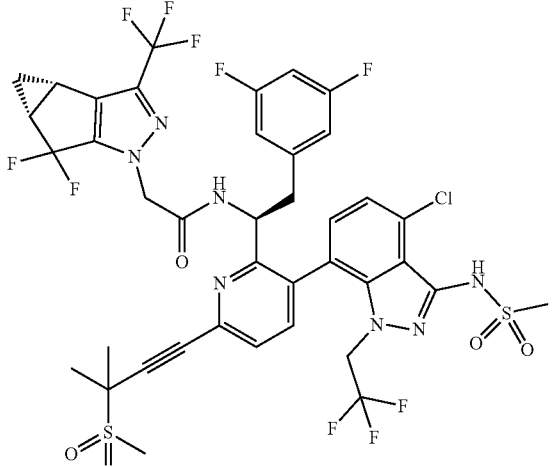

(Ia)

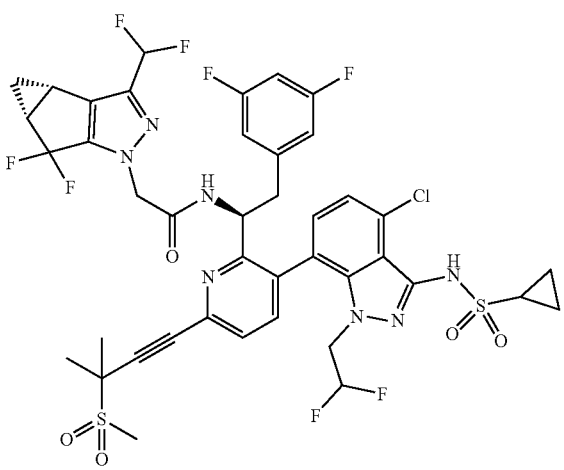

(Ib)

or a pharmaceutically acceptable salt thereof, where the patient had been previously treated with an HIV treatment regimen including administration of at least one antiretroviral medication and failed the treatment regimen; and administration of the compound results in a reduction in HIV viral load in the patient.

In some embodiments of the method, the multidrug resistant HIV-1 is resistant to at least one antiretroviral medication from each of two different classes of antiretroviral medications. In some embodiments of the method, the multidrug resistant HIV-1 is resistant to at least one antiretroviral medication from each of three different classes of antiretroviral medications. In some embodiment, the different classes of antiretroviral medications are selected from a nucleoside reverse transcriptase inhibitor (NRTI), a non-nucleoside reverse transcriptase inhibitor (NNRTI), a protease inhibitor (PI), and an integrase strand transfer inhibitor (INSTI).

In some embodiments, the patient had been previously treated with at least one antiretroviral medication for at least 3 months, at least 6 months, at least 9 months, or at least 12 months. In some embodiments, the prior treatment regimen included administration of at least one antiretroviral medication from each of two different classes of antiretroviral medications. In some embodiments, the prior treatment regimen included administration of at least one antiretroviral medication from each of three different classes of antiretroviral medications. In some embodiments, the different classes of antiretroviral medications are selected from a nucleoside reverse transcriptase inhibitor (NRTI), a non-nucleoside reverse transcriptase inhibitor (NNRTI), a protease inhibitor (PI), and an integrase strand transfer inhibitor (INSTI).

Provided in the present disclosure is a method of treating human immunodeficiency virus-1 (HIV-1) infection in a heavily treatment-experienced patient with multidrug resistant HIV-1, the method including administering to the patient a therapeutically effective amount of a compound of Formula (Ia) or Formula (Ib):

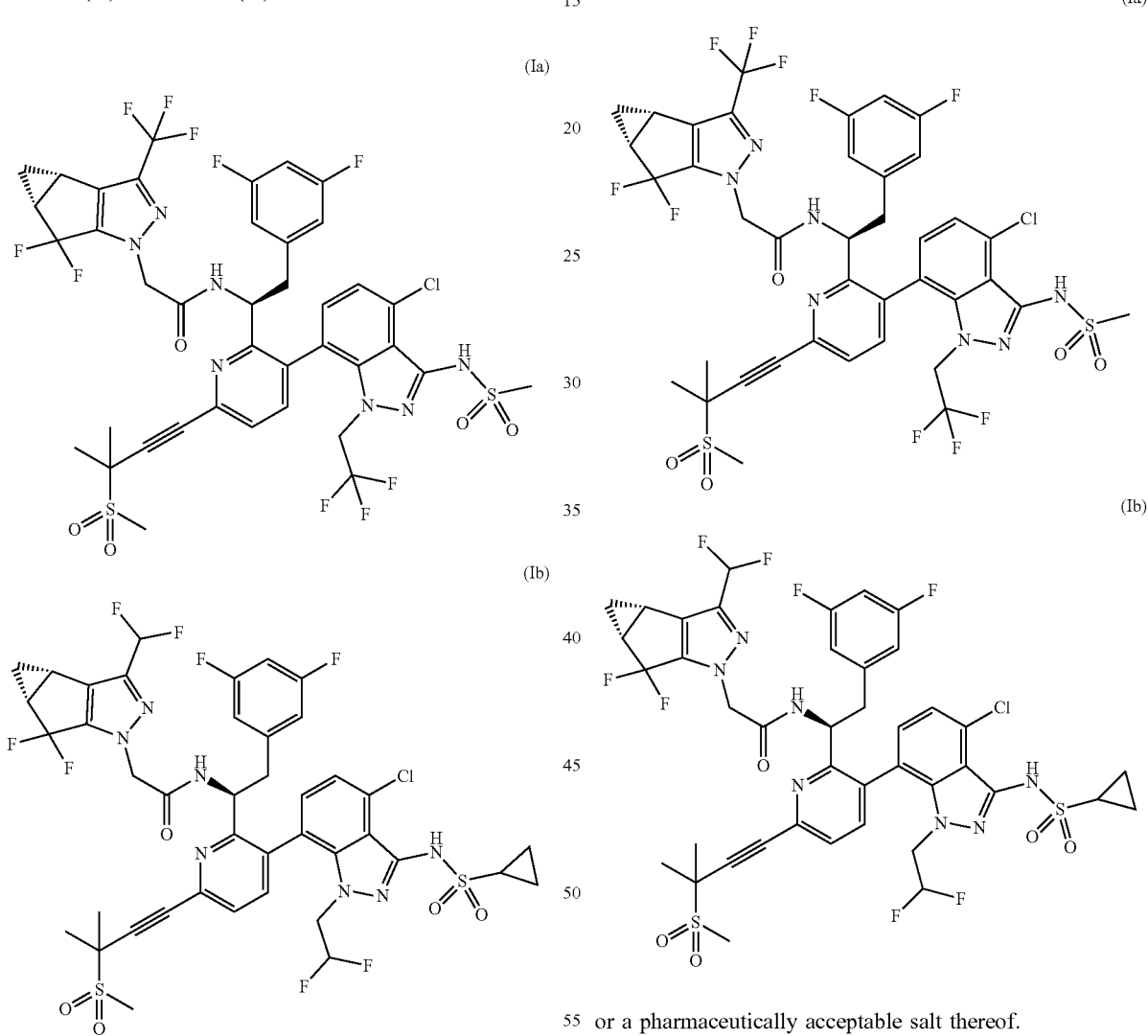

or a pharmaceutically acceptable salt thereof, where the multidrug resistant HIV-1 is resistant to at least one antiretroviral medication from each of two different classes of antiretroviral medications, where the different classes of antiretroviral medications are selected from a nucleoside reverse transcriptase inhibitor (NRTI), a non-nucleoside reverse transcriptase inhibitor (NNRTI), a protease inhibitor (PI), and an integrase strand transfer inhibitor (INSTI); the patient had been previously treated with an HIV treatment regimen including administration of at least one antiretroviral medication and failed the treatment regimen; the patient has a viral load of greater than about 200 copies of HIV-1 RNA/mL at the time of beginning administration of the compound of Formula (Ia) or Formula (Ib); and administration of the compound results in a reduction in HIV viral load in the patient.

Also provided is a method of reducing the viral load associated with an HIV infection in a heavily treatment-experienced patient with multidrug resistant HIV, the method including administering to the patient a therapeutically effective amount of a compound of Formula (Ia) or Formula (Ib):

or a pharmaceutically acceptable salt thereof.

Additional embodiments of the current disclosure are disclosed herein.

DETAILED DESCRIPTION

Figure 1:
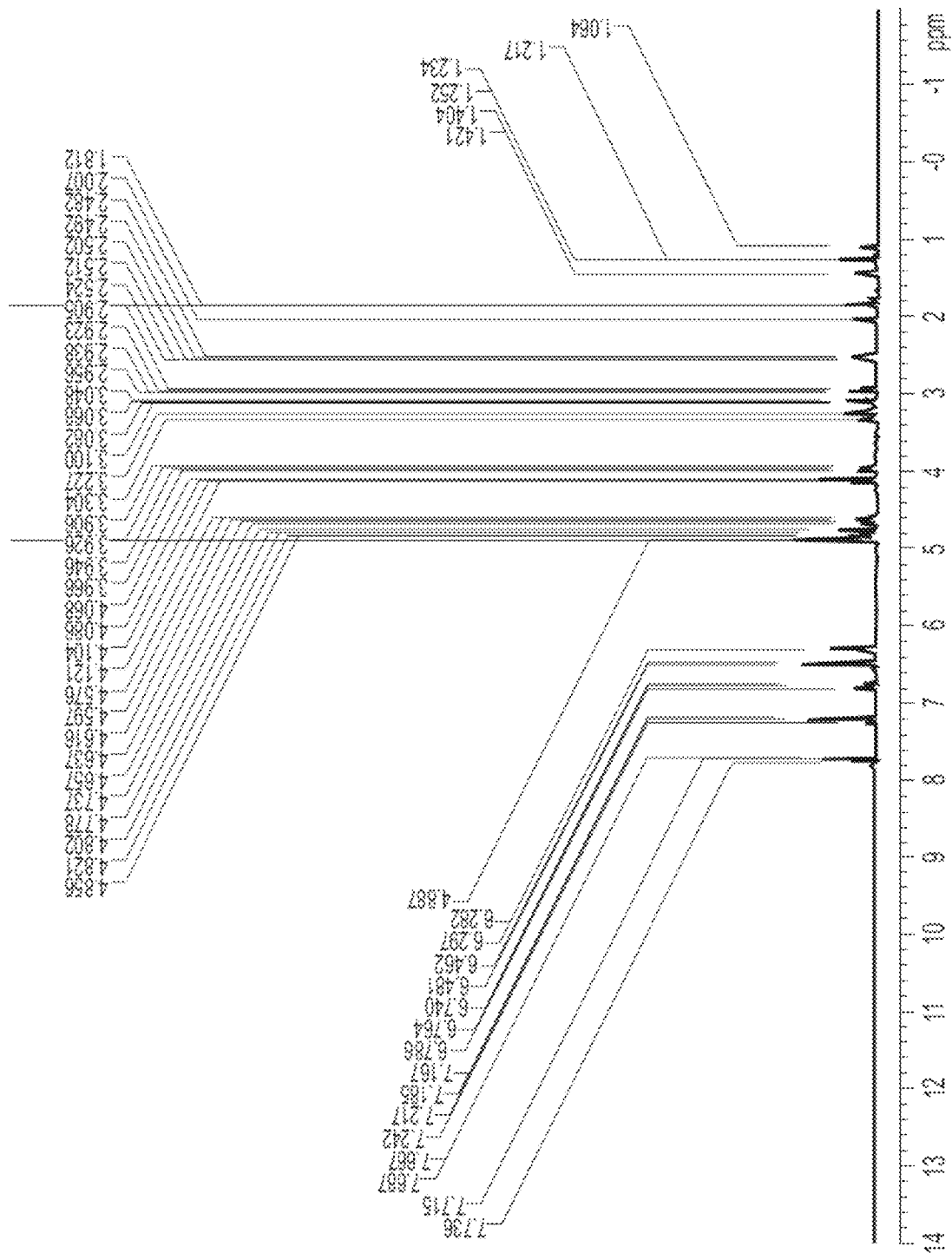
FIG. 1 shows the $^1$H NMR (400 MHz, methanol-d4) of the compound of Formula (Ia): N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide.
Figure 2:
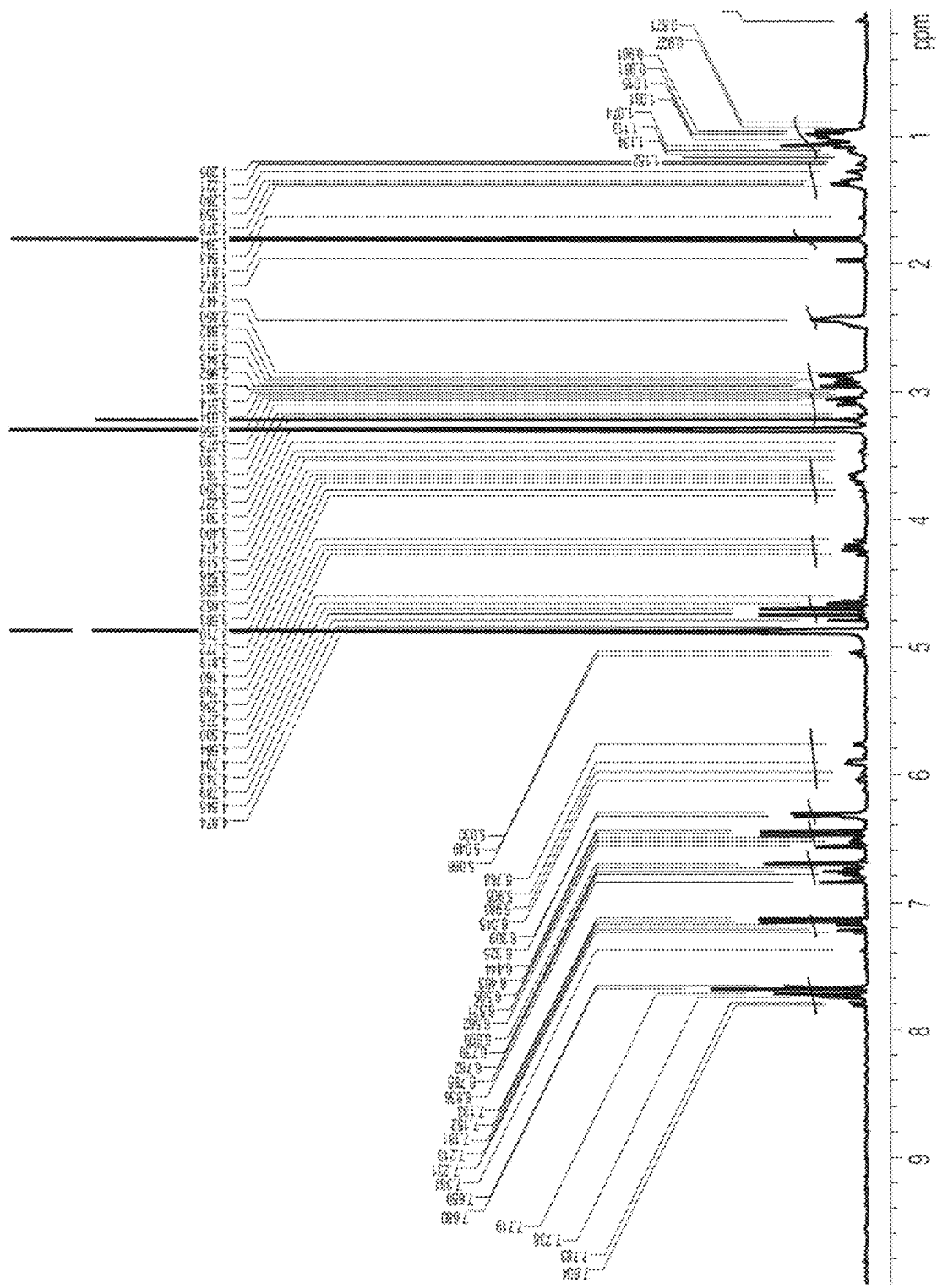
FIG. 2 shows the $^1$H NMR (400 MHz, methanol-d4) of the compound of Formula (Ib): N—((S)-1-(3-(4-chloro-3-(cyclopropanesulfonamido)-1-(2,2-difluoroethyl)-1H-indazol-'7-yl)-6-(3-methyl-3-(methylsulfonyl)but-1-yn-1-yl) pyridin-2-yl)-2-(3,5-difluorophenyl)ethyl)-2-((3b S,4aR)-5, 5-difluoro-3-(trifluoromethyl)-3b,4,4a,5-tetrahydro-1H-cyclopropa[3,4]cyclopenta[1,2-c]pyrazol-1-yl)acetamide.

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art.

When trade names are used herein, it is intended to independently include the tradename product and the active pharmaceutical ingredient(s) of the tradename product.

Reference to "about" a value or parameter herein includes (and describes) embodiments that are directed to that value or parameter per se. In certain embodiments, the term "about" includes the indicated amount±10%. In other embodiments, the term "about" includes the indicated amount±8%. In other embodiments, the term "about" includes the indicated amount±5%. In other embodiments, the term "about" includes the indicated amount±3%. In certain other embodiments, the term "about" includes the indicated amount±1%. Also, the term "about X" includes description of "X".

As used herein and in the appended claims, the singular forms "a" and "an" and "the" include plural referents unless the context clearly dictates otherwise. Thus, for example, reference to "the compound" includes a plurality of such compounds and reference to "the assay" includes reference to one or more assays, and so forth.

As an additional example, reference to "a pharmaceutically acceptable excipient" includes both a single pharmaceutically acceptable excipient and a plurality of pharmaceutically acceptable excipients.

As used herein, "HIV" or "Human Immunodeficiency Virus" refers to HIV-1 and/or to HIV-2.

As used herein, a "heavily treatment-experienced patient" refers to an HIV-infected patient who has limited treatment options due to a multidrug resistant HIV infection. For example, in some embodiments, the "heavily treatment-experienced patient" is a patient with HIV who has developed resistance to an antiretroviral medication from at least one class of antiretroviral medications selected from the group consisting of NRTIs, NNRTIs, PIs, and INSTIs.

In some embodiments, "multidrug resistant HIV infection" means resistance to an antiretroviral medication from at least one class of antiretroviral medications selected from the group consisting of NRTIs, NNRTIs, PIs, and INSTIs. In some embodiments, "multidrug resistant HIV infection" means resistance to at least one antiretroviral medication from two classes of antiretroviral medications selected from the group consisting of NRTIs, NNRTIs, PIs, and INSTIs. In some embodiments, "multidrug resistant HIV infection" means resistance to at least one antiretroviral medication from three classes of antiretroviral medications selected from the group consisting of NRTIs, NNRTIs, PIs, and INSTIs. In some embodiments, "multidrug resistant HIV infection" means resistance to at least one antiretroviral medication from each of the four classes of antiretroviral medications selected from the group consisting of NRTIs, NNRTIs, PIs, and INSTIs.

As used herein, the term "NRTI(s)" refers to nucleoside reverse transcriptase inhibitor(s) or nucleotide reverse transcriptase inhibitor(s).

As used herein, the term "NNRTI(s)" refers to non-nucleoside reverse transcriptase inhibitor(s) or non-nucleotide reverse transcriptase inhibitor(s).

As used herein, the term "PI(s)" refers to protease inhibitor(s).

As used herein, the term "INSTI(s)" refers to integrase strand transfer inhibitor(s).

As used herein, the term "fail" or "failed" when referring to HIV therapy or an HIV treatment regimen means a treatment outcome which precludes the use of the same agent or class in the future in a patient with HIV. This could be due to inadequate initial viral response due to pre-existing viral resistance, viral rebound due to emergent viral resistance, or inability of a patient to continue a treatment due to intolerability or safety issues.

As used herein, the term "$C_{max}$" refers to the maximum observed plasma/serum concentration of drug.

"Pharmaceutically acceptable" refers to compounds, salts, compositions, dosage forms and other materials that are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-naphthalenesulfonic acid, oleic acid, palmitic acid, propionic acid, stearic acid, succinic acid, tartaric acid, p-toluenesulfonic acid, trifluoroacetic acid, trimethylacetic acid, and the like, and salts formed when an acidic proton present in the parent compound is replaced by either a metal ion, for example, an alkali metal ion (for example, a sodium or potassium), an alkaline earth ion (for example, calcium or magnesium), or an aluminum ion; or coordinates with an organic base such as diethanolamine, triethanolamine, N-methylglucamine and the like. Also included in this definition are ammonium and substituted or quaternary ammonium salts (e.g., quaternary ammonium salts containing the N,N,N-trimethylethanolammonium (choline) cation). Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, PA, (2005), at p. 732, Table 38-5, both of which are hereby incorporated by reference herein.

"Patient" and "patients" refer to humans, domestic animals (for example, dogs and cats), farm animals (for example, cattle, horses, sheep, goats and pigs), laboratory animals (for example, mice, rats, hamsters, guinea pigs, pigs, rabbits, dogs, and monkeys), and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (for example, decreasing one or more symptoms resulting from the disease or condition, and/or diminishing the extent of the disease or condition); b) slowing or arresting the development of one or more symptoms associated with the disease or condition (for example, stabilizing the disease or condition, delaying the worsening or progression of the disease or condition); and/or c) relieving the disease or condition, for example, causing the regression of clinical symptoms, ameliorating the disease state, delaying the progression of the disease, increasing the quality of life, and/or prolonging survival.

As used herein, the term "therapeutically effective amount" or "effective amount" refers to an amount that is effective to elicit the desired biological or medical response, including the amount of a compound that, when administered to a patient for treating a disease, is sufficient to effect such treatment for the disease or to an amount that is effective to protect against the contracting or onset of a disease. The effective amount will vary depending on the compound, the disease, and its severity and the age, weight, etc., of the patient to be treated. The effective amount can include a range of amounts. As is understood in the art, an effective amount may be in one or more doses, for example, a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (for example, additive or synergistic effects) of the compounds.

Except as expressly defined otherwise, the present disclosure includes all tautomers of compounds detailed herein, even if only one tautomer is expressly represented (for example, both tautomeric forms are intended and described by the presentation of one tautomeric form where a pair of two tautomers may exist). For example, if reference is made to a compound containing an amide (for example, by structure or chemical name), it is understood that the corresponding imidic acid tautomer is included by this disclosure and described the same as if the amide were expressly recited either alone or together with the imidic acid. Where more than two tautomers may exist, the present disclosure includes all such tautomers even if only a single tautomeric form is depicted by chemical name and/or structure.

It is understood by one skilled in the art that this disclosure also includes any compound disclosed herein (for example, a compound of Formula (Ia) or Formula (Ib), or a pharmaceutically acceptable salt thereof) that can be enriched at any or all atoms above naturally occurring isotopic ratios with one or more isotopes such as, but not limited to, deuterium ($^2H$ or D).

Disclosed are also compounds in which from 1 to n hydrogen atoms attached to a carbon atom can be replaced by a deuterium atom or D, in which n is the number of hydrogen atoms in the molecule. As known in the art, the deuterium atom is a non-radioactive isotope of the hydrogen atom. Such compounds can increase resistance to metabolism, and thus can be useful for increasing the half-life of the compounds when administered to a mammal. See, for example, Foster, "Deuterium Isotope Effects in Studies of Drug Metabolism," Trends Pharmacol. Sci., 5(12):524-527 (1984). Such compounds are synthesized by means well known in the art, for example, by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, a N, can be useful in positron emission tomography (PET) studies for examining substrate receptor occupancy. Isotopically-labeled compounds of Formula (Ia) or Formula (Ib), or a pharmaceutically acceptable salt thereof, can generally be prepared by conventional techniques known to those skilled in the art or by processes analogous to those described in the Examples as set out below using an appropriate isotopically-labeled reagent in place of the non-labeled reagent previously employed.

Compounds described herein can have chiral centers and/or geometric isomeric centers (E- and Z-isomers), and it is to be understood that all such optical, enantiomeric, diastereoisomeric and geometric isomers are encompassed. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s).

Also provided are also pharmaceutically acceptable hydrates, solvates, tautomeric forms, polymorphs, and prodrugs of the compounds described herein.

In an embodiment, the current disclosure relates to the use of the compound of Formula (Ia) or Formula (Ib), or a pharmaceutically acceptable salt thereof, in treating an infection caused by the HIV virus comprising administering a therapeutically effective amount to a patient in need thereof, where the patient is a heavily treatment-experienced patient that has a multidrug resistant HIV infection.

The present disclosure includes methods of using a compound of Formula (Ia), N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, having the following structure:

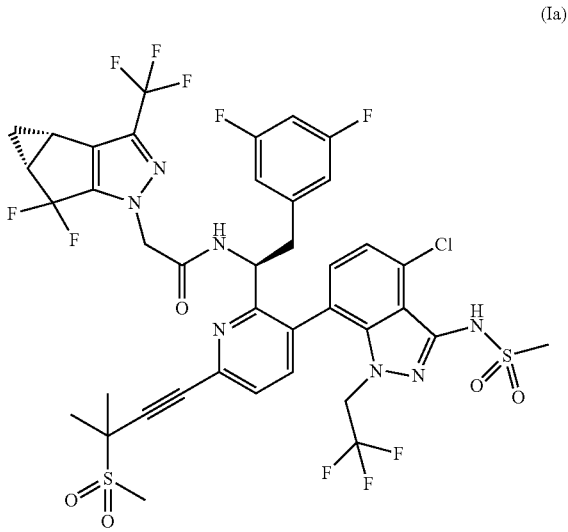 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

(Ia)

or pharmaceutically acceptable salt thereof, for the treatment of an HIV infection in heavily treatment-experienced patients with multidrug resistant HIV infection.

The present disclosure also includes methods of using a compound of Formula (Ib), N—((S)-1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3b S,4aR)-3-(difluoromethyl)-5,5-difluoro-3b,4,4a,5-tetrahydro-1H-cyclopropa[3,4]cyclopenta[1,2-c]pyrazol-1-yl)acetamide, having the following structure:

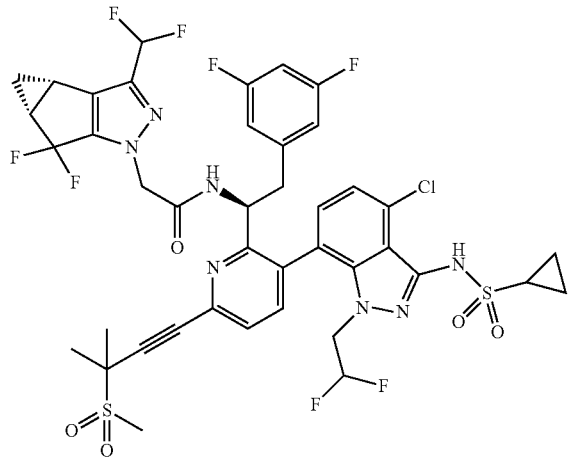

(Ib)

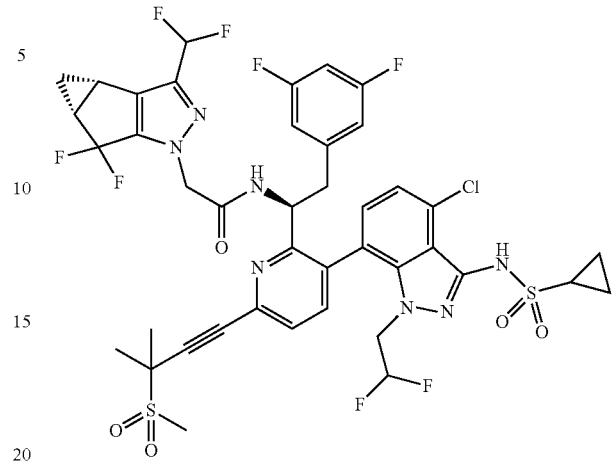

(Ib)

or pharmaceutically acceptable salt thereof, for the treatment of an HIV infection in heavily treatment-experienced patients with multidrug resistant HIV infection.

In some embodiments, the compound is a pharmaceutically acceptable salt of the compound of Formula (Ia) or Formula (Ib). Non-limiting examples of pharmaceutically acceptable salts of the compound of Formula (Ia) and Formula (Ib) include sodium salts and trifluoroacetic acid salts. In some embodiments, the compound of Formula (Ia) is a sodium salt. In some embodiments, the compound of Formula (Ib) is a trifluoroacetic acid salt.

The compounds used in the methods disclosed herein (for example, a compound of Formula (Ia) or Formula (Ib), or a pharmaceutically acceptable salt thereof) are active against major HIV-1 mutants selected by protease inhibitors (PIs), nucleoside reverse transcriptase inhibitors (NRTIs), non-nucleoside reverse transcriptase inhibitors (NNRTIs), and/or integrase inhibitors (INSTIs).

Methods of Treatment

Provided in this disclosure is a method of treating human immunodeficiency virus (HIV) infection in a heavily treatment-experienced patient that includes administering to the patient a therapeutically effective amount of a compound of Formula (Ia) or Formula (Ib):

(Ia)

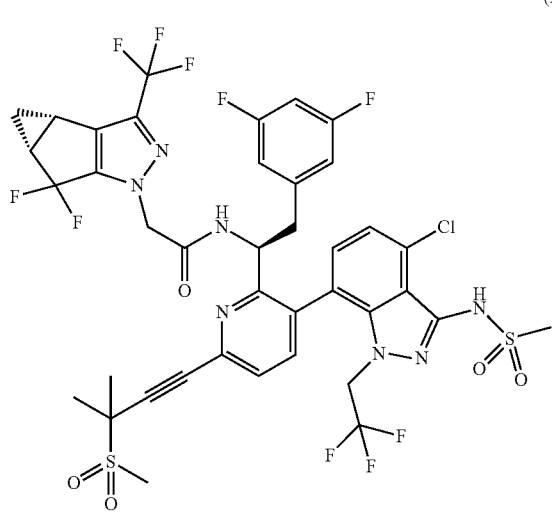

or a pharmaceutically acceptable salt thereof.

In the disclosed methods, the heavily treatment-experienced patient is infected with multidrug resistant HIV. In some embodiments, the heavily treatment-experienced patient has a multidrug resistant HIV infection and is on a failing HIV treatment regimen. In some embodiments, the heavily treatment-experienced patient has a viral load greater than about 1,000 copies of HIV RNA/mL.

In some embodiments, the HIV infection is an HIV-1 infection. In some embodiments, the HIV-1 infection is characterized by HIV-1 mutant resistance to an antiretroviral medication, for example, to one, two, three, four, or more classes of antiretroviral medications (e.g., PIs, NRTIs, NNRTIs, INSTIs, etc.). In some embodiments, the HIV-1 infection is characterized by HIV-1 mutant resistance to one or more classes of antiretroviral medications. In some embodiments, the HIV-1 infection is characterized by HIV-1 mutant resistance to two or more classes of antiretroviral medications. In some embodiments, the HIV-1 infection is characterized by HIV-1 mutant resistance to three or more classes of antiretroviral medications.

In some embodiments, the HIV-1 infection is characterized by an HIV-1 mutant that includes, but is not limited to:

(a) an HIV-1 mutant resistant to a PI (e.g., I50V, 184V/L90M, G48V/V82A/L90M, G48V/V82S, etc.);
(b) an HIV-1 mutant resistant to an NRTI (e.g., K65R, M184V, 6TAMs, etc.);
(c) an HIV-1 mutant resistant to an NNRTI (e.g., K103N, Y181C, Y188L, L100I/K103N, K103N/Y181C, etc.); and/or
(d) an HIV-1 mutant resistant to an INSTI (Y143R, E138K/Q148K, G140S/Q148R, E92Q/N155H, N155H/Q148R, R263K/M50I, etc.).

In some embodiments, the patient is infected with HIV-1 that is resistant to at least one antiretroviral medication. In some embodiments, the patient is infected with multidrug resistant HIV-1. In some embodiments, the patient is infected with multidrug resistant HIV-1 that is resistant to at least one, two, three, four, or more antiretroviral medications. In some embodiments, the patient is infected with multidrug resistant HIV-1 that is resistant to at least one antiretroviral medication from each of two different classes of antiretroviral medications. In some embodiments, the patient is infected with multidrug resistant HIV-1 that is resistant to at least one antiretroviral medication from each of three different classes of antiretroviral medications. In some embodiments, the different classes of antiretroviral medications are selected from a nucleoside reverse transcriptase inhibitor (NRTI), a non-nucleoside reverse transcriptase inhibitor (NNRTI), a protease inhibitor (PI), and an integrase strand transfer inhibitor (INSTI). In some embodiments, the different classes of antiretroviral medications are selected from an NRTI, an NNRTI, and a PI. In some embodiments, the patient is infected with multidrug resistant HIV-1 that is resistant to at least one NRTI and at least one NNRTI. In some embodiments, the patient is infected with multidrug resistant HIV-1 that is resistant to at least one NRTI and at least one PI. In some embodiments, the patient is infected with multidrug resistant HIV-1 that is resistant to at least one NRTI and at least one INSTI. In some embodiments, the patient is infected with multidrug resistant HIV-1 that is resistant to at least one NNRTI and at least one PI. In some embodiments, the patient is infected with multidrug resistant HIV-1 that is resistant to at least one NNRTI and at least one INSTI. In some embodiments, the patient is infected with multidrug resistant HIV-1 that is resistant to at least one PI and at least one INSTI. In some embodiments, the patient is infected with multidrug resistant HIV-1 that is resistant to at least one NRTI, at least one NNRTI, and at least one PI. In some embodiments, the patient is infected with multidrug resistant HIV-1 that is resistant to at least one NRTI, at least one NNRTI, and at least one INSTI. In some embodiments, the patient is infected with multidrug resistant HIV-1 that is resistant to at least one NRTI, at least one PI, and at least one INSTI. In some embodiments, the patient is infected with multidrug resistant HIV-1 that is resistant to at least one NNRTI, at least one PI, and at least one INSTI. In some embodiments, the patient is infected with multidrug resistant HIV-1 that is resistant to at least one NRTI, at least one NNRTI, at least one PI, and at least one INSTI.

In some embodiments, the patient is infected with multidrug resistant HIV-1 that is resistant to at least one antiretroviral medication that is an NRTI. Examples of NRTIs include, but are not limited to, emtricitabine (FTC; Emtriva®), lamivudine (3TC; Epivir®), zidovudine (azidothymidine (AZT); Retrovir®), didanosine (ddI; Videx-EC®), dideoxyinosine (Videx®), tenofovir, tenofovir alafenamide (Vemlidy®), tenofovir disoproxil fumarate (Viread®), stavudine (d4T; Zerit®), zalcitabine (dideoxycytidine, ddC; Hivid®), and abacavir (Ziagen®).

In some embodiments, the patient is infected with multidrug resistant HIV-1 that is resistant to at least one antiretroviral medication that is an NNRTI. Examples of NNRTIs include, but are not limited to, efavirenz (Sustiva®), etravirine (Intelence®), rilpivirine (Edurant®), nevirapine (Viramune®), and delavirdine (Rescriptor®).

In some embodiments, the patient is infected with multidrug resistant HIV-1 that is resistant to at least one antiretroviral medication that is a PI. Examples of PIs include, but are not limited to, amprenavir (Agenerase®), atazanavir (Reyataz®), darunavir (Prezista®), fosamprenavir (Telzir®, Lexiva®), indinavir (Crixivan®), lopinavir (Kaletra®), nelfinavir (Viracept®), ritonavir (Norvir®), saquinavir (Invirase®), and tipranavir (Aptivus®).

In some embodiments, the patient is infected with multidrug resistant HIV-1 that is resistant to at least one antiretroviral medication that is an INSTI. Examples of INSTIs include, but are not limited to, raltegravir (Isentress®), elvitegravir (Vitekta®), dolutegravir (Tivicay®), cabotegravir, and bictegravir.

In some embodiments, the patient is infected with multidrug resistant HIV-1 that is resistant to at least one antiretroviral medication that is a gp41 fusion inhibitor. Examples of gp41 fusion inhibitors include, but are not limited to, albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

In some embodiments, the patient is infected with multidrug resistant HIV-1 that is resistant to at least one antiretroviral medication that is a CCR5 co-receptor antagonist. Examples of CCR5 co-receptor antagonists include, but are not limited to, aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

In some embodiments of the disclosed methods, the patient has been previously treated with at least one antiretroviral medication before being treated with a compound of Formula (Ia) or Formula (Ib), or a pharmaceutically acceptable salt thereof. In some embodiments, the patient has been previously treated with at least one antiretroviral medication for at least 3 months, such as at least 4 months, at least 5 months, at least 6 months, at least 7 months, at least 8 months, at least 9 months, at least 10 months, at least 11 months, at least 12 months, at least 18 months, or at least 24 months. In some embodiments, the patient has been previously treated with at least one antiretroviral medication for at least 3 months. In some embodiments, the patient has been previously treated with at least one antiretroviral medication for at least 6 months. In some embodiments, the patient has been previously treated with at least one antiretroviral medication for at least 9 months. In some embodiments, the patient has been previously treated with at least one antiretroviral medication for at least 12 months. In some embodiments, the patient has been previously treated with at least one antiretroviral medication for at least 18 months. In some embodiments, the patient has been previously treated with at least one antiretroviral medication for at least 24 months. In some embodiments, the patient has been previously treated with at least one antiretroviral medication for at least 30 months. In some embodiments, the patient has been previously treated with at least one antiretroviral medication for at least 36 months.

In some embodiments of the disclosed methods, the patient has failed or is failing an HIV treatment regimen before being treated with a compound of Formula (Ia) or Formula (Ib), or a pharmaceutically acceptable salt thereof. In some embodiments, the prior HIV treatment regimen included administering at least one antiretroviral medication. In some embodiments, the patient infected with HIV has relapsed after an initial response to the prior HIV treatment regimen, for example, antiretroviral therapy. In some embodiments, the patient has a viral load of greater than about 50 copies of HIV RNA/mL after about 48 weeks of therapy, for example, antiretroviral therapy, before being treated with a compound of Formula (Ia) or Formula (Ib), or a pharmaceutically acceptable salt thereof.

In some embodiments, the prior treatment regimen includes administering at least one antiretroviral medication from each of two different classes of antiretroviral medications. In some embodiments, the prior treatment regimen includes administering at least one antiretroviral medication from each of three different classes of antiretroviral medications. In some embodiments, the different classes of antiretroviral medications are selected from a nucleoside reverse transcriptase inhibitor (NRTI), a non-nucleoside reverse transcriptase inhibitor (NNRTI), a protease inhibitor (PI), and an integrase strand transfer inhibitor (INSTI). In some embodiments, the different classes of antiretroviral medications are selected from an NRTI, an NNRTI, and a PI. In some embodiments, the prior treatment regimen includes administering at least one NRTI and at least one NNRTI. In some embodiments, the prior treatment regimen includes administering at least one NRTI and at least one PI. In some embodiments, the prior treatment regimen includes administering at least one NRTI and at least one INSTI. In some embodiments, the prior treatment regimen includes administering at least one NNRTI and at least one PI. In some embodiments, the prior treatment regimen includes administering at least one NNRTI and at least one INSTI. In some embodiments, the prior treatment regimen includes administering at least one PI and at least one INSTI. In some embodiments, the prior treatment regimen includes administering at least one NRTI, at least one NNRTI, and at least one PI. In some embodiments, the prior treatment regimen includes administering at least one NRTI, at least one NNRTI, and at least one INSTI. In some embodiments, the prior treatment regimen includes administering at least one NRTI, at least one PI, and at least one INSTI. In some embodiments, the prior treatment regimen includes administering at least one NNRTI, at least one PI, and at least one INSTI.

In some embodiments, the prior treatment regimen includes administering at least one antiretroviral medication that is a gp41 fusion inhibitor.

In some embodiments, the prior treatment regimen includes administering at least one antiretroviral medication that is a CCR5 co-receptor antagonist.

In some embodiments, the prior treatment regimen includes administering at least one antiretroviral medication that is an NRTI. Examples of NRTIs include, but are not limited to, emtricitabine (FTC; Emtriva®), lamivudine (3TC; Epivir®), zidovudine (azidothymidine (AZT); Retrovir®), didanosine (ddI; Videx-EC®), dideoxyinosine (Videx®), tenofovir, tenofovir alafenamide (Vemlidy®), tenofovir disoproxil fumarate (Viread®), stavudine (d4T; Zerit®), zalcitabine (dideoxycytidine, ddC; Hivid®), and abacavir (Ziagen®).

In some embodiments, the prior treatment regimen includes administering at least one antiretroviral medication that is an NNRTI. Examples of NNRTIs include, but are not limited to, efavirenz (Sustiva®), etravirine (Intelence®), rilpivirine (Edurant®), nevirapine (Viramune®), and delavirdine (Rescriptor®).

In some embodiments, the prior treatment regimen includes administering at least one antiretroviral medication that is a PI. Examples of PIs include, but are not limited to, amprenavir (Agenerase®), atazanavir (Reyataz®), darunavir (Prezista®), fosamprenavir (Telzir®, Lexiva®), indinavir (Crixivan®), lopinavir (Kaletra®), nelfinavir (Viracept®), ritonavir (Norvir®), saquinavir (Invirase®), and tipranavir (Aptivus®).

In some embodiments, the prior treatment regimen includes administering at least one antiretroviral medication that is an INSTI. Examples of INSTIs include, but are not limited to, raltegravir (Isentress®), elvitegravir (Vitekta®), dolutegravir (Tivicay®), cabotegravir, and bictegravir.

In some embodiments, the prior treatment regimen includes administering at least one antiretroviral medication that is a gp41 fusion inhibitor. Examples of gp41 fusion inhibitors include, but are not limited to, albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

In some embodiments, the prior treatment regimen includes administering at least one antiretroviral medication that is a CCR5 co-receptor antagonist. Examples of CCR5 co-receptor antagonists include, but are not limited to, aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

In some embodiments of the disclosed methods, the heavily treatment-experienced patient infected with HIV has a viral load of about 200 copies of HIV-1 RNA/mL (c/mL) to about 1,000,000 c/mL at the time of beginning administration of the compound of Formula (Ia) or Formula (Ib), or a pharmaceutically acceptable salt thereof, such as a viral load of about 200 c/mL to about 500,000 c/mL, about 200 c/mL to about 250,000 c/mL, about 200 c/mL to about 100,000 c/mL, about 200 c/mL to about 50,000 c/mL, about 200 c/mL to about 25,000 c/mL, about 200 c/mL to about 10,000 c/mL, about 200 c/mL to about 5,000 c/mL, about 200 c/mL to about 3,000 c/mL, about 200 c/mL to about 2,000 c/mL, about 200 c/mL to about 1,000 c/mL, about 200 c/mL to about 750 c/mL, about 200 c/mL to about 500 c/mL, about 500 c/mL to about 1,000,000 c/mL, about 500 c/mL to about 500,000 c/mL, about 500 c/mL to about 250,000 c/mL, about 500 c/mL to about 100,000 c/mL, about 500 c/mL to about 50,000 c/mL, about 500 c/mL to about 25,000 c/mL, about 500 c/mL to about 10,000 c/mL, about 500 c/mL to about 5,000 c/mL, about 500 c/mL to about 3,000 c/mL, about 500 c/mL to about 2,000 c/mL, about 500 c/mL to about 1,000 c/mL, about 500 c/mL to about 750 c/mL, about 750 c/mL to about 1,000,000 c/mL, about 750 c/mL to about 500,000 c/mL, about 750 c/mL to about 250,000 c/mL, about 750 c/mL to about 100,000 c/mL, about 750 c/mL to about 50,000 c/mL, about 750 c/mL to about 25,000 c/mL, about 750 c/mL to about 10,000 c/mL, about 750 c/mL to about 5,000 c/mL, about 750 c/mL to about 3,000 c/mL, about 750 c/mL to about 2,000 c/mL, about 750 c/mL to about 1,000 c/mL, about 1,000 c/mL to about 1,000,000 c/mL, about 1,000 c/mL to about 500,000 c/mL, about 1,000 c/mL to about 250,000 c/mL, about 1,000 c/mL to about 100,000 c/mL, about 1,000 c/mL to about 50,000 c/mL, about 1,000 c/mL to about 25,000 c/mL, about 1,000 c/mL to about 10,000 c/mL, about 1,000 c/mL to about 5,000 c/mL, about 1,000 c/mL to about 3,000 c/mL, about 1,000 c/mL to about 2,000 c/mL, about 2,000 c/mL to about 1,000,000 c/mL, about 2,000 c/mL to about 500,000 c/mL, about 2,000 c/mL to about 250,000 c/mL, about 2,000 c/mL to about 100,000 c/mL, about 2,000 c/mL to about 50,000 c/mL, about 2,000 c/mL to about 25,000 c/mL, about 2,000 c/mL to about 10,000 c/mL, about 2,000 c/mL to about 5,000 c/mL, about 2,000 c/mL to about 3,000 c/mL, about 3,000 c/mL to about 1,000,000 c/mL, about 3,000 c/mL to about 500,000 c/mL, about 3,000 c/mL to about 250,000 c/mL, about 3,000 c/mL to about 100,000 c/mL, about 3,000 c/mL to about 50,000 c/mL, about 3,000 c/mL to about 25,000 c/mL, about 3,000 c/mL to about 10,000 c/mL, about 3,000 c/mL to about 5,000 c/mL, about 5,000 c/mL to about 1,000,000 c/mL, about 5,000 c/mL to about 500,000 c/mL, about 5,000 c/mL to about 250,000 c/mL, about 5,000 c/mL to about 100,000 c/mL, about 5,000 c/mL to about 50,000 c/mL, about 5,000 c/mL to about 25,000 c/mL, about 5,000 c/mL to about 10,000 c/mL, about 10,000 c/mL to about 1,000,000 c/mL, about 10,000 c/mL to about 500,000 c/mL, about 10,000 c/mL to about 250,000 c/mL, about 10,000 c/mL to about 100,000 c/mL, about 10,000 c/mL to about 50,000 c/mL, about 10,000 c/mL to about 25,000 c/mL, about 25,000 c/mL to about 1,000,000 c/mL, about 25,000 c/mL to about 500,000 c/mL, about 25,000 c/mL to about 250,000 c/mL, about 25,000 c/mL to about 100,000 c/mL, about 25,000 c/mL to about 50,000 c/mL, about 50,000 c/mL to about 1,000,000 c/mL, about 50,000 c/mL to about 500,000 c/mL, about 50,000 c/mL to about 250,000 c/mL, about 50,000 c/mL to about 100,000 c/mL, about 100,000 c/mL to about 1,000,000 c/mL, about 100,000 c/mL to about 500,000 c/mL, about 100,000 c/mL to about 250,000 c/mL, about 250,000 c/mL to about 1,000,000 c/mL, about 250,000 c/mL to about 500,000 c/mL, or about 500,000 c/mL to about 1,000,000 c/mL.

In some embodiments, the patient has a viral load of greater than about 200 copies of HIV-1 RNA/mL (c/mL) at the time of beginning administration of the compound of Formula (Ia) or Formula (Ib), or a pharmaceutically acceptable salt thereof, such as a viral load greater than about 500 c/mL, about 750 c/mL, about 1,000 c/mL, about 2,000 c/mL, about 3,000 c/mL, about 5,000 c/mL, about 10,000 c/mL, about 25,000 c/mL, about 50,000 c/mL, about 100,000 c/mL, about 250,000 c/mL, about 500,000 c/mL, or greater than about 1,000,000 c/mL at the time of beginning administration of the compound of Formula (Ia) or Formula (Ib), or a pharmaceutically acceptable salt thereof. In some embodiments, the patient has a viral load of greater than about 200 c/mL at the time of beginning administration of the compound of Formula (Ia) or Formula (Ib), or a pharmaceutically acceptable salt thereof. In some embodiments, the patient has a viral load of greater than about 500 c/mL at the time of beginning administration of the compound of Formula (Ia) or Formula (Ib), or a pharmaceutically acceptable salt thereof. In some embodiments, the patient has a viral load of greater than about 750 c/mL at the time of beginning administration of the compound of Formula (Ia) or Formula (Ib), or a pharmaceutically acceptable salt thereof. In some embodiments, the patient has a viral load of greater than about 1,000 c/mL at the time of beginning administration of the compound of Formula (Ia) or Formula (Ib), or a pharmaceutically acceptable salt thereof. In some embodiments, the patient has a viral load of greater than about 2,000 c/mL at the time of beginning administration of the compound of Formula (Ia) or Formula (Ib), or a pharmaceutically acceptable salt thereof.

The compound of Formula (Ia) or Formula (Ib), or a pharmaceutically acceptable salt thereof, can be administered to a patient in accordance with an effective dosing regimen for a desired period of time or duration, such as at least about one day, at least about one week, at least about one month, at least about 2 months, at least about 3 months, at least about 4 months, at least about 6 months, or at least about 12 months, or longer. In some embodiments, the compound of Formula (Ia) or Formula (Ib), or a pharmaceutically acceptable salt thereof, is administered on a daily or intermittent schedule. In some embodiments, the compound of Formula (Ia) or Formula (Ib), or a pharmaceutically acceptable salt thereof, is administered weekly. In some embodiments, the compound of Formula (Ia) or Formula (Ib), or a pharmaceutically acceptable salt thereof, is administered bi-monthly (i.e., every two weeks). In some embodiments, the compound of Formula (Ia) or Formula (Ib), or a pharmaceutically acceptable salt thereof, is administered monthly. In some embodiments, the compound of Formula (Ia) or Formula (Ib), or a pharmaceutically acceptable salt thereof, is administered every two months. In some embodiments, the compound of Formula (Ia) or Formula (Ib), or a pharmaceutically acceptable salt thereof, is administered every three months. In some embodiments, the compound of Formula (Ia) or Formula (Ib), or a pharmaceutically acceptable salt thereof, is administered every four months. In some embodiments, the compound of Formula (Ia) or Formula (Ib), or a pharmaceutically acceptable salt thereof, is administered every five months. In some embodiments, the compound of Formula (Ia) or Formula (Ib), or a pharmaceutically acceptable salt thereof, is administered every 6 months. In some embodiments, the compound of Formula (Ia) or Formula (Ib), or a pharmaceutically acceptable salt thereof, is administered every five months. In some embodiments, the compound of Formula (Ia) or Formula (Ib), or a pharmaceutically acceptable salt thereof, is administered every 12 months.

In some embodiments, the compound of Formula (Ia) or Formula (Ib), or a pharmaceutically acceptable salt thereof, is administered every nine months.

In some embodiments of the disclosed methods, administration of the compound of Formula (Ia) or Formula (Ib), or a pharmaceutically acceptable salt thereof, results in a decrease in the viral load in the patient. In some embodiments, the viral load is decreased by about 0.5 $\log_{10}$ to about 2.5 $\log_{10}$ after administration of the compound of Formula (Ia) or Formula (Ib), or a pharmaceutically acceptable salt thereof, for a certain amount of time as compared to the viral load at the time of beginning administration of the compound of Formula (Ia) or Formula (Ib), or a pharmaceutically acceptable salt thereof. For example, the viral load is decreased by about 0.5 $\log_{10}$, about 1 $\log_{10}$, about 1.5 $\log_{10}$, about 2 $\log_{10}$, or about 2.5 $\log_{10}$ after administration of the compound of Formula (Ia) or Formula (Ib), or a pharmaceutically acceptable salt thereof, for a certain amount of time as compared to the viral load at the time of beginning administration of the compound of Formula (Ia) or Formula (Ib), or a pharmaceutically acceptable salt thereof. In some embodiments, the viral load is decreased by about 0.5 $\log_{10}$ after administration of the compound of Formula (Ia) or Formula (Ib), or a pharmaceutically acceptable salt thereof, for about 24 weeks as compared to the viral load at the time of beginning administration of the compound of Formula (Ia) or Formula (Ib), or a pharmaceutically acceptable salt thereof. In some embodiments, the viral load is decreased by about 1 $\log_{10}$ after administration of the compound of Formula (Ia) or Formula (Ib), or a pharmaceutically acceptable salt thereof, for about 24 weeks as compared to the viral load at the time of beginning administration of the compound of Formula (Ia) or Formula (Ib), or a pharmaceutically acceptable salt thereof. In some embodiments, the viral load is decreased by about 1.5 $\log_{10}$ after administration of the compound of Formula (Ia) or Formula (Ib), or a pharmaceutically acceptable salt thereof, for about 24 weeks as compared to the viral load at the time of beginning administration of the compound of Formula (Ia) or Formula (Ib), or a pharmaceutically acceptable salt thereof. In some embodiments, the viral load is decreased by about 2 $\log_{10}$ after administration of the compound of Formula (Ia) or Formula (Ib), or a pharmaceutically acceptable salt thereof, for about 24 weeks as compared to the viral load at the time of beginning administration of the compound of Formula (Ia) or Formula (Ib), or a pharmaceutically acceptable salt thereof. In some embodiments, the viral load is decreased by about 2.5 $\log_{10}$ after administration of the compound of Formula (Ia) or Formula (Ib), or a pharmaceutically acceptable salt thereof, for about 24 weeks as compared to the viral load at the time of beginning administration of the compound of Formula (Ia) or Formula (Ib), or a pharmaceutically acceptable salt thereof.

In some embodiments of the disclosed methods, the viral load in the patient is about 200 c/mL or less after administration of the compound of Formula (Ia) or Formula (Ib), or a pharmaceutically acceptable salt thereof, for a certain amount of time, such as about 175 c/mL or less, about 150 c/mL or less, about 125 c/mL or less, about 100 c/mL or less, about 75 c/mL or less, or about 50 c/mL or less. In some embodiments, the viral load in the patient is about 200 c/mL or less after administration of the compound of Formula (Ia) or Formula (Ib), or a pharmaceutically acceptable salt thereof, for about 24 weeks. In some embodiments, the viral load in the patient is about 200 c/mL or less after administration of the compound of Formula (Ia) or Formula (Ib), or a pharmaceutically acceptable salt thereof, for about 24 weeks. In some embodiments, the viral load in the patient is about 100 c/mL or less after administration of the compound of Formula (Ia) or Formula (Ib), or a pharmaceutically acceptable salt thereof, for about 24 weeks. In some embodiments, the viral load in the patient is about 50 c/mL or less after administration of the compound of Formula (Ia) or Formula (Ib), or a pharmaceutically acceptable salt thereof, for about 24 weeks.

In certain embodiments of the disclosed methods, the heavily treatment-experienced patient is concurrently being treated with at least one additional antiretroviral medication. In some embodiments, the antiretroviral medication is selected from an NRTI, an NNRTI, a PI, an INSTI, a gp41 fusion inhibitor, and a CCR5 co-receptor antagonist.

In some embodiments, the patient is concurrently being treated with at least one NRTI. Examples of NRTIs include, but are not limited to, emtricitabine (FTC; Emtriva®), lamivudine (3TC; Epivir®), zidovudine (azidothymidine (AZT); Retrovir®), didanosine (ddI; Videx-EC®), dideoxyinosine (Videx®), tenofovir, tenofovir alafenamide (Vemlidy®), tenofovir disoproxil fumarate (Viread®), stavudine (d4T; Zerit®), zalcitabine (dideoxycytidine, ddC; Hivid®), and abacavir (Ziagen®).

In some embodiments, the patient is concurrently being treated with at least one NNRTI. Examples of NNRTIs include, but are not limited to, efavirenz (Sustiva®), etravirine (Intelence®), rilpivirine (Edurant®), nevirapine (Viramune®), and delavirdine (Rescriptor®).

In some embodiments, the patient is concurrently being treated with at least one PI. Examples of PIs include, but are not limited to, amprenavir (Agenerase®), atazanavir (Reyataz®), darunavir (Prezista®), fosamprenavir (Telzir®, Lexiva®), indinavir (Crixivan®), lopinavir (Kaletra®), nelfinavir (Viracept®), ritonavir (Norvir®), saquinavir (Invirase®), and tipranavir (Aptivus®).

In some embodiments, the patient is concurrently being treated with at least one INSTI. Examples of INSTIs include, but are not limited to, raltegravir (Isentress®), elvitegravir (Vitekta®), dolutegravir (Tivicay®), cabortegravir, and bictegravir.

In some embodiments, the patient is concurrently being treated with at least one gp41 fusion inhibitor. Examples of gp41 fusion inhibitors include, but are not limited to, albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer, and sifuvirtide.

In some embodiments, the patient is concurrently being treated with at least one CCR5 co-receptor antagonist. Examples of CCR5 co-receptor antagonists include, but are not limited to, aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Also provided in this disclosure is a method of treating an HIV-1 infection in a heavily treatment-experienced patient with multidrug resistant HIV-1 that includes administering a therapeutically effective amount of a compound of Formula (Ia) or Formula (Ib), or a pharmaceutically acceptable salt thereof, to a patient that had been previously treated with an HIV treatment regimen that includes the administration of at least one antiretroviral medication and had failed the treatment regimen. In some embodiments, the HIV treatment regimen includes administration of at least one antiretroviral medication such as those described herein. In some embodiments of the method, administration of the compound or Formula (Ia) or Formula (Ib), or a pharmaceutically acceptable salt thereof, results in a reduction in HIV viral load in the patient.

Also disclosed is a method of treating an HIV-1 infection in a heavily treatment-experienced patient with multidrug resistant HIV-1 that includes administering a therapeutically effective amount of a compound of Formula (Ia) or Formula (Ib), or a pharmaceutically acceptable salt thereof, to a patient that had been previously treated with an HIV treatment regimen that includes the administration of at least one antiretroviral medication and had failed the treatment regimen, where the multidrug resistant HIV-1 is resistant to at least one antiretroviral medication from each of two different classes of antiretroviral medications. In some embodiments, the different classes of antiretroviral medications are selected from an NRTI, an NNRTI, a PI, and an INSTI. In some embodiments, the patient has a viral load of greater than about 200 c/mL at the time of beginning administration of the compound of Formula (Ia) or Formula (Ib), or a pharmaceutically acceptable salt thereof, and administration of the compound results in a reduction in HIV viral load in the patient.

In some embodiments, disclosed is a method of treating an HIV-1 infection in a heavily treatment-experienced patient with multidrug resistant HIV-1 that includes administering a therapeutically effective amount of a compound of Formula (Ia) or Formula (Ib), or a pharmaceutically acceptable salt thereof, to a patient that had been previously treated with an HIV treatment regimen that includes the administration of at least one antiretroviral medication, and had failed the treatment regimen, where the multidrug resistant HIV-1 is resistant to at least one antiretroviral medication from each of three different classes of antiretroviral medications. In some embodiments, the different classes of antiretroviral medications are selected from an NRTI, an NNRTI, a PI, and an INSTI. In some embodiments, the patient has a viral load of greater than about 200 c/mL at the time of beginning administration of the compound of Formula (Ia) or Formula (Ib), or a pharmaceutically acceptable salt thereof, and administration of the compound results in a reduction in HIV viral load in the patient.

Pharmaceutical Compositions

Pharmaceutical compositions disclosed herein contain a compound disclosed herein (for example, a compound of Formula (Ia) or Formula (Ib), or a pharmaceutically acceptable salt thereof), together with one or more pharmaceutically acceptable excipients and optionally other therapeutic agents. Pharmaceutical compositions containing the active ingredient may be in any form suitable for the intended method of administration.

Pharmaceutical compositions comprising the compound disclosed herein (for example, a compound of Formula (Ia) or Formula (Ib), or a pharmaceutically acceptable salt thereof), can be prepared with conventional carriers (for example, inactive ingredient or excipient material) which can be selected in accord with ordinary practice. Tablets can contain excipients including glidants, fillers, binders and the like. Aqueous compositions can be prepared in sterile form, and when intended for delivery by other than oral administration generally can be isotonic. All compositions can optionally contain excipients such as those set forth in the Rowe et al., Handbook of Pharmaceutical Excipients, 5$^{th}$ edition, American Pharmacists Association, 1986. Excipients can include ascorbic acid and other antioxidants, chelating agents such as EDTA, carbohydrates such as dextrin, hydroxyalkylcellulose, hydroxyalkylmethylcellulose, stearic acid and the like.

In some embodiments, tablets can contain excipients including glidants, fillers, binders, polymers and the like. Injectable solutions and suspensions can be prepared in sterile form, and when intended for delivery by other than oral administration generally can be isotonic. All compositions can optionally contain excipients such as those set forth in the Rowe et al., Handbook of Pharmaceutical Excipients, 5$^{th}$ edition, American Pharmacists Association, 1986. Excipients can include ascorbic acid and other antioxidants, chelating agents such as EDTA, carbohydrates such as dextrin, hydroxyalkylcellulose, hydroxyalkylmethylcellulose, stearic acid and the like.

While it is possible for the active ingredient (for example, the compound of Formula (Ia) or Formula (Ib), or a pharmaceutically acceptable salt thereof) to be administered alone, it may be preferable to present the active ingredient as a pharmaceutical composition. The composition, both for veterinary and for human use, contains at least the compound of Formula (Ia) or Formula (Ib), or a pharmaceutically acceptable salt thereof, together with one or more acceptable carriers and optionally other therapeutic ingredients. In one embodiment, the pharmaceutical composition comprises a compound of Formula (Ia) or Formula (Ib), or a pharmaceutically acceptable salt thereof, a pharmaceutically acceptable excipient and a therapeutically effective amount of one or more (for example, one, two, three, or four; or one or two; or one to three; or one to four) additional therapeutic agents as defined herein. In some embodiments, the pharmaceutical composition comprises a compound of Formula (Ia) or Formula (Ib), or a pharmaceutically acceptable salt thereof, a pharmaceutically acceptable excipient and one other therapeutic ingredient. The carrier(s) are "acceptable" in the sense of being compatible with the other ingredients of the composition and physiologically innocuous to the recipient thereof.

In some embodiments, the pharmaceutical compositions disclosed herein comprise a compound of Formula (Ia) or Formula (Ib), or a pharmaceutically acceptable salt thereof, a pharmaceutically acceptable excipient and one other therapeutic agent selected from the group consisting of tenofovir alafenamide, tenofovir alafenamide hemifumarate, and bictegravir. In some embodiments, the pharmaceutical compositions disclosed herein comprise a compound of Formula (Ia) or Formula (Ib), or a pharmaceutically acceptable salt thereof, a pharmaceutically acceptable excipient and one other therapeutic agent selected from the group consisting of tenofovir alafenamide hemifumarate and bictegravir. In some embodiments, the pharmaceutical compositions disclosed herein comprise a compound of Formula (Ia) or Formula (Ib), or a pharmaceutically acceptable salt thereof, a pharmaceutically acceptable excipient and tenofovir alafenamide. In some embodiments, the pharmaceutical compositions disclosed herein comprise a compound of Formula (Ia) or Formula (Ib), or a pharmaceutically acceptable salt thereof, a pharmaceutically acceptable excipient and tenofovir alafenamide hemifumarate. In some embodiments, the pharmaceutical compositions disclosed herein comprise a compound of Formula (Ia) or Formula (Ib), or a pharmaceutically acceptable salt thereof, a pharmaceutically acceptable excipient and bictegravir.

In some embodiments, the pharmaceutical compositions disclosed herein comprise a compound of Formula (Ia) or Formula (Ib), a pharmaceutically acceptable excipient and one other therapeutic agent selected from the group consisting of tenofovir alafenamide, tenofovir alafenamide hemifumarate, and bictegravir. In some embodiments, the pharmaceutical compositions disclosed herein comprise a compound of Formula (Ia) or Formula (Ib), a pharmaceutically acceptable excipient and one other therapeutic agent selected from the group consisting of tenofovir alafenamide hemifumarate and bictegravir. In some embodiments, the pharmaceutical compositions disclosed herein comprise a compound of Formula (Ia) or Formula (Ib), a pharmaceutically acceptable excipient and tenofovir alafenamide. In some embodiments, the pharmaceutical compositions disclosed herein comprise a compound of Formula (Ia) or Formula (Ib), a pharmaceutically acceptable excipient and tenofovir alafenamide hemifumarate. In some embodiments, the pharmaceutical compositions disclosed herein comprise a compound of Formula (Ia) or Formula (Ib), a pharmaceutically acceptable excipient and bictegravir.

In some embodiments, the pharmaceutical compositions disclosed herein comprise a sodium salt of the compound of Formula (Ia), a pharmaceutically acceptable excipient and one other therapeutic agent selected from the group consisting of tenofovir alafenamide, tenofovir alafenamide hemifumarate, and bictegravir. In some embodiments, the pharmaceutical compositions disclosed herein comprise a sodium salt of the compound of Formula (Ia), a pharmaceutically acceptable excipient and one other therapeutic agent selected from the group consisting of tenofovir alafenamide hemifumarate and bictegravir. In some embodiments, the pharmaceutical compositions disclosed herein comprise a sodium salt of the compound of Formula (Ia), a pharmaceutically acceptable excipient and tenofovir alafenamide. In some embodiments, the pharmaceutical compositions disclosed herein comprise a sodium salt of the compound of Formula (Ia), a pharmaceutically acceptable excipient and tenofovir alafenamide hemifumarate. In some embodiments, the pharmaceutical compositions disclosed herein comprise a sodium salt of the compound of Formula (Ia), a pharmaceutically acceptable excipient and bictegravir.

In some embodiments, the pharmaceutical compositions disclosed herein comprise a trifluoroacetic acid salt of the compound of Formula (Ib), a pharmaceutically acceptable excipient and one other therapeutic agent selected from the group consisting of tenofovir alafenamide, tenofovir alafenamide hemifumarate, and bictegravir. In some embodiments, the pharmaceutical compositions disclosed herein comprise a trifluoroacetic acid salt of the compound of Formula (Ib), a pharmaceutically acceptable excipient and one other therapeutic agent selected from the group consisting of tenofovir alafenamide hemifumarate and bictegravir. In some embodiments, the pharmaceutical compositions disclosed herein comprise a trifluoroacetic acid salt of the compound of Formula (Ib), a pharmaceutically acceptable excipient and tenofovir alafenamide. In some embodiments, the pharmaceutical compositions disclosed herein comprise a trifluoroacetic acid salt of the compound of Formula (Ib), a pharmaceutically acceptable excipient and tenofovir alafenamide hemifumarate. In some embodiments, the pharmaceutical compositions disclosed herein comprise a trifluoroacetic acid salt of the compound of Formula (Ib), a pharmaceutically acceptable excipient and bictegravir.

The compositions include those suitable for various administration routes. The compositions can conveniently be presented in unit dosage form and can be prepared by any of the methods well known in the art of pharmacy. Such methods include the step of bringing into association the active ingredient (for example, a compound of Formula (Ia) or Formula (Ib) or a pharmaceutically acceptable salt thereof) with one or more inactive ingredients (for example, a carrier, pharmaceutical excipient, etc.). The compositions can be prepared by uniformly and intimately bringing into association the active ingredient with liquid carriers or finely divided solid carriers or both, and then, if necessary, shaping the product. Techniques and formulations generally are found in Remington: The Science and Practice of Pharmacy, 21$^{st}$ Edition, Lippincott Williams and Wilkins, Philadelphia, Pa., 2006.

Compositions described herein that are suitable for oral administration can be presented as discrete units (a unit dosage form) including, but not limited to, capsules, cachets, or tablets, each containing a predetermined amount of the active ingredient.

When formulated for oral administration, tablets, troches, lozenges, aqueous or oil suspensions, dispersible powders or granules, emulsions, hard or soft capsules, syrups or elixirs can be prepared. Compositions intended for oral use can be prepared according to any method known in the art for the manufacture of pharmaceutical compositions. Such compositions can contain one or more agents, including sweetening agents, flavoring agents, coloring agents, and preserving agents, in order to provide a palatable preparation. Tablets containing the active ingredient in admixture with non-toxic pharmaceutically acceptable excipients which are suitable for manufacture of tablets are acceptable. These excipients can be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets can be uncoated or can be coated by known techniques that include microencapsulation to delay disintegration and adsorption in the gastrointestinal tract and thereby provide a sustained action over a longer period. For example, a time delay material such as glyceryl monostearate or glyceryl distearate alone or with a wax may be employed.

In some embodiments, disclosed herein are oral dosage forms (for example, tablets), which can be prepared from hot melt extrusion or spray-drying dispersion (SDD) technologies.

In some embodiments, disclosed herein are capsules filled with powder, beads, or granules containing the active ingredient in admixture with non-toxic pharmaceutically acceptable excipient which are suitable for manufacture of hard or soft capsules. These excipients can be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. In some embodiments, the capsule is a hard capsule. In some embodiments, the capsule is a soft capsule.

In some embodiments, disclosed herein are hard or soft capsules filled with liquid or semi-solid mixtures containing the active ingredient in admixture with non-toxic pharmaceutically acceptable excipient which are suitable for manufacture of hard or soft capsules. These excipients can be, for example, solubilizing oils such as maize oil, sesame oil, or corn oil; medium chain triglycerides and related esters, such as, derivitized palm kernel oil or coconut oil; self-emulsifying lipid systems (SEDDS or SMEDDS), such as caprylic triglyceride or propylene glycol monocaprylate and polyethylene glycol esters of medium chain triglycerides; viscosity modifiers, such as, cetyl alcohol, steryl alcohol, glycerol stearate; mixtures of medium chain mono- and di-glycerides; mixtures of monoglycerides, diglycerides, and triglycerides, such as caprylic/capric monoglycerides and diglycerides; and solubilizing agents and surfactants, such as polyethylene glycol, propylene glycol, glycerin, ethanol, polyethoxylated castor oil, poloxamers, or polysorbates. In some embodiments, the capsule is a hard capsule. In some embodiments, the capsule is a soft capsule.

In some embodiments, the hard or soft capsules comprise a compound of Formula (Ia) or (Ib), or a pharmaceutically acceptable salt thereof and one or more pharmaceutically acceptable excipients. In some embodiments, the one or more pharmaceutically acceptable excipients of the hard or soft capsules disclosed herein are water-soluble and/or water-insoluble. Examples of water-soluble excipients include, but are not limited to, dimethylacetamide (DMA), dimethyl sulfoxide (DMSO), ethanol, N-methyl-2-pyrrolidone (NMP), PEG 300, PEG 400, PEG 600, propylene glycol, hydroxypropyl-β-cyclodextrin, sulfobutylether-β-cyclodextrin, glycerin, diethylene glycol monoethyl ether (e.g., Transcutol® HP), and phospholipids. Examples of phospholipids include, but are not limited to, hydrogenated soy phosphatidylcholine (HSPC), di stearoylphosphatidylglycerol (DSPG), L-α-dimyristoylphosphatidyl-choline (DMPC), and L-α-dimyristoylphosphatidyl-glycerol (DMPG). Examples of water-insoluble excipients include, but are not limited to, beeswax, oleic acid, soy fatty acids, vitamin E, corn oil mono-di-tridiglycerides, medium chain C$_{8-10}$ monoglycerides and diglycerides, propylene glycol dicaprylate/dicaprate, glyceryl monolinoleate, glyceryl monooleate, long-chain triglycerides, and medium-chain triglycerides. Examples of long-chain triglycerides include, but are not limited to, sesame oil, castor oil, corn oil, cottonseed oil, olive oil, peanut oil, peppermint oil, soybean oil, hydrogenated soybean oil, and hydrogenated vegetable oils. Examples of medium-chain triglycerides include, but are not limited to, caprylic/capric triglycerides derived from coconut oil or palm seed oil.

In some embodiments, the one or more pharmaceutically acceptable excipients of the hard or soft capsule disclosed herein include one or more surfactants. Examples of a surfactant include, but are not limited to, d-α-tocopheryl polyethylene glycol 1000 succinate (TPGS), polysorbate 20, polysorbate 80, polyoxyl 35 castor oil (e.g., Cremophor® EL), polyoxyl 40 hydrogenated castor oil (e.g., Cremophor® RH 40, Cremophor® RH 60), Solutol® HS-15, sorbitan monooleate (e.g., Span® 20), PEG 300 caprylic/capric glycerides (e.g., Softigen® 767), PEG 400 caprylic/capric glycerides (e.g., Labrasol®), PEG 300 oleic glycerides (e.g., Labrafil® M-1944CS), PEG 300 linoleic glycerides (e.g., Labrafil® M-2125CS), PEG 300 lauric glycerides (e.g., Labrafil® M2130CS), polyoxyl 8 stearate (e.g., PEG 400 monosterate), polyoxyl 40 stearate (e.g., PEG 1750 monosterate), povidone K-90, polyoxyl stearate, Type I (e.g., Gelucire® 48/16), polyglyceryl-3 dioleate, propylene glycol monolaurate, Type I, propylene glycol monolaurate, Type II, propylene glycol monocaprylate, Type II (e.g., Capryol™ 90), propylene glycol monocaprylate, Type I (e.g., Capryol™ PGMC), lauroyl polyoxylglycerides (e.g., Gelucire® 44/14), stearoyl polyoxylglycerides (e.g., Gelucire® 50/13), poloxamer 124, poloxamer 188, and poloxamer 407.

The pharmaceutical compositions of the present disclosure can be in the form of a sterile injectable preparation, such as a solution or sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that can be employed are water, Ringer's solution, and isotonic sodium chloride solution. In addition, sterile fixed oils can conventionally be employed as a solvent or suspending medium. For this purpose any bland fixed oil can be employed, including synthetic mono- or diglycerides. In addition, fatty acids such as oleic acid can likewise be used in the preparation of injectables.

In some embodiments, the sterile injectable preparation disclosed herein can also be a sterile injectable solution or suspension prepared from a reconstituted lyophilized powder in a non-toxic parenterally acceptable diluent or solvent, such as a solution in 1,3-butane-diol. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents. In certain embodiments, the suspension is a microsuspension. In certain embodiments, the suspension is a nanosuspension.

In some embodiments, the pharmaceutical compositions of the present disclosure can be in the form of a solution formulation. In some embodiments, the solution comprises N-methyl-2-pyrrolidone (NMP), polyethylene glycol (PEG), water and/or glycofurol. In some embodiments, the solution comprises PEG 200, ethanol, and water. In some embodiments, the solution comprises PEG 300 and water. In some embodiments, the amount of water in the solution comprising PEG 300 and water is about 25 w/w %, about 23 w/w %, about 20 w/w %, about 17 w/w %, about 15 w/w %, about 10 w/w %, about 9 w/w %, about 8 w/w %, or about 5 w/w %. In some embodiments, the amount of PEG 300 in the solution comprising PEG 300 and water is about 90 w/w %, about 85 w/w %, about 80 w/w %, about 75 w/w %, about 70 w/w %, about 65 w/w %, about 60 w/w %, about 55 w/w %, about 50 w/w %, or about 45 w/w %. In some embodiments, the solution comprising PEG 300 and water comprises about 85 w/w % PEG 300 and about 15 w/w % water. In some embodiments, the solution comprising PEG 300 and water further comprises a base. In some embodiments, the solution comprising PEG 300 and water further comprises an inorganic base. In some embodiments, the inorganic base is sodium hydroxide or sodium ethoxide. In some embodiments, the sodium hydroxide or sodium ethoxide is in an amount of about 3 w/w %, about 2 w/w %, about 1 w/w %, or about 0.5 w/w %.

In some embodiments, formulations suitable for parenteral administration (for example, intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and can be found, for example, in the Handbook of Pharmaceutical Excipients (eds. Rowe, Sheskey & Quinn), 6th edition 2009.

Examples of solubilizing excipients in a parenteral formulation (for example, an SC or IM formulation) include, but are not limited to, polysorbates (such as polysorbate 20 or 80) and poloxamers (such as poloxamer 338, 188, or 207). In some embodiments, disclosed herein is a parenteral administration (for example, an SC or IM formulation) that comprises a compound of Formula (Ia) or Formula (Ib), or a pharmaceutically acceptable salt thereof, and a poloxamer. In some embodiments, the poloxamer is poloxamer 338. In some embodiments, the poloxamer is poloxamer 188. In some embodiments, the amount of poloxamer in a parenteral administration disclosed herein is less than about 5%, such as less than about 3%, about 2%, about 1%, or about 0.5%.

In certain embodiments, excipients include N-methyl-2-pyrrolidone (NMP), dimethyl sulfoxide, polyethylene glycol and/or tetraglycol/glycofurol.

In general, poloxamers are synthetic non-ionic triblock of linear copolymers having a central hydrophobic chain of polyoxypropylene adjacent to two hydrophilic polypropylene oxide, in certain instances in a 4:2:4 weight ratio. Accordingly, in certain embodiments, the compositions disclosed herein include a compound of Formula (Ia) or Formula (Ib), or a pharmaceutically acceptable salt thereof, and a block copolymer comprised of one polyoxypropylene segment and two hydrophilic polypropylene oxide segments. In certain embodiments, the ratio of the polyoxypropylene segment to the two hydrophilic polypropylene oxide segments is 4:2:4 (hydrophilic polypropylene oxide: polyoxypropylene: hydrophilic polypropylene oxide). Poloxamers are generally understood to have the following structure:

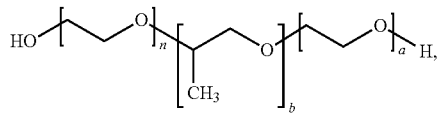

where a and b are integers. For example, a is between about 2 and about 130 and b is between about 15 and about 67. Poloxamer 188, for example, is understood to have a molecular weight from about 7680 to about 9510 Daltons (where a is about 80 and b is about 27) (see, for example, International Journal of PharmTech Research, Vol. 1, No. 2, pp 299-303, April-June 2009). In some instances, poloxamer 188 has an average molecular weight of about 8400 Daltons. Poloxamer 338 has a molecular weight in the range of from about 12700 Da to about 17400 Da (where a is about 141 and b is about 44).

In some embodiments, poloxamers are synthetic nonionic triblock of linear copolymers having a central hydrophobic chain of polypropylene oxide (PPO) adjacent to two hydrophilic chains of polyethylene oxide (PEO), in certain instances in a 4:2:4 weight ratio. Accordingly, in certain embodiments, the compositions disclosed herein include a compound of Formula (Ia) or Formula (Ib), or a pharmaceutically acceptable salt thereof, and a block copolymer comprised of one PPO segment and two PEO segments. In certain embodiments, the ratio of the PPO segment to the two PEO segments is 4:2:4 (PEO:PPO:PEO). Poloxamers are generally understood to have the following structure:

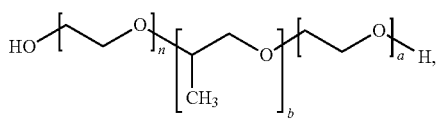

where a and b are integers. For example, a is between about 2 and about 130 and b is between about 15 and about 67. Poloxamer 188, for example, is understood to have a molecular weight from about 7680 to about 9510 Daltons (where a is about 80 and b is about 27) (see, for example, International Journal of PharmTech Research, Vol. 1, No. 2, pp 299-303, April-June 2009). In some instances, poloxamer 188 has an average molecular weight of about 8400 Daltons. Poloxamer 338 has a molecular weight in the range of from about 12700 Da to about 17400 Da (where a is about 141 and b is about 44).

In some embodiments, the pharmaceutical compositions disclosed herein comprise a compound of Formula (Ia) or Formula (Ib), or a pharmaceutically acceptable salt thereof, a poloxamer, and a pharmaceutically acceptable excipient. In some embodiments, the pharmaceutical compositions disclosed herein comprise a compound of Formula (Ia) or Formula (Ib), or a pharmaceutically acceptable salt thereof, poloxamer 188, and a pharmaceutically acceptable excipient. In some embodiments, the pharmaceutical compositions disclosed herein do not comprise a poloxamer. In some embodiments, the pharmaceutical compositions disclosed herein do not compromise poloxamer 188. In some embodiments, the pharmaceutical compositions disclosed herein are solutions that comprise a compound of Formula (Ia) or Formula (Ib), or a pharmaceutically acceptable salt thereof, and a pharmaceutically acceptable excipient. In some embodiments, the pharmaceutical compositions disclosed herein are solutions that comprise a compound of Formula (Ia) or Formula (Ib), or a pharmaceutically acceptable salt thereof, a poloxamer, and a pharmaceutically acceptable excipient. In some embodiments, the pharmaceutical compositions disclosed herein are solutions that comprise a compound of Formula (Ia) or Formula (Ib), or a pharmaceutically acceptable salt thereof, poloxamer 188, and a pharmaceutically acceptable excipient. In some embodiments, the pharmaceutical compositions disclosed herein are solutions that do not comprise a poloxamer. In some embodiments, the pharmaceutical compositions disclosed herein are solutions that do not comprise poloxamer 188.

Examples of excipients in a parenteral formulation (for example, an SC or an IM formulation) include polyethylene glycol. In general, polyethylene glycol (PEG) is a polyether having a general formula H—(O—CH$_2$—CH$_2$)$_n$—OH. In certain embodiments, the PEG may be "capped" by an alkyl group. In those embodiments, the capped PEG is of the formula alkyl-(0-CH$_2$—CH$_2$)$_n$—O-alkyl (for example, CH$_3$—(O—CH$_2$—CH$_2$)$_n$—OCH$_3$). The pharmaceutical compositions of the present disclosure can include PEG having an average molecular weight of about 100 to about 1000. In some embodiments, the average molecular weight of PEG within the pharmaceutical composition is about 100 to about 800. In some embodiments, the average molecular weight of PEG within the pharmaceutical composition is about 200 to about 600. In some embodiments, the average molecular weight of PEG within the pharmaceutical composition is about 400. In some embodiments, the average molecular weight of PEG within the pharmaceutical composition is about 300. In some embodiments, the average molecular weight of PEG within the pharmaceutical composition is about 200. In some embodiments of the pharmaceutical composition, different molecular weight PEG can be combined to obtain a desired property or properties (for example, viscosity). Specific examples of PEG include, but are not limited to, PEG 100, PEG 200, PEG 300, PEG 400, PEG 500, and PEG 600. PEG 100, for example, refers to a polyethylene glycol with an average molecular weight of about 100.

As noted above, in some embodiments, the pharmaceutical compositions comprising a compound of Formula (Ia) or Formula (Ib), or a pharmaceutically acceptable salt thereof, disclosed herein are in the form of a solution.

In some embodiments, the concentration of a compound of Formula (Ia) or Formula (Ib), or a pharmaceutically acceptable salt thereof, in the solution disclosed herein is about 50 mg/ml to about 500 mg/ml. In some embodiments, the concentration of a compound of Formula (Ia) or Formula (Ib), or a pharmaceutically acceptable salt thereof, in the solution disclosed herein is about 75 mg/ml to about 500 mg/ml. In some embodiments, the concentration of a compound of Formula (Ia) or Formula (Ib), or a pharmaceutically acceptable salt thereof, in the solution disclosed herein is about 50 mg/ml to about 400 mg/ml. In some embodiments, the concentration of a compound of Formula (Ia) or Formula (Ib), or a pharmaceutically acceptable salt thereof, in the solution disclosed herein is about 50 mg/ml to about 300 mg/ml. In some embodiments, the concentration of a compound of Formula (Ia) or Formula (Ib), or a pharmaceutically acceptable salt thereof, in the solution disclosed herein is about 75 mg/ml to about 400 mg/ml. In some embodiments, the concentration of a compound of Formula (Ia) or Formula (Ib), or a pharmaceutically acceptable salt thereof, in the solution disclosed herein is about 75 mg/ml to about 300 mg/ml. In some embodiments, the concentration of a compound of Formula (Ia) or Formula (Ib), or a pharmaceutically acceptable salt thereof, in the solution disclosed herein is about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, about 160 mg/ml, about 165 mg/ml, about 170 mg/ml, about 175 mg/ml, about 180 mg/ml, about 185 mg/ml, about 190 mg/ml, about 195 mg/ml, about 200 mg/ml, about 205 mg/ml, about 210 mg/ml, about 215 mg/ml, about 220 mg/ml, about 225 mg/ml, about 230 mg/ml, about 235 mg/ml, about 240 mg/ml, about 245 mg/ml, about 250 mg/ml, about 255 mg/ml, about 260 mg/ml, about 265 mg/ml, about 270 mg/ml, about 275 mg/ml, about 280 mg/ml, about 285 mg/ml, about 290 mg/ml, about 295 mg/ml, about 300 mg/ml, about 325 mg/ml, about 350 mg/ml, about 375 mg/ml, about 400 mg/ml, about 425 mg/ml, about 450 mg/ml, about 475 mg/ml, or about 500 mg/ml. In some embodiments, the concentration of a compound of Formula (Ia) or Formula (Ib), or a pharmaceutically acceptable salt thereof, in the solution disclosed herein is about 50 mg/ml. In some embodiments, the concentration of a compound of Formula (Ia) or Formula (Ib), or a pharmaceutically acceptable salt thereof, in the solution disclosed herein is about 75 mg/ml. In some embodiments, the concentration of a compound of Formula (Ia) or Formula (Ib), or a pharmaceutically acceptable salt thereof, in the solution disclosed herein is about 100 mg/ml. In some embodiments, the concentration of a compound of Formula (Ia) or Formula (Ib), or a pharmaceutically acceptable salt thereof, in the solution disclosed herein is about 125 mg/ml. In some embodiments, the concentration of a compound of Formula (Ia) or Formula (Ib), or a pharmaceutically acceptable salt thereof, in the solution disclosed herein is about 150 mg/ml. In some embodiments, the concentration of a compound of Formula (Ia) or Formula (Ib), or a pharmaceutically acceptable salt thereof, in the solution disclosed herein is about 175 mg/ml. In some embodiments, the concentration of a compound of Formula (Ia) or Formula (Ib), or a pharmaceutically acceptable salt thereof, in the solution disclosed herein is about 200 mg/ml. In some embodiments, the concentration of a compound of Formula (Ia) or Formula (Ib), or a pharmaceutically acceptable salt thereof, in the solution disclosed herein is about 225 mg/ml. In some embodiments, the concentration of a compound of Formula (Ia) or Formula (Ib), or a pharmaceutically acceptable salt thereof, in the solution disclosed herein is about 250 mg/ml. In some embodiments, the concentration of a compound of Formula (Ia) or Formula (Ib), or a pharmaceutically acceptable salt thereof, in the solution disclosed herein is about 275 mg/ml. In some embodiments, the concentration of a compound of Formula (Ia) or Formula (Ib), or a pharmaceutically acceptable salt thereof, in the solution disclosed herein is about 300 mg/ml. In some embodiments, the concentration of a compound of Formula (Ia) or Formula (Ib), or a pharmaceutically acceptable salt thereof, in the solution disclosed herein is about 325 mg/ml. In some embodiments, the concentration of a compound of Formula (Ia) or Formula (Ib), or a pharmaceutically acceptable salt thereof, in the solution disclosed herein is about 350 mg/ml. In some embodiments, the concentration of a compound of Formula (Ia) or Formula (Ib), or a pharmaceutically acceptable salt thereof, in the solution disclosed herein is about 375 mg/ml. In some embodiments, the concentration of a compound of Formula (Ia) or Formula (Ib), or a pharmaceutically acceptable salt thereof, in the solution disclosed herein is about 400 mg/ml. In some embodiments, the concentration of a compound of Formula (Ia) or Formula (Ib), or a pharmaceutically acceptable salt thereof, in the solution disclosed herein is about 425 mg/ml. In some embodiments, the concentration of a compound of Formula (Ia) or Formula (Ib), or a pharmaceutically acceptable salt thereof, in the solution disclosed herein is about 450 mg/ml. In some embodiments, the concentration of a compound of Formula (Ia) or Formula (Ib), or a pharmaceutically acceptable salt thereof, in the solution disclosed herein is about 475 mg/ml. In some embodiments, the concentration of a compound of Formula (Ia) or Formula (Ib), or a pharmaceutically acceptable salt thereof, in the solution disclosed herein is about 500 mg/ml.

In some embodiments, the solution disclosed herein comprises a compound of Formula (Ia) or Formula (Ib), or a pharmaceutically acceptable salt thereof, PEG 300, and water. In some embodiments, the solution disclosed herein comprises a compound of Formula (Ia) or a pharmaceutically acceptable salt thereof, PEG 300, and water. In some embodiments, the solution disclosed herein comprises a compound of Formula (Ib), or a pharmaceutically acceptable salt thereof, PEG 300, and water. In some embodiments, the solution disclosed herein comprises a sodium salt of the compound of Formula (Ia), PEG 300, and water. In some embodiments, the solution disclosed herein comprises a trifluoroacetic acid salt of the compound of Formula (Ib), PEG 300, and water. In some embodiments, the solution disclosed herein comprises a compound of Formula (Ib), PEG 300, and water.

In some embodiments, the solution disclosed herein comprises a compound of Formula (Ia), PEG 300, and water. In some embodiments, the concentration of the compound of Formula (Ia) in the solution comprising a compound of Formula (Ia), PEG 300, and water is about 50 mg/ml to about 500 mg/ml. In some embodiments, the concentration of the compound of Formula (Ia) in the solution comprising a compound of Formula (Ia), PEG 300, and water is about 50 mg/ml to about 400 mg/ml. In some embodiments, the concentration of the compound of Formula (Ia) in the solution comprising a compound of Formula (Ia), PEG 300, and water is about 50 mg/ml to about 300 mg/ml. In some embodiments, the concentration of the compound of Formula (Ia) in the solution comprising a compound of Formula (Ia), PEG 300, and water is about 75 mg/ml to about 300 mg/ml. In some embodiments, the concentration of the compound of Formula (Ia) in the solution comprising a compound of Formula (Ia), PEG 300, and water is about 50 mg/ml. In some embodiments, the concentration of the compound of Formula (Ia) in the solution comprising a compound of Formula (Ia), PEG 300, and water is about 75 mg/ml. In some embodiments, the concentration of the compound of Formula (Ia) in the solution comprising a compound of Formula (Ia), PEG 300, and water is about 100 mg/ml. In some embodiments, the concentration of the compound of Formula (Ia) in the solution comprising a compound of Formula (Ia), PEG 300, and water is about 125 mg/ml. In some embodiments, the concentration of the compound of Formula (Ia) in the solution comprising a compound of Formula (Ia), PEG 300, and water is about 150 mg/ml. In some embodiments, the concentration of the compound of Formula (Ia) in the solution comprising a compound of Formula (Ia), PEG 300, and water is about 175 mg/ml. In some embodiments, the concentration of the compound of Formula (Ia) in the solution comprising a compound of Formula (Ia), PEG 300, and water is about 200 mg/ml. In some embodiments, the concentration of the compound of Formula (Ia) in the solution comprising a compound of Formula (Ia), PEG 300, and water is about 225 mg/ml. In some embodiments, the concentration of the compound of Formula (Ia) in the solution comprising a compound of Formula (Ia), PEG 300, and water is about 250 mg/ml. In some embodiments, the concentration of the compound of Formula (Ia) in the solution comprising a compound of Formula (Ia), PEG 300, and water is about 275 mg/ml. In some embodiments, the concentration of the compound of Formula (Ia) in the solution comprising a compound of Formula (Ia), PEG 300, and water is about 300 mg/ml. In some embodiments, the concentration of the compound of Formula (Ia) in the solution comprising a compound of Formula (Ia), PEG 300, and water is about 325 mg/ml. In some embodiments, the concentration of the compound of Formula (Ia) in the solution comprising a compound of Formula (Ia), PEG 300, and water is about 350 mg/ml. In some embodiments, the concentration of the compound of Formula (Ia) in the solution comprising a compound of Formula (Ia), PEG 300, and water is about 375 mg/ml. In some embodiments, the concentration of the compound of Formula (Ia) in the solution comprising a compound of Formula (Ia), PEG 300, and water is about 400 mg/ml. In some embodiments, the concentration of the compound of Formula (Ia) in the solution comprising a compound of Formula (Ia), PEG 300, and water is about 425 mg/ml. In some embodiments, the concentration of the compound of Formula (Ia) in the solution comprising a compound of Formula (Ia), PEG 300, and water is about 450 mg/ml. In some embodiments, the concentration of the compound of Formula (Ia) in the solution comprising a compound of Formula (Ia), PEG 300, and water is about 475 mg/ml. In some embodiments, the concentration of the compound of Formula (Ia) in the solution comprising a compound of Formula (Ia), PEG 300, and water is about 500 mg/ml.

In some embodiments, the amount of water in the solution comprising a compound of Formula (Ia), PEG 300, and water is about 5 w/w % to about 15 w/w %. In some embodiments, the amount of water in the solution comprising a compound of Formula (Ia), PEG 300, and water is about 5 w/w % to about 10 w/w %. In some embodiments, the amount of water in the solution comprising a compound of Formula (Ia), PEG 300, and water is about 8 w/w % to about 12 w/w %. In some embodiments, the amount of water in the solution comprising a compound of Formula (Ia), PEG 300, and water is about 9 w/w % to about 10 w/w %. In some embodiments, the amount of water in the solution comprising a compound of Formula (Ia), PEG 300, and water is about 8.0 w/w %, about 8.1 w/w %, about 8.2 w/w %, about 8.3 w/w %, about 8.4 w/w %, about 8.5 w/w %, about 8.6 w/w %, about 8.7 w/w %, about 8.8 w/w %, about 8.9 w/w %, about 9.0 w/w %, about 9.1 w/w %, about 9.2 w/w %, about 9.3 w/w %, about 9.4 w/w %, about 9.5 w/w %, about 9.6 w/w %, about 9.7 w/w %, about 9.8 w/w %, about 9.9 w/w %, about 10.0 w/w %, about 10.1 w/w %, about 10.2 w/w %, about 10.3 w/w %, about 10.4 w/w %, about 10.5 w/w %, about 10.6 w/w %, about 10.7 w/w %, about 10.8 w/w %, about 10.9 w/w %, about 11.0 w/w %, about 11.1 w/w %, about 11.2 w/w %, about 11.3 w/w %, about 11.4 w/w %, about 11.5 w/w %, about 11.6 w/w %, about 11.7 w/w %, about 11.8 w/w %, about 11.9 w/w %, or about 12.0 w/w %. In some embodiments, the amount of water in the solution comprising a compound of Formula (Ia), PEG 300, and water is about 9.0 w/w %, about 9.1 w/w %, about 9.2 w/w %, about 9.3 w/w %, about 9.4 w/w %, about 9.5 w/w %, about 9.6 w/w %, about 9.7 w/w %, about 9.8 w/w %, about 9.9 w/w %, or about 10.0 w/w %. In some embodiments, the amount of water in the solution comprising a compound of Formula (Ia), PEG 300, and water is about 9.5 w/w %, about 9.6 w/w %, about 9.7 w/w %, about 9.8 w/w %, about 9.9 w/w %, or about 10.0 w/w %. In some embodiments, the amount of water in the solution comprising a compound of Formula (Ia), PEG 300, and water is about 9.8 w/w %. In some embodiments, the amount of water in the solution comprising a compound of Formula (Ia), PEG 300, and water is about 10 w/w %.

In some embodiments, the amount of PEG 300 in the solution comprising a compound of Formula (Ia), PEG 300, and water is about 50 w/w % to about 85 w/w %. In some embodiments, the amount of PEG 300 in the solution comprising a compound of Formula (Ia), PEG 300, and water is about 60 w/w % to about 80 w/w %. In some embodiments, the amount of PEG 300 in the solution comprising a compound of Formula (Ia), PEG 300, and water is about 60 w/w % to about 70 w/w %. In some embodiments, the amount of PEG 300 in the solution comprising a compound of Formula (Ia), PEG 300, and water is about 50 w/w %, about 55 w/w %, about 60 w/w %, about 65 w/w %, about 70 w/w %, about 75 w/w %, about 80 w/w %, or about 85 w/w %. In some embodiments, the amount of PEG 300 in the solution comprising a compound of Formula (Ia), PEG 300, and water is about 65 w/w %. In some embodiments, the amount of PEG 300 in the solution comprising a compound of Formula (Ia), PEG 300, and water is about 65.0 w/w %.

In some embodiments, the amount of the compound of Formula (Ia) in the solution comprising a compound of Formula (Ia), PEG 300, and water is about 15 w/w % to about 35 w/w %. In some embodiments, the amount of the compound of Formula (Ia) in the solution comprising a compound of Formula (Ia), PEG 300, and water is about 20 w/w % to about 35 w/w %. In some embodiments, the amount of the compound of Formula (Ia) in the solution comprising a compound of Formula (Ia), PEG 300, and water is about 24 w/w % to about 26 w/w %. In some embodiments, the amount of the compound of Formula (Ia) in the solution comprising a compound of Formula (Ia), PEG 300, and water is about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, or about 25.5 w/w %. In some embodiments, the amount of the compound of Formula (Ia) in the solution comprising a compound of Formula (Ia), PEG 300, and water is about 25 w/w %. In some embodiments, the amount of the compound of Formula (Ia) in the solution comprising a compound of Formula (Ia), PEG 300, and water is about 25.2 w/w %.

In some embodiments, the solution disclosed herein comprises about 5 w/w % to about 15 w/w % water, about 50 w/w % to about 85 w/w % PEG 300, and about 15 w/w % to about 35 w/w % of a compound of Formula (Ia). In some embodiments, the solution comprises about 5 w/w % to about 10 w/w % water, about 60 w/w % to about 80 w/w % PEG 300, and about 20 w/w % to about 35 w/w % of a compound of Formula (Ia). In some embodiments, the solution comprises about 8 w/w % to about 12 w/w % water, about 60 w/w % to about 70 w/w % PEG 300, and about 15 w/w % to about 35 w/w % of a compound of Formula (Ia). In some embodiments, the solution comprises about 9 w/w % to about 10 w/w % water, about 60 w/w % to about 70 w/w % PEG 300, and about 24 w/w % to about 26 w/w % of a compound of Formula (Ia). In some embodiments, the solution comprises about 9.8 w/w % water, about 65.0 w/w % PEG 300, and about 25.2 w/w % of a compound of Formula (Ia). In some embodiments, the solution comprises about 10 w/w % water, about 65.0 w/w % PEG 300, and about 25 w/w % of a compound of Formula (Ia).

In some embodiments, the solution disclosed herein comprises a sodium salt of the compound of Formula (Ia), PEG 300, and water. In some embodiments, the concentration of the compound of Formula (Ia) in the solution comprising a sodium salt of the compound of Formula (Ia), PEG 300, and water is about 50 mg/ml to about 500 mg/ml. In some embodiments, the concentration of the compound of Formula (Ia) in the solution comprising a sodium salt of the compound of Formula (Ia), PEG 300, and water is about 50 mg/ml to about 300 mg/ml. In some embodiments, the concentration of the compound of Formula (Ia) in the solution comprising a sodium salt of the compound of Formula (Ia), PEG 300, and water is about 75 mg/ml to about 300 mg/ml. In some embodiments, the concentration of the compound of Formula (Ia) in the solution comprising a sodium salt of the compound of Formula (Ia), PEG 300, and water is about 50 mg/ml. In some embodiments, the concentration of the compound of Formula (Ia) in the solution comprising a sodium salt of the compound of Formula (Ia), PEG 300, and water is about 75 mg/ml. In some embodiments, the concentration of the compound of Formula (Ia) in the solution comprising a sodium salt of the compound of Formula (Ia), PEG 300, and water is about 100 mg/ml. In some embodiments, the concentration of the compound of Formula (Ia) in the solution comprising a sodium salt of the compound of Formula (Ia), PEG 300, and water is about 125 mg/ml. In some embodiments, the concentration of the compound of Formula (Ia) in the solution comprising a sodium salt of the compound of Formula (Ia), PEG 300, and water is about 150 mg/ml. In some embodiments, the concentration of the compound of Formula (Ia) in the solution comprising a sodium salt of the compound of Formula (Ia), PEG 300, and water is about 175 mg/ml. In some embodiments, the concentration of the compound of Formula (Ia) in the solution comprising a sodium salt of the compound of Formula (Ia), PEG 300, and water is about 200 mg/ml. In some embodiments, the concentration of the compound of Formula (Ia) in the solution comprising a sodium salt of the compound of Formula (Ia), PEG 300, and water is about 225 mg/ml. In some embodiments, the concentration of the compound of Formula (Ia) in the solution comprising a sodium salt of the compound of Formula (Ia), PEG 300, and water is about 250 mg/ml. In some embodiments, the concentration of the compound of Formula (Ia) in the solution comprising a sodium salt of the compound of Formula (Ia), PEG 300, and water is about 275 mg/ml. In some embodiments, the concentration of the compound of Formula (Ia) in the solution comprising a sodium salt of the compound of Formula (Ia), PEG 300, and water is about 300 mg/ml. In some embodiments, the concentration of the compound of Formula (Ia) in the solution comprising a sodium salt of the compound of Formula (Ia), PEG 300, and water is about 325 mg/ml. In some embodiments, the concentration of the compound of Formula (Ia) in the solution comprising a sodium salt of the compound of Formula (Ia), PEG 300, and water is about 350 mg/ml. In some embodiments, the concentration of the compound of Formula (Ia) in the solution comprising a sodium salt of the compound of Formula (Ia), PEG 300, and water is about 375 mg/ml. In some embodiments, the concentration of the compound of Formula (Ia) in the solution comprising a sodium salt of the compound of Formula (Ia), PEG 300, and water is about 400 mg/ml. In some embodiments, the concentration of the compound of Formula (Ia) in the solution comprising a sodium salt of the compound of Formula (Ia), PEG 300, and water is about 425 mg/ml. In some embodiments, the concentration of the compound of Formula (Ia) in the solution comprising a sodium salt of the compound of Formula (Ia), PEG 300, and water is about 450 mg/ml. In some embodiments, the concentration of the compound of Formula (Ia) in the solution comprising a sodium salt of the compound of Formula (Ia), PEG 300, and water is about 475 mg/ml. In some embodiments, the concentration of the compound of Formula (Ia) in the solution comprising a sodium salt of the compound of Formula (Ia), PEG 300, and water is about 500 mg/ml.

In some embodiments, the amount of water in the solution comprising a sodium salt of the compound of Formula (Ia), PEG 300, and water is about 10 w/w % to about 40 w/w %. In some embodiments, the amount of water in the solution comprising a sodium salt of the compound of Formula (Ia), PEG 300, and water is about 15 w/w % to about 35 w/w %. In some embodiments, the amount of water in the solution comprising a sodium salt of the compound of Formula (Ia), PEG 300, and water is about 20 w/w % to about 30 w/w %. In some embodiments, the amount of water in the solution comprising a sodium salt of the compound of Formula (Ia), PEG 300, and water is about 21 w/w % to about 29 w/w %. In some embodiments, the amount of water in the solution comprising a sodium salt of the compound of Formula (Ia), PEG 300, and water is about 23.4 w/w % to about 27.5 w/w %. In some embodiments, the amount of water in the solution comprising a sodium salt of the compound of Formula (Ia), PEG 300, and water is about 23.41 w/w % to about 27.47 w/w %. In some embodiments, the amount of water in the solution comprising a sodium salt of the compound of Formula (Ia), PEG 300, and water is about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of water in the solution comprising a sodium salt of the compound of Formula (Ia), PEG 300, and water is about 23.4 w/w %. In some embodiments, the amount of water in the solution comprising a sodium salt of the compound of Formula (Ia), PEG 300, and water is about 23.41 w/w %. In some embodiments, the amount of water in the solution comprising a sodium salt of the compound of Formula (Ia), PEG 300, and water is about 27.47 w/w %. In some embodiments, the amount of water in the solution comprising a sodium salt of the compound of Formula (Ia), PEG 300, and water is about 27.5 w/w %.

In some embodiments, the amount of PEG 300 in the solution comprising a sodium salt of the compound of Formula (Ia), PEG 300, and water is about 35 w/w % to about 75 w/w %. In some embodiments, the amount of PEG 300 in the solution comprising a sodium salt of the compound of Formula (Ia), PEG 300, and water is about 45 w/w % to about 65 w/w %. In some embodiments, the amount of PEG 300 in the solution comprising a sodium salt of the compound of Formula (Ia), PEG 300, and water is about 48 w/w % to about 60 w/w %. In some embodiments, the amount of PEG 300 in the solution comprising a sodium salt of the compound of Formula (Ia), PEG 300, and water is about 50 w/w % to about 59 w/w %. In some embodiments, the amount of PEG 300 in the solution comprising a sodium salt of the compound of Formula (Ia), PEG 300, and water is about 50.1 w/w % to about 58.8 w/w %. In some embodiments, the amount of PEG 300 in the solution comprising a sodium salt of the compound of Formula (Ia), PEG 300, and water is about 50.13 w/w % to about 58.84 w/w %. In some embodiments, the amount of PEG 300 in the solution comprising a sodium salt of the compound of Formula (Ia), PEG 300, and water is about 45 w/w %, about 46 w/w %, about 47 w/w %, about 48 w/w %, about 49 w/w %, about 50 w/w %, about 51 w/w %, about 52 w/w %, about 53 w/w %, about 54 w/w %, about 55 w/w %, about 56 w/w %, about 57 w/w %, about 58 w/w %, about 59 w/w %, about 60 w/w %, about 61 w/w %, about 62 w/w %, about 63 w/w %, about 64 w/w %, or about 65 w/w %. In some embodiments, the amount of PEG 300 in the solution comprising a sodium salt of the compound of Formula (Ia), PEG 300, and water is about 50.1 w/w %. In some embodiments, the amount of PEG 300 in the solution comprising a sodium salt of the compound of Formula (Ia), PEG 300, and water is about 50.13 w/w %. In some embodiments, the amount of PEG 300 in the solution comprising a sodium salt of the compound of Formula (Ia), PEG 300, and water is about 58.8 w/w %. In some embodiments, the amount of PEG 300 in the solution comprising a sodium salt of the compound of Formula (Ia), PEG 300, and water is about 58.84 w/w %.

In some embodiments, the amount of the sodium salt of the compound of Formula (Ia) in the solution comprising a sodium salt of the compound of Formula (Ia), PEG 300, and water is about 5 w/w % to about 35 w/w %. In some embodiments, the amount of the sodium salt of the compound of Formula (Ia) in the solution comprising a sodium salt of the compound of Formula (Ia), PEG 300, and water is about 10 w/w % to about 30 w/w %. In some embodiments, the amount of the sodium salt of the compound of Formula (Ia) in the solution comprising a sodium salt of the compound of Formula (Ia), PEG 300, and water is about 11 w/w % to about 28 w/w %. In some embodiments, the amount of the sodium salt of the compound of Formula (Ia) in the solution comprising a sodium salt of the compound of Formula (Ia), PEG 300, and water is about 13 w/w % to about 27 w/w %. In some embodiments, the amount of the sodium salt of the compound of Formula (Ia) in the solution comprising a sodium salt of the compound of Formula (Ia), PEG 300, and water is about 13.69 w/w % to about 26.46 w/w %. In some embodiments, the amount of the sodium salt of the compound of Formula (Ia) in the solution comprising a sodium salt of the compound of Formula (Ia), PEG 300, and water is about 13.7 w/w % to about 26.5 w/w %. In some embodiments, the amount of the sodium salt of the compound of Formula (Ia) in the solution comprising a sodium salt of the compound of Formula (Ia), PEG 300, and water is about 13.0 w/w %, about 13.1 w/w %, about 13.2 w/w %, about 13.3 w/w %, about 13.4 w/w %, about 13.5 w/w %, about 13.6 w/w %, about 13.7 w/w %, about 13.8 w/w %, about 13.9 w/w %, about 14.0 w/w %, about 14.1 w/w %, about 14.2 w/w %, about 14.3 w/w %, about 14.4 w/w %, about 14.5 w/w %, about 14.6 w/w %, about 14.7 w/w %, about 14.8 w/w %, about 14.9 w/w %, about 15.0 w/w %, about 15.1 w/w %, about 15.2 w/w %, about 15.3 w/w %, about 15.4 w/w %, about 15.5 w/w %, about 15.6 w/w %, about 15.7 w/w %, about 15.8 w/w %, about 15.9 w/w %, about 16.0 w/w %, about 16.1 w/w %, about 16.2 w/w %, about 16.3 w/w %, about 16.4 w/w %, about 16.5 w/w %, about 16.6 w/w %, about 16.7 w/w %, about 16.8 w/w %, about 16.9 w/w %, about 17.0 w/w %, about 17.1 w/w %, about 17.2 w/w %, about 17.3 w/w %, about 17.4 w/w %, about 17.5 w/w %, about 17.6 w/w %, about 17.7 w/w %, about 17.8 w/w %, about 17.9 w/w %, about 18.0 w/w %, about 18.1 w/w %, about 18.2 w/w %, about 18.3 w/w %, about 18.4 w/w %, about 18.5 w/w %, about 18.6 w/w %, about 18.7 w/w %, about 18.8 w/w %, about 18.9 w/w %, about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of the sodium salt of the compound of Formula (Ia) in the solution comprising a sodium salt of the compound of Formula (Ia), PEG 300, and water is about 13.69 w/w %. In some embodiments, the amount of the sodium salt of the compound of Formula (Ia) in the solution comprising a sodium salt of the compound of Formula (Ia), PEG 300, and water is about 13.7 w/w %. In some embodiments, the amount of the sodium salt of the compound of Formula (Ia) in the solution comprising a sodium salt of the compound of Formula (Ia), PEG 300, and water is about 26.46 w/w %. In some embodiments, the amount of the sodium salt of the compound of Formula (Ia) in the solution comprising a sodium salt of the compound of Formula (Ia), PEG 300, and water is about 26.5 w/w %.

In some embodiments, the solution disclosed herein comprises about 10 w/w % to about 40 w/w % water, about 35 w/w % to about 75 w/w % PEG 300, and about 5 w/w % to about 35 w/w % of a sodium salt of the compound of Formula (Ia). In some embodiments, the solution comprises about 15 w/w % to about 35 w/w % water, about 45 w/w % to about 65 w/w % PEG 300, and about 10 w/w % to about 30 w/w % of a sodium salt of the compound of Formula (Ia). In some embodiments, the solution comprises about 20 w/w % to about 30 w/w % water, about 48 w/w % to about 60 w/w % PEG 300, and about 11 w/w % to about 28 w/w % of a sodium salt of the compound of Formula (Ia). In some embodiments, the solution comprises about 21 w/w % to about 29 w/w % water, about 50 w/w % to about 59 w/w % PEG 300, and about 13 w/w % to about 27 w/w % of a sodium salt of the compound of Formula (Ia). In some embodiments, the solution comprises about 23.4 w/w % to about 27.5 w/w % water, about 50.1 w/w % to about 58.8 w/w % PEG 300, and about 13.7 w/w % to about 26.5 w/w % of a sodium salt of the compound of Formula (Ia). In some embodiments, the solution comprises about 23.41 w/w % to about 27.47 w/w % water, about 50.13 w/w % to about 58.84 w/w % PEG 300, and about 13.69 w/w % to about 26.46 w/w % of a sodium salt of the compound of Formula (Ia). In some embodiments, the solution comprises about 27.5 w/w % water, about 58.8 w/w % PEG 300, and about 13.7 w/w % of a sodium salt of the compound of Formula (Ia). In some embodiments, the solution comprises about 27.47 w/w % water, about 58.84 w/w % PEG 300, and about 13.69 w/w % of a sodium salt of the compound of Formula (Ia). In some embodiments, the solution comprises about 23.4 w/w % water, about 50.1 w/w % PEG 300, and about 26.5 w/w % of a sodium salt of the compound of Formula (Ia). In some embodiments, the solution comprises about 23.41 w/w % water, about 50.13 w/w % PEG 300, and about 26.46 w/w % of a sodium salt of the compound of Formula (Ia).

In some embodiments, the solution disclosed herein comprises a compound of Formula (Ia) or Formula (Ib), or a pharmaceutically acceptable salt thereof, PEG 300, poloxamer 188, and water. In some embodiments, the solution disclosed herein comprises a compound of Formula (Ia) or a pharmaceutically acceptable salt thereof, PEG 300, poloxamer 188, and water. In some embodiments, the solution disclosed herein comprises a compound of Formula (Ib), or a pharmaceutically acceptable salt thereof, PEG 300, poloxamer 188, and water. In some embodiments, the solution disclosed herein comprises a compound of Formula (Ia), PEG 300, poloxamer 188, and water. In some embodiments, the solution disclosed herein comprises a trifluoroacetic acid salt of the compound of Formula (Ib), PEG 300, poloxamer 188, and water. In some embodiments, the solution disclosed herein comprises a compound of Formula (Ib), PEG 300, poloxamer 188, and water.

In some embodiments, the solution disclosed herein comprises a sodium salt of the compound of Formula (Ia), PEG 300, poloxamer 188, and water. In some embodiments, the concentration of the compound of Formula (Ia) in the solution comprising a sodium salt of the compound of Formula (Ia), PEG 300, poloxamer 188, and water is about 50 mg/ml to about 500 mg/ml. In some embodiments, the concentration of the compound of Formula (Ia) in the solution comprising a sodium salt of the compound of Formula (Ia), PEG 300, poloxamer 188, and water is about 50 mg/ml to about 400 mg/ml. In some embodiments, the concentration of the compound of Formula (Ia) in the solution comprising a sodium salt of the compound of Formula (Ia), PEG 300, poloxamer 188, and water is about 50 mg/ml to about 300 mg/ml. In some embodiments, the concentration of the compound of Formula (Ia) in the solution comprising a sodium salt of the compound of Formula (Ia), PEG 300, poloxamer 188, and water is about 75 mg/ml to about 300 mg/ml. In some embodiments, the concentration of the compound of Formula (Ia) in the solution comprising a sodium salt of the compound of Formula (Ia), PEG 300, poloxamer 188, and water is about 50 mg/ml. In some embodiments, the concentration of the compound of Formula (Ia) in the solution comprising a sodium salt of the compound of Formula (Ia), PEG 300, poloxamer 188, and water is about 75 mg/ml. In some embodiments, the concentration of the compound of Formula (Ia) in the solution comprising a sodium salt of the compound of Formula (Ia), PEG 300, poloxamer 188, and water is about 100 mg/ml. In some embodiments, the concentration of the compound of Formula (Ia) in the solution comprising a sodium salt of the compound of Formula (Ia), PEG 300, poloxamer 188, and water is about 125 mg/ml. In some embodiments, the concentration of the compound of Formula (Ia) in the solution comprising a sodium salt of the compound of Formula (Ia), PEG 300, poloxamer 188, and water is about 150 mg/ml. In some embodiments, the concentration of the compound of Formula (Ia) in the solution comprising a sodium salt of the compound of Formula (Ia), PEG 300, poloxamer 188, and water is about 175 mg/ml. In some embodiments, the concentration of the compound of Formula (Ia) in the solution comprising a sodium salt of the compound of Formula (Ia), PEG 300, poloxamer 188, and water is about 200 mg/ml. In some embodiments, the concentration of the compound of Formula (Ia) in the solution comprising a sodium salt of the compound of Formula (Ia), PEG 300, poloxamer 188, and water is about 225 mg/ml. In some embodiments, the concentration of the compound of Formula (Ia) in the solution comprising a sodium salt of the compound of Formula (Ia), PEG 300, poloxamer 188, and water is about 250 mg/ml. In some embodiments, the concentration of the compound of Formula (Ia) in the solution comprising a sodium salt of the compound of Formula (Ia), PEG 300, poloxamer 188, and water is about 275 mg/ml. In some embodiments, the concentration of the compound of Formula (Ia) in the solution comprising a sodium salt of the compound of Formula (Ia), PEG 300, poloxamer 188, and water is about 300 mg/ml. In some embodiments, the concentration of the compound of Formula (Ia) in the solution comprising a sodium salt of the compound of Formula (Ia), PEG 300, poloxamer 188, and water is about 325 mg/ml. In some embodiments, the concentration of the compound of Formula (Ia) in the solution comprising a sodium salt of the compound of Formula (Ia), PEG 300, poloxamer 188, and water is about 350 mg/ml. In some embodiments, the concentration of the compound of Formula (Ia) in the solution comprising a sodium salt of the compound of Formula (Ia), PEG 300, poloxamer 188, and water is about 375 mg/ml. In some embodiments, the concentration of the compound of Formula (Ia) in the solution comprising a sodium salt of the compound of Formula (Ia), PEG 300, poloxamer 188, and water is about 400 mg/ml. In some embodiments, the concentration of the compound of Formula (Ia) in the solution comprising a sodium salt of the compound of Formula (Ia), PEG 300, poloxamer 188, and water is about 425 mg/ml. In some embodiments, the concentration of the compound of Formula (Ia) in the solution comprising a sodium salt of the compound of Formula (Ia), PEG 300, poloxamer 188, and water is about 450 mg/ml. In some embodiments, the concentration of the compound of Formula (Ia) in the solution comprising a sodium salt of the compound of Formula (Ia), PEG 300, poloxamer 188, and water is about 475 mg/ml. In some embodiments, the concentration of the compound of Formula (Ia) in the solution comprising a sodium salt of the compound of Formula (Ia), PEG 300, poloxamer 188, and water is about 500 mg/ml.

In some embodiments, the amount of water in the solution comprising a sodium salt of the compound of Formula (Ia), PEG 300, poloxamer 188, and water is about 10 w/w % to about 45 w/w %. In some embodiments, the amount of water in the solution comprising a sodium salt of the compound of Formula (Ia), PEG 300, poloxamer 188, and water is about 15 w/w % to about 35 w/w %. In some embodiments, the amount of water in the solution comprising a sodium salt of the compound of Formula (Ia), PEG 300, poloxamer 188, and water is about 20 w/w % to about 35 w/w %. In some embodiments, the amount of water in the solution comprising a sodium salt of the compound of Formula (Ia), PEG 300, poloxamer 188, and water is about 20 w/w % to about 31 w/w %. In some embodiments, the amount of water in the solution comprising a sodium salt of the compound of Formula (Ia), PEG 300, poloxamer 188, and water is about 21.9 w/w % to about 30.1 w/w %. In some embodiments, the amount of water in the solution comprising a sodium salt of the compound of Formula (Ia), PEG 300, poloxamer 188, and water is about 21.87 w/w % to about 30.07 w/w %. In some embodiments, the amount of water in the solution comprising a sodium salt of the compound of Formula (Ia), PEG 300, poloxamer 188, and water is about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 20.1 w/w %, about 20.2 w/w %, about 20.3 w/w %, about 20.4 w/w %, about 20.5 w/w %, about 20.6 w/w %, about 20.7 w/w %, about 20.8 w/w %, about 20.9 w/w %, about 21.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, about 29.0 w/w %, about 29.1 w/w %, about 29.2 w/w %, about 29.3 w/w %, about 29.4 w/w %, about 29.5 w/w %, about 29.6 w/w %, about 29.7 w/w %, about 29.8 w/w %, about 29.9 w/w %, about 30.0 w/w %, about 30.1 w/w %, about 30.2 w/w %, about 30.3 w/w %, about 30.4 w/w %, about 30.5 w/w %, about 30.6 w/w %, about 30.7 w/w %, about 30.8 w/w %, about 30.9 w/w %, about 31.0 w/w %, about 31.1 w/w %, about 31.2 w/w %, about 31.3 w/w %, about 31.4 w/w %, about 31.5 w/w %, about 31.6 w/w %, about 31.7 w/w %, about 31.8 w/w %, about 31.9 w/w %, about 32.0 w/w %, about 32.1 w/w %, about 32.2 w/w %, about 32.3 w/w %, about 32.4 w/w %, about 32.5 w/w %, about 32.6 w/w %, about 32.7 w/w %, about 32.8 w/w %, about 32.9 w/w %, or about 33.0 w/w %. In some embodiments, the amount of water in the solution comprising a sodium salt of the compound of Formula (Ia), PEG 300, poloxamer 188, and water is about 21.87 w/w %. In some embodiments, the amount of water in the solution comprising a sodium salt of the compound of Formula (Ia), PEG 300, poloxamer 188, and water is about 21.9 w/w %. In some embodiments, the amount of water in the solution comprising a sodium salt of the compound of Formula (Ia), PEG 300, poloxamer 188, and water is about 26.68 w/w %. In some embodiments, the amount of water in the solution comprising a sodium salt of the compound of Formula (Ia), PEG 300, poloxamer 188, and water is about 26.7 w/w %. In some embodiments, the amount of water in the solution comprising a sodium salt of the compound of Formula (Ia), PEG 300, and poloxamer 188, and water is about 27.5 w/w %. In some embodiments, the amount of water in the solution comprising a sodium salt of the compound of Formula (Ia), PEG 300, poloxamer 188, and water is about 27.51 w/w %. In some embodiments, the amount of water in the solution comprising a sodium salt of the compound of Formula (Ia), PEG 300, poloxamer 188, and water is about 28.36 w/w %. In some embodiments, the amount of water in the solution comprising a sodium salt of the compound of Formula (Ia), PEG 300, poloxamer 188, and water is about 28.4 w/w %. In some embodiments, the amount of water in the solution comprising a sodium salt of the compound of Formula (Ia), PEG 300, poloxamer 188, and water is about 29.2 w/w %. In some embodiments, the amount of water in the solution comprising a sodium salt of the compound of Formula (Ia), PEG 300, poloxamer 188, and water is about 29.21 w/w %. In some embodiments, the amount of water in the solution comprising a sodium salt of the compound of Formula (Ia), PEG 300, poloxamer 188, and water is about 30.07 w/w %. In some embodiments, the amount of water in the solution comprising a sodium salt of the compound of Formula (Ia), PEG 300, poloxamer 188, and water is about 30.1 w/w %.

In some embodiments, the amount of PEG 300 in the solution comprising a sodium salt of the compound of Formula (Ia), PEG 300, poloxamer 188, and water is about 30 w/w % to about 85 w/w %. In some embodiments, the amount of PEG 300 in the solution comprising a sodium salt of the compound of Formula (Ia), PEG 300, poloxamer 188, and water is about 35 w/w % to about 75 w/w %. In some embodiments, the amount of PEG 300 in the solution comprising a sodium salt of the compound of Formula (Ia), PEG 300, poloxamer 188, and water is about 40 w/w % to about 70 w/w %. In some embodiments, the amount of PEG 300 in the solution comprising a sodium salt of the compound of Formula (Ia), PEG 300, poloxamer 188, and water is about 45 w/w % to about 68 w/w %. In some embodiments, the amount of PEG 300 in the solution comprising a sodium salt of the compound of Formula (Ia), PEG 300, poloxamer 188, and water is about 46.8 w/w % to about 64.4 w/w %. In some embodiments, the amount of PEG 300 in the solution comprising a sodium salt of the compound of Formula (Ia), PEG 300, poloxamer 188, and water is about 46.84 w/w % to about 64.40 w/w %. In some embodiments, the amount of PEG 300 in the solution comprising a sodium salt of the compound of Formula (Ia), PEG 300, poloxamer 188, and water is about 40 w/w %, about 41 w/w %, about 42 w/w %, about 43 w/w %, about 44 w/w %, about 45 w/w %, about 46 w/w %, about 47 w/w %, about 48 w/w %, about 49 w/w %, about 50 w/w %, about 51 w/w %, about 52 w/w %, about 53 w/w %, about 54 w/w %, about 55 w/w %, about 56 w/w %, about 57 w/w %, about 58 w/w %, about 59 w/w %, about 60 w/w %, about 61 w/w %, about 62 w/w %, about 63 w/w %, about 64 w/w %, about 65 w/w %, about 66 w/w %, about 67 w/w %, about 68 w/w %, about 69 w/w %, or about 70 w/w %. In some embodiments, the amount of PEG 300 in the solution comprising a sodium salt of the compound of Formula (Ia), PEG 300, poloxamer 188, and water is about 46.8 w/w %. In some embodiments, the amount of PEG 300 in the solution comprising a sodium salt of the compound of Formula (Ia), PEG 300, poloxamer 188, and water is about 46.84 w/w %. In some embodiments, the amount of PEG 300 in the solution comprising a sodium salt of the compound of Formula (Ia), PEG 300, poloxamer 188, and water is about 57.1 w/w %. In some embodiments, the amount of PEG 300 in the solution comprising a sodium salt of the compound of Formula (Ia), PEG 300, poloxamer 188, and water is about 57.13 w/w %. In some embodiments, the amount of PEG 300 in the solution comprising a sodium salt of the compound of Formula (Ia), PEG 300, poloxamer 188, and water is about 58.9 w/w %. In some embodiments, the amount of PEG 300 in the solution comprising a sodium salt of the compound of Formula (Ia), PEG 300, poloxamer 188, and water is about 58.92 w/w %. In some embodiments, the amount of PEG 300 in the solution comprising a sodium salt of the compound of Formula (Ia), PEG 300, poloxamer 188, and water is about 60.7 w/w %. In some embodiments, the amount of PEG 300 in the solution comprising a sodium salt of the compound of Formula (Ia), PEG 300, poloxamer 188, and water is about 60.73 w/w %. In some embodiments, the amount of PEG 300 in the solution comprising a sodium salt of the compound of Formula (Ia), PEG 300, poloxamer 188, and water is about 62.55 w/w %. In some embodiments, the amount of PEG 300 in the solution comprising a sodium salt of the compound of Formula (Ia), PEG 300, poloxamer 188, and water is about 62.6 w/w %. In some embodiments, the amount of PEG 300 in the solution comprising a sodium salt of the compound of Formula (Ia), PEG 300, poloxamer 188, and water is about 64.4 w/w %. In some embodiments, the amount of PEG 300 in the solution comprising a sodium salt of the compound of Formula (Ia), PEG 300, poloxamer 188, and water is about 64.40 w/w %.

In some embodiments, the amount of the sodium salt of the compound of Formula (Ia) in the solution comprising a sodium salt of the compound of Formula (Ia), PEG 300, poloxamer 188, and water is about 0.5 w/w % to about 40 w/w %. In some embodiments, the amount of the sodium salt of the compound of Formula (Ia) in the solution comprising a sodium salt of the compound of Formula (Ia), PEG 300, poloxamer 188, and water is about 1 w/w % to about 35 w/w %. In some embodiments, the amount of the sodium salt of the compound of Formula (Ia) in the solution comprising a sodium salt of the compound of Formula (Ia), PEG 300, poloxamer 188, and water is about 1 w/w % to about 30 w/w %. In some embodiments, the amount of the sodium salt of the compound of Formula (Ia) in the solution comprising a sodium salt of the compound of Formula (Ia), PEG 300, poloxamer 188, and water is about 3 w/w % to about 28 w/w %. In some embodiments, the amount of the sodium salt of the compound of Formula (Ia) in the solution comprising a sodium salt of the compound of Formula (Ia), PEG 300, poloxamer 188, and water is about 4 w/w % to about 27 w/w %. In some embodiments, the amount of the sodium salt of the compound of Formula (Ia) in the solution comprising a sodium salt of the compound of Formula (Ia), PEG 300, poloxamer 188, and water is about 4.68 w/w % to about 26.47 w/w %. In some embodiments, the amount of the sodium salt of the compound of Formula (Ia) in the solution comprising a sodium salt of the compound of Formula (Ia), PEG 300, poloxamer 188, and water is about 4.7 w/w % to about 26.5 w/w %. In some embodiments, the amount of the sodium salt of the compound of Formula (Ia) in the solution comprising a sodium salt of the compound of Formula (Ia), PEG 300, poloxamer 188, and water is about 3.0 w/w %, about 3.1 w/w %, about 3.2 w/w %, about 3.3 w/w %, about 3.4 w/w %, about 3.5 w/w %, about 3.6 w/w %, about 3.7 w/w %, about 3.8 w/w %, about 3.9 w/w %, about 4.0 w/w %, about 4.1 w/w %, about 4.2 w/w %, about 4.3 w/w %, about 4.4 w/w %, about 4.5 w/w %, about 4.6 w/w %, about 4.7 w/w %, about 4.8 w/w %, about 4.9 w/w %, about 5.0 w/w %, about 5.1 w/w %, about 5.2 w/w %, about 5.3 w/w %, about 5.4 w/w %, about 5.5 w/w %, about 5.6 w/w %, about 5.7 w/w %, about 5.8 w/w %, about 5.9 w/w %, about 6.0 w/w %, about 6.1 w/w %, about 6.2 w/w %, about 6.3 w/w %, about 6.4 w/w %, about 6.5 w/w %, about 6.6 w/w %, about 6.7 w/w %, about 6.8 w/w %, about 6.9 w/w %, about 7.0 w/w %, about 7.1 w/w %, about 7.2 w/w %, about 7.3 w/w %, about 7.4 w/w %, about 7.5 w/w %, about 7.6 w/w %, about 7.7 w/w %, about 7.8 w/w %, about 7.9 w/w %, about 8.0 w/w %, about 8.1 w/w %, about 8.2 w/w %, about 8.3 w/w %, about 8.4 w/w %, about 8.5 w/w %, about 8.6 w/w %, about 8.7 w/w %, about 8.8 w/w %, about 8.9 w/w %, about 9.0 w/w %, about 9.1 w/w %, about 9.2 w/w %, about 9.3 w/w %, about 9.4 w/w %, about 9.5 w/w %, about 9.6 w/w %, about 9.7 w/w %, about 9.8 w/w %, about 9.9 w/w %, about 10.0 w/w %, about 10.1 w/w %, about 10.2 w/w %, about 10.3 w/w %, about 10.4 w/w %, about 10.5 w/w %, about 10.6 w/w %, about 10.7 w/w %, about 10.8 w/w %, about 10.9 w/w %, about 11.0 w/w %, about 11.1 w/w %, about 11.2 w/w %, about 11.3 w/w %, about 11.4 w/w %, about 11.5 w/w %, about 11.6 w/w %, about 11.7 w/w %, about 11.8 w/w %, about 11.9 w/w %, about 12.0 w/w %, about 12.1 w/w %, about 12.2 w/w %, about 12.3 w/w %, about 12.4 w/w %, about 12.5 w/w %, about 12.6 w/w %, about 12.7 w/w %, about 12.8 w/w %, about 12.9 w/w %, about 13.0 w/w %, about 13.1 w/w %, about 13.2 w/w %, about 13.3 w/w %, about 13.4 w/w %, about 13.5 w/w %, about 13.6 w/w %, about 13.7 w/w %, about 13.8 w/w %, about 13.9 w/w %, about 14.0 w/w %, about 14.1 w/w %, about 14.2 w/w %, about 14.3 w/w %, about 14.4 w/w %, about 14.5 w/w %, about 14.6 w/w %, about 14.7 w/w %, about 14.8 w/w %, about 14.9 w/w %, about 15.0 w/w %, about 15.1 w/w %, about 15.2 w/w %, about 15.3 w/w %, about 15.4 w/w %, about 15.5 w/w %, about 15.6 w/w %, about 15.7 w/w %, about 15.8 w/w %, about 15.9 w/w %, about 16.0 w/w %, about 16.1 w/w %, about 16.2 w/w %, about 16.3 w/w %, about 16.4 w/w %, about 16.5 w/w %, about 16.6 w/w %, about 16.7 w/w %, about 16.8 w/w %, about 16.9 w/w %, about 17.0 w/w %, about 17.1 w/w %, about 17.2 w/w %, about 17.3 w/w %, about 17.4 w/w %, about 17.5 w/w %, about 17.6 w/w %, about 17.7 w/w %, about 17.8 w/w %, about 17.9 w/w %, about 18.0 w/w %, about 18.1 w/w %, about 18.2 w/w %, about 18.3 w/w %, about 18.4 w/w %, about 18.5 w/w %, about 18.6 w/w %, about 18.7 w/w %, about 18.8 w/w %, about 18.9 w/w %, about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 20.1 w/w %, about 20.2 w/w %, about 20.3 w/w %, about 20.4 w/w %, about 20.5 w/w %, about 20.6 w/w %, about 20.7 w/w %, about 20.8 w/w %, about 20.9 w/w %, about 21.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of the sodium salt of the compound of Formula (Ia) in the solution comprising a sodium salt of the compound of Formula (Ia), PEG 300, poloxamer 188, and water is about 4.68 w/w %. In some embodiments, the amount of the sodium salt of the compound of Formula (Ia) in the solution comprising a sodium salt of the compound of Formula (Ia), PEG 300, poloxamer 188, and water is about 4.7 w/w %. In some embodiments, the amount of the sodium salt of the compound of Formula (Ia) in the solution comprising a sodium salt of the compound of Formula (Ia), PEG 300, poloxamer 188, and water is about 6.97 w/w %. In some embodiments, the amount of the sodium salt of the compound of Formula (Ia) in the solution comprising a sodium salt of the compound of Formula (Ia), PEG 300, poloxamer 188, and water is about 7 w/w %. In some embodiments, the amount of the sodium salt of the compound of Formula (Ia) in the solution comprising a sodium salt of the compound of Formula (Ia), PEG 300, poloxamer 188, and water is about 9.2 w/w %. In some embodiments, the amount of the sodium salt of the compound of Formula (Ia) in the solution comprising a sodium salt of the compound of Formula (Ia), PEG 300, poloxamer 188, and water is about 9.23 w/w %. In some embodiments, the amount of the sodium salt of the compound of Formula (Ia) in the solution comprising a sodium salt of the compound of Formula (Ia), PEG 300, poloxamer 188, and water is about 11.48 w/w %. In some embodiments, the amount of the sodium salt of the compound of Formula (Ia) in the solution comprising a sodium salt of the compound of Formula (Ia), PEG 300, poloxamer 188, and water is about 11.5 w/w %. In some embodiments, the amount of the sodium salt of the compound of Formula (Ia) in the solution comprising a sodium salt of the compound of Formula (Ia), PEG 300, poloxamer 188, and water is about 13.7 w/w %. In some embodiments, the amount of the sodium salt of the compound of Formula (Ia) in the solution comprising a sodium salt of the compound of Formula (Ia), PEG 300, poloxamer 188, and water is about 13.70 w/w %. In some embodiments, the amount of the sodium salt of the compound of Formula (Ia) in the solution comprising a sodium salt of the compound of Formula (Ia), PEG 300, poloxamer 188, and water is about 26.47 w/w %. In some embodiments, the amount of the sodium salt of the compound of Formula (Ia) in the solution comprising a sodium salt of the compound of Formula (Ia), PEG 300, poloxamer 188, and water is about 26.5 w/w %.

In some embodiments, the amount of poloxamer 188 in the solution comprising a sodium salt of the compound of Formula (Ia), PEG 300, poloxamer 188, and water is about 0.1 w/w % to about 10 w/w %. In some embodiments, the amount of poloxamer 188 in the solution comprising a sodium salt of the compound of Formula (Ia), PEG 300, poloxamer 188, and water is about 0.3 w/w % to about 8 w/w %. In some embodiments, the amount of poloxamer 188 in the solution comprising a sodium salt of the compound of Formula (Ia), PEG 300, poloxamer 188, and water is about 0.5 w/w % to about 7 w/w %. In some embodiments, the amount of poloxamer 188 in the solution comprising a sodium salt of the compound of Formula (Ia), PEG 300, poloxamer 188, and water is about 0.6 w/w % to about 7 w/w %. In some embodiments, the amount of poloxamer 188 in the solution comprising a sodium salt of the compound of Formula (Ia), PEG 300, poloxamer 188, and water is about 0.85 w/w % to about 4.82 w/w %. In some embodiments, the amount of poloxamer 188 in the solution comprising a sodium salt of the compound of Formula (Ia), PEG 300, poloxamer 188, and water is about 0.9 w/w % to about 4.8 w/w %. In some embodiments, the amount of poloxamer 188 in the solution comprising a sodium salt of the compound of Formula (Ia), PEG 300, poloxamer 188, and water is about 0.5 w/w %, about 0.6 w/w %, about 0.7 w/w %, about 0.8 w/w %, about 0.9 w/w %, about 1.0 w/w %, about 1.1 w/w %, about 1.2 w/w %, about 1.3 w/w %, about 1.4 w/w %, about 1.5 w/w %, about 1.6 w/w %, about 1.7 w/w %, about 1.8 w/w %, about 1.9 w/w %, about 2.0 w/w %, about 2.1 w/w %, about 2.2 w/w %, about 2.3 w/w %, about 2.4 w/w %, about 2.5 w/w %, about 2.6 w/w %, about 2.7 w/w %, about 2.8 w/w %, about 2.9 w/w %, about 3.0 w/w %, about 3.1 w/w %, about 3.2 w/w %, about 3.3 w/w %, about 3.4 w/w %, about 3.5 w/w %, about 3.6 w/w %, about 3.7 w/w %, about 3.8 w/w %, about 3.9 w/w %, about 4.0 w/w %, about 4.1 w/w %, about 4.2 w/w %, about 4.3 w/w %, about 4.4 w/w %, about 4.5 w/w %, about 4.6 w/w %, about 4.7 w/w %, about 4.8 w/w %, about 4.9 w/w %, about 5.0 w/w %, about 5.1 w/w %, about 5.2 w/w %, about 5.3 w/w %, about 5.4 w/w %, about 5.5 w/w %, about 5.6 w/w %, about 5.7 w/w %, about 5.8 w/w %, about 5.9 w/w %, about 6.0 w/w %, about 6.1 w/w %, about 6.2 w/w %, about 6.3 w/w %, about 6.4 w/w %, about 6.5 w/w %, about 6.6 w/w %, about 6.7 w/w %, about 6.8 w/w %, about 6.9 w/w %, or about 7.0 w/w %. In some embodiments, the amount of poloxamer 188 in the solution comprising a sodium salt of the compound of Formula (Ia), PEG 300, poloxamer 188, and water is about 0.85 w/w %. In some embodiments, the amount of poloxamer 188 in the solution comprising a sodium salt of the compound of Formula (Ia), PEG 300, poloxamer 188, and water is about 0.9 w/w %. In some embodiments, the amount of poloxamer 188 in the solution comprising a sodium salt of the compound of Formula (Ia), PEG 300, poloxamer 188, and water is about 1.27 w/w %. In some embodiments, the amount of poloxamer 188 in the solution comprising a sodium salt of the compound of Formula (Ia), PEG 300, poloxamer 188, and water is about 1.3 w/w %. In some embodiments, the amount of poloxamer 188 in the solution comprising a sodium salt of the compound of Formula (Ia), PEG 300, poloxamer 188, and water is about 1.68 w/w %. In some embodiments, the amount of poloxamer 188 in the solution comprising a sodium salt of the compound of Formula (Ia), PEG 300, poloxamer 188, and water is about 1.7 w/w %. In some embodiments, the amount of poloxamer 188 in the solution comprising a sodium salt of the compound of Formula (Ia), PEG 300, poloxamer 188, and water is about 2.09 w/w %. In some embodiments, the amount of poloxamer 188 in the solution comprising a sodium salt of the compound of Formula (Ia), PEG 300, poloxamer 188, and water is about 2.1 w/w %. In some embodiments, the amount of poloxamer 188 in the solution comprising a sodium salt of the compound of Formula (Ia), PEG 300, poloxamer 188, and water is about 2.49 w/w %. In some embodiments, the amount of poloxamer 188 in the solution comprising a sodium salt of the compound of Formula (Ia), PEG 300, poloxamer 188, and water is about 2.5 w/w %. In some embodiments, the amount of poloxamer 188 in the solution comprising a sodium salt of the compound of Formula (Ia), PEG 300, poloxamer 188, and water is about 4.8 w/w %. In some embodiments, the amount of poloxamer 188 in the solution comprising a sodium salt of the compound of Formula (Ia), PEG 300, poloxamer 188, and water is about 4.82 w/w %.

In some embodiments, the solution disclosed herein comprises about 10 w/w % to about 45 w/w % water, about 30 w/w % to about 85 w/w % PEG 300, about 0.5 w/w % to about 40 w/w % of a sodium salt of a compound of Formula (Ia), and about 0.1 w/w % to about 10 w/w % of poloxamer 188. In some embodiments, the solution comprises about 15 w/w % to about 35 w/w % water, about 35 w/w % to about 75 w/w % PEG 300, about 1 w/w % to about 35 w/w % of a sodium salt of a compound of Formula (Ia), and about 0.3 w/w % to about 8 w/w % of poloxamer 188. In some embodiments, the solution comprises about 20 w/w % to about 35 w/w % water, about 40 w/w % to about 70 w/w % PEG 300, about 1 w/w % to about 30 w/w % of a sodium salt of a compound of Formula (Ia), and about 0.5 w/w % to about 7 w/w % of poloxamer 188. In some embodiments, the solution comprises about 20 w/w % to about 31 w/w % water, about 45 w/w % to about 68 w/w % PEG 300, about 3 w/w % to about 28 w/w % of a sodium salt of a compound of Formula (Ia), and about 0.6 w/w % to about 7 w/w % of poloxamer 188. In some embodiments, the solution comprises about 21.9 w/w % to about 30.1 w/w % water, about 46.8 w/w % to about 64.4 w/w % PEG 300, about 4.7 w/w % to about 26.5 w/w % of a sodium salt of a compound of Formula (Ia), and about 0.9 w/w % to about 4.8 w/w % of poloxamer 188. In some embodiments, the solution comprises about 21.87 w/w % to about 30.07 w/w % water, about 46.84 w/w % to about 64.40 w/w % PEG 300, about 4.68 w/w % to about 26.47 w/w % of a sodium salt of a compound of Formula (Ia), and about 0.85 w/w % to about 4.82 w/w % of poloxamer 188. In some embodiments, the solution comprises about 30.1 w/w % water, about 64.4 w/w % PEG 300, about 4.7 w/w % of a sodium salt of a compound of Formula (Ia), and about 0.9 w/w % of poloxamer 188. In some embodiments, the solution comprises about 30.07 w/w % water, about 64.40 w/w % PEG 300, about 4.68 w/w % of a sodium salt of a compound of Formula (Ia), and about 0.85 w/w % of poloxamer 188. In some embodiments, the solution comprises about 29.2 w/w % water, about 62.6 w/w % PEG 300, about 7 w/w % of a sodium salt of a compound of Formula (Ia), and about 1.3 w/w % of poloxamer 188. In some embodiments, the solution comprises about 29.21 w/w % water, about 62.55 w/w % PEG 300, about 6.97 w/w % of a sodium salt of a compound of Formula (Ia), and about 1.27 w/w % of poloxamer 188. In some embodiments, the solution comprises about 28.4 w/w % water, about 60.7 w/w % PEG 300, about 9.2 w/w % of a sodium salt of a compound of Formula (Ia), and about 1.7 w/w % of poloxamer 188. In some embodiments, the solution comprises about 28.36 w/w % water, about 60.73 w/w % PEG 300, about 9.23 w/w % of a sodium salt of a compound of Formula (Ia), and about 1.68 w/w % of poloxamer 188. In some embodiments, the solution comprises about 27.5 w/w % water, about 58.9 w/w % PEG 300, about 11.5 w/w % of a sodium salt of a compound of Formula (Ia), and about 2.1 w/w % of poloxamer 188. In some embodiments, the solution comprises about 27.51 w/w % water, about 58.92 w/w % PEG 300, about 11.48 w/w % of a sodium salt of a compound of Formula (Ia), and about 2.09 w/w % of poloxamer 188. In some embodiments, the solution comprises about 26.7 w/w % water, about 57.1 w/w % PEG 300, about 13.7 w/w % of a sodium salt of a compound of Formula (Ia), and about 2.5 w/w % of poloxamer 188. In some embodiments, the solution comprises about 26.68 w/w % water, about 57.13 w/w % PEG 300, about 13.70 w/w % of a sodium salt of a compound of Formula (Ia), and about 2.49 w/w % of poloxamer 188. In some embodiments, the solution comprises about 21.9 w/w % water, about 46.8 w/w % PEG 300, about 26.5 w/w % of a sodium salt of a compound of Formula (Ia), and about 4.8 w/w % of poloxamer 188. In some embodiments, the solution comprises about 21.87 w/w % water, about 46.84 w/w % PEG 300, about 26.47 w/w % of a sodium salt of a compound of Formula (Ia), and about 4.82 w/w % of poloxamer 188.

In some embodiments, the parenteral formulation (for example, an SC or IM formulation) disclosed herein is an aqueous suspension. In some embodiments, the parenteral formulation (for example, an SC or IM formulation) disclosed herein is an aqueous suspension that includes a compound of Formula (Ia) or Formula (Ib), or a pharmaceutically acceptable salt thereof, and saline. In some embodiments, the parenteral formulation (for example, an SC or IM formulation) disclosed herein is an aqueous suspension that comprises a compound of Formula (Ia) or Formula (Ib), or a pharmaceutically acceptable salt thereof, saline, and a suspending agent. In some embodiments, the parenteral formulation (for example, an SC or IM formulation) disclosed herein is an aqueous suspension that comprises a compound of Formula (Ia) or Formula (Ib), or a pharmaceutically acceptable salt thereof, saline, and a poloxamer (such as poloxamer 338, 188, or 207).

In some embodiments, a suspension comprising a compound of Formula (Ia) or Formula (Ib), or a pharmaceutically acceptable salt thereof, in a poloxamer and saline is provided. In some embodiments, the concentration of poloxamer in saline is from about 0.1% to about 20%. In some embodiments, the concentration of poloxamer in saline is from about 0.1% to about 10%. In some embodiments, the concentration of poloxamer in saline is about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10%. In certain embodiments, the concentration of poloxamer in saline is about 2%. In certain embodiments, the poloxamer is poloxamer 188. In certain embodiments, the compound is a compound of Formula (Ia), or a pharmaceutically acceptable salt thereof. In certain embodiments, the compound is a compound of Formula (Ia). In certain embodiments, the compound is a sodium salt of the compound of Formula (Ia). In certain embodiments, the compound is a compound of Formula (Ib), or a pharmaceutically acceptable salt thereof. In certain embodiments, the compound is a compound of Formula (Ib). In certain embodiments, the compound is a trifluoroacetic acid salt of the compound of Formula (Ib).

In some embodiments, a suspension comprising a compound of Formula (Ia) or Formula (Ib), or a pharmaceutically acceptable salt thereof, in a poloxamer and mannitol is provided. In some embodiments, the concentration of poloxamer in mannitol is from about 0.1% to about 20%. In some embodiments, the concentration of poloxamer in mannitol is from about 0.1% to about 10%. In some embodiments, the concentration of poloxamer in mannitol is about 0.1%, about 0.2%, about 0.3%, about 0.4%, about 0.5%, about 0.6%, about 0.7%, about 0.8%, about 0.9%, about 1%, about 2,%, about 3%, about 4%, about 5%, about 6%, about 7%, about 8%, about 9%, or about 10%. In certain embodiments, the concentration of poloxamer in mannitol is about 2%. In certain embodiments, the poloxamer is poloxamer 188. In certain embodiments, the compound is a compound of Formula (Ia), or a pharmaceutically acceptable salt thereof. In certain embodiments, the compound is a compound of Formula (Ia). In certain embodiments, the compound is a sodium salt of the compound of Formula (Ia). In certain embodiments, the compound is a compound of Formula (Ib), or a pharmaceutically acceptable salt thereof. In certain embodiments, the compound is a compound of Formula (Ib). In certain embodiments, the compound is a trifluoroacetic acid salt of the compound of Formula (Ib).

In certain embodiments, the composition is formulated as a solid dosage form. In some embodiments, the solid dosage form is a solid injectable dosage form, such as a solid depot form.

In certain embodiments, the active ingredient (for example, a compound of Formula (Ia) or Formula (Ib)) is present as a free acid. In certain embodiments, the active ingredient (for example, a compound of Formula (Ia) or Formula (Ib)) is present as a sodium salt. In certain embodiments, the active ingredient (for example, a compound of Formula (Ia) or Formula (Ib)) is present as a trifluoroacetic acid salt. In some embodiments, the active ingredient is a compound of Formula (Ia). In some embodiments, the active ingredient is a compound of Formula (Ib).

In certain embodiments, the pharmaceutical composition disclosed herein is a parenteral formulation. In certain embodiments, the formulation is administered subcutaneously to a patient in need thereof. In certain embodiments, the formulation is administered intramuscularly to a patient in need thereof.

In certain embodiments, the parenteral formulation comprises N-methyl-2-pyrrolidone (NMP). In certain embodiments, the parenteral formulation consists essentially of N-methyl-2-pyrrolidone. In certain embodiments, the parenteral formulation comprises dimethyl sulfoxide (DMSO). In some embodiments, the parenteral formulation comprises polyethylene glycol (PEG) or glycofurol. In some embodiments, the solution comprises PEG 200, ethanol, and water. In some embodiments, the solution comprises PEG 300 and water. In some embodiments, the solution comprises poloxamer in saline. In some embodiments, the solution comprises 2% poloxamer 188 in normal saline.

In certain embodiments, the parenteral formulation comprises a compound of Formula (Ia) or Formula (Ib), or a pharmaceutically acceptable salt thereof, and water. In certain embodiments, the parenteral formulation comprises a compound of Formula (Ia), or a pharmaceutically acceptable salt thereof, and water. In certain embodiments, the parenteral formulation comprises a compound of Formula (Ib), or a pharmaceutically acceptable salt thereof, and water. In certain embodiments, the parenteral formulation further contains an alcohol. In certain embodiments, the alcohol is ethanol. In certain embodiments, the parenteral formulation further contains polyethylene glycol. In certain embodiments, the polyethylene glycol has an average molecular weight of about 200 g/mol (for example, polyethylene glycol 200). In certain embodiments, the parenteral formulation further contains an inorganic base. In certain embodiments, the inorganic base is sodium hydroxide (NaOH). In certain embodiments, the inorganic base is sodium ethoxide (NaOEt). In certain embodiments, the formulation comprises from about 0.1 molar equivalents to about 1.5 molar equivalents of the inorganic base. In certain embodiments, the formulation comprises from about 0.5 molar equivalents to about 1.5 molar equivalents of the inorganic base. In certain embodiments, the formulation comprises from about 0.75 molar equivalents to about 1.2 molar equivalents of the inorganic base. In certain embodiments, the formulation comprises about 1.0 molar equivalents inorganic base. In certain embodiments, the formulation comprises about 1.2 molar equivalents inorganic base. In some embodiments, the inorganic base is NaOH or NaOEt.

In certain embodiments, the parenteral formulation comprises a compound of Formula (Ia), or a pharmaceutically acceptable salt thereof, water and polyethylene glycol PEG 300. In certain embodiments, the parenteral formulation comprises a compound of Formula (Ib), or a pharmaceutically acceptable salt thereof, water, and polyethylene glycol PEG 300.

In certain embodiments, the parenteral formulation comprises a compound of Formula (Ia), or a pharmaceutically acceptable salt thereof, water, and polyethylene glycol PEG 300 (polyethylene glycol with an average molecular weight of 300 g/mol), and NaOH. In certain embodiments, the parenteral formulation comprises a compound of Formula (Ia), or a pharmaceutically acceptable salt thereof, water, and polyethylene glycol (PEG) 300, and NaOEt. In certain embodiments, the formulation includes from about 0.1 molar equivalents to about 1.5 molar equivalents of NaOH or NaOEt. In certain embodiments, the formulation includes from about 0.5 molar equivalents to about 1.5 molar equivalents of NaOH or NaOEt. In certain embodiments, the formulation includes from about 0.75 molar equivalents to about 1.2 molar equivalents of NaOH or NaOEt. In certain embodiments, the formulation comprises about 1.0 molar equivalents of NaOH or NaOEt. In certain embodiments, the formulation includes about 1.2 molar equivalents of NaOH or NaOEt.

In certain embodiments, the parenteral formulation is a solution formulation that includes a mixture of ethanol, water, and polyethylene glycol. In certain embodiments, the parenteral formulation is a solution formulation that includes a mixture of ethanol, water, and PEG 200. In certain embodiments, the solution formulation includes about 5% to about 20% ethanol, about 5% to about 20% water, and about 60% to about 90% PEG 200. In certain embodiments, the solution formulation comprises about 10% to about 15% ethanol, about 10% to about 15% water, and about 70% to about 80% PEG 200. In certain embodiments, the solution formulation includes about 10% ethanol, about 12% water, and about 78% PEG 200. In certain embodiments, the solution formulation further includes an inorganic base. In certain embodiments, the solution formulation includes about 10% ethanol, about 13% water, and about 77% PEG 200. In certain embodiments, the solution formulation further includes an inorganic base. In certain embodiments, the formulation includes from about 0.1 molar equivalents to about 1.5 molar equivalents of the inorganic base. In certain embodiments, the formulation comprises from about 0.5 molar equivalents to about 1.5 molar equivalents of the inorganic base. In certain embodiments, the formulation comprises from about 1.0 molar equivalents to about 1.2 molar equivalents of the inorganic base. In certain embodiments, the formulation comprises about 1.2 molar equivalents inorganic base. In certain embodiments, the inorganic base is sodium hydroxide or sodium ethoxide. In certain embodiments, the inorganic base is sodium hydroxide.

In certain embodiments, the parenteral formulation is a solution formulation that includes a mixture of water and polyethylene glycol. In certain embodiments, the parenteral formulation is a solution formulation that includes a mixture of water and PEG 300. In certain embodiments, the solution formulation includes about 5% w/w to about 25% w/w water, and about 75% w/w to about 95% w/w PEG 300. In some embodiments, the solution formulation further includes an inorganic base. In certain embodiments, the formulation includes from about 0.1 molar equivalents to about 1.5 molar equivalents of the inorganic base. In certain embodiments, the formulation comprises from about 0.5 molar equivalents to about 1.5 molar equivalents of the inorganic base. In certain embodiments, the formulation comprises from about 0.75 molar equivalents to about 1.2 molar equivalents of the inorganic base. In certain embodiments, the formulation comprises about 1.0 molar equivalents inorganic base. In certain embodiments, the formulation comprises about 1.2 molar equivalents inorganic base. In certain embodiments, the inorganic base is sodium hydroxide or sodium ethoxide. In certain embodiments, the inorganic base is sodium hydroxide.

In some embodiments, the solution disclosed herein comprises a compound of Formula (Ia) or Formula (Ib), or a pharmaceutically acceptable salt thereof, PEG 300, sodium hydroxide, and water. In some embodiments, the solution disclosed herein comprises a compound of Formula (Ia) or a pharmaceutically acceptable salt thereof, PEG 300, sodium hydroxide, and water. In some embodiments, the solution disclosed herein comprises a compound of Formula (Ib), or a pharmaceutically acceptable salt thereof, PEG 300, sodium hydroxide, and water. In some embodiments, the solution disclosed herein comprises a sodium salt of the compound of Formula (Ia), PEG 300, sodium hydroxide, and water. In some embodiments, the solution disclosed herein comprises a trifluoroacetic acid salt of the compound of Formula (Ib), PEG 300, sodium hydroxide, and water. In some embodiments, the solution disclosed herein comprises a compound of Formula (Ib), PEG 300, sodium hydroxide, and water.

In some embodiments, the solution disclosed herein comprises a compound of Formula (Ia), PEG 300, sodium hydroxide, and water. In some embodiments, the concentration of the compound of Formula (Ia) in the solution comprising a compound of Formula (Ia), PEG 300, sodium hydroxide, and water is about 50 mg/ml to about 500 mg/ml. In some embodiments, the concentration of the compound of Formula (Ia) in the solution comprising a compound of Formula (Ia), PEG 300, sodium hydroxide, and water is about 50 mg/ml to about 400 mg/ml. In some embodiments, the concentration of the compound of Formula (Ia) in the solution comprising a compound of Formula (Ia), PEG 300, sodium hydroxide, and water is about 50 mg/ml to about 300 mg/ml. In some embodiments, the concentration of the compound of Formula (Ia) in the solution comprising a compound of Formula (Ia), PEG 300, sodium hydroxide, and water is about 75 mg/ml to about 300 mg/ml. In some embodiments, the concentration of the compound of Formula (Ia) in the solution comprising a compound of Formula (Ia), PEG 300, sodium hydroxide, and water is about 50 mg/ml. In some embodiments, the concentration of the compound of Formula (Ia) in the solution comprising a compound of Formula (Ia), PEG 300, sodium hydroxide, and water is about 75 mg/ml. In some embodiments, the concentration of the compound of Formula (Ia) in the solution comprising a compound of Formula (Ia), PEG 300, sodium hydroxide, and water is about 100 mg/ml. In some embodiments, the concentration of the compound of Formula (Ia) in the solution comprising a compound of Formula (Ia), PEG 300, sodium hydroxide, and water is about 125 mg/ml. In some embodiments, the concentration of the compound of Formula (Ia) in the solution comprising a compound of Formula (Ia), PEG 300, sodium hydroxide, and water is about 150 mg/ml. In some embodiments, the concentration of the compound of Formula (Ia) in the solution comprising a compound of Formula (Ia), PEG 300, sodium hydroxide, and water is about 175 mg/ml. In some embodiments, the concentration of the compound of Formula (Ia) in the solution comprising a compound of Formula (Ia), PEG 300, sodium hydroxide, and water is about 200 mg/ml. In some embodiments, the concentration of the compound of Formula (Ia) in the solution comprising a compound of Formula (Ia), PEG 300, sodium hydroxide, and water is about 225 mg/ml. In some embodiments, the concentration of the compound of Formula (Ia) in the solution comprising a compound of Formula (Ia), PEG 300, sodium hydroxide, and water is about 250 mg/ml. In some embodiments, the concentration of the compound of Formula (Ia) in the solution comprising a compound of Formula (Ia), PEG 300, sodium hydroxide, and water is about 275 mg/ml. In some embodiments, the concentration of the compound of Formula (Ia) in the solution comprising a compound of Formula (Ia), PEG 300, sodium hydroxide, and water is about 300 mg/ml. In some embodiments, the concentration of the compound of Formula (Ia) in the solution comprising a compound of Formula (Ia), PEG 300, sodium hydroxide, and water is about 325 mg/ml. In some embodiments, the concentration of the compound of Formula (Ia) in the solution comprising a compound of Formula (Ia), PEG 300, sodium hydroxide, and water is about 350 mg/ml. In some embodiments, the concentration of the compound of Formula (Ia) in the solution comprising a compound of Formula (Ia), PEG 300, sodium hydroxide, and water is about 375 mg/ml. In some embodiments, the concentration of the compound of Formula (Ia) in the solution comprising a compound of Formula (Ia), PEG 300, sodium hydroxide, and water is about 400 mg/ml. In some embodiments, the concentration of the compound of Formula (Ia) in the solution comprising a compound of Formula (Ia), PEG 300, sodium hydroxide, and water is about 425 mg/ml. In some embodiments, the concentration of the compound of Formula (Ia) in the solution comprising a compound of Formula (Ia), PEG 300, sodium hydroxide, and water is about 450 mg/ml. In some embodiments, the concentration of the compound of Formula (Ia) in the solution comprising a compound of Formula (Ia), PEG 300, sodium hydroxide, and water is about 475 mg/ml. In some embodiments, the concentration of the compound of Formula (Ia) in the solution comprising a compound of Formula (Ia), PEG 300, sodium hydroxide, and water is about 500 mg/ml.

In some embodiments, the amount of water in the solution comprising a compound of Formula (Ia), PEG 300, sodium hydroxide, and water is about 10 w/w % to about 40 w/w %. In some embodiments, the amount of water in the solution comprising a compound of Formula (Ia), PEG 300, sodium hydroxide, and water is about 15 w/w % to about 35 w/w %. In some embodiments, the amount of water in the solution comprising a compound of Formula (Ia), PEG 300, sodium hydroxide, and water is about 20 w/w % to about 30 w/w %. In some embodiments, the amount of water in the solution comprising a compound of Formula (Ia), PEG 300, sodium hydroxide, and water is about 21 w/w % to about 29 w/w %. In some embodiments, the amount of water in the solution comprising a compound of Formula (Ia), PEG 300, sodium hydroxide, and water is about 23.2 w/w % to about 27.9 w/w %. In some embodiments, the amount of water in the solution comprising a compound of Formula (Ia), PEG 300, sodium hydroxide, and water is about 23.2 w/w % to about 27.92 w/w %. In some embodiments, the amount of water in the solution comprising a compound of Formula (Ia), PEG 300, sodium hydroxide, and water is about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of water in the solution comprising a compound of Formula (Ia), PEG 300, sodium hydroxide, and water is about 23.2 w/w %. In some embodiments, the amount of water in the solution comprising a compound of Formula (Ia), PEG 300, sodium hydroxide, and water is about 27.9 w/w %. In some embodiments, the amount of water in the solution comprising a compound of Formula (Ia), PEG 300, sodium hydroxide, and water is about 27.92 w/w %.

In some embodiments, the amount of PEG 300 in the solution comprising compound of Formula (Ia), PEG 300, sodium hydroxide, and water is about 35 w/w % to about 75 w/w %. In some embodiments, the amount of PEG 300 in the solution comprising a compound of Formula (Ia), PEG 300, sodium hydroxide, and water is about 45 w/w % to about 65 w/w %. In some embodiments, the amount of PEG 300 in the solution comprising a compound of Formula (Ia), PEG 300, sodium hydroxide, and water is about 48 w/w % to about 60 w/w %. In some embodiments, the amount of PEG 300 in the solution comprising a compound of Formula (Ia), PEG 300, sodium hydroxide, and water is about 49 w/w % to about 59 w/w %. In some embodiments, the amount of PEG 300 in the solution comprising a compound of Formula (Ia), PEG 300, sodium hydroxide, and water is about 50.0 w/w % to about 58.0 w/w %. In some embodiments, the amount of PEG 300 in the solution comprising a compound of Formula (Ia), PEG 300, sodium hydroxide, and water is about 50.0 w/w % to about 58.04 w/w %. In some embodiments, the amount of PEG 300 in the solution comprising a compound of Formula (Ia), PEG 300, sodium hydroxide, and water is about 45 w/w %, about 46 w/w %, about 47 w/w %, about 48 w/w %, about 49 w/w %, about 50 w/w %, about 51 w/w %, about 52 w/w %, about 53 w/w %, about 54 w/w %, about 55 w/w %, about 56 w/w %, about 57 w/w %, about 58 w/w %, about 59 w/w %, about 60 w/w %, about 61 w/w %, about 62 w/w %, about 63 w/w %, about 64 w/w %, or about 65 w/w %. In some embodiments, the amount of PEG 300 in the solution comprising a compound of Formula (Ia), PEG 300, sodium hydroxide, and water is about 50.0 w/w %. In some embodiments, the amount of PEG 300 in the solution comprising a compound of Formula (Ia), PEG 300, sodium hydroxide, and water is about 58.0 w/w %. In some embodiments, the amount of PEG 300 in the solution comprising a compound of Formula (Ia), PEG 300, sodium hydroxide, and water is about 58.04 w/w %.

In some embodiments, the amount of the compound of Formula (Ia) in the solution comprising a compound of Formula (Ia), PEG 300, sodium hydroxide, and water is about 5 w/w % to about 35 w/w %. In some embodiments, the amount of the compound of Formula (Ia) in the solution comprising a compound of Formula (Ia), PEG 300, sodium hydroxide, and water is about 10 w/w % to about 30 w/w %. In some embodiments, the amount of the compound of Formula (Ia) in the solution comprising a compound of Formula (Ia), PEG 300, sodium hydroxide, and water is about 11 w/w % to about 28 w/w %. In some embodiments, the amount of the compound of Formula (Ia) in the solution comprising a compound of Formula (Ia), PEG 300, sodium hydroxide, and water is about 13 w/w % to about 27 w/w %. In some embodiments, the amount of the compound of Formula (Ia) in the solution comprising a compound of Formula (Ia), PEG 300, sodium hydroxide, and water is about 13.5 w/w % to about 25.7 w/w %. In some embodiments, the amount of the compound of Formula (Ia) in the solution comprising a compound of Formula (Ia), PEG 300, sodium hydroxide, and water is about 13.47 w/w % to about 25.7 w/w %. In some embodiments, the amount of the compound of Formula (Ia) in the solution comprising a compound of Formula (Ia), PEG 300, sodium hydroxide, and water is about 13.0 w/w %, about 13.1 w/w %, about 13.2 w/w %, about 13.3 w/w %, about 13.4 w/w %, about 13.5 w/w %, about 13.6 w/w %, about 13.7 w/w %, about 13.8 w/w %, about 13.9 w/w %, about 14.0 w/w %, about 14.1 w/w %, about 14.2 w/w %, about 14.3 w/w %, about 14.4 w/w %, about 14.5 w/w %, about 14.6 w/w %, about 14.7 w/w %, about 14.8 w/w %, about 14.9 w/w %, about 15.0 w/w %, about 15.1 w/w %, about 15.2 w/w %, about 15.3 w/w %, about 15.4 w/w %, about 15.5 w/w %, about 15.6 w/w %, about 15.7 w/w %, about 15.8 w/w %, about 15.9 w/w %, about 16.0 w/w %, about 16.1 w/w %, about 16.2 w/w %, about 16.3 w/w %, about 16.4 w/w %, about 16.5 w/w %, about 16.6 w/w %, about 16.7 w/w %, about 16.8 w/w %, about 16.9 w/w %, about 17.0 w/w %, about 17.1 w/w %, about 17.2 w/w %, about 17.3 w/w %, about 17.4 w/w %, about 17.5 w/w %, about 17.6 w/w %, about 17.7 w/w %, about 17.8 w/w %, about 17.9 w/w %, about 18.0 w/w %, about 18.1 w/w %, about 18.2 w/w %, about 18.3 w/w %, about 18.4 w/w %, about 18.5 w/w %, about 18.6 w/w %, about 18.7 w/w %, about 18.8 w/w %, about 18.9 w/w %, about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of the compound of Formula (Ia) in the solution comprising a compound of Formula (Ia), PEG 300, sodium hydroxide, and water is about 13.47 w/w %. In some embodiments, the amount of the compound of Formula (Ia) in the solution comprising a compound of Formula (Ia), PEG 300, sodium hydroxide, and water is about 13.5 w/w %. In some embodiments, the amount of the compound of Formula (Ia) in the solution comprising a compound of Formula (Ia), PEG 300, sodium hydroxide, and water is about 25.7 w/w %.

In some embodiments, the amount of sodium hydroxide in the solution comprising a compound of Formula (Ia), PEG 300, sodium hydroxide, and water is about 0.05 w/w % to about 2 w/w %. In some embodiments, the amount of sodium hydroxide in the solution comprising a compound of Formula (Ia), PEG 300, sodium hydroxide, and water is about 0.1 w/w % to about 1.5 w/w %. In some embodiments, the amount of sodium hydroxide in the solution comprising a compound of Formula (Ia), PEG 300, sodium hydroxide, and water is about 0.3 w/w % to about 1.3 w/w %. In some embodiments, the amount of sodium hydroxide in the solution comprising a compound of Formula (Ia), PEG 300, sodium hydroxide, and water is about 0.5 w/w % to about 1.2 w/w %. In some embodiments, the amount of sodium hydroxide in the solution comprising a compound of Formula (Ia), PEG 300, sodium hydroxide, and water is about 0.6 w/w % to about 1.1 w/w %. In some embodiments, the amount of sodium hydroxide in the solution comprising a compound of Formula (Ia), PEG 300, sodium hydroxide, and water is about 0.58 w/w % to about 1.1 w/w %. In some embodiments, the amount of sodium hydroxide in the solution comprising a compound of Formula (Ia), PEG 300, sodium hydroxide, and water is about 0.1 w/w %, about 0.2 w/w %, about 0.3 w/w %, about 0.4 w/w %, about 0.5 w/w %, about 0.6 w/w %, about 0.7 w/w %, about 0.8 w/w %, about 0.9 w/w %, about 1.0 w/w %, about 1.1 w/w %, about 1.2 w/w %, about 1.3 w/w %, about 1.4 w/w %, about 1.5 w/w %, about 1.6 w/w %, about 1.7 w/w %, about 1.8 w/w %, about 1.9 w/w %, or about 2.0 w/w %. In some embodiments, the amount of sodium hydroxide in the solution comprising a compound of Formula (Ia), PEG 300, sodium hydroxide, and water is about 0.58 w/w %. In some embodiments, the amount of sodium hydroxide in the solution comprising a compound of Formula (Ia), PEG 300, sodium hydroxide, and water is about 0.6 w/w %. In some embodiments, the amount of sodium hydroxide in the solution comprising a compound of Formula (Ia), PEG 300, sodium hydroxide, and water is about 1.1 w/w %. In some embodiments, the solution disclosed herein comprises about 10 w/w % to about 40 w/w % water, about 35 w/w % to about 75 w/w % PEG 300, about 5 w/w % to about 35 w/w % of a compound of Formula (Ia), and about 0.05 w/w % to about 2 w/w % of sodium hydroxide. In some embodiments, the solution comprises about 15 w/w % to about 35 w/w % water, about 45 w/w % to about 65 w/w % PEG 300, about 10 w/w % to about 30 w/w % of a compound of Formula (Ia), and about 0.1 w/w % to about 1.5 w/w % of sodium hydroxide. In some embodiments, the solution comprises about 20 w/w % to about 30 w/w % water, about 48 w/w % to about 60 w/w % PEG 300, about 11 w/w % to about 28 w/w % of a compound of Formula (Ia), and about 0.3 w/w % to about 1.3 w/w % of sodium hydroxide. In some embodiments, the solution comprises about 21 w/w % to about 29 w/w % water, about 49 w/w % to about 59 w/w % PEG 300, about 13 w/w % to about 27 w/w % of a compound of Formula (Ia), and about 0.5 w/w % to about 1.2 w/w % of sodium hydroxide. In some embodiments, the solution comprises about 23.2 w/w % to about 27.9 w/w % water, about 50 w/w % to about 58 w/w % PEG 300, about 13.5 w/w % to about 25.7 w/w % of a compound of Formula (Ia), and about 0.6 w/w % to about 1.1 w/w % of sodium hydroxide. In some embodiments, the solution comprises about 23.2 w/w % to about 27.92 w/w % water, about 50.0 w/w % to about 58.04 w/w % PEG 300, about 13.47 w/w % to about 25.7 w/w % of a compound of Formula (Ia), and about 0.58 w/w % to about 1.1 w/w % of sodium hydroxide. In some embodiments, the solution comprises about 27.9 w/w % water, about 58 w/w % PEG 300, about 13.5 w/w % of a compound of Formula (Ia), and about 0.6 w/w % of sodium hydroxide. In some embodiments, the solution comprises about 27.92 w/w % water, about 58.04 w/w % PEG 300, about 13.47 w/w % of a compound of Formula (Ia), and about 0.58 w/w % of sodium hydroxide. In some embodiments, the solution comprises about 23.2 w/w % water, about 50.0 w/w % PEG 300, about 25.7 w/w % of a compound of Formula (Ia), and about 1.1 w/w % of sodium hydroxide.

In some embodiments, the compound of Formula (Ia) becomes ionized in situ to a sodium salt of the compound of Formula (Ia) in the presence of sodium hydroxide in the solution comprising a compound of Formula (Ia), PEG 300, sodium hydroxide, and water. Thus, in some embodiments, the compound of Formula (Ia) is present as a sodium salt of the compound of Formula (Ia) in the solution comprising a compound of Formula (Ia), PEG 300, sodium hydroxide, and water.

In some embodiments, the pharmaceutical compositions disclosed herein comprise a compound of Formula (Ia) or Formula (Ib), or a pharmaceutically acceptable salt thereof, a poloxamer, and a pharmaceutically acceptable excipient. In some embodiments, the pharmaceutical compositions disclosed herein comprise a compound of Formula (Ia) or Formula (Ib), or a pharmaceutically acceptable salt thereof, poloxamer 188, and a pharmaceutically acceptable excipient. In some embodiments, the pharmaceutical compositions disclosed herein are solutions that comprise a compound of Formula (Ia) or Formula (Ib), or a pharmaceutically acceptable salt thereof, a poloxamer, and a pharmaceutically acceptable excipient. In some embodiments, the pharmaceutical compositions disclosed herein are solutions that comprise a compound of Formula (Ia) or Formula (Ib), or a pharmaceutically acceptable salt thereof, poloxamer 188, and a pharmaceutically acceptable excipient.

In some embodiments, the solution disclosed herein comprises a compound of Formula (Ia) or Formula (Ib), or a pharmaceutically acceptable salt thereof, PEG 300, sodium hydroxide, poloxamer 188, and water. In some embodiments, the solution disclosed herein comprises a compound of Formula (Ia) or a pharmaceutically acceptable salt thereof, PEG 300, sodium hydroxide, poloxamer 188, and water. In some embodiments, the solution disclosed herein comprises a compound of Formula (Ib), or a pharmaceutically acceptable salt thereof, PEG 300, sodium hydroxide, poloxamer 188, and water. In some embodiments, the solution disclosed herein comprises a sodium salt of the compound of Formula (Ia), PEG 300, sodium hydroxide, poloxamer 188, and water. In some embodiments, the solution disclosed herein comprises a trifluoroacetic acid salt of the compound of Formula (Ib), PEG 300, sodium hydroxide, poloxamer 188, and water.

In some embodiments, the solution disclosed herein comprises a compound of Formula (Ia), PEG 300, sodium hydroxide, poloxamer 188, and water. In some embodiments, the concentration of the compound of Formula (Ia) in the solution comprising a compound of Formula (Ia), PEG 300, sodium hydroxide, poloxamer 188, and water is about 50 mg/ml to about 500 mg/ml. In some embodiments, the concentration of the compound of Formula (Ia) in the solution comprising a compound of Formula (Ia), PEG 300, sodium hydroxide, poloxamer 188, and water is about 50 mg/ml to about 400 mg/ml. In some embodiments, the concentration of the compound of Formula (Ia) in the solution comprising a compound of Formula (Ia), PEG 300, sodium hydroxide, poloxamer 188, and water is about 50 mg/ml to about 300 mg/ml. In some embodiments, the concentration of the compound of Formula (Ia) in the solution comprising a compound of Formula (Ia), PEG 300, sodium hydroxide, poloxamer 188, and water is about 75 mg/ml to about 300 mg/ml. In some embodiments, the concentration of the compound of Formula (Ia) in the solution comprising a compound of Formula (Ia), PEG 300, sodium hydroxide, poloxamer 188, and water is about 50 mg/ml. In some embodiments, the concentration of the compound of Formula (Ia) in the solution comprising a compound of Formula (Ia), PEG 300, sodium hydroxide, poloxamer 188, and water is about 75 mg/ml. In some embodiments, the concentration of the compound of Formula (Ia) in the solution comprising a compound of Formula (Ia), PEG 300, sodium hydroxide, poloxamer 188, and water is about 100 mg/ml. In some embodiments, the concentration of the compound of Formula (Ia) in the solution comprising a compound of Formula (Ia), PEG 300, sodium hydroxide, poloxamer 188, and water is about 125 mg/ml. In some embodiments, the concentration of the compound of Formula (Ia) in the solution comprising a compound of Formula (Ia), PEG 300, sodium hydroxide, poloxamer 188, and water is about 150 mg/ml. In some embodiments, the concentration of the compound of Formula (Ia) in the solution comprising a compound of Formula (Ia), PEG 300, sodium hydroxide, poloxamer 188, and water is about 175 mg/ml. In some embodiments, the concentration of the compound of Formula (Ia) in the solution comprising a compound of Formula (Ia), PEG 300, sodium hydroxide, poloxamer 188, and water is about 200 mg/ml. In some embodiments, the concentration of the compound of Formula (Ia) in the solution comprising a compound of Formula (Ia), PEG 300, sodium hydroxide, poloxamer 188, and water is about 225 mg/ml. In some embodiments, the concentration of the compound of Formula (Ia) in the solution comprising a compound of Formula (Ia), PEG 300, sodium hydroxide, poloxamer 188, and water is about 250 mg/ml. In some embodiments, the concentration of the compound of Formula (Ia) in the solution comprising a compound of Formula (Ia), PEG 300, sodium hydroxide, poloxamer 188, and water is about 275 mg/ml. In some embodiments, the concentration of the compound of Formula (Ia) in the solution comprising a compound of Formula (Ia), PEG 300, sodium hydroxide, poloxamer 188, and water is about 300 mg/ml. In some embodiments, the concentration of the compound of Formula (Ia) in the solution comprising a compound of Formula (Ia), PEG 300, sodium hydroxide, poloxamer 188, and water is about 325 mg/ml. In some embodiments, the concentration of the compound of Formula (Ia) in the solution comprising a compound of Formula (Ia), PEG 300, sodium hydroxide, poloxamer 188, and water is about 350 mg/ml. In some embodiments, the concentration of the compound of Formula (Ia) in the solution comprising a compound of Formula (Ia), PEG 300, sodium hydroxide, poloxamer 188, and water is about 375 mg/ml. In some embodiments, the concentration of the compound of Formula (Ia) in the solution comprising a compound of Formula (Ia), PEG 300, sodium hydroxide, poloxamer 188, and water is about 400 mg/ml. In some embodiments, the concentration of the compound of Formula (Ia) in the solution comprising a compound of Formula (Ia), PEG 300, sodium hydroxide, poloxamer 188, and water is about 425 mg/ml. In some embodiments, the concentration of the compound of Formula (Ia) in the solution comprising a compound of Formula (Ia), PEG 300, sodium hydroxide, poloxamer 188, and water is about 450 mg/ml. In some embodiments, the concentration of the compound of Formula (Ia) in the solution comprising a compound of Formula (Ia), PEG 300, sodium hydroxide, poloxamer 188, and water is about 475 mg/ml. In some embodiments, the concentration of the compound of Formula (Ia) in the solution comprising a compound of Formula (Ia), PEG 300, sodium hydroxide, poloxamer 188, and water is about 500 mg/ml.

In some embodiments, the amount of water in the solution comprising a compound of Formula (Ia), PEG 300, sodium hydroxide, poloxamer 188, and water is about 10 w/w % to about 45 w/w %. In some embodiments, the amount of water in the solution comprising a of Formula (Ia), PEG 300, sodium hydroxide, poloxamer 188, and water is about 15 w/w % to about 35 w/w %. In some embodiments, the amount of water in the solution comprising a compound of Formula (Ia), PEG 300, sodium hydroxide, poloxamer 188, and water is about 20 w/w % to about 35 w/w %. In some embodiments, the amount of water in the solution comprising a compound of Formula (Ia), PEG 300, sodium hydroxide, poloxamer 188, and water is about 20 w/w % to about 31 w/w %. In some embodiments, the amount of water in the solution comprising a compound of Formula (Ia), PEG 300, sodium hydroxide, poloxamer 188, and water is about 22 w/w % to about 30.1 w/w %. In some embodiments, the amount of water in the solution comprising a compound of Formula (Ia), PEG 300, sodium hydroxide, poloxamer 188, and water is about 21.97 w/w % to about 30.07 w/w %. In some embodiments, the amount of water in the solution comprising a compound of Formula (Ia), PEG 300, sodium hydroxide, poloxamer 188, and water is about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 20.1 w/w %, about 20.2 w/w %, about 20.3 w/w %, about 20.4 w/w %, about 20.5 w/w %, about 20.6 w/w %, about 20.7 w/w %, about 20.8 w/w %, about 20.9 w/w %, about 21.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, about 29.0 w/w %, about 29.1 w/w %, about 29.2 w/w %, about 29.3 w/w %, about 29.4 w/w %, about 29.5 w/w %, about 29.6 w/w %, about 29.7 w/w %, about 29.8 w/w %, about 29.9 w/w %, about 30.0 w/w %, about 30.1 w/w %, about 30.2 w/w %, about 30.3 w/w %, about 30.4 w/w %, about 30.5 w/w %, about 30.6 w/w %, about 30.7 w/w %, about 30.8 w/w %, about 30.9 w/w %, about 31.0 w/w %, about 31.1 w/w %, about 31.2 w/w %, about 31.3 w/w %, about 31.4 w/w %, about 31.5 w/w %, about 31.6 w/w %, about 31.7 w/w %, about 31.8 w/w %, about 31.9 w/w %, about 32.0 w/w %, about 32.1 w/w %, about 32.2 w/w %, about 32.3 w/w %, about 32.4 w/w %, about 32.5 w/w %, about 32.6 w/w %, about 32.7 w/w %, about 32.8 w/w %, about 32.9 w/w %, or about 33.0 w/w %. In some embodiments, the amount of water in the solution comprising a compound of Formula (Ia), PEG 300, sodium hydroxide, poloxamer 188, and water is about 21.97 w/w %. In some embodiments, the amount of water in the solution comprising a compound of Formula (Ia), PEG 300, sodium hydroxide, poloxamer 188, and water is about 22 w/w %. In some embodiments, the amount of water in the solution comprising a compound of Formula (Ia), PEG 300, sodium hydroxide, poloxamer 188, and water is about 30.07 w/w %. In some embodiments, the amount of water in the solution comprising a compound of Formula (Ia), PEG 300, sodium hydroxide, poloxamer 188, and water is about 30.1 w/w %.

In some embodiments, the amount of PEG 300 in the solution comprising a compound of Formula (Ia), PEG 300, sodium hydroxide, poloxamer 188, and water is about 30 w/w % to about 85 w/w %. In some embodiments, the amount of PEG 300 in the solution comprising a compound of Formula (Ia), PEG 300, sodium hydroxide, poloxamer 188, and water is about 35 w/w % to about 75 w/w %. In some embodiments, the amount of PEG 300 in the solution comprising a compound of Formula (Ia), PEG 300, sodium hydroxide, poloxamer 188, and water is about 40 w/w % to about 70 w/w %. In some embodiments, the amount of PEG 300 in the solution comprising a compound of Formula (Ia), PEG 300, sodium hydroxide, poloxamer 188, and water is about 45 w/w % to about 68 w/w %. In some embodiments, the amount of PEG 300 in the solution comprising a compound of Formula (Ia), PEG 300, sodium hydroxide, poloxamer 188, and water is about 47.1 w/w % to about 64.4 w/w %. In some embodiments, the amount of PEG 300 in the solution comprising a compound of Formula (Ia), PEG 300, sodium hydroxide, poloxamer 188, and water is about 47.05 w/w % to about 64.41 w/w %. In some embodiments, the amount of PEG 300 in the solution comprising a compound of Formula (Ia), PEG 300, sodium hydroxide, poloxamer 188, and water is about 40 w/w %, about 41 w/w %, about 42 w/w %, about 43 w/w %, about 44 w/w %, about 45 w/w %, about 46 w/w %, about 47 w/w %, about 48 w/w %, about 49 w/w %, about 50 w/w %, about 51 w/w %, about 52 w/w %, about 53 w/w %, about 54 w/w %, about 55 w/w %, about 56 w/w %, about 57 w/w %, about 58 w/w %, about 59 w/w %, about 60 w/w %, about 61 w/w %, about 62 w/w %, about 63 w/w %, about 64 w/w %, about 65 w/w %, about 66 w/w %, about 67 w/w %, about 68 w/w %, about 69 w/w %, or about 70 w/w %. In some embodiments, the amount of PEG 300 in the solution comprising a compound of Formula (Ia), PEG 300, sodium hydroxide, poloxamer 188, and water is about 47.05 w/w %. In some embodiments, the amount of PEG 300 in the solution comprising a compound of Formula (Ia), PEG 300, sodium hydroxide, poloxamer 188, and water is about 47.1 w/w %. In some embodiments, the amount of PEG 300 in the solution comprising a compound of Formula (Ia), PEG 300, sodium hydroxide, poloxamer 188, and water is about 64.4 w/w %. In some embodiments, the amount of PEG 300 in the solution comprising a compound of Formula (Ia), PEG 300, sodium hydroxide, poloxamer 188, and water is about 64.41 w/w %.

In some embodiments, the amount of the compound of Formula (Ia) in the solution comprising a compound of Formula (Ia), PEG 300, sodium hydroxide, poloxamer 188, and water is about 0.5 w/w % to about 40 w/w %. In some embodiments, the amount of the compound of Formula (Ia) in the solution comprising a compound of Formula (Ia), PEG 300, sodium hydroxide, poloxamer 188, and water is about 1 w/w % to about 35 w/w %. In some embodiments, the amount of the compound of Formula (Ia) in the solution comprising a compound of Formula (Ia), PEG 300, sodium hydroxide, poloxamer 188, and water is about 1 w/w % to about 30 w/w %. In some embodiments, the amount of the compound of Formula (Ia) in the solution comprising a compound of Formula (Ia), PEG 300, sodium hydroxide, poloxamer 188, and water is about 3 w/w % to about 28 w/w %. In some embodiments, the amount of the compound of Formula (Ia) in the solution comprising a compound of Formula (Ia), PEG 300, sodium hydroxide, poloxamer 188, and water is about 4 w/w % to about 26 w/w %. In some embodiments, the amount of the compound of Formula (Ia) in the solution comprising a compound of Formula (Ia), PEG 300, sodium hydroxide, poloxamer 188, and water is about 4.6 w/w % to about 25.2 w/w %. In some embodiments, the amount of the compound of Formula (Ia) in the solution comprising a compound of Formula (Ia), PEG 300, sodium hydroxide, poloxamer 188, and water is about 4.57 w/w % to about 25.21 w/w %. In some embodiments, the amount of the compound of Formula (Ia) in the solution comprising a compound of Formula (Ia), PEG 300, sodium hydroxide, poloxamer 188, and water is about 3.0 w/w %, about 3.1 w/w %, about 3.2 w/w %, about 3.3 w/w %, about 3.4 w/w %, about 3.5 w/w %, about 3.6 w/w %, about 3.7 w/w %, about 3.8 w/w %, about 3.9 w/w %, about 4.0 w/w %, about 4.1 w/w %, about 4.2 w/w %, about 4.3 w/w %, about 4.4 w/w %, about 4.5 w/w %, about 4.6 w/w %, about 4.7 w/w %, about 4.8 w/w %, about 4.9 w/w %, about 5.0 w/w %, about 5.1 w/w %, about 5.2 w/w %, about 5.3 w/w %, about 5.4 w/w %, about 5.5 w/w %, about 5.6 w/w %, about 5.7 w/w %, about 5.8 w/w %, about 5.9 w/w %, about 6.0 w/w %, about 6.1 w/w %, about 6.2 w/w %, about 6.3 w/w %, about 6.4 w/w %, about 6.5 w/w %, about 6.6 w/w %, about 6.7 w/w %, about 6.8 w/w %, about 6.9 w/w %, about 7.0 w/w %, about 7.1 w/w %, about 7.2 w/w %, about 7.3 w/w %, about 7.4 w/w %, about 7.5 w/w %, about 7.6 w/w %, about 7.7 w/w %, about 7.8 w/w %, about 7.9 w/w %, about 8.0 w/w %, about 8.1 w/w %, about 8.2 w/w %, about 8.3 w/w %, about 8.4 w/w %, about 8.5 w/w %, about 8.6 w/w %, about 8.7 w/w %, about 8.8 w/w %, about 8.9 w/w %, about 9.0 w/w %, about 9.1 w/w %, about 9.2 w/w %, about 9.3 w/w %, about 9.4 w/w %, about 9.5 w/w %, about 9.6 w/w %, about 9.7 w/w %, about 9.8 w/w %, about 9.9 w/w %, about 10.0 w/w %, about 10.1 w/w %, about 10.2 w/w %, about 10.3 w/w %, about 10.4 w/w %, about 10.5 w/w %, about 10.6 w/w %, about 10.7 w/w %, about 10.8 w/w %, about 10.9 w/w %, about 11.0 w/w %, about 11.1 w/w %, about 11.2 w/w %, about 11.3 w/w %, about 11.4 w/w %, about 11.5 w/w %, about 11.6 w/w %, about 11.7 w/w %, about 11.8 w/w %, about 11.9 w/w %, about 12.0 w/w %, about 12.1 w/w %, about 12.2 w/w %, about 12.3 w/w %, about 12.4 w/w %, about 12.5 w/w %, about 12.6 w/w %, about 12.7 w/w %, about 12.8 w/w %, about 12.9 w/w %, about 13.0 w/w %, about 13.1 w/w %, about 13.2 w/w %, about 13.3 w/w %, about 13.4 w/w %, about 13.5 w/w %, about 13.6 w/w %, about 13.7 w/w %, about 13.8 w/w %, about 13.9 w/w %, about 14.0 w/w %, about 14.1 w/w %, about 14.2 w/w %, about 14.3 w/w %, about 14.4 w/w %, about 14.5 w/w %, about 14.6 w/w %, about 14.7 w/w %, about 14.8 w/w %, about 14.9 w/w %, about 15.0 w/w %, about 15.1 w/w %, about 15.2 w/w %, about 15.3 w/w %, about 15.4 w/w %, about 15.5 w/w %, about 15.6 w/w %, about 15.7 w/w %, about 15.8 w/w %, about 15.9 w/w %, about 16.0 w/w %, about 16.1 w/w %, about 16.2 w/w %, about 16.3 w/w %, about 16.4 w/w %, about 16.5 w/w %, about 16.6 w/w %, about 16.7 w/w %, about 16.8 w/w %, about 16.9 w/w %, about 17.0 w/w %, about 17.1 w/w %, about 17.2 w/w %, about 17.3 w/w %, about 17.4 w/w %, about 17.5 w/w %, about 17.6 w/w %, about 17.7 w/w %, about 17.8 w/w %, about 17.9 w/w %, about 18.0 w/w %, about 18.1 w/w %, about 18.2 w/w %, about 18.3 w/w %, about 18.4 w/w %, about 18.5 w/w %, about 18.6 w/w %, about 18.7 w/w %, about 18.8 w/w %, about 18.9 w/w %, about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of the compound of Formula (Ia) in the solution comprising a compound of Formula (Ia), PEG 300, sodium hydroxide, poloxamer 188, and water is about 4.57 w/w %. In some embodiments, the amount of the compound of Formula (Ia) in the solution comprising a compound of Formula (Ia), PEG 300, sodium hydroxide, poloxamer 188, and water is about 4.6 w/w %. In some embodiments, the amount of the compound of Formula (Ia) in the solution comprising a compound of Formula (Ia), PEG 300, sodium hydroxide, poloxamer 188, and water is about 25.2 w/w %. In some embodiments, the amount of the compound of Formula (Ia) in the solution comprising a compound of Formula (Ia), PEG 300, sodium hydroxide, poloxamer 188, and water is about 25.21 w/w %.

In some embodiments, the amount of sodium hydroxide in the solution comprising a compound of Formula (Ia), PEG 300, sodium hydroxide, poloxamer 188, and water is about 0.01 w/w % to about 3.0 w/w %. In some embodiments, the amount of sodium hydroxide in the solution comprising a compound of Formula (Ia), PEG 300, sodium hydroxide, poloxamer 188, and water is about 0.01 w/w % to about 2.0 w/w %. In some embodiments, the amount of sodium hydroxide in the solution comprising a compound of Formula (Ia), PEG 300, sodium hydroxide, poloxamer 188, and water is about 0.05 w/w % to about 1.5 w/w %. In some embodiments, the amount of sodium hydroxide in the solution comprising a compound of Formula (Ia), PEG 300, sodium hydroxide, poloxamer 188, and water is about 0.05 w/w % to about 1.2 w/w %. In some embodiments, the amount of sodium hydroxide in the solution comprising a compound of Formula (Ia), PEG 300, sodium hydroxide, poloxamer 188, and water is about 0.1 w/w % to about 1.1 w/w %. In some embodiments, the amount of sodium hydroxide in the solution comprising a compound of Formula (Ia), PEG 300, sodium hydroxide, poloxamer 188, and water is about 0.10 w/w % to about 1.08 w/w %. In some embodiments, the amount of sodium hydroxide in the solution comprising a compound of Formula (Ia), PEG 300, sodium hydroxide, poloxamer 188, and water is about 0.01 w/w %, about 0.02 w/w %, about 0.03 w/w %, about 0.04 w/w %, about 0.05 w/w %, about 0.06 w/w %, about 0.07 w/w %, about 0.08 w/w %, about 0.09 w/w %, about 0.1 w/w %, about 0.2 w/w %, about 0.3 w/w %, about 0.4 w/w %, about 0.5 w/w %, about 0.6 w/w %, about 0.7 w/w %, about 0.8 w/w %, about 0.9 w/w %, about 1.0 w/w %, about 1.1 w/w %, about 1.2 w/w %, about 1.3 w/w %, about 1.4 w/w %, about 1.5 w/w %, about 1.6 w/w %, about 1.7 w/w %, about 1.8 w/w %, about 1.9 w/w %, or about 2.0 w/w %. In some embodiments, the amount of sodium hydroxide in the solution comprising a compound of Formula (Ia), PEG 300, sodium hydroxide, poloxamer 188, and water is about 0.1 w/w %. In some embodiments, the amount of sodium hydroxide in the solution comprising a compound of Formula (Ia), PEG 300, sodium hydroxide, poloxamer 188, and water is about 0.10 w/w %. In some embodiments, the amount of sodium hydroxide in the solution comprising a compound of Formula (Ia), PEG 300, sodium hydroxide, poloxamer 188, and water is about 1.08 w/w %. In some embodiments, the amount of sodium hydroxide in the solution comprising a compound of Formula (Ia), PEG 300, sodium hydroxide, poloxamer 188, and water is about 1.1 w/w %.

In some embodiments, the amount of poloxamer 188 in the solution comprising a compound of Formula (Ia), PEG 300, sodium hydroxide, poloxamer 188, and water is about 0.1 w/w % to about 10 w/w %. In some embodiments, the amount of poloxamer 188 in the solution comprising a compound of Formula (Ia), PEG 300, sodium hydroxide, poloxamer 188, and water is about 0.3 w/w % to about 8 w/w %. In some embodiments, the amount of poloxamer 188 in the solution comprising a compound of Formula (Ia), PEG 300, sodium hydroxide, poloxamer 188, and water is about 0.5 w/w % to about 7 w/w %. In some embodiments, the amount of poloxamer 188 in the solution comprising a compound of Formula (Ia), PEG 300, sodium hydroxide, poloxamer 188, and water is about 0.6 w/w % to about 7 w/w %. In some embodiments, the amount of poloxamer 188 in the solution comprising a compound of Formula (Ia), PEG 300, sodium hydroxide, poloxamer 188, and water is about 0.85 w/w % to about 4.69 w/w %. In some embodiments, the amount of poloxamer 188 in the solution comprising a compound of Formula (Ia), PEG 300, sodium hydroxide, poloxamer 188, and water is about 0.9 w/w % to about 4.7 w/w %. In some embodiments, the amount of poloxamer 188 in the solution comprising a compound of Formula (Ia), PEG 300, sodium hydroxide, poloxamer 188, and water is about 0.5 w/w %, about 0.6 w/w %, about 0.7 w/w %, about 0.8 w/w %, about 0.9 w/w %, about 1.0 w/w %, about 1.1 w/w %, about 1.2 w/w %, about 1.3 w/w %, about 1.4 w/w %, about 1.5 w/w %, about 1.6 w/w %, about 1.7 w/w %, about 1.8 w/w %, about 1.9 w/w %, about 2.0 w/w %, about 2.1 w/w %, about 2.2 w/w %, about 2.3 w/w %, about 2.4 w/w %, about 2.5 w/w %, about 2.6 w/w %, about 2.7 w/w %, about 2.8 w/w %, about 2.9 w/w %, about 3.0 w/w %, about 3.1 w/w %, about 3.2 w/w %, about 3.3 w/w %, about 3.4 w/w %, about 3.5 w/w %, about 3.6 w/w %, about 3.7 w/w %, about 3.8 w/w %, about 3.9 w/w %, about 4.0 w/w %, about 4.1 w/w %, about 4.2 w/w %, about 4.3 w/w %, about 4.4 w/w %, about 4.5 w/w %, about 4.6 w/w %, about 4.7 w/w %, about 4.8 w/w %, about 4.9 w/w %, about 5.0 w/w %, about 5.1 w/w %, about 5.2 w/w %, about 5.3 w/w %, about 5.4 w/w %, about 5.5 w/w %, about 5.6 w/w %, about 5.7 w/w %, about 5.8 w/w %, about 5.9 w/w %, about 6.0 w/w %, about 6.1 w/w %, about 6.2 w/w %, about 6.3 w/w %, about 6.4 w/w %, about 6.5 w/w %, about 6.6 w/w %, about 6.7 w/w %, about 6.8 w/w %, about 6.9 w/w %, or about 7.0 w/w %. In some embodiments, the amount of poloxamer 188 in the solution comprising a compound of Formula (Ia), PEG 300, sodium hydroxide, poloxamer 188, and water is about 0.85 w/w %. In some embodiments, the amount of poloxamer 188 in the solution comprising a compound of Formula (Ia), PEG 300, sodium hydroxide, poloxamer 188, and water is about 0.9 w/w %. In some embodiments, the amount of poloxamer 188 in the solution comprising a compound of Formula (Ia), PEG 300, sodium hydroxide, poloxamer 188, and water is about 4.69 w/w %. In some embodiments, the amount of poloxamer 188 in the solution comprising a compound of Formula (Ia), PEG 300, sodium hydroxide, poloxamer 188, and water is about 4.7 w/w %.

In some embodiments, the solution disclosed herein comprises about 10 w/w % to about 45 w/w % water, about 30 w/w % to about 85 w/w % PEG 300, about 0.5 w/w % to about 40 w/w % of a compound of Formula (Ia), about 0.01 w/w % to about 3.0 w/w % of sodium hydroxide, and about 0.1 w/w % to about 10 w/w % of poloxamer 188. In some embodiments, the solution comprises about 15 w/w % to about 35 w/w % water, about 35 w/w % to about 75 w/w % PEG 300, about 1 w/w % to about 35 w/w % of a compound of Formula (Ia), about 0.01 w/w % to about 2.0 w/w % of sodium hydroxide, and about 0.3 w/w % to about 8 w/w % of poloxamer 188. In some embodiments, the solution comprises about 20 w/w % to about 35 w/w % water, about 40 w/w % to about 70 w/w % PEG 300, about 1 w/w % to about 30 w/w % of a compound of Formula (Ia), about 0.05 w/w % to about 1.5 w/w % of sodium hydroxide, and about 0.5 w/w % to about 7 w/w % of poloxamer 188. In some embodiments, the solution comprises about 20 w/w % to about 31 w/w % water, about 45 w/w % to about 68 w/w % PEG 300, about 3 w/w % to about 28 w/w % of a compound of Formula (Ia), about 0.05 w/w % to about 1.2 w/w % of sodium hydroxide, and about 0.6 w/w % to about 7 w/w % of poloxamer 188. In some embodiments, the solution comprises about 22 w/w % to about 30.1 w/w % water, about 47.1 w/w % to about 64.4 w/w % PEG 300, about 4.6 w/w % to about 25.2 w/w % of a compound of Formula (Ia), about 0.1 w/w % to about 1.1 w/w % of sodium hydroxide, and about 0.9 w/w % to about 4.7 w/w % of poloxamer 188. In some embodiments, the solution comprises about 21.97 w/w % to about 30.07 w/w % water, about 47.05 w/w % to about 64.41 w/w % PEG 300, about 4.57 w/w % to about 25.21 w/w % of a compound of Formula (Ia), about 0.10 w/w % to about 1.08 w/w % of sodium hydroxide, and about 0.85 w/w % to about 4.69 w/w % of poloxamer 188. In some embodiments, the solution comprises about 30.1 w/w % water, about 64.4 w/w % PEG 300, about 4.6 w/w % of a compound of Formula (Ia), about 0.1 w/w % of sodium hydroxide, and about 0.9 w/w % of poloxamer 188. In some embodiments, the solution comprises about 30.07 w/w % water, about 64.41 w/w % PEG 300, about 4.57 w/w % of a compound of Formula (Ia), about 0.10 w/w % of sodium hydroxide, and about 0.85 w/w % of poloxamer 188. In some embodiments, the solution comprises about 22 w/w % water, about 47.1 w/w % PEG 300, about 25.2 w/w % of a compound of Formula (Ia), about 1.1 w/w % of sodium hydroxide, and about 4.7 w/w % of poloxamer 188. In some embodiments, the solution comprises about 21.97 w/w % water, about 47.05 w/w % PEG 300, about 25.21 w/w % of a compound of Formula (Ia), about 1.08 w/w % of sodium hydroxide, and about 4.69 w/w % of poloxamer 188.

In some embodiments, the compound of Formula (Ia) becomes ionized in situ to a sodium salt of the compound of Formula (Ia) in the presence of sodium hydroxide in the solution comprising a compound of Formula (Ia), PEG 300, sodium hydroxide, poloxamer 188, and water. Thus, in some embodiments, the compound of Formula (Ia) is present as a sodium salt of the compound of Formula (Ia) in the solution comprising a compound of Formula (Ia), PEG 300, sodium hydroxide, poloxamer 188, and water.

In some embodiments, the solution formulation comprises about 50 mg/mL of the compound of Formula (Ia) or Formula (Ib), or a pharmaceutically acceptable salt thereof. In some embodiments, the solution formulation comprises about 75 mg/mL of the compound of Formula (Ia) or Formula (Ib), or a pharmaceutically acceptable salt thereof. In some embodiments, the solution formulation comprises about 125 mg/mL of the compound of Formula (Ia) or Formula (Ib), or a pharmaceutically acceptable salt thereof. In some embodiments, the solution formulation comprises about 175 mg/mL of the compound of Formula (Ia) or Formula (Ib), or a pharmaceutically acceptable salt thereof. In some embodiments, the solution formulation comprises about 225 mg/mL of the compound of Formula (Ia) or Formula (Ib), or a pharmaceutically acceptable salt thereof. In some embodiments, the solution formulation comprises about 250 mg/mL of the compound of Formula (Ia) or Formula (Ib), or a pharmaceutically acceptable salt thereof. In some embodiments, the solution formulation comprises about 275 mg/mL of the compound of Formula (Ia) or Formula (Ib), or a pharmaceutically acceptable salt thereof.

In some embodiments, the solution formulation comprises about 325 mg/mL of the compound of Formula (Ia) or Formula (Ib), or a pharmaceutically acceptable salt thereof. In some embodiments, the solution formulation comprises about 350 mg/mL of the compound of Formula (Ia) or Formula (Ib), or a pharmaceutically acceptable salt thereof. In some embodiments, the solution formulation comprises about 375 mg/mL of the compound of Formula (Ia) or Formula (Ib), or a pharmaceutically acceptable salt thereof. In some embodiments, the solution formulation comprises about 100 mg/mL of the compound of Formula (Ia) or Formula (Ib), or a pharmaceutically acceptable salt thereof. In some embodiments, the solution formulation comprises about 150 mg/mL of the compound of Formula (Ia) or Formula (Ib), or a pharmaceutically acceptable salt thereof. In some embodiments, the solution formulation comprises about 200 mg/mL of the compound of Formula (Ia) or Formula (Ib), or a pharmaceutically acceptable salt thereof. In some embodiments, the solution formulation comprises about 300 mg/mL of the compound of Formula (Ia) or Formula (Ib), or a pharmaceutically acceptable salt thereof. In some embodiments, the solution formulation comprises about 400 mg/mL of the compound of Formula (Ia) or Formula (Ib), or a pharmaceutically acceptable salt thereof.

In some embodiments, the solution formulation comprises about 425 mg/mL of the compound of Formula (Ia) or Formula (Ib), or a pharmaceutically acceptable salt thereof. In some embodiments, the solution formulation comprises about 450 mg/mL of the compound of Formula (Ia) or Formula (Ib), or a pharmaceutically acceptable salt thereof. In some embodiments, the solution formulation comprises about 475 mg/mL of the compound of Formula (Ia) or Formula (Ib), or a pharmaceutically acceptable salt thereof. In some embodiments, the solution formulation comprises about 500 mg/mL of the compound of Formula (Ia) or Formula (Ib), or a pharmaceutically acceptable salt thereof.

In some embodiments, the solutions disclosed herein are administered through subcutaneous injection. In some embodiments, the solutions disclosed herein are administered through intramuscular injection.

In certain embodiments, an oral formulation of a compound of Formula (Ia) or Formula (Ib), or a pharmaceutically acceptable salt thereof, and at least one excipient is provided. Excipients can include ethanol, medium chain triglycerides, vitamin E d-α-tocopheryl polyethylene glycol 1000 succinate (TPGS), glycerol monocaprylocaprate, glycerin, and/or pharmaceutically acceptable oils. Examples of suitable medium chain triglycerides include, but are not limited to, MIGLYOL 810, MIGLYOL 821, and MIGLYOL 840. Examples of suitable pharmaceutically acceptable oils include, but are not limited to, sesame oil, castor oil, safflower oil, vegetable oil, and soybean oil. Oral formulations disclosed herein can include any combination of one or more suitable excipients. Excipients taken together can be present in greater than about 65% by weight of the total oral formulation, greater than about 70% by weight of the total oral formulation, greater than about 80% by weight of the total oral formulation, greater than about 90% by weight of the total oral formulation, or greater than about 95% by weight of the total oral formulation.

In some embodiments, the oral formulation of a compound of Formula (Ia) or Formula (Ib), or a pharmaceutically acceptable salt thereof, and at least one excipient as disclosed herein is prepared in hard or soft capsules. In some embodiments, the hard or soft capsules comprise a compound of Formula (Ia) or Formula (Ib), or a pharmaceutically acceptable salt thereof, and one or more excipients selected from the group consisting of ethanol, propylene glycol, glycerine, d-α-tocopheryl polyethylene glycol 1000 succinate (TPGS), polyoxyl 35 castor oil (e.g., Kolliphor® EL), glycerol monocapryolocaprate (e.g., Capmul® MCM), PEG 400 caprylic/capric glycerides (e.g., Labrasol®), PEG 400, diethylene glycol monoethyl ether (e.g., Transcutol®), propylene glycol monocaprylate, Type II (e.g., Capryol® 90), glyceryl monooleate, Type 40 (e.g., Peceol™), medium chain triglycerides (e.g., Miglyol® 812N), glyceryl monolinoleate (e.g., Maisine®), and polysorbate 80. In some embodiments, the hard or soft capsules comprise a compound of Formula (Ia) or Formula (Ib), or a pharmaceutically acceptable salt thereof, and one or more excipients selected from the group consisting of ethanol, medium chain triglycerides (e.g., Miglyol® 812N), d-α-tocopheryl polyethylene glycol 1000 succinate (TPGS), glycerol monocapryolocaprate (e.g., Capmul® MCM), PEG 400 caprylic/capric glycerides (e.g., Labrasol®), and PEG 400.

In some embodiments, the hard or soft capsules further comprise a capsule shell. In some embodiments, the capsule shell comprises one or more pharmaceutically acceptable excipients. In some embodiments, the one or more pharmaceutically acceptable excipients of the capsule shell is selected from the group consisting of a gelatin shell, a plasticizer, an opacifier, and a colorant. Plasticizers, opacifiers, and colorants are well-known in the art. In some embodiments, the capsule shell comprises one or more pharmaceutically acceptable excipients selected from the group consisting of gelatin, glycerin, titanium dioxide, and iron oxide. In some embodiments, the iron oxide comprises iron oxide (yellow).

In some embodiments, an oral formulation of a compound of Formula (Ia) or Formula (Ib), or a pharmaceutically acceptable salt thereof, is provided. In certain embodiments, the oral formulation comprises a compound of Formula (Ia) or Formula (Ib), or a pharmaceutically acceptable salt thereof, and glycerol monocaprylocaprate. In certain embodiments, the oral formulation includes a compound of Formula (Ia) or Formula (Ib), or a pharmaceutically acceptable salt thereof, about 5% to about 20% ethanol, about 10% to about 30% vitamin E TPGS, and about 50% to about 85% MIGLYOL 812. In some embodiments, the oral formulation includes a compound of Formula (Ia) or Formula (Ib), or a pharmaceutically acceptable salt thereof, about 8% to about 15% ethanol, about 15% to about 25% vitamin E TPGS, and about 60% to about 77% MIGLYOL 812. In certain embodiments, the oral formulation includes a compound of Formula (Ia) or Formula (Ib), or a pharmaceutically acceptable salt thereof, in about 10% ethanol, about 20% vitamin E TPGS, and about 70% MIGLYOL 812. In certain embodiments, the oral formulation is prepared in hard gelatin capsules. In certain embodiments, the oral formulation is prepared in soft gelatin capsules.

In some embodiments, the hard gelatin or soft gelatin capsule disclosed herein comprises a compound of Formula (Ia) or Formula (Ib), or a pharmaceutically acceptable salt thereof, and a pharmaceutically acceptable excipient as disclosed herein. In some embodiments, the hard gelatin or soft gelatin capsule disclosed herein comprises a compound of Formula (Ia) or Formula (Ib), or a pharmaceutically acceptable salt thereof, and glycerol monocaprylocaprate. In some embodiments, the concentration of a compound of Formula (Ia) or Formula (Ib), or a pharmaceutically acceptable salt thereof, in the hard gelatin or soft gelatin capsule disclosed herein is about 10 mg/ml to about 500 mg/ml. In some embodiments, the concentration of a compound of Formula (Ia) or Formula (Ib), or a pharmaceutically acceptable salt thereof, in the hard gelatin or soft gelatin capsule disclosed herein is about 10 mg/ml to about 400 mg/ml. In some embodiments, the concentration of a compound of Formula (Ia) or Formula (Ib), or a pharmaceutically acceptable salt thereof, in the hard gelatin or soft gelatin capsule disclosed herein is about 50 mg/ml to about 300 mg/ml. In some embodiments, the concentration of a compound of Formula (Ia) or Formula (Ib), or a pharmaceutically acceptable salt thereof, in the hard gelatin or soft gelatin capsule disclosed herein is about 50 mg/ml to about 200 mg/ml. In some embodiments, the concentration of a compound of Formula (Ia) or Formula (Ib), or a pharmaceutically acceptable salt thereof, in the hard gelatin or soft gelatin capsule disclosed herein is about 50 mg/ml to about 100 mg/ml. In some embodiments, the concentration of a compound of Formula (Ia) or Formula (Ib), or a pharmaceutically acceptable salt thereof, in the hard gelatin or soft gelatin capsule disclosed herein is about 10 mg/ml, about 15 mg/ml, about 20 mg/ml, about 25 mg/ml, about 30 mg/ml, about 30 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, about 160 mg/ml, about 165 mg/ml, about 170 mg/ml, about 175 mg/ml, about 180 mg/ml, about 185 mg/ml, about 190 mg/ml, about 195 mg/ml, about 200 mg/ml, 205 mg/ml, about 210 mg/ml, about 215 mg/ml, about 220 mg/ml, about 225 mg/ml, about 230 mg/ml, about 235 mg/ml, about 240 mg/ml, about 245 mg/ml, about 250 mg/ml, about 255 mg/ml, about 260 mg/ml, about 265 mg/ml, about 270 mg/ml, about 275 mg/ml, about 280 mg/ml, about 285 mg/ml, about 290 mg/ml, about 295 mg/ml, about 300 mg/ml, about 305 mg/ml, about 310 mg/ml, about 315 mg/ml, about 320 mg/ml, about 325 mg/ml, about 330 mg/ml, about 335 mg/ml, about 340 mg/ml, about 345 mg/ml, about 350 mg/ml, about 355 mg/ml, about 360 mg/ml, about 365 mg/ml, about 370 mg/ml, about 375 mg/ml, about 380 mg/ml, about 385 mg/ml, about 390 mg/ml, about 395 mg/ml, about 400 mg/ml, about 405 mg/ml, about 410 mg/ml, about 415 mg/ml, about 420 mg/ml, about 425 mg/ml, about 430 mg/ml, about 435 mg/ml, about 440 mg/ml, about 445 mg/ml, about 450 mg/ml, about 455 mg/ml, about 460 mg/ml, about 465 mg/ml, about 470 mg/ml, about 475 mg/ml, about 480 mg/ml, about 485 mg/ml, about 490 mg/ml, about 495 mg/ml, or about 500 mg/ml. In some embodiments, the concentration of a compound of Formula (Ia) or Formula (Ib), or a pharmaceutically acceptable salt thereof, in the hard gelatin or soft gelatin capsule disclosed herein is about 10 mg/ml. In some embodiments, the concentration of a compound of Formula (Ia) or Formula (Ib), or a pharmaceutically acceptable salt thereof, in the hard gelatin or soft gelatin capsule disclosed herein is about 20 mg/ml. In some embodiments, the concentration of a compound of Formula (Ia) or Formula (Ib), or a pharmaceutically acceptable salt thereof, in the hard gelatin or soft gelatin capsule disclosed herein is about 30 mg/ml. In some embodiments, the concentration of a compound of Formula (Ia) or Formula (Ib), or a pharmaceutically acceptable salt thereof, in the hard gelatin or soft gelatin capsule disclosed herein is about 40 mg/ml. In some embodiments, the concentration of a compound of Formula (Ia) or Formula (Ib), or a pharmaceutically acceptable salt thereof, in the hard gelatin or soft gelatin capsule disclosed herein is about 50 mg/ml. In some embodiments, the concentration of a compound of Formula (Ia) or Formula (Ib), or a pharmaceutically acceptable salt thereof, in the hard gelatin or soft gelatin capsule disclosed herein is about 75 mg/ml. In some embodiments, the concentration of a compound of Formula (Ia) or Formula (Ib), or a pharmaceutically acceptable salt thereof, in the hard gelatin or soft gelatin capsule disclosed herein is about 100 mg/ml. In some embodiments, the concentration of a compound of Formula (Ia) or Formula (Ib), or a pharmaceutically acceptable salt thereof, in the hard gelatin or soft gelatin capsule disclosed herein is about 125 mg/ml. In some embodiments, the concentration of a compound of Formula (Ia) or Formula (Ib), or a pharmaceutically acceptable salt thereof, in the hard gelatin or soft gelatin capsule disclosed herein is about 150 mg/ml. In some embodiments, the concentration of a compound of Formula (Ia) or Formula (Ib), or a pharmaceutically acceptable salt thereof, in the hard gelatin or soft gelatin capsule disclosed herein is about 175 mg/ml. In some embodiments, the concentration of a compound of Formula (Ia) or Formula (Ib), or a pharmaceutically acceptable salt thereof, in the hard gelatin or soft gelatin capsule disclosed herein is about 200 mg/ml. In some embodiments, the concentration of a compound of Formula (Ia) or Formula (Ib), or a pharmaceutically acceptable salt thereof, in the hard gelatin or soft gelatin capsule disclosed herein is about 225 mg/ml. In some embodiments, the concentration of a compound of Formula (Ia) or Formula (Ib), or a pharmaceutically acceptable salt thereof, in the hard gelatin or soft gelatin capsule disclosed herein is about 250 mg/ml. In some embodiments, the concentration of a compound of Formula (Ia) or Formula (Ib), or a pharmaceutically acceptable salt thereof, in the hard gelatin or soft gelatin capsule disclosed herein is about 275 mg/ml. In some embodiments, the concentration of a compound of Formula (Ia) or Formula (Ib), or a pharmaceutically acceptable salt thereof, in the hard gelatin or soft gelatin capsule disclosed herein is about 300 mg/ml. In some embodiments, the concentration of a compound of Formula (Ia) or Formula (Ib), or a pharmaceutically acceptable salt thereof, in the hard gelatin or soft gelatin capsule disclosed herein is about 325 mg/ml. In some embodiments, the concentration of a compound of Formula (Ia) or Formula (Ib), or a pharmaceutically acceptable salt thereof, in the hard gelatin or soft gelatin capsule disclosed herein is about 350 mg/ml. In some embodiments, the concentration of a compound of Formula (Ia) or Formula (Ib), or a pharmaceutically acceptable salt thereof, in the hard gelatin or soft gelatin capsule disclosed herein is about 375 mg/ml. In some embodiments, the concentration of a compound of Formula (Ia) or Formula (Ib), or a pharmaceutically acceptable salt thereof, in the hard gelatin or soft gelatin capsule disclosed herein is about 400 mg/ml. In some embodiments, the concentration of a compound of Formula (Ia) or Formula (Ib), or a pharmaceutically acceptable salt thereof, in the hard gelatin or soft gelatin capsule disclosed herein is about 425 mg/ml. In some embodiments, the concentration of a compound of Formula (Ia) or Formula (Ib), or a pharmaceutically acceptable salt thereof, in the hard gelatin or soft gelatin capsule disclosed herein is about 450 mg/ml. In some embodiments, the concentration of a compound of Formula (Ia) or Formula (Ib), or a pharmaceutically acceptable salt thereof, in the hard gelatin or soft gelatin capsule disclosed herein is about 475 mg/ml. In some embodiments, the concentration of a compound of Formula (Ia) or Formula (Ib), or a pharmaceutically acceptable salt thereof, in the hard gelatin or soft gelatin capsule disclosed herein is about 500 mg/ml.

In some embodiments, the hard gelatin or soft gelatin capsule disclosed herein comprises a compound of Formula (Ib), or a pharmaceutically acceptable salt thereof, and glycerol monocaprylocaprate. In some embodiments, the hard gelatin or soft gelatin capsule disclosed herein comprises a trifluoroacetic acid salt of the compound of Formula (Ib) and glycerol monocaprylocaprate.

In some embodiments, the hard gelatin or soft gelatin capsule disclosed herein comprises a compound of Formula (Ia) and glycerol monocaprylocaprate. In some embodiments, the concentration of the compound of Formula (Ia) in the hard gelatin or soft gelatin capsule comprising a compound of Formula (Ia) and glycerol monocaprylocaprate is about 10 mg/ml to about 500 mg/ml. In some embodiments, the concentration of the compound of Formula (Ia) in the hard gelatin or soft gelatin capsule comprising a compound of Formula (Ia) and glycerol monocaprylocaprate is about 10 mg/ml to about 400 mg/ml. In some embodiments, the concentration of the compound of Formula (Ia) in the hard gelatin or soft gelatin capsule comprising a compound of Formula (Ia) and glycerol monocaprylocaprate is about 50 mg/ml to about 300 mg/ml. In some embodiments, the concentration of the compound of Formula (Ia) in the hard gelatin or soft gelatin capsule comprising a compound of Formula (Ia) and glycerol monocaprylocaprate is about 75 mg/ml to about 300 mg/ml. In some embodiments, the concentration of the compound of Formula (Ia) in the hard gelatin or soft gelatin capsule comprising a compound of Formula (Ia) and glycerol monocaprylocaprate is about 50 mg/ml to about 200 mg/ml. In some embodiments, the concentration of the compound of Formula (Ia) in the hard gelatin or soft gelatin capsule comprising a compound of Formula (Ia) and glycerol monocaprylocaprate is about 50 mg/ml to about 100 mg/ml. In some embodiments, the concentration of the compound of Formula (Ia) in the hard gelatin or soft gelatin capsule comprising a compound of Formula (Ia) and glycerol monocaprylocaprate is about 10 mg/ml. In some embodiments, the concentration of the compound of Formula (Ia) in the hard gelatin or soft gelatin capsule comprising a compound of Formula (Ia) and glycerol monocaprylocaprate is about 20 mg/ml. In some embodiments, the concentration of the compound of Formula (Ia) in the hard gelatin or soft gelatin capsule comprising a compound of Formula (Ia) and glycerol monocaprylocaprate is about 30 mg/ml. In some embodiments, the concentration of the compound of Formula (Ia) in the hard gelatin or soft gelatin capsule comprising a compound of Formula (Ia) and glycerol monocaprylocaprate is about 40 mg/ml. In some embodiments, the concentration of the compound of Formula (Ia) in the hard gelatin or soft gelatin capsule comprising a compound of Formula (Ia) and glycerol monocaprylocaprate is about 50 mg/ml. In some embodiments, the concentration of the compound of Formula (Ia) in the hard gelatin or soft gelatin capsule comprising a compound of Formula (Ia) and glycerol monocaprylocaprate is about 75 mg/ml. In some embodiments, the concentration of the compound of Formula (Ia) in the hard gelatin or soft gelatin capsule comprising a compound of Formula (Ia) and glycerol monocaprylocaprate is about 100 mg/ml. In some embodiments, the concentration of a compound of Formula (Ia) in the hard gelatin or soft gelatin capsule comprising a compound of Formula (Ia) and glycerol monocaprylocaprate is about 125 mg/ml. In some embodiments, the concentration of a compound of Formula (Ia) in the hard gelatin or soft gelatin capsule comprising a compound of Formula (Ia) and glycerol monocaprylocaprate is about 150 mg/ml. In some embodiments, the concentration of a compound of Formula (Ia) in the hard gelatin or soft gelatin capsule comprising a compound of Formula (Ia) and glycerol monocaprylocaprate is about 175 mg/ml. In some embodiments, the concentration of a compound of Formula (Ia) in the hard gelatin or soft gelatin capsule comprising a compound of Formula (Ia) and glycerol monocaprylocaprate is about 200 mg/ml. In some embodiments, the concentration of a compound of Formula (Ia) in the hard gelatin or soft gelatin capsule comprising a compound of Formula (Ia) and glycerol monocaprylocaprate is about 225 mg/ml. In some embodiments, the concentration of a compound of Formula (Ia) in the hard gelatin or soft gelatin capsule comprising a compound of Formula (Ia) and glycerol monocaprylocaprate is about 250 mg/ml. In some embodiments, the concentration of a compound of Formula (Ia) in the hard gelatin or soft gelatin capsule comprising a compound of Formula (Ia) and glycerol monocaprylocaprate is about 275 mg/ml. In some embodiments, the concentration of a compound of Formula (Ia) in the hard gelatin or soft gelatin capsule comprising a compound of Formula (Ia) and glycerol monocaprylocaprate is about 300 mg/ml. In some embodiments, the concentration of a compound of Formula (Ia) in the hard gelatin or soft gelatin capsule comprising a compound of Formula (Ia) and glycerol monocaprylocaprate is about 325 mg/ml. In some embodiments, the concentration of a compound of Formula (Ia) in the hard gelatin or soft gelatin capsule comprising a compound of Formula (Ia) and glycerol monocaprylocaprate is about 350 mg/ml. In some embodiments, the concentration of a compound of Formula (Ia) in the hard gelatin or soft gelatin capsule comprising a compound of Formula (Ia) and glycerol monocaprylocaprate is about 375 mg/ml. In some embodiments, the concentration of a compound of Formula (Ia) in the hard gelatin or soft gelatin capsule comprising a compound of Formula (Ia) and glycerol monocaprylocaprate is about 400 mg/ml. In some embodiments, the concentration of a compound of Formula (Ia) in the hard gelatin or soft gelatin capsule comprising a compound of Formula (Ia) and glycerol monocaprylocaprate is about 425 mg/ml. In some embodiments, the concentration of a compound of Formula (Ia) in the hard gelatin or soft gelatin capsule comprising a compound of Formula (Ia) and glycerol monocaprylocaprate is about 450 mg/ml. In some embodiments, the concentration of a compound of Formula (Ia) in the hard gelatin or soft gelatin capsule comprising a compound of Formula (Ia) and glycerol monocaprylocaprate is about 475 mg/ml. In some embodiments, the concentration of a compound of Formula (Ia) in the hard gelatin or soft gelatin capsule comprising a compound of Formula (Ia) and glycerol monocaprylocaprate is about 500 mg/ml.

In some embodiments, the amount of glycerol monocaprylocaprate in the hard gelatin or soft gelatin capsule comprising a compound of Formula (Ia) and glycerol monocaprylocaprate is about 30 w/w % to about 85 w/w %. In some embodiments, the amount of glycerol monocaprylocaprate in the hard gelatin or soft gelatin capsule comprising a compound of Formula (Ia) and glycerol monocaprylocaprate is about 40 w/w % to about 80 w/w %. In some embodiments, the amount of glycerol monocaprylocaprate in the hard gelatin or soft gelatin capsule comprising a compound of Formula (Ia) and glycerol monocaprylocaprate is about 50 w/w % to about 80 w/w %. In some embodiments, the amount of glycerol monocaprylocaprate in the hard gelatin or soft gelatin capsule comprising a compound of Formula (Ia) and glycerol monocaprylocaprate is about 60 w/w % to about 70 w/w %. In some embodiments, the amount of glycerol monocaprylocaprate in the hard gelatin or soft gelatin capsule comprising a compound of Formula (Ia) and glycerol monocaprylocaprate is about 65.9 w/w %. In some embodiments, the amount of glycerol monocaprylocaprate in the hard gelatin or soft gelatin capsule comprising a compound of Formula (Ia) and glycerol monocaprylocaprate is about 65.94 w/w %.

In some embodiments, the amount of the compound of Formula (Ia) in the hard gelatin or soft gelatin capsule comprising a compound of Formula (Ia) and glycerol monocaprylocaprate is about 1 w/w % to about 40 w/w %. In some embodiments, the amount of the compound of Formula (Ia) in the hard gelatin or soft gelatin capsule comprising a compound of Formula (Ia) and glycerol monocaprylocaprate is about 1 w/w % to about 35 w/w %. In some embodiments, the amount of the compound of Formula (Ia) in the hard gelatin or soft gelatin capsule comprising a compound of Formula (Ia) and glycerol monocaprylocaprate is about 2 w/w % to about 30 w/w %. In some embodiments, the amount of the compound of Formula (Ia) in the hard gelatin or soft gelatin capsule comprising a compound of Formula (Ia) and glycerol monocaprylocaprate is about 3 w/w % to about 28 w/w %. In some embodiments, the amount of the compound of Formula (Ia) in the hard gelatin or soft gelatin capsule comprising a compound of Formula (Ia) and glycerol monocaprylocaprate is about 3.4 w/w %. In some embodiments, the amount of the compound of Formula (Ia) in the hard gelatin or soft gelatin capsule comprising a compound of Formula (Ia) and glycerol monocaprylocaprate is about 3.42 w/w %.

In some embodiments, the hard gelatin or soft gelatin capsule comprising a compound of Formula (Ia) and glycerol monocaprylocaprate further comprises a capsule shell. In some embodiments, the capsule shell comprises one or more pharmaceutically acceptable excipients. In some embodiments, the one or more pharmaceutically acceptable excipients of the capsule shell is selected from the group consisting of a gelatin shell, a plasticizer, an opacifier, and a colorant. In some embodiments, the hard gelatin or soft gelatin capsule comprising a compound of Formula (Ia) and glycerol monocaprylocaprate further comprises one or more of a pharmaceutically acceptable excipient selected from the group consisting of gelatin, glycerin, titanium dioxide, and iron oxide. In some embodiments, the hard gelatin or soft gelatin capsule comprising a compound of Formula (Ia) and glycerol monocaprylocaprate further comprises gelatin. In some embodiments, the hard gelatin or soft gelatin capsule comprising a compound of Formula (Ia) and glycerol monocaprylocaprate further comprises glycerin. In some embodiments, the hard gelatin or soft gelatin capsule comprising a compound of Formula (Ia) and glycerol monocaprylocaprate further comprises titanium dioxide. In some embodiments, the hard gelatin or soft gelatin capsule comprising a compound of Formula (Ia) and glycerol monocaprylocaprate further comprises iron oxide. In some embodiments, the hard gelatin or soft gelatin capsule comprising a compound of Formula (Ia) and glycerol monocaprylocaprate further comprises gelatin and glycerin. In some embodiments, the hard gelatin or soft gelatin capsule comprising a compound of Formula (Ia) and glycerol monocaprylocaprate further comprises gelatin, glycerin, and titanium dioxide. In some embodiments, the hard gelatin or soft gelatin capsule comprising a compound of Formula (Ia) and glycerol monocaprylocaprate further comprises gelatin, glycerin, titanium dioxide, and iron oxide. In some embodiments, the iron oxide of the hard gelatin or soft gelatin capsule comprising a compound of Formula (Ia), glycerol monocaprylocaprate, gelatin, glycerin, titanium dioxide, and iron oxide comprises iron oxide (yellow).

In some embodiments, the amount of gelatin in the hard gelatin or soft gelatin capsule comprising a compound of Formula (Ia), glycerol monocaprylocaprate, gelatin, glycerin, titanium dioxide, and iron oxide is about 10 w/w % to about 40 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 10 w/w % to about 30 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 15 w/w % to about 25 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 18 w/w % to about 22 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 19.6 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 19.60 w/w %.

In some embodiments, the amount of glycerin in the hard gelatin or soft gelatin capsule comprising a compound of Formula (Ia), glycerol monocaprylocaprate, gelatin, glycerin, titanium dioxide, and iron oxide is about 3 w/w % to about 25 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 5 w/w % to about 20 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 5 w/w % to about 15 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 8 w/w % to about 12 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 10.8 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 10.80 w/w %.

In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.01 w/w % to about 2 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.05 w/w % to about 1.5 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.1 w/w % to about 1.0 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.1 w/w % to about 0.5 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.2 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.22 w/w %.

In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.01 w/w % to about 1 w/w %. In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.01 w/w % to about 0.5 w/w %. In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.01 w/w % to about 0.15 w/w %. In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.01 w/w % to about 0.1 w/w %. In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.02 w/w %.

In some embodiments, the hard gelatin or soft capsule disclosed herein comprises about 30 w/w % to about 85 w/w % of glycerol monocaprylocaprate and about 1 w/w % to about 40 w/w % of a compound of Formula (Ia). In some embodiments, the hard gelatin or soft gelatin capsule disclosed herein comprises about 40 w/w % to about 80 w/w % of glycerol monocaprylocaprate and about 1 w/w % to about 35 w/w % of a compound of Formula (Ia). In some embodiments, the hard gelatin or soft capsule disclosed herein comprises about 50 w/w % to about 80 w/w % of glycerol monocaprylocaprate and about 2 w/w % to about 30 w/w % of a compound of Formula (Ia). In some embodiments, the hard gelatin or soft capsule disclosed herein comprises about 60 w/w % to about 70 w/w % of glycerol monocaprylocaprate and about 3 w/w % to about 28 w/w % of a compound of Formula (Ia). In some embodiments, the hard gelatin or soft gelatin capsule disclosed herein comprises about 65.9 w/w % of glycerol monocaprylocaprate and about 3.4 w/w % of a compound of Formula (Ia). In some embodiments, the hard gelatin or soft gelatin capsule disclosed herein comprises about 65.94 w/w % of glycerol monocaprylocaprate and about 3.42 w/w % of a compound of Formula (Ia).

In some embodiments, the hard gelatin or soft capsule disclosed herein comprises about 30 w/w % to about 85 w/w % of glycerol monocaprylocaprate, about 1 w/w % to about 40 w/w % of a compound of Formula (Ia), about 10 w/w % to about 40 w/w % of gelatin, about 3 w/w % to about 25 w/w % of glycerin, about 0.01 w/w % to about 2 w/w % of titanium dioxide, and about 0.01 w/w % to about 1 w/w % of iron oxide. In some embodiments, the hard gelatin or soft capsule disclosed herein comprises about 40 w/w % to about 80 w/w % of glycerol monocaprylocaprate, about 1 w/w % to about 35 w/w % of a compound of Formula (Ia), about 10 w/w % to about 30 w/w % of gelatin, about 5 w/w % to about 20 w/w % of glycerin, about 0.05 w/w % to about 1.5 w/w % of titanium dioxide, and about 0.01 w/w % to about 0.5 w/w % of iron oxide. In some embodiments, the hard gelatin or soft capsule disclosed herein comprises about 50 w/w % to about 80 w/w % of glycerol monocaprylocaprate, about 2 w/w % to about 30 w/w % of a compound of Formula (Ia), about 15 w/w % to about 25 w/w % of gelatin, about 5 w/w % to about 15 w/w % of glycerin, about 0.1 w/w % to about 1.0 w/w % of titanium dioxide, and about 0.01 w/w % to about 0.15 w/w % of iron oxide. In some embodiments, the hard gelatin or soft capsule disclosed herein comprises about 60 w/w % to about 70 w/w % of glycerol monocaprylocaprate, about 3 w/w % to about 28 w/w % of a compound of Formula (Ia), about 18 w/w % to about 22 w/w % of gelatin, about 8 w/w % to about 12 w/w % of glycerin, about 0.1 w/w % to about 0.5 w/w % of titanium dioxide, and about 0.01 w/w % to about 0.1 w/w % of iron oxide. In some embodiments, the hard gelatin or soft capsule disclosed herein comprises about 65.9 w/w % of glycerol monocaprylocaprate, about 3.4 w/w % of a compound of Formula (Ia), about 19.6 w/w % of gelatin, about 10.8 w/w % of glycerin, about 0.2 w/w % of titanium dioxide, and about 0.02 w/w % of iron oxide. In some embodiments, the hard gelatin or soft capsule disclosed herein comprises about 65.94 w/w % of glycerol monocaprylocaprate, about 3.42 w/w % of a compound of Formula (Ia), about 19.60 w/w % of gelatin, about 10.80 w/w % of glycerin, about 0.22 w/w % of titanium dioxide, and about 0.02 w/w % of iron oxide.

In some embodiments, the iron oxide in the hard gelatin or soft gelatin capsule comprising a compound of Formula (Ia), glycerol monocaprylocaprate, gelatin, glycerin, titanium dioxide, and iron oxide comprises iron oxide (yellow). In some embodiments, the hard gelatin or soft capsule disclosed herein comprises about 65.9 w/w % of glycerol monocaprylocaprate, about 3.4 w/w % of a compound of Formula (Ia), about 19.6 w/w % of gelatin, about 10.8 w/w % of glycerin, about 0.2 w/w % of titanium dioxide, and about 0.02 w/w % of iron oxide (yellow). In some embodiments, the hard gelatin or soft capsule disclosed herein comprises about 65.94 w/w % of glycerol monocaprylocaprate, about 3.42 w/w % of a compound of Formula (Ia), about 19.60 w/w % of gelatin, about 10.80 w/w % of glycerin, about 0.22 w/w % of titanium dioxide, and about 0.02 w/w % of iron oxide (yellow).

In some embodiments, the hard gelatin or soft gelatin capsule disclosed herein comprises a sodium salt of the compound of Formula (Ia) and glycerol monocaprylocaprate. In some embodiments, the concentration of the compound of Formula (Ia) in the hard gelatin or soft gelatin capsule comprising a sodium salt of the compound of Formula (Ia) and glycerol monocaprylocaprate is about 10 mg/ml to about 500 mg/ml. In some embodiments, the concentration of the compound of Formula (Ia) in the hard gelatin or soft gelatin capsule comprising a sodium salt of the compound of Formula (Ia) and glycerol monocaprylocaprate is about 10 mg/ml to about 400 mg/ml. In some embodiments, the concentration of the compound of Formula (Ia) in the hard gelatin or soft gelatin capsule comprising a sodium salt of the compound of Formula (Ia) and glycerol monocaprylocaprate is about 50 mg/ml to about 300 mg/ml. In some embodiments, the concentration of the compound of Formula (Ia) in the hard gelatin or soft gelatin capsule comprising a sodium salt of the compound of Formula (Ia) and glycerol monocaprylocaprate is about 75 mg/ml to about 300 mg/ml. In some embodiments, the concentration of the compound of Formula (Ia) in the hard gelatin or soft gelatin capsule comprising a sodium salt of the compound of Formula (Ia) and glycerol monocaprylocaprate is about 10 mg/ml. In some embodiments, the concentration of the compound of Formula (Ia) in the hard gelatin or soft gelatin capsule comprising a sodium salt of the compound of Formula (Ia) and glycerol monocaprylocaprate is about 20 mg/ml. In some embodiments, the concentration of the compound of Formula (Ia) in the hard gelatin or soft gelatin capsule comprising a sodium salt of the compound of Formula (Ia) and glycerol monocaprylocaprate is about 30 mg/ml. In some embodiments, the concentration of the compound of Formula (Ia) in the hard gelatin or soft gelatin capsule comprising a sodium salt of the compound of Formula (Ia) and glycerol monocaprylocaprate is about 40 mg/ml. In some embodiments, the concentration of the compound of Formula (Ia) in the hard gelatin or soft gelatin capsule comprising a sodium salt of the compound of Formula (Ia) and glycerol monocaprylocaprate is about 50 mg/ml. In some embodiments, the concentration of the compound of Formula (Ia) in the hard gelatin or soft gelatin capsule comprising a sodium salt of the compound of Formula (Ia) and glycerol monocaprylocaprate is about 75 mg/ml. In some embodiments, the concentration of the compound of Formula (Ia) in the hard gelatin or soft gelatin capsule comprising a sodium salt of the compound of Formula (Ia) and glycerol monocaprylocaprate is about 100 mg/ml. In some embodiments, the concentration of the compound of Formula (Ia) in the hard gelatin or soft gelatin capsule comprising a sodium salt of the compound of Formula (Ia) and glycerol monocaprylocaprate is about 125 mg/ml. In some embodiments, the concentration of the compound of Formula (Ia) in the hard gelatin or soft gelatin capsule comprising a sodium salt of the compound of Formula (Ia) and glycerol monocaprylocaprate is about 150 mg/ml. In some embodiments, the concentration of the compound of Formula (Ia) in the hard gelatin or soft gelatin capsule comprising a sodium salt of the compound of Formula (Ia) and glycerol monocaprylocaprate is about 175 mg/ml. In some embodiments, the concentration of the compound of Formula (Ia) in the hard gelatin or soft gelatin capsule comprising a sodium salt of the compound of Formula (Ia) and glycerol monocaprylocaprate is about 200 mg/ml. In some embodiments, the concentration of the compound of Formula (Ia) in the hard gelatin or soft gelatin capsule comprising a sodium salt of the compound of Formula (Ia) and glycerol monocaprylocaprate is about 225 mg/ml. In some embodiments, the concentration of the compound of Formula (Ia) in the hard gelatin or soft gelatin capsule comprising a sodium salt of the compound of Formula (Ia) and glycerol monocaprylocaprate is about 250 mg/ml. In some embodiments, the concentration of the compound of Formula (Ia) in the hard gelatin or soft gelatin capsule comprising a sodium salt of the compound of Formula (Ia) and glycerol monocaprylocaprate is about 275 mg/ml. In some embodiments, the concentration of the compound of Formula (Ia) in the hard gelatin or soft gelatin capsule comprising a sodium salt of the compound of Formula (Ia) and glycerol monocaprylocaprate is about 300 mg/ml. In some embodiments, the concentration of the compound of Formula (Ia) in the hard gelatin or soft gelatin capsule comprising a sodium salt of the compound of Formula (Ia) and glycerol monocaprylocaprate is about 325 mg/ml. In some embodiments, the concentration of the compound of Formula (Ia) in the hard gelatin or soft gelatin capsule comprising a sodium salt of the compound of Formula (Ia) and glycerol monocaprylocaprate is about 350 mg/ml. In some embodiments, the concentration of the compound of Formula (Ia) in the hard gelatin or soft gelatin capsule comprising a sodium salt of the compound of Formula (Ia) and glycerol monocaprylocaprate is about 375 mg/ml. In some embodiments, the concentration of the compound of Formula (Ia) in the hard gelatin or soft gelatin capsule comprising a sodium salt of the compound of Formula (Ia) and glycerol monocaprylocaprate is about 400 mg/ml. In some embodiments, the concentration of the compound of Formula (Ia) in the hard gelatin or soft gelatin capsule comprising a sodium salt of the compound of Formula (Ia) and glycerol monocaprylocaprate is about 425 mg/ml. In some embodiments, the concentration of the compound of Formula (Ia) in the hard gelatin or soft gelatin capsule comprising a sodium salt of the compound of Formula (Ia) and glycerol monocaprylocaprate is about 450 mg/ml. In some embodiments, the concentration of the compound of Formula (Ia) in the hard gelatin or soft gelatin capsule comprising a sodium salt of the compound of Formula (Ia) and glycerol monocaprylocaprate is about 475 mg/ml. In some embodiments, the concentration of the compound of Formula (Ia) in the hard gelatin or soft gelatin capsule comprising a sodium salt of the compound of Formula (Ia) and glycerol monocaprylocaprate is about 500 mg/ml.

In some embodiments, the amount of glycerol monocaprylocaprate in the hard gelatin or soft gelatin capsule comprising a sodium salt of the compound of Formula (Ia) and glycerol monocaprylocaprate is about 30 w/w % to about 99 w/w %. In some embodiments, the amount of glycerol monocaprylocaprate in the hard gelatin or soft gelatin capsule comprising a sodium salt of the compound of Formula (Ia) and glycerol monocaprylocaprate is about 50 w/w % to about 99 w/w %. In some embodiments, the amount of glycerol monocaprylocaprate in the hard gelatin or soft gelatin capsule comprising a sodium salt of the compound of Formula (Ia) and glycerol monocaprylocaprate is about 60 w/w % to about 99 w/w %. In some embodiments, the amount of glycerol monocaprylocaprate in the hard gelatin or soft gelatin capsule comprising a sodium salt of the compound of Formula (Ia) and glycerol monocaprylocaprate is about 75 w/w % to about 98 w/w %. In some embodiments, the amount of glycerol monocaprylocaprate in the hard gelatin or soft gelatin capsule comprising a sodium salt of the compound of Formula (Ia) and glycerol monocaprylocaprate is about 80.09 w/w % to about 94.85 w/w %. In some embodiments, the amount of glycerol monocaprylocaprate in the hard gelatin or soft gelatin capsule comprising a sodium salt of the compound of Formula (Ia) and glycerol monocaprylocaprate is about 80.1 w/w % to about 94.9 w/w %. In some embodiments, the amount of glycerol monocaprylocaprate in the hard gelatin or soft gelatin capsule comprising a sodium salt of the compound of Formula (Ia) and glycerol monocaprylocaprate is about 80.09 w/w %. In some embodiments, the amount of glycerol monocaprylocaprate in the hard gelatin or soft gelatin capsule comprising a sodium salt of the compound of Formula (Ia) and glycerol monocaprylocaprate is about 80.1 w/w %. In some embodiments, the amount of glycerol monocaprylocaprate in the hard gelatin or soft gelatin capsule comprising a sodium salt of the compound of Formula (Ia) and glycerol monocaprylocaprate is about 94.85 w/w %. In some embodiments, the amount of glycerol monocaprylocaprate in the hard gelatin or soft gelatin capsule comprising a sodium salt of the compound of Formula (Ia) and glycerol monocaprylocaprate is about 94.9 w/w %.

In some embodiments, the amount of the sodium salt of the compound of Formula (Ia) in the hard gelatin or soft gelatin capsule comprising a sodium salt of the compound of Formula (Ia) and glycerol monocaprylocaprate is about 1 w/w % to about 40 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 1 w/w % to about 35 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 2 w/w % to about 30 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 3 w/w % to about 28 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 5.15 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 5.2 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 19.9 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 19.91 w/w %.

In some embodiments, the hard gelatin or soft gelatin capsule comprising a sodium salt of the compound of Formula (Ia) and glycerol monocaprylocaprate further comprises a capsule shell. In some embodiments, the capsule shell comprises one or more pharmaceutically acceptable excipients. In some embodiments, the one or more pharmaceutically acceptable excipients of the capsule shell is selected from the group consisting of a gelatin shell, a plasticizer, an opacifier, and a colorant. In some embodiments, the hard gelatin or soft gelatin capsule comprising a sodium salt of the compound of Formula (Ia) and glycerol monocaprylocaprate further comprises one or more of a pharmaceutically acceptable excipient selected from the group consisting of gelatin, glycerin, titanium dioxide, and iron oxide. In some embodiments, the hard gelatin or soft gelatin capsule comprising a sodium salt of the compound of Formula (Ia) and glycerol monocaprylocaprate further comprises gelatin. In some embodiments, the hard gelatin or soft gelatin capsule comprising a sodium salt of the compound of Formula (Ia) and glycerol monocaprylocaprate further comprises glycerin. In some embodiments, the hard gelatin or soft gelatin capsule comprising a sodium salt of the compound of Formula (Ia) and glycerol monocaprylocaprate further comprises titanium dioxide. In some embodiments, the hard gelatin or soft gelatin capsule comprising a sodium salt of the compound of Formula (Ia) and glycerol monocaprylocaprate further comprises iron oxide. In some embodiments, the hard gelatin or soft gelatin capsule comprising a sodium salt of the compound of Formula (Ia) and glycerol monocaprylocaprate further comprises gelatin and glycerin. In some embodiments, the hard gelatin or soft gelatin capsule comprising a sodium salt of the compound of Formula (Ia) and glycerol monocaprylocaprate further comprises gelatin, glycerin, and titanium dioxide. In some embodiments, the hard gelatin or soft gelatin capsule comprising a sodium salt of the compound of Formula (Ia) and glycerol monocaprylocaprate further comprises gelatin, glycerin, titanium dioxide, and iron oxide. In some embodiments, the iron oxide of the hard gelatin or soft gelatin capsule comprising a sodium salt of the compound of Formula (Ia), glycerol monocaprylocaprate, gelatin, glycerin, titanium dioxide, and iron oxide comprises iron oxide (yellow).

In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 10 w/w % to about 40 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 10 w/w % to about 30 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 15 w/w % to about 25 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 18 w/w % to about 22 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 19.6 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 19.60 w/w %.

In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 3 w/w % to about 25 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 5 w/w % to about 20 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 5 w/w % to about 15 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 8 w/w % to about 12 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 10.8 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 10.80 w/w %.

In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 2 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.05 w/w % to about 1.5 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.1 w/w % to about 1.0 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.1 w/w % to about 0.5 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.2 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.22 w/w %.

In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 1 w/w %. In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 0.5 w/w %. In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 0.15 w/w %. In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 0.1 w/w %. In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.02 w/w %.

In some embodiments, the hard gelatin or soft capsule disclosed herein comprises about 30 w/w % to about 99 w/w % of glycerol monocaprylocaprate and about 1 w/w % to about 40 w/w % of a sodium salt of the compound of Formula (Ia). In some embodiments, the hard gelatin or soft capsule disclosed herein comprises about 50 w/w % to about 99 w/w % of glycerol monocaprylocaprate and about 1 w/w % to about 35 w/w % of a sodium salt of the compound of Formula (Ia). In some embodiments, the hard gelatin or soft capsule disclosed herein comprises about 60 w/w % to about 99 w/w % of glycerol monocaprylocaprate and about 2 w/w % to about 30 w/w % of a sodium salt of the compound of Formula (Ia). In some embodiments, the hard gelatin or soft capsule disclosed herein comprises about 75 w/w % to about 98 w/w % of glycerol monocaprylocaprate and about 3 w/w % to about 28 w/w % of a sodium salt of the compound of Formula (Ia). In some embodiments, the hard gelatin or soft capsule disclosed herein comprises about 80.09 w/w % to about 94.85 w/w % of glycerol monocaprylocaprate and about 5.15 w/w % to about 19.91 w/w % of a sodium salt of the compound of Formula (Ia). In some embodiments, the hard gelatin or soft capsule disclosed herein comprises about 80.1 w/w % to about 94.9 w/w % of glycerol monocaprylocaprate and about 5.2 w/w % to about 19.9 w/w % of a sodium salt of the compound of Formula (Ia). In some embodiments, the hard gelatin or soft capsule disclosed herein comprises about 94.85 w/w % of glycerol monocaprylocaprate and about 5.15 w/w % of a sodium salt of the compound of Formula (Ia). In some embodiments, the hard gelatin or soft capsule disclosed herein comprises about 94.9 w/w % of glycerol monocaprylocaprate and about 5.2 w/w % of a sodium salt of the compound of Formula (Ia). In some embodiments, the hard gelatin or soft capsule disclosed herein comprises about 80.09 w/w % of glycerol monocaprylocaprate and about 19.91 w/w % of a sodium salt of the compound of Formula (Ia). In some embodiments, the hard gelatin or soft capsule disclosed herein comprises about 80.1 w/w % of glycerol monocaprylocaprate and about 19.9 w/w % of a sodium salt of the compound of Formula (Ia).

In some embodiments, the iron oxide in the hard gelatin or soft gelatin capsule comprising a sodium salt of the compound of Formula (Ia), glycerol monocaprylocaprate, gelatin, glycerin, titanium dioxide, and iron oxide comprises iron oxide (yellow).

In some embodiments, the hard gelatin or soft gelatin capsules disclosed herein may be taken with food. In some embodiments, the hard gelatin or soft gelatin capsules disclosed herein exhibit an increase in $C_{max}$ when taken with food (compared to when taken without food). In some embodiments, the hard gelatin or soft gelatin capsules disclosed herein exhibit about a 2-10 fold increase in $C_{max}$ when taken with food (compared to when taken without food). In some embodiments, the hard gelatin or soft gelatin capsules disclosed herein exhibit about a 2-fold increase in $C_{max}$ when taken with food (compared to when taken without food). In some embodiments, the hard gelatin or soft gelatin capsules disclosed herein exhibit about a 3-fold increase in $C_{max}$ when taken with food (compared to when taken without food). In some embodiments, the hard gelatin or soft gelatin capsules disclosed herein exhibit about a 4-fold increase in $C_{max}$ when taken with food (compared to when taken without food). In some embodiments, the hard gelatin or soft gelatin capsules disclosed herein exhibit about a 5-fold increase in $C_{max}$ when taken with food (compared to when taken without food). In some embodiments, the hard gelatin or soft gelatin capsules disclosed herein exhibit about a 6-fold increase in $C_{max}$ when taken with food (compared to when taken without food). In some embodiments, the hard gelatin or soft gelatin capsules disclosed herein exhibit about a 7-fold increase in $C_{max}$ when taken with food (compared to when taken without food). In some embodiments, the hard gelatin or soft gelatin capsules disclosed herein exhibit about a 8-fold increase in $C_{max}$ when taken with food (compared to when taken without food).

In some embodiments, the food taken with the hard gelatin or soft gelatin capsules disclosed herein comprises any food that is ranging from low in fat to high in fat. In some embodiments, the food taken with the hard gelatin or soft gelatin capsules disclosed herein comprises any food that is low in fat. In some embodiments, the food taken with the hard gelatin or soft gelatin capsules disclosed herein comprises any food that is moderate in fat. In some embodiments, the food taken with the hard gelatin or soft gelatin capsules disclosed herein comprises any food that is high in fat. In some embodiments, the food taken with the hard gelatin or soft gelatin capsules disclosed herein is low in fat. In some embodiments, the food taken with the hard gelatin or soft gelatin capsules disclosed herein is moderate in fat.

In some embodiments, the food taken with the hard gelatin or soft gelatin capsules disclosed herein is high in fat.

In some embodiments, the hard gelatin or soft gelatin capsules disclosed herein are hard gelatin capsules. In some embodiments, the hard gelatin or soft gelatin capsules disclosed herein are soft gelatin capsules.

In some embodiments, the oral formulation of a compound of Formula (Ia) or Formula (Ib), or a pharmaceutically acceptable salt thereof, disclosed herein is a tablet prepared from a spray-dried dispersion of a compound of Formula (Ia) or Formula (Ib), or a pharmaceutically acceptable salt thereof. In some embodiments, the amount of a compound of Formula (Ia) or Formula (Ib), or a pharmaceutically acceptable salt thereof, in the tablet disclosed herein is about 5 mg to about 500 mg. In some embodiments, the amount of a compound of Formula (Ia) or Formula (Ib), or a pharmaceutically acceptable salt thereof, in the tablet disclosed herein is about 25 mg to about 500 mg. In some embodiments, the amount of a compound of Formula (Ia) or Formula (Ib), or a pharmaceutically acceptable salt thereof, in the tablet disclosed herein is about 25 mg to about 400 mg. In some embodiments, the amount of a compound of Formula (Ia) or Formula (Ib), or a pharmaceutically acceptable salt thereof, in the tablet disclosed herein is about 25 mg to about 300 mg. In some embodiments, the amount of a compound of Formula (Ia) or Formula (Ib), or a pharmaceutically acceptable salt thereof, in the tablet disclosed herein is about 50 mg to about 500 mg. In some embodiments, the amount of a compound of Formula (Ia) or Formula (Ib), or a pharmaceutically acceptable salt thereof, in the tablet disclosed herein is about 75 mg to about 500 mg. In some embodiments, the amount of a compound of Formula (Ia) or Formula (Ib), or a pharmaceutically acceptable salt thereof, in the tablet disclosed herein is about 50 mg to about 400 mg. In some embodiments, the amount of a compound of Formula (Ia) or Formula (Ib), or a pharmaceutically acceptable salt thereof, in the tablet disclosed herein is about 50 mg to about 300 mg. In some embodiments, the amount of a compound of Formula (Ia) or Formula (Ib), or a pharmaceutically acceptable salt thereof, in the tablet disclosed herein is about 75 mg to about 400 mg. In some embodiments, the amount of a compound of Formula (Ia) or Formula (Ib), or a pharmaceutically acceptable salt thereof, in the tablet disclosed herein is about 75 mg to about 300 mg. In some embodiments, the amount of a compound of Formula (Ia) or Formula (Ib), or a pharmaceutically acceptable salt thereof, in the tablet disclosed herein is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, or about 500 mg. In some embodiments, the amount of a compound of Formula (Ia) or Formula (Ib), or a pharmaceutically acceptable salt thereof, in the tablet disclosed herein is about 5 mg. In some embodiments, the amount of a compound of Formula (Ia) or Formula (Ib), or a pharmaceutically acceptable salt thereof, in the tablet disclosed herein is about 10 mg. In some embodiments, the amount of a compound of Formula (Ia) or Formula (Ib), or a pharmaceutically acceptable salt thereof, in the tablet disclosed herein is about 20 mg. In some embodiments, the amount of a compound of Formula (Ia) or Formula (Ib), or a pharmaceutically acceptable salt thereof, in the tablet disclosed herein is about 25 mg. In some embodiments, the amount of a compound of Formula (Ia) or Formula (Ib), or a pharmaceutically acceptable salt thereof, in the tablet disclosed herein is about 30 mg. In some embodiments, the amount of a compound of Formula (Ia) or Formula (Ib), or a pharmaceutically acceptable salt thereof, in the tablet disclosed herein is about 40 mg. In some embodiments, the amount of a compound of Formula (Ia) or Formula (Ib), or a pharmaceutically acceptable salt thereof, in the tablet disclosed herein is about 50 mg. In some embodiments, the amount of a compound of Formula (Ia) or Formula (Ib), or a pharmaceutically acceptable salt thereof, in the tablet disclosed herein is about 75 mg. In some embodiments, the amount of a compound of Formula (Ia) or Formula (Ib), or a pharmaceutically acceptable salt thereof, in the tablet disclosed herein is about 100 mg. In some embodiments, the amount of a compound of Formula (Ia) or Formula (Ib), or a pharmaceutically acceptable salt thereof, in the tablet disclosed herein is about 125 mg. In some embodiments, the amount of a compound of Formula (Ia) or Formula (Ib), or a pharmaceutically acceptable salt thereof, in the tablet disclosed herein is about 150 mg. In some embodiments, the amount of a compound of Formula (Ia) or Formula (Ib), or a pharmaceutically acceptable salt thereof, in the tablet disclosed herein is about 175 mg. In some embodiments, the amount of a compound of Formula (Ia) or Formula (Ib), or a pharmaceutically acceptable salt thereof, in the tablet disclosed herein is about 200 mg. In some embodiments, the amount of a compound of Formula (Ia) or Formula (Ib), or a pharmaceutically acceptable salt thereof, in the tablet disclosed herein is about 225 mg. In some embodiments, the amount of a compound of Formula (Ia) or Formula (Ib), or a pharmaceutically acceptable salt thereof, in the tablet disclosed herein is about 250 mg. In some embodiments, the amount of a compound of Formula (Ia) or Formula (Ib), or a pharmaceutically acceptable salt thereof, in the tablet disclosed herein is about 275 mg. In some embodiments, the amount of a compound of Formula (Ia) or Formula (Ib), or a pharmaceutically acceptable salt thereof, in the tablet disclosed herein is about 300 mg. In some embodiments, the amount of a compound of Formula (Ia) or Formula (Ib), or a pharmaceutically acceptable salt thereof, in the tablet disclosed herein is about 325 mg. In some embodiments, the amount of a compound of Formula (Ia) or Formula (Ib), or a pharmaceutically acceptable salt thereof, in the tablet disclosed herein is about 350 mg. In some embodiments, the amount of a compound of Formula (Ia) or Formula (Ib), or a pharmaceutically acceptable salt thereof, in the tablet disclosed herein is about 375 mg. In some embodiments, the amount of a compound of Formula (Ia) or Formula (Ib), or a pharmaceutically acceptable salt thereof, in the tablet disclosed herein is about 400 mg. In some embodiments, the amount of a compound of Formula (Ia) or Formula (Ib), or a pharmaceutically acceptable salt thereof, in the tablet disclosed herein is about 425 mg. In some embodiments, the amount of a compound of Formula (Ia) or Formula (Ib), or a pharmaceutically acceptable salt thereof, in the tablet disclosed herein is about 450 mg. In some embodiments, the amount of a compound of Formula (Ia) or Formula (Ib), or a pharmaceutically acceptable salt thereof, in the tablet disclosed herein is about 475 mg. In some embodiments, the amount of a compound of Formula (Ia) or Formula (Ib), or a pharmaceutically acceptable salt thereof, in the tablet disclosed herein is about 500 mg.

In some embodiments, the tablet disclosed herein comprises a compound of Formula (Ia) or Formula (Ib), or a pharmaceutically acceptable salt thereof, and one or more pharmaceutically acceptable excipients. In some embodiments, the tablet disclosed herein comprises a compound of Formula (Ia) or a pharmaceutically acceptable salt thereof, and one or more pharmaceutically acceptable excipients. In some embodiments, the tablet disclosed herein comprises a compound of Formula (Ia) and one or more pharmaceutically acceptable excipients. In some embodiments, the tablet disclosed herein comprises a sodium salt of the compound of Formula (Ia) and one or more pharmaceutically acceptable excipients. In some embodiments, the tablet disclosed herein comprises a compound of Formula (Ib) and one or more pharmaceutically acceptable excipients. In some embodiments, the tablet disclosed herein comprises a trifluoroacetic acid salt of the compound of Formula (Ib) and one or more pharmaceutically acceptable excipients.

The pharmaceutically acceptable excipients of the tablets disclosed herein should be compatible with the other ingredients of the formulation and physiologically innocuous to the recipient thereof. Examples of suitable excipients are well known to the person skilled in the art of tablet formulation and may be found e.g. in *Handbook of Pharmaceutical Excipients* (eds. Rowe, Sheskey & Quinn), 6th edition 2009. As used herein the term "excipients" is intended to refer to inter alia basifying agents, solubilisers, glidants, fillers, binders, lubricant, diluents, preservatives, surface active agents, dispersing agents and the like. The term also includes agents such as sweetening agents, flavoring agents, coloring agents and preserving agents. Such components will generally be present in admixture within the tablet.

Examples of solubilisers include, but are not limited to, surfactants (including both ionic and non-ionic surfactants) such as sodium lauryl sulphate, cetyltrimethylammonium bromide, polysorbates (such as polysorbate 20 or 80), poloxamers (such as poloxamer 188 or 207), and macrogols. Examples of lubricants, glidants and flow aids include, but are not limited to, magnesium stearate, calcium stearate, stearic acid, hydrogenated vegetable oil, glyceryl palmitostearate, glyceryl behenate, sodium stearyl fumarate, colloidal silicon dioxide, and talc. Examples of disintegrants include, but are not limited to, starches, celluloses, cross-linked PVP, sodium starch glycolate, croscarmellose sodium, and the like. Examples of fillers (also known as bulking agents or diluents) include, but are not limited to, starches, maltodextrins, polyols (such as lactose), and celluloses. Examples of binders include, but are not limited to, cross-linked PVP, HPMC, microcrystalline cellulose, sucrose, starches, and the like.

In some embodiments, the tablets disclosed herein comprise a compound of Formula (Ia) or Formula (Ib), or a pharmaceutically acceptable salt thereof, and one or more pharmaceutically acceptable excipients selected from the group consisting of a matrix former, a surfactant, a filler, a disintegrant, and a lubricant. In some embodiments, the tablet comprises about 1 w/w % to about 10 w/w % of a matrix former. In some embodiments, the matrix former comprises copovidone. In some embodiments, the tablet comprises about 0.01 w/w % to about 10 w/w % of a surfactant. In some embodiments, the surfactant comprises poloxamer 407. In some embodiments, the tablet comprises about 25-85 w/w % of one or more fillers. In some embodiments, the one or more fillers comprises microcrystalline cellulose and/or mannitol. In some embodiments, the tablet comprises about 1 w/w % to about 30 w/w % of a disintegrant. In some embodiments, the disintegrant comprises croscarmellose sodium. In some embodiments, the tablet comprises about 0.01 w/w % to about 10 w/w % of a lubricant. In some embodiments, the lubricant comprises magnesium stearate.

The tablets disclosed herein may be uncoated or coated (in which case they include an outer film coat). Although uncoated tablets may be used, it is more usual to provide a coated tablet, in which case a conventional non-enteric coating may be used. Film coatings are known in the art and can be composed of hydrophilic polymer materials, but are not limited to, polysaccharide materials, such as hydroxypropylmethyl cellulose (HPMC), methylcellulose, hydroxyethyl cellulose (HEC), hydroxypropyl cellulose (HPC), poly(vinylalcohol-co-ethylene glycol) and other water soluble polymers. Though the water soluble material included in the film coating of the tablets disclosed herein may include a single polymer material, it may also be formed using a mixture of more than one polymer. The coating may be white or colored. Suitable coatings include, but are not limited to, polymeric film coatings such as those comprising polyvinyl alcohol e.g. 'Opadry® II' (which includes part-hydrolysed PVA, titanium dioxide, macrogol 3350 and talc, with optional colouring such as iron oxide or indigo carmine or iron oxide yellow or FD&C yellow #6). The amount of coating will generally be between about 1-8% of the uncoated tablet's weight.

In some embodiments, the tablet disclosed herein comprises a compound of Formula (Ia) or a pharmaceutically acceptable salt thereof, and one or more pharmaceutically acceptable excipients. In some embodiments, the one or more pharmaceutically acceptable excipients is selected from the group consisting of copovidone, poloxamer 407, microcrystalline cellulose, mannitol, croscarmellose sodium, and magnesium stearate. In some embodiments, the one or more pharmaceutically acceptable excipient comprises copovidone. In some embodiments, the one or more pharmaceutically acceptable excipient comprises poloxamer 407. In some embodiments, the one or more pharmaceutically acceptable excipient comprises microcrystalline cellulose. In some embodiments, the one or more pharmaceutically acceptable excipient comprises mannitol. In some embodiments, the one or more pharmaceutically acceptable excipient comprises croscarmellose sodium. In some embodiments, the one or more pharmaceutically acceptable excipient comprises magnesium stearate. In some embodiments, the one or more pharmaceutically acceptable excipient comprises copovidone and poloxamer 407. In some embodiments, the one or more pharmaceutically acceptable excipient comprises copovidone, poloxamer 407, and microcrystalline cellulose. In some embodiments, the one or more pharmaceutically acceptable excipient comprises copovidone, poloxamer 407, microcrystalline cellulose, and mannitol. In some embodiments, the one or more pharmaceutically acceptable excipient comprises copovidone, poloxamer 407, microcrystalline cellulose, mannitol, and croscarmellose sodium. In some embodiments, the one or more pharmaceutically acceptable excipient comprises copovidone, poloxamer 407, microcrystalline cellulose, mannitol, croscarmellose sodium, and magnesium stearate.

In some embodiments, the tablet disclosed herein comprises a compound of Formula (Ia) or a pharmaceutically acceptable salt thereof, copovidone, poloxamer 407, microcrystalline cellulose, mannitol, croscarmellose sodium, and magnesium stearate. In some embodiments, the tablet disclosed herein comprises a compound of Formula (Ib), or a pharmaceutically acceptable salt thereof, copovidone, poloxamer 407, microcrystalline cellulose, mannitol, croscarmellose sodium, and magnesium stearate. In some embodiments, the tablet disclosed herein comprises a trifluoroacetic acid salt of the compound of Formula (Ib), copovidone, poloxamer 407, microcrystalline cellulose, mannitol, croscarmellose sodium, and magnesium stearate. In some embodiments, the tablet disclosed herein comprises a compound of Formula (Ia), copovidone, poloxamer 407, microcrystalline cellulose, mannitol, croscarmellose sodium, and magnesium stearate. In some embodiments, the tablet disclosed herein comprises a compound of Formula (Ib), copovidone, poloxamer 407, microcrystalline cellulose, mannitol, croscarmellose sodium, and magnesium stearate.

In some embodiments, the tablet disclosed herein comprises a sodium salt of the compound of Formula (Ia), copovidone, poloxamer 407, microcrystalline cellulose, mannitol, croscarmellose sodium, and magnesium stearate. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 5 mg to about 500 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 25 mg to about 500 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 25 mg to about 400 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 25 mg to about 300 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 50 mg to about 300 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 5 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 10 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 20 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 25 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 30 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 40 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 50 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 75 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 100 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 125 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 150 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 175 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 200 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 225 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 250 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 275 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 300 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 325 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 350 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 375 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 400 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 425 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 450 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 475 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 500 mg.

In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 5 w/w % to about 45 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 10 w/w % to about 40 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 15 w/w % to about 35 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 15 w/w % to about 25 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 20.46 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 20.5 w/w %.

In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 1 w/w % to about 10 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 2 w/w % to about 10 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 3 w/w % to about 8 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 3 w/w % to about 6 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 4.88 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 4.9 w/w %.

In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 0.01 w/w % to about 10 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 0.05 w/w % to about 8 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 0.5 w/w % to about 4 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 0.5 w/w % to about 3.0 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 1.3 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 1.33 w/w %.

In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 5 w/w % to about 45 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 10 w/w % to about 40 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 15 w/w % to about 35 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 18 w/w % to about 30 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 21.28 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 21.3 w/w %.

In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 15 w/w % to about 70 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 20 w/w % to about 60 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 30 w/w % to about 55 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 40 w/w % to about 50 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 42.55 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 42.6 w/w %.

In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 1 w/w % to about 30 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 1 w/w % to about 20 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 4 w/w % to about 16 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 6 w/w % to about 10 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 8.0 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 8.00 w/w %.

In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 0.01 w/w % to about 10 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 0.05 w/w % to about 8 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 0.5 w/w % to about 4 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 1.0 w/w % to about 3.0 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 1.5 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 1.50 w/w %.

In some embodiments, the tablet disclosed herein comprises about 5 w/w % to about 45 w/w % of a sodium salt of the compound of Formula (Ia), about 1 w/w % to about 10 w/w % of copovidone, about 0.01 w/w % to about 10 w/w % of poloxamer 407, about 5 w/w % to about 45 w/w % of microcrystalline cellulose, about 15 w/w % to about 70 w/w % of mannitol, about 1 w/w % to about 30 w/w % of croscarmellose sodium, and about 0.01 w/w % to about 10 w/w % of magnesium stearate. In some embodiments, the tablet disclosed herein comprises about 10 w/w % to about 40 w/w % of a sodium salt of the compound of Formula (Ia), about 2 w/w % to about 10 w/w % of copovidone, about 0.05 w/w % to about 8 w/w % of poloxamer 407, about 10 w/w % to about 40 w/w % of microcrystalline cellulose, about 20 w/w % to about 60 w/w % of mannitol, about 1 w/w % to about 20 w/w % of croscarmellose sodium, and about 0.05 w/w % to about 8 w/w % of magnesium stearate. In some embodiments, the tablet disclosed herein comprises about 15 w/w % to about 35 w/w % of a sodium salt of the compound of Formula (Ia), about 3 w/w % to about 8 w/w % of copovidone, about 0.5 w/w % to about 4 w/w % of poloxamer 407, about 15 w/w % to about 35 w/w % of microcrystalline cellulose, about 30 w/w % to about 55 w/w % of mannitol, about 4 w/w % to about 16 w/w % of croscarmellose sodium, and about 0.5 w/w % to about 4 w/w % of magnesium stearate. In some embodiments, the tablet disclosed herein comprises about 15 w/w % to about 25 w/w % of a sodium salt of the compound of Formula (Ia), about 3 w/w % to about 6 w/w % of copovidone, about 0.5 w/w % to about 3.0 w/w % of poloxamer 407, about 18 w/w % to about 30 w/w % of microcrystalline cellulose, about 40 w/w % to about 50 w/w % of mannitol, about 6 w/w % to about 10 w/w % of croscarmellose sodium, and about 1.0 w/w % to about 3.0 w/w % of magnesium stearate. In some embodiments, the tablet disclosed herein comprises about 20.5 w/w % of a sodium salt of the compound of Formula (Ia), about 4.9 w/w % of copovidone, about 1.3 w/w % of poloxamer 407, about 21.3 w/w % of microcrystalline cellulose, about 42.6 w/w % of mannitol, about 8.0 w/w % of croscarmellose sodium, and about 1.5 w/w % of magnesium stearate. In some embodiments, the tablet disclosed herein comprises about 20.46 w/w % of a sodium salt of the compound of Formula (Ia), about 4.88 w/w % of copovidone, about 1.33 w/w % of poloxamer 407, about 21.28 w/w % of microcrystalline cellulose, about 42.55 w/w % of mannitol, about 8.00 w/w % of croscarmellose sodium, and about 1.50 w/w % of magnesium stearate.

In some embodiments, the tablet disclosed herein further comprises an outer film coat. In some embodiments, the tablet comprising a sodium salt of the compound of Formula (Ia), copovidone, poloxamer 407, microcrystalline cellulose, mannitol, croscarmellose sodium, and magnesium stearate further comprises an outer film coat. In some embodiments, the outer film coat provides from about 1% to about 8% weight gain based on the uncoated tablet. In some embodiments, the outer film coat provides from about 2% to about 6% weight gain based on the uncoated tablet. In some embodiments, the outer film coat provides from about 2% to about 4% weight gain based on the uncoated tablet. In some embodiments, the outer film coat provides from about 4% to about 6% weight gain based on the uncoated tablet. In some embodiments, the outer film coat provides about 1%, about 2%, about 3%, about 4%, about 5%, about 6%, about 7%, or about 8% weight gain based on the uncoated tablet. In some embodiments, the outer film coat provides about 1% weight gain based on the uncoated tablet. In some embodiments, the outer film coat provides about 2% weight gain based on the uncoated tablet. In some embodiments, the outer film coat provides about 3% weight gain based on the uncoated tablet. In some embodiments, the outer film coat provides about 4% weight gain based on the uncoated tablet. In some embodiments, the outer film coat provides about 5% weight gain based on the uncoated tablet. In some embodiments, the outer film coat provides about 6% weight gain based on the uncoated tablet. In some embodiments, the outer film coat provides about 7% weight gain based on the uncoated tablet. In some embodiments, the outer film coat provides about 8% weight gain based on the uncoated tablet. In some embodiments, the outer film coat comprises Opadry® II. In some embodiments, the outer film coat comprises Opadry® II White. In some embodiments, the outer film coat comprises Opadry® II White 85F18422.

In some embodiments, the tablets disclosed herein may be taken with food. In some embodiments, the tablets disclosed herein exhibit an increase in $C_{max}$ when taken with food (compared to when taken without food). In some embodiments, the tablets disclosed herein exhibit about a 2-10 fold increase in $C_{max}$ when taken with food (compared to when taken without food). In some embodiments, the tablets disclosed herein exhibit about a 2-fold increase in $C_{max}$ when taken with food (compared to when taken without food). In some embodiments, the tablets disclosed herein exhibit about a 3-fold increase in $C_{max}$ when taken with food (compared to when taken without food). In some embodiments, the tablets disclosed herein exhibit about a 4-fold increase in $C_{max}$ when taken with food (compared to when taken without food). In some embodiments, the tablets disclosed herein exhibit about a 5-fold increase in $C_{max}$ when taken with food (compared to when taken without food). In some embodiments, the tablets disclosed herein exhibit about a 6-fold increase in $C_{max}$ when taken with food (compared to when taken without food). In some embodiments, the tablets disclosed herein exhibit about a 7-fold increase in $C_{max}$ when taken with food (compared to when taken without food). In some embodiments, the tablets disclosed herein exhibit about a 8-fold increase in $C_{max}$ when taken with food (compared to when taken without food).

In some embodiments, the food taken with the tablets disclosed herein comprises any food that is ranging from low in fat to high in fat. In some embodiments, the food taken with the tablets disclosed herein comprises any food that is low in fat. In some embodiments, the food taken with the tablets disclosed herein comprises any food that is moderate in fat. In some embodiments, the food taken with the tablets disclosed herein comprises any food that is high in fat. In some embodiments, the food taken with the tablets disclosed herein is low in fat. In some embodiments, the food taken with the tablets disclosed herein is moderate in fat. In some embodiments, the food taken with the tablets disclosed herein is high in fat.

The amount of active ingredient that can be combined with the inactive ingredients to produce a dosage form can vary depending upon the intended treatment patient and the particular mode of administration. For example, in some embodiments, a dosage form for oral administration to humans can contain approximately 1 mg to about 1000 mg of active material formulated with an appropriate and convenient amount of carrier material (for example, inactive ingredient or excipient material). In certain embodiments, the carrier material varies from about 5% to about 95% of the total weight of the composition.

It should be understood that in addition to the ingredients particularly mentioned above, the compositions of these embodiments can include other agents conventional in the art having regard to the type of composition in question. For example, those suitable for oral administration can include flavoring agents.

In certain embodiments, a composition comprising an active ingredient disclosed herein (for example, a compound of Formula (Ia) or Formula (Ib), or a pharmaceutically acceptable salt thereof) in one variation does not contain an agent that affects the rate at which the active ingredient is metabolized. Thus, it is understood that compositions containing a compound of Formula (Ia) or Formula (Ib), or a pharmaceutically acceptable salt thereof, in certain embodiments do not comprise an agent that would affect (for example, slow, hinder, or retard) the metabolism of a compound of Formula (Ia) or Formula (Ib), or a pharmaceutically acceptable salt thereof, or any other active ingredient administered separately, sequentially, or simultaneously with a compound of Formula (Ia) or Formula (Ib), or a pharmaceutically acceptable salt thereof. It is also understood that any of the methods, kits, articles of manufacture and the like detailed herein in certain embodiments do not contain an agent that would affect (for example, slow, hinder, or retard) the metabolism of a compound of Formula (Ia) or Formula (Ib), or a pharmaceutically acceptable salt thereof, or any other active ingredient administered separately, sequentially, or simultaneously with a compound of any one of Formula (Ia) or Formula (Ib), or a pharmaceutically acceptable salt thereof.

In one aspect, disclosed herein are methods for preparing the suspensions, solutions, hard gelatin or soft gelatin capsules, and tablets disclosed herein. Methods of preparing suspensions, solutions, hard gelatin or soft gelatin capsules, and tablets (prepared from spray-dried dispersion technology) are well known in the art.

In some embodiments, the solutions disclosed herein may be prepared by mixing the individual ingredients together and heating the resulting mixture.

In some embodiments, the hard gelatin or soft gelatin capsules disclosed herein may be prepared by mixing the individual ingredients together and homogenizing the mixture. The homogenized mixture may be deaerated, heated, and then dispensed into gelatin capsules while being heated.

In some embodiments, the tablets disclosed herein may be prepared by mixing the compound of Formula (Ia) or Formula (Ib), or a pharmaceutically acceptable salt thereof, with one or more pharmaceutically acceptable excipients and spray drying the mixture into a powder, which is then dried. The dried powder may be combined with one or more additional pharmaceutically acceptable excipients. The resulting mixture may be milled and compressed into tablets.

Routes of Administration

The compound of the Formula (Ia) or Formula (Ib), or a pharmaceutically acceptable salt thereof, can be administered by any route appropriate to the condition to be treated. Suitable routes include oral, rectal, nasal, topical (including buccal and sublingual), transdermal, vaginal, and parenteral (including subcutaneous, intramuscular, intravenous, intradermal, intrathecal and epidural), and the like. It will be appreciated that the preferred route can vary with, for example, the condition of the recipient. In certain embodiments, the compounds disclosed are dosed parenterally. In certain embodiments, the compounds disclosed are dosed intravenously, subcutaneously, or intramuscularly. In some embodiments, the compound of Formula (Ia) or Formula (Ib), or a pharmaceutically acceptable salt thereof, is administered subcutaneously. In some embodiments, the compound of Formula (Ia) or Formula (Ib), or a pharmaceutically acceptable salt thereof, is administered intravenously. In some embodiments, the compound of Formula (Ia) or Formula (Ib), or a pharmaceutically acceptable salt thereof, is administered intramuscularly. In some embodiments, the compound of Formula (Ia) or Formula (Ib), or a pharmaceutically acceptable salt thereof, is administered orally.

In some embodiments, the compound of the Formula (Ia) or Formula (Ib), or a pharmaceutically acceptable salt thereof, is administered via injection, using an injection device. In some embodiments, the injection device is or includes a syringe, which can be employed manually, or as part of a syringe-containing injection device. A wide variety of injection devices can be used, including, but not limited to, a handheld or wearable autoinjector, a handheld or wearable manual injector, an on-body injector, a syrette, a jet injector, or a pen injector, each of which can be reusable or disposable.

In some embodiments, the compound of Formula (Ia) or Formula (Ib), or a pharmaceutically acceptable salt thereof, can be administered with a syringe suitable for administration of the compound. In some embodiments, the syringe is disposable. In some embodiments, the syringe is reusable. In some embodiments, the syringe is pre-filled with the compound of Formula (Ia) or Formula (Ib), or a pharmaceutically acceptable salt thereof.

In some embodiments, the compound of Formula (Ia) or Formula (Ib), or a pharmaceutically acceptable salt thereof, can be administered with an auto-injector comprising a syringe. In some embodiments, the syringe is disposable. In some embodiments, the syringe is reusable. In some embodiments, the syringe is pre-filled with the compound of Formula (Ia) or Formula (Ib), or a pharmaceutically acceptable salt thereof.

In some embodiments, the compound of Formula (Ia) or Formula (Ib), or a pharmaceutically acceptable salt thereof, is formulated for subcutaneous administration. In some embodiments, the compound of Formula (Ia) or Formula (Ib), or a pharmaceutically acceptable salt thereof, is formulated as a solution or suspension. In some embodiments, the compound of Formula (Ia) or Formula (Ib), or a pharmaceutically acceptable salt thereof, is formulated as a solution for subcutaneous administration. In some embodiments, the compound of Formula (Ia) or Formula (Ib), or a pharmaceutically acceptable salt thereof, is formulated as a suspension for subcutaneous administration. In some embodiments, the compound of Formula (Ia) or Formula (Ib), or a pharmaceutically acceptable salt thereof, is formulated at a concentration of about 50 mg/mL to about 500 mg/mL, such as about 50 mg/mL to about 400 mg/mL, about 50 mg/mL to about 300 mg/mL, about 50 mg/mL to about 200 mg/mL, about 50 mg/mL to about 150 mg/mL, about 50 mg/mL to about 100 mg/mL, about 100 mg/mL to about 500 mg/mL, about 100 mg/mL to about 400 mg/mL, about 100 mg/mL to about 300 mg/mL, about 100 mg/mL to about 200 mg/mL, about 200 mg/mL to about 500 mg/mL, about 200 mg/mL to about 400 mg/mL, about 200 mg/mL to about 300 mg/mL, about 300 mg/mL to about 500 mg/mL, about 300 mg/mL to about 400 mg/mL, or about 400 mg/mL to about 500 mg/mL, or about 50 mg/mL, about 100 mg/mL, about 150 mg/mL, about 200 mg/mL, about 300 mg/mL, about 400 mg/mL, or about 500 mg/mL. In some embodiments, the compound of Formula (Ia) or Formula (Ib), or a pharmaceutically acceptable salt thereof, is formulated at a concentration of about 100 mg/mL. In some embodiments, the compound of Formula (Ia) or Formula (Ib), or a pharmaceutically acceptable salt thereof, is formulated at a concentration of about 150 mg/mL. In some embodiments, the compound of Formula (Ia) or Formula (Ib), or a pharmaceutically acceptable salt thereof, is formulated at a concentration of about 300 mg/mL.

In some embodiments, the compound of Formula (Ia) or Formula (Ib), or a pharmaceutically acceptable salt thereof, is formulated at a concentration of about 50 mg/mL. In some embodiments, the compound of Formula (Ia) or Formula (Ib), or a pharmaceutically acceptable salt thereof, is formulated at a concentration of about 75 mg/mL. In some embodiments, the compound of Formula (Ia) or Formula (Ib), or a pharmaceutically acceptable salt thereof, is formulated at a concentration of about 125 mg/mL. In some embodiments, the compound of Formula (Ia) or Formula (Ib), or a pharmaceutically acceptable salt thereof, is formulated at a concentration of about 175 mg/mL. In some embodiments, the compound of Formula (Ia) or Formula (Ib), or a pharmaceutically acceptable salt thereof, is formulated at a concentration of about 200 mg/mL. In some embodiments, the compound of Formula (Ia) or Formula (Ib), or a pharmaceutically acceptable salt thereof, is formulated at a concentration of about 225 mg/mL. In some embodiments, the compound of Formula (Ia) or Formula (Ib), or a pharmaceutically acceptable salt thereof, is formulated at a concentration of about 250 mg/mL. In some embodiments, the compound of Formula (Ia) or Formula (Ib), or a pharmaceutically acceptable salt thereof, is formulated at a concentration of about 275 mg/mL. In some embodiments, the compound of Formula (Ia) or Formula (Ib), or a pharmaceutically acceptable salt thereof, is formulated at a concentration of about 325 mg/mL. In some embodiments, the compound of Formula (Ia) or Formula (Ib), or a pharmaceutically acceptable salt thereof, is formulated at a concentration of about 350 mg/mL. In some embodiments, the compound of Formula (Ia) or Formula (Ib), or a pharmaceutically acceptable salt thereof, is formulated at a concentration of about 375 mg/mL. In some embodiments, the compound of Formula (Ia) or Formula (Ib), or a pharmaceutically acceptable salt thereof, is formulated at a concentration of about 400 mg/mL. In some embodiments, the compound of Formula (Ia) or Formula (Ib), or a pharmaceutically acceptable salt thereof, is formulated at a concentration of about 425 mg/mL. In some embodiments, the compound of Formula (Ia) or Formula (Ib), or a pharmaceutically acceptable salt thereof, is formulated at a concentration of about 450 mg/mL. In some embodiments, the compound of Formula (Ia) or Formula (Ib), or a pharmaceutically acceptable salt thereof, is formulated at a concentration of about 475 mg/mL. In some embodiments, the compound of Formula (Ia) or Formula (Ib), or a pharmaceutically acceptable salt thereof, is formulated at a concentration of about 500 mg/mL.

In some embodiments, the compound of Formula (Ia) or Formula (Ib), or a pharmaceutically acceptable salt thereof, is formulated for oral administration. In some embodiments, the compound of Formula (Ia) or Formula (Ib), or a pharmaceutically acceptable salt thereof, is formulated as a hard gelatin capsule. In some embodiments, the compound of Formula (Ia) or Formula (Ib), or a pharmaceutically acceptable salt thereof, is formulated as a soft gelatin capsule. In some embodiments, the compound of Formula (Ia) or Formula (Ib), or a pharmaceutically acceptable salt thereof, is formulated as a hard gelatin capsule for oral administration. In some embodiments, the compound of Formula (Ia) or Formula (Ib), or a pharmaceutically acceptable salt thereof, is formulated as a soft gelatin capsule for oral administration. In some embodiments, the compound of Formula (Ia) or Formula (Ib), or a pharmaceutically acceptable salt thereof, is formulated at a concentration of about 20 mg/mL to about 100 mg/mL, such as about 20 mg/mL to about 75 mg/mL, about 20 mg/mL to about 50 mg/mL, about 20 mg/mL to about 30 mg/mL, about 30 mg/mL to about 100 mg/mL, about 30 mg/mL to about 75 mg/mL, about 30 mg/mL to about 50 mg/mL, about 50 mg/mL to about 100 mg/mL, about 50 mg/mL to about 75 mg/mL, or about 75 mg/mL to about 100 mg/mL, or about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL. In some embodiments, the compound of Formula (Ia) or Formula (Ib), or a pharmaceutically acceptable salt thereof, is formulated for oral administration at a concentration of about 30 mg/mL. In some embodiments, the compound of Formula (Ia) or Formula (Ib), or a pharmaceutically acceptable salt thereof, is formulated for oral administration at a concentration of about 50 mg/mL.

In some embodiments, the compound of Formula (Ia) or Formula (Ib), or a pharmaceutically acceptable salt thereof, is formulated for oral administration at a concentration of about 10 mg/ml to about 500 mg/mL.

In some embodiments, the compound of Formula (Ia) or Formula (Ib), or a pharmaceutically acceptable salt thereof, is formulated for oral administration at a concentration of about 10 mg/mL. In some embodiments, the compound of Formula (Ia) or Formula (Ib), or a pharmaceutically acceptable salt thereof, is formulated for oral administration at a concentration of about 25 mg/mL. In some embodiments, the compound of Formula (Ia) or Formula (Ib), or a pharmaceutically acceptable salt thereof, is formulated for oral administration at a concentration of about 75 mg/mL. In some embodiments, the compound of Formula (Ia) or Formula (Ib), or a pharmaceutically acceptable salt thereof, is formulated for oral administration at a concentration of about 100 mg/mL. In some embodiments, the compound of Formula (Ia) or Formula (Ib), or a pharmaceutically acceptable salt thereof, is formulated for oral administration at a concentration of about 125 mg/mL. In some embodiments, the compound of Formula (Ia) or Formula (Ib), or a pharmaceutically acceptable salt thereof, is formulated for oral administration at a concentration of about 150 mg/mL. In some embodiments, the compound of Formula (Ia) or Formula (Ib), or a pharmaceutically acceptable salt thereof, is formulated for oral administration at a concentration of about 175 mg/mL. In some embodiments, the compound of Formula (Ia) or Formula (Ib), or a pharmaceutically acceptable salt thereof, is formulated for oral administration at a concentration of about 200 mg/mL. In some embodiments, the compound of Formula (Ia) or Formula (Ib), or a pharmaceutically acceptable salt thereof, is formulated for oral administration at a concentration of about 225 mg/mL. In some embodiments, the compound of Formula (Ia) or Formula (Ib), or a pharmaceutically acceptable salt thereof, is formulated for oral administration at a concentration of about 250 mg/mL. In some embodiments, the compound of Formula (Ia) or Formula (Ib), or a pharmaceutically acceptable salt thereof, is formulated for oral administration at a concentration of about 275 mg/mL. In some embodiments, the compound of Formula (Ia) or Formula (Ib), or a pharmaceutically acceptable salt thereof, is formulated for oral administration at a concentration of about 300 mg/mL. In some embodiments, the compound of Formula (Ia) or Formula (Ib), or a pharmaceutically acceptable salt thereof, is formulated for oral administration at a concentration of about 325 mg/mL. In some embodiments, the compound of Formula (Ia) or Formula (Ib), or a pharmaceutically acceptable salt thereof, is formulated for oral administration at a concentration of about 350 mg/mL. In some embodiments, the compound of Formula (Ia) or Formula (Ib), or a pharmaceutically acceptable salt thereof, is formulated for oral administration at a concentration of about 375 mg/mL. In some embodiments, the compound of Formula (Ia) or Formula (Ib), or a pharmaceutically acceptable salt thereof, is formulated for oral administration at a concentration of about 400 mg/mL. In some embodiments, the compound of Formula (Ia) or Formula (Ib), or a pharmaceutically acceptable salt thereof, is formulated for oral administration at a concentration of about 425 mg/mL. In some embodiments, the compound of Formula (Ia) or Formula (Ib), or a pharmaceutically acceptable salt thereof, is formulated for oral administration at a concentration of about 450 mg/mL. In some embodiments, the compound of Formula (Ia) or Formula (Ib), or a pharmaceutically acceptable salt thereof, is formulated for oral administration at a concentration of about 475 mg/mL. In some embodiments, the compound of Formula (Ia) or Formula (Ib), or a pharmaceutically acceptable salt thereof, is formulated for oral administration at a concentration of about 500 mg/mL.

Dosing Regimen

In some embodiments, the compound of Formula (Ia) or Formula (Ib), or a pharmaceutically acceptable salt thereof, is administered to a patient in accordance with an effective dosing regimen for a desired period of time or duration. In some embodiments, the dosing regimen includes administration of the compound of Formula (Ia) or Formula (Ib), or a pharmaceutically acceptable salt thereof, for at least about 1 week, about 2 weeks, about 4 weeks, about 8 weeks, about 12 weeks, about 16 weeks, about 20 weeks, about 24 weeks, or about 48 weeks, or longer.

In some embodiments, the dosing regimen includes administration of the compound of Formula (Ia) or Formula (Ib), or a pharmaceutically acceptable salt thereof, for at least about 1 year, 2 years, 3 years, 4 years, 5 years, 10 years, or longer. In some embodiments, the dosing regimen includes a permanent administration of the compound of Formula (Ia) or Formula (Ib), or a pharmaceutically acceptable salt thereof.

In some embodiments, the compound of Formula (Ia) or Formula (Ib), or a pharmaceutically acceptable salt thereof, is administered on a daily or intermittent schedule. In some embodiments, the compound of Formula (Ia) or Formula (Ib), or a pharmaceutically acceptable salt thereof, is administered once daily. In some embodiments, the compound of Formula (Ia) or Formula (Ib), or a pharmaceutically acceptable salt thereof, is administered on a monthly schedule. In some embodiments, the compound of Formula (Ia) or Formula (Ib), or a pharmaceutically acceptable salt thereof, is administered once about every 1 week, about every 2 weeks, about every 4 weeks, about every 8 weeks, about every 12 weeks, about every 16 weeks, about every 20 weeks, about every 24 weeks, or once about every 48 weeks. In some embodiments, the compound of Formula (Ia) or Formula (Ib), or a pharmaceutically acceptable salt thereof, is administered once every 4 weeks (or monthly). In some embodiments, the compound of Formula (Ia) or Formula (Ib), or a pharmaceutically acceptable salt thereof, is administered once every 8 weeks (or 2 months). In some embodiments, the compound of Formula (Ia) or Formula (Ib), or a pharmaceutically acceptable salt thereof, is administered once every 12 weeks (or three months). In some embodiments, the compound of Formula (Ia) or Formula (Ib), or a pharmaceutically acceptable salt thereof, is administered once every 16 weeks (or four months). In some embodiments, the compound of Formula (Ia) or Formula (Ib), or a pharmaceutically acceptable salt thereof, is administered once every 20 weeks (or five months). In some embodiments, the compound of Formula (Ia) or Formula (Ib), or a pharmaceutically acceptable salt thereof, is administered every 24 weeks (or 6 months). In some embodiments, the compound of Formula (Ia) or Formula (Ib), or a pharmaceutically acceptable salt thereof, is administered every 52 weeks (or yearly).

In some embodiments, the compound of Formula (Ia) or Formula (Ib), or a pharmaceutically acceptable salt thereof, is subcutaneously administered to a patient for at least about one month. In some embodiments, the compound of Formula (Ia) or Formula (Ib), or a pharmaceutically acceptable salt thereof, is subcutaneously or intramuscularly administered to a patient for at least about 2 months, at least about 3 months, at least about 4 months, or at least about 6 months. In some embodiments, the compound of Formula (Ia) or Formula (Ib), or a pharmaceutically acceptable salt thereof, is subcutaneously administered to a patient once about every month. In some embodiments, the compound of Formula (Ia) or Formula (Ib), or a pharmaceutically acceptable salt thereof, is subcutaneously or intramuscularly administered to a patient once about every 3 months. In some embodiments, the compound of Formula (Ia) or Formula (Ib), or a pharmaceutically acceptable salt thereof, is subcutaneously or intramuscularly administered to a patient once about every 6 months.

In some embodiments, the compound of Formula (Ia) or Formula (Ib), or a pharmaceutically acceptable salt thereof, is intramuscularly administered to a patient once about every month. In some embodiments, the compound of Formula (Ia) or Formula (Ib), or a pharmaceutically acceptable salt thereof, is subcutaneously administered to a patient once about every 3 months. In some embodiments, the compound of Formula (Ia) or Formula (Ib), or a pharmaceutically acceptable salt thereof, is intramuscularly administered to a patient once about every 3 months. In some embodiments, the compound of Formula (Ia) or Formula (Ib), or a pharmaceutically acceptable salt thereof, is subcutaneously administered to a patient once about every 6 months. In some embodiments, the compound of Formula (Ia) or Formula (Ib), or a pharmaceutically acceptable salt thereof, is intramuscularly administered to a patient once about every 6 months. In some embodiments, the compound of Formula (Ia) or Formula (Ib), or a pharmaceutically acceptable salt thereof, is subcutaneously administered to a patient once about every year. In some embodiments, the compound of Formula (Ia) or Formula (Ib), or a pharmaceutically acceptable salt thereof, is intramuscularly administered to a patient once about every year.

In some embodiments, the compound of Formula (Ia) or Formula (Ib), or a pharmaceutically acceptable salt thereof, is orally administered to a patient once daily. In some embodiments, the compound of Formula (Ia) or Formula (Ib), or a pharmaceutically acceptable salt thereof, is orally administered to a patient once about every 1 week, about every 2 weeks, about every 4 weeks, about every 8 weeks, about every 12 weeks, about every 16 weeks, about every 20 weeks, about every 24 weeks, about every 48 weeks, or about every year. In some embodiments, the compound of Formula (Ia) or Formula (Ib), or a pharmaceutically acceptable salt thereof, is orally administered to a patient once about every 1 week. In some embodiments, the compound of Formula (Ia) or Formula (Ib), or a pharmaceutically acceptable salt thereof, is orally administered to a patient once about every month. In some embodiments, the compound of Formula (Ia) or Formula (Ib), or a pharmaceutically acceptable salt thereof, is orally administered to a patient once about every 3 months. In some embodiments, the compound of Formula (Ia) or Formula (Ib), or a pharmaceutically acceptable salt thereof, is orally administered to a patient once about every 6 months. In some embodiments, the compound of Formula (Ia) or Formula (Ib), or a pharmaceutically acceptable salt thereof, is orally administered to a patient once about every year.

The dosage or dosing frequency of a compound of Formula (Ia) or Formula (Ib), or a pharmaceutically acceptable salt thereof, can be adjusted over the course of the treatment, based on the judgment of the administering physician.

In some embodiments, the compound of Formula (Ia) or Formula (Ib), or a pharmaceutically acceptable salt thereof, is administered to a patient (for example, a human) in a therapeutically effective amount. In some embodiments, the compound of Formula (Ia) or Formula (Ib), or a pharmaceutically acceptable salt thereof, is administered once daily. In some embodiments, the compound of Formula (Ia) or Formula (Ib), or a pharmaceutically acceptable salt thereof, is administered monthly. In some embodiments, the compound of Formula (Ia) or Formula (Ib), or a pharmaceutically acceptable salt thereof, is administered every two months. In some embodiments, the compound of Formula (Ia) or Formula (Ib), or a pharmaceutically acceptable salt thereof, is administered every three months. In some embodiments, the compound of Formula (Ia) or Formula (Ib), or a pharmaceutically acceptable salt thereof, is administered every four months. In some embodiments, the compound of Formula (Ia) or Formula (Ib), or a pharmaceutically acceptable salt thereof, is administered every six months. In some embodiments, the compound of Formula (Ia) or Formula (Ib), or a pharmaceutically acceptable salt thereof, is administered yearly.

In some embodiments, the compound of Formula (Ia) or Formula (Ib), or a pharmaceutically acceptable salt thereof, is administered in a dosage amount that is effective. In some embodiments, the dosage is from about 1 mg to about 1000 mg of the compound of Formula (Ia) or Formula (Ib), or a pharmaceutically acceptable salt thereof. In certain embodiments, the dosage amount is about 1 mg, about 10 mg, about 20 mg, about 30 mg, about 40 mg, about 50 mg, about 60 mg, about 70 mg, about 80 mg, about 90 mg, about 95 mg, about 100 mg, about 105 mg, about 110 mg, about 120 mg, about 130 mg, about 140 mg, or about 150 mg of the compound of Formula (Ia) or Formula (Ib), or a pharmaceutically acceptable salt thereof. In certain embodiments, the dosage amount is about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg of the compound of Formula (Ia) or Formula (Ib), or a pharmaceutically acceptable salt thereof.

In certain embodiments, the dosage amount is about 1 mg, about 5 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 2000 mg, about 2050 mg, or about 3000 mg of the compound of Formula (Ia) or Formula (Ib), or a pharmaceutically acceptable salt thereof.

In some embodiments, the dosage amount of the compound of Formula (Ia) or Formula (Ib), or a pharmaceutically acceptable salt thereof, is about 1 mg to about 2500 mg. In some embodiments, the dosage amount of the compound of Formula (Ia) or Formula (Ib), or a pharmaceutically acceptable salt thereof, is about 5 mg to about 2400 mg. In some embodiments, the dosage amount of the compound of Formula (Ia) or Formula (Ib), or a pharmaceutically acceptable salt thereof, is about 5 mg to about 2000 mg. In some embodiments, the dosage amount of the compound of Formula (Ia) or Formula (Ib), or a pharmaceutically acceptable salt thereof, is about 5 mg to about 1500 mg. In some embodiments, the dosage amount of the compound of Formula (Ia) or Formula (Ib), or a pharmaceutically acceptable salt thereof, is about 5 mg to about 1200 mg. In some embodiments, the dosage amount of the compound of Formula (Ia) or Formula (Ib), or a pharmaceutically acceptable salt thereof, is about 5 mg to about 1000 mg. In some embodiments, the dosage amount of the compound of Formula (Ia) or Formula (Ib), or a pharmaceutically acceptable salt thereof, is about 5 mg to about 500 mg. In some embodiments, the dosage amount of the compound of Formula (Ia) or Formula (Ib), or a pharmaceutically acceptable salt thereof, is about 5 mg to about 300 mg. In some embodiments, the dosage amount of the compound of Formula (Ia) or Formula (Ib), or a pharmaceutically acceptable salt thereof, is about 5 mg to about 200 mg. In some embodiments, the dosage amount of the compound of Formula (Ia) or Formula (Ib), or a pharmaceutically acceptable salt thereof, is about 5 mg to about 100 mg. In some embodiments, the dosage amount of the compound of Formula (Ia) or Formula (Ib), or a pharmaceutically acceptable salt thereof, is about 5 mg to about 50 mg.

In some embodiments, the compound of Formula (Ia) or Formula (Ib), or a pharmaceutically acceptable salt thereof, is administered in a once daily dose of about 1 mg to about 1500 mg. In some embodiments, the compound of Formula (Ia) or Formula (Ib), or a pharmaceutically acceptable salt thereof, is administered in a once daily dose of about 5 mg to about 1200 mg. In some embodiments, the compound of Formula (Ia) or Formula (Ib), or a pharmaceutically acceptable salt thereof, is administered in a once daily dose of about 100 mg to about 1200 mg. In some embodiments, the compound of Formula (Ia) or Formula (Ib), or a pharmaceutically acceptable salt thereof, is administered in a once daily dose of about 200 mg to about 1200 mg. In some embodiments, the compound of Formula (Ia) or Formula (Ib), or a pharmaceutically acceptable salt thereof, is administered in a once daily dose of about 300 mg to about 1200 mg. In some embodiments, the compound of Formula (Ia) or Formula (Ib), or a pharmaceutically acceptable salt thereof, is administered in a once daily dose of about 500 mg to about 1200 mg.

In some embodiments, the compound of Formula (Ia) or Formula (Ib), or a pharmaceutically acceptable salt thereof, is administered in a once daily dose of about 1 mg to about 200 mg. In some embodiments, the compound of Formula (Ia) or Formula (Ib), or a pharmaceutically acceptable salt thereof, is administered in a once daily dose of about 5 mg to about 200 mg. In some embodiments, the compound of Formula (Ia) or Formula (Ib), or a pharmaceutically acceptable salt thereof, is administered in a once daily dose of about 10 mg to about 200 mg. In some embodiments, the compound of Formula (Ia) or Formula (Ib), or a pharmaceutically acceptable salt thereof, is administered in a once daily dose of about 50 mg to about 200 mg. In some embodiments, the compound of Formula (Ia) or Formula (Ib), or a pharmaceutically acceptable salt thereof, is administered in a once daily dose of about 100 mg to about 200 mg.

In some embodiments, the compound of Formula (Ia) or Formula (Ib), or a pharmaceutically acceptable salt thereof, is administered in a once daily dose of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg.

In some embodiments, the compound of Formula (Ia) or Formula (Ib), or a pharmaceutically acceptable salt thereof, is administered in a once daily dose of about 1 mg.

In some embodiments, the compound of Formula (Ia) or Formula (Ib), or a pharmaceutically acceptable salt thereof, is administered in a once daily dose of about 5 mg. In some embodiments, the compound of Formula (Ia) or Formula (Ib), or a pharmaceutically acceptable salt thereof, is administered in a once daily dose of about 10 mg. In some embodiments, the compound of Formula (Ia) or Formula (Ib), or a pharmaceutically acceptable salt thereof, is administered in a once daily dose of about 15 mg. In some embodiments, the compound of Formula (Ia) or Formula (Ib), or a pharmaceutically acceptable salt thereof, is administered in a once daily dose of about 20 mg. In some embodiments, the compound of Formula (Ia) or Formula (Ib), or a pharmaceutically acceptable salt thereof, is administered in a once daily dose of about 25 mg. In some embodiments, the compound of Formula (Ia) or Formula (Ib), or a pharmaceutically acceptable salt thereof, is administered in a once daily dose of about 50 mg. In some embodiments, the compound of Formula (Ia) or Formula (Ib), or a pharmaceutically acceptable salt thereof, is administered in a once daily dose of about 75 mg. In some embodiments, the compound of Formula (Ia) or Formula (Ib), or a pharmaceutically acceptable salt thereof, is administered in a once daily dose of about 100 mg. In some embodiments, the compound of Formula (Ia) or Formula (Ib), or a pharmaceutically acceptable salt thereof, is administered in a once daily dose of about 125 mg. In some embodiments, the compound of Formula (Ia) or Formula (Ib), or a pharmaceutically acceptable salt thereof, is administered in a once daily dose of about 150 mg. In some embodiments, the compound of Formula (Ia) or Formula (Ib), or a pharmaceutically acceptable salt thereof, is administered in a once daily dose of about 175 mg. In some embodiments, the compound of Formula (Ia) or Formula (Ib), or a pharmaceutically acceptable salt thereof, is administered in a once daily dose of about 200 mg. In some embodiments, the compound of Formula (Ia) or Formula (Ib), or a pharmaceutically acceptable salt thereof, is administered in a once daily dose of about 300 mg. In some embodiments, the compound of Formula (Ia) or Formula (Ib), or a pharmaceutically acceptable salt thereof, is administered in a once daily dose of about 400 mg. In some embodiments, the compound of Formula (Ia) or Formula (Ib), or a pharmaceutically acceptable salt thereof, is administered in a once daily dose of about 500 mg. In some embodiments, the compound of Formula (Ia) or Formula (Ib), or a pharmaceutically acceptable salt thereof, is administered in a once daily dose of about 600 mg. In some embodiments, the compound of Formula (Ia) or Formula (Ib), or a pharmaceutically acceptable salt thereof, is administered in a once daily dose of about 700 mg. In some embodiments, the compound of Formula (Ia) or Formula (Ib), or a pharmaceutically acceptable salt thereof, is administered in a once daily dose of about 800 mg. In some embodiments, the compound of Formula (Ia) or Formula (Ib), or a pharmaceutically acceptable salt thereof, is administered in a once daily dose of about 900 mg. In some embodiments, the compound of Formula (Ia) or Formula (Ib), or a pharmaceutically acceptable salt thereof, is administered in a once daily dose of about 1000 mg. In some embodiments, the compound of Formula (Ia) or Formula (Ib), or a pharmaceutically acceptable salt thereof, is administered in a once daily dose of about 1100 mg. In some embodiments, the compound of Formula (Ia) or Formula (Ib), or a pharmaceutically acceptable salt thereof, is administered in a once daily dose of about 1200 mg. In some embodiments, the compound of Formula (Ia) or Formula (Ib), or a pharmaceutically acceptable salt thereof, is administered in a once daily dose of about 1300 mg. In some embodiments, the compound of Formula (Ia) or Formula (Ib), or a pharmaceutically acceptable salt thereof, is administered in a once daily dose of about 1400 mg. In some embodiments, the compound of Formula (Ia) or Formula (Ib), or a pharmaceutically acceptable salt thereof, is administered in a once daily dose of about 1500 mg.

In some embodiments, the compound of Formula (Ia) or Formula (Ib), or a pharmaceutically acceptable salt thereof, is administered weekly at a dose of about 100 mg to about 2500 mg. In some embodiments, the compound of Formula (Ia) or Formula (Ib), or a pharmaceutically acceptable salt thereof, is administered weekly at a dose of about 100 mg to about 2400 mg. In some embodiments, the compound of Formula (Ia) or Formula (Ib), or a pharmaceutically acceptable salt thereof, is administered weekly at a dose of about 100 mg to about 2000 mg. In some embodiments, the compound of Formula (Ia) or Formula (Ib), or a pharmaceutically acceptable salt thereof, is administered weekly at a dose of about 300 mg to about 2500 mg. In some embodiments, the compound of Formula (Ia) or Formula (Ib), or a pharmaceutically acceptable salt thereof, is administered weekly at a dose of about 500 mg to about 2500 mg. In some embodiments, the compound of Formula (Ia) or Formula (Ib), or a pharmaceutically acceptable salt thereof, is administered weekly at a dose of about 800 mg to about 2500 mg. In some embodiments, the compound of Formula (Ia) or Formula (Ib), or a pharmaceutically acceptable salt thereof, is administered weekly at a dose of about 1000 mg to about 2500 mg. In some embodiments, the compound of Formula (Ia) or Formula (Ib), or a pharmaceutically acceptable salt thereof, is administered weekly at a dose of about 100 mg to about 1200 mg. In some embodiments, the compound of Formula (Ia) or Formula (Ib), or a pharmaceutically acceptable salt thereof, is administered weekly at a dose of about 150 mg to about 1200 mg. In some embodiments, the compound of Formula (Ia) or Formula (Ib), or a pharmaceutically acceptable salt thereof, is administered weekly at a dose of about 200 mg to about 1200 mg. In some embodiments, the compound of Formula (Ia) or Formula (Ib), or a pharmaceutically acceptable salt thereof, is administered weekly at a dose of about 300 mg to about 1200 mg. In some embodiments, the compound of Formula (Ia) or Formula (Ib), or a pharmaceutically acceptable salt thereof, is administered weekly at a dose of about 500 mg to about 1200 mg. In some embodiments, the compound of Formula (Ia) or Formula (Ib), or a pharmaceutically acceptable salt thereof, is administered weekly at a dose of about 600 mg to about 1200 mg. In some embodiments, the compound of Formula (Ia) or Formula (Ib), or a pharmaceutically acceptable salt thereof, is administered weekly at a dose of about 800 mg to about 1200 mg. In some embodiments, the compound of Formula (Ia) or Formula (Ib), or a pharmaceutically acceptable salt thereof, is administered weekly at a dose of about 1000 mg to about 1200 mg. In some embodiments, the compound of Formula (Ia) or Formula (Ib), or a pharmaceutically acceptable salt thereof, is administered weekly at a dose of about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, or about 2500 mg.

In some embodiments, the compound of Formula (Ia) or Formula (Ib), or a pharmaceutically acceptable salt thereof, is administered weekly at a dose of about 100 mg. In some embodiments, the compound of Formula (Ia) or Formula (Ib), or a pharmaceutically acceptable salt thereof, is administered weekly at a dose of about 150 mg. In some embodiments, the compound of Formula (Ia) or Formula (Ib), or a pharmaceutically acceptable salt thereof, is administered weekly at a dose of about 175 mg. In some embodiments, the compound of Formula (Ia) or Formula (Ib), or a pharmaceutically acceptable salt thereof, is administered weekly at a dose of about 200 mg. In some embodiments, the compound of Formula (Ia) or Formula (Ib), or a pharmaceutically acceptable salt thereof, is administered weekly at a dose of about 300 mg.

In some embodiments, the compound of Formula (Ia) or Formula (Ib), or a pharmaceutically acceptable salt thereof, is administered weekly at a dose of about 400 mg. In some embodiments, the compound of Formula (Ia) or Formula (Ib), or a pharmaceutically acceptable salt thereof, is administered weekly at a dose of about 500 mg.

In some embodiments, the compound of Formula (Ia) or Formula (Ib), or a pharmaceutically acceptable salt thereof, is administered weekly at a dose of about 600 mg.

In some embodiments, the compound of Formula (Ia) or Formula (Ib), or a pharmaceutically acceptable salt thereof, is administered weekly at a dose of about 700 mg.

In some embodiments, the compound of Formula (Ia) or Formula (Ib), or a pharmaceutically acceptable salt thereof, is administered weekly at a dose of about 800 mg.

In some embodiments, the compound of Formula (Ia) or Formula (Ib), or a pharmaceutically acceptable salt thereof, is administered weekly at a dose of about 900 mg.

In some embodiments, the compound of Formula (Ia) or Formula (Ib), or a pharmaceutically acceptable salt thereof, is administered weekly at a dose of about 1000 mg. In some embodiments, the compound of Formula (Ia) or Formula (Ib), or a pharmaceutically acceptable salt thereof, is administered weekly at a dose of about 1100 mg. In some embodiments, the compound of Formula (Ia) or Formula (Ib), or a pharmaceutically acceptable salt thereof, is administered weekly at a dose of about 1200 mg. In some embodiments, the compound of Formula (Ia) or Formula (Ib), or a pharmaceutically acceptable salt thereof, is administered weekly at a dose of about 1300 mg. In some embodiments, the compound of Formula (Ia) or Formula (Ib), or a pharmaceutically acceptable salt thereof, is administered weekly at a dose of about 1400 mg. In some embodiments, the compound of Formula (Ia) or Formula (Ib), or a pharmaceutically acceptable salt thereof, is administered weekly at a dose of about 1500 mg.

In some embodiments, the compound of Formula (Ia) or Formula (Ib), or a pharmaceutically acceptable salt thereof, is administered weekly at a dose of about 1600 mg. In some embodiments, the compound of Formula (Ia) or Formula (Ib), or a pharmaceutically acceptable salt thereof, is administered weekly at a dose of about 1700 mg. In some embodiments, the compound of Formula (Ia) or Formula (Ib), or a pharmaceutically acceptable salt thereof, is administered weekly at a dose of about 1800 mg. In some embodiments, the compound of Formula (Ia) or Formula (Ib), or a pharmaceutically acceptable salt thereof, is administered weekly at a dose of about 1900 mg. In some embodiments, the compound of Formula (Ia) or Formula (Ib), or a pharmaceutically acceptable salt thereof, is administered weekly at a dose of about 2000 mg. In some embodiments, the compound of Formula (Ia) or Formula (Ib), or a pharmaceutically acceptable salt thereof, is administered weekly at a dose of about 2100 mg. In some embodiments, the compound of Formula (Ia) or Formula (Ib), or a pharmaceutically acceptable salt thereof, is administered weekly at a dose of about 2200 mg. In some embodiments, the compound of Formula (Ia) or Formula (Ib), or a pharmaceutically acceptable salt thereof, is administered weekly at a dose of about 2300 mg. In some embodiments, the compound of Formula (Ia) or Formula (Ib), or a pharmaceutically acceptable salt thereof, is administered weekly at a dose of about 2400 mg. In some embodiments, the compound of Formula (Ia) or Formula (Ib), or a pharmaceutically acceptable salt thereof, is administered weekly at a dose of about 2500 mg.

In some embodiments, the compound of Formula (Ia) or Formula (Ib), or a pharmaceutically acceptable salt thereof, is administered monthly at a dose of about 100 mg to about 3000 mg. In some embodiments, the compound of Formula (Ia) or Formula (Ib), or a pharmaceutically acceptable salt thereof, is administered monthly at a dose of about 100 mg to about 2500 mg. In some embodiments, the compound of Formula (Ia) or Formula (Ib), or a pharmaceutically acceptable salt thereof, is administered monthly at a dose of about 100 mg to about 2400 mg. In some embodiments, the compound of Formula (Ia) or Formula (Ib), or a pharmaceutically acceptable salt thereof, is administered monthly at a dose of about 100 mg to about 2000 mg. In some embodiments, the compound of Formula (Ia) or Formula (Ib), or a pharmaceutically acceptable salt thereof, is administered monthly at a dose of about 300 mg to about 2500 mg. In some embodiments, the compound of Formula (Ia) or Formula (Ib), or a pharmaceutically acceptable salt thereof, is administered monthly at a dose of about 500 mg to about 2500 mg. In some embodiments, the compound of Formula (Ia) or Formula (Ib), or a pharmaceutically acceptable salt thereof, is administered monthly at a dose of about 800 mg to about 2500 mg. In some embodiments, the compound of Formula (Ia) or Formula (Ib), or a pharmaceutically acceptable salt thereof, is administered monthly at a dose of about 1000 mg to about 2500 mg.

In some embodiments, the compound of Formula (Ia) or Formula (Ib), or a pharmaceutically acceptable salt thereof, is administered monthly at a dose of about 200 mg to about 2000 mg. In some embodiments, the compound of Formula (Ia) or Formula (Ib), or a pharmaceutically acceptable salt thereof, is administered monthly at a dose of about 300 mg to about 2000 mg. In some embodiments, the compound of Formula (Ia) or Formula (Ib), or a pharmaceutically acceptable salt thereof, is administered monthly at a dose of about 400 mg to about 2000 mg. In some embodiments, the compound of Formula (Ia) or Formula (Ib), or a pharmaceutically acceptable salt thereof, is administered monthly at a dose of about 500 mg to about 2000 mg. In some embodiments, the compound of Formula (Ia) or Formula (Ib), or a pharmaceutically acceptable salt thereof, is administered monthly at a dose of about 800 mg to about 2000 mg. In some embodiments, the compound of Formula (Ia) or Formula (Ib), or a pharmaceutically acceptable salt thereof, is administered monthly at a dose of about 1000 mg to about 2000 mg. In some embodiments, the compound of Formula (Ia) or Formula (Ib), or a pharmaceutically acceptable salt thereof, is administered monthly at a dose of about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, or about 3000 mg.

In some embodiments, the compound of Formula (Ia) or Formula (Ib), or a pharmaceutically acceptable salt thereof, is administered monthly at a dose of about 100 mg.

In some embodiments, the compound of Formula (Ia) or Formula (Ib), or a pharmaceutically acceptable salt thereof, is administered monthly at a dose of about 150 mg.

In some embodiments, the compound of Formula (Ia) or Formula (Ib), or a pharmaceutically acceptable salt thereof, is administered monthly at a dose of about 200 mg.

In some embodiments, the compound of Formula (Ia) or Formula (Ib), or a pharmaceutically acceptable salt thereof, is administered monthly at a dose of about 300 mg. In some embodiments, the compound of Formula (Ia) or Formula (Ib), or a pharmaceutically acceptable salt thereof, is administered monthly at a dose of about 400 mg. In some embodiments, the compound of Formula (Ia) or Formula (Ib), or a pharmaceutically acceptable salt thereof, is administered monthly at a dose of about 500 mg. In some embodiments, the compound of Formula (Ia) or Formula (Ib), or a pharmaceutically acceptable salt thereof, is administered monthly at a dose of about 800 mg.
In some embodiments, the compound of Formula (Ia) or Formula (Ib), or a pharmaceutically acceptable salt thereof, is administered monthly at a dose of about 1000 mg. In some embodiments, the compound of Formula (Ia) or Formula (Ib), or a pharmaceutically acceptable salt thereof, is administered monthly at a dose of about 1100 mg. In some embodiments, the compound of Formula (Ia) or Formula (Ib), or a pharmaceutically acceptable salt thereof, is administered monthly at a dose of about 1200 mg. In some embodiments, the compound of Formula (Ia) or Formula (Ib), or a pharmaceutically acceptable salt thereof, is administered monthly at a dose of about 1500 mg. In some embodiments, the compound of Formula (Ia) or Formula (Ib), or a pharmaceutically acceptable salt thereof, is administered monthly at a dose of about 1800 mg. In some embodiments, the compound of Formula (Ia) or Formula (Ib), or a pharmaceutically acceptable salt thereof, is administered monthly at a dose of about 2000 mg. In some embodiments, the compound of Formula (Ia) or Formula (Ib), or a pharmaceutically acceptable salt thereof, is administered monthly at a dose of about 2100 mg. In some embodiments, the compound of Formula (Ia) or Formula (Ib), or a pharmaceutically acceptable salt thereof, is administered monthly at a dose of about 2200 mg. In some embodiments, the compound of Formula (Ia) or Formula (Ib), or a pharmaceutically acceptable salt thereof, is administered monthly at a dose of about 2300 mg. In some embodiments, the compound of Formula (Ia) or Formula (Ib), or a pharmaceutically acceptable salt thereof, is administered monthly at a dose of about 2400 mg. In some embodiments, the compound of Formula (Ia) or Formula (Ib), or a pharmaceutically acceptable salt thereof, is administered monthly at a dose of about 2500 mg. In some embodiments, the compound of Formula (Ia) or Formula (Ib), or a pharmaceutically acceptable salt thereof, is administered monthly at a dose of about 2600 mg. In some embodiments, the compound of Formula (Ia) or Formula (Ib), or a pharmaceutically acceptable salt thereof, is administered monthly at a dose of about 2700 mg. In some embodiments, the compound of Formula (Ia) or Formula (Ib), or a pharmaceutically acceptable salt thereof, is administered monthly at a dose of about 2800 mg. In some embodiments, the compound of Formula (Ia) or Formula (Ib), or a pharmaceutically acceptable salt thereof, is administered monthly at a dose of about 2900 mg. In some embodiments, the compound of Formula (Ia) or Formula (Ib), or a pharmaceutically acceptable salt thereof, is administered monthly at a dose of about 3000 mg.

In some embodiments, the compound of Formula (Ia) or Formula (Ib), or a pharmaceutically acceptable salt thereof, is administered every 6 months at a dose of about 600 mg.

In some embodiments, the dosage and/or dose amounts disclosed herein of the compound of Formula (Ia) or Formula (Ib), or a pharmaceutically acceptable salt thereof, is administered orally or parenterally. In some embodiments, the dosage and/or dose amounts disclosed herein of the compound of Formula (Ia) or Formula (Ib), or a pharmaceutically acceptable salt thereof, is administered orally. In some embodiments, the dosage and/or dose amounts disclosed herein of the compound of Formula (Ia) or Formula (Ib), or a pharmaceutically acceptable salt thereof, is administered through one or more tablets as disclosed herein. In some embodiments, the dosage and/or dose amounts disclosed herein of the compound of Formula (Ia) or Formula (Ib), or a pharmaceutically acceptable salt thereof, is administered through one or more capsules as disclosed herein. In some embodiments, the dosage and/or dose amounts disclosed herein of the compound of Formula (Ia) or Formula (Ib), or a pharmaceutically acceptable salt thereof, is administered through one or more hard gelatin or soft gelatin capsules as disclosed herein.

In some embodiments, the dosage and/or dose amounts disclosed herein of the compound of Formula (Ia) or Formula (Ib), or a pharmaceutically acceptable salt thereof, is administered parenterally. In some embodiments, the dosage and/or dose amounts disclosed herein of the compound of Formula (Ia) or Formula (Ib), or a pharmaceutically acceptable salt thereof, is administered through an injection. In some embodiments, the dosage and/or dose amounts disclosed herein of the compound of Formula (Ia) or Formula (Ib), or a pharmaceutically acceptable salt thereof, is administered through a subcutaneous injection.

Combination Therapy

In certain embodiments, a method for treating or preventing an HIV infection in a human having or at risk of having the infection is provided, comprising administering to the human a therapeutically effective amount of a compound disclosed herein (for example, a compound of Formula (Ia) or Formula (Ib), or a pharmaceutically acceptable salt thereof), in combination with a therapeutically effective amount of one or more (for example, one, two, three, or four; or one or two; or one to three; or one to four) additional therapeutic agents. In one embodiment, a method for treating an HIV infection in a human having or at risk of having the infection is provided, comprising administering to the human a therapeutically effective amount of a compound disclosed herein (for example, a compound of Formula (Ia) or Formula (Ib), or a pharmaceutically acceptable salt thereof, in combination with a therapeutically effective amount of one or more (for example, one, two, three, or four; or one or two; or one to three; or one to four) additional therapeutic agents.

In some embodiments, a method for treating or preventing an HIV infection in a human having or at risk of having the infection is provided, comprising administering to the human a therapeutically effective amount of a compound disclosed herein (for example, a compound of Formula (Ia) or Formula (Ib), or a pharmaceutically acceptable salt thereof, in combination with a therapeutically effective amount of one or more (for example, one, two, three, or four; or one or two; or one to three; or one to four) additional therapeutic agents. In one embodiment, a method for treating an HIV infection in a human having or at risk of having the infection is provided, comprising administering to the human a therapeutically effective amount of a compound disclosed herein (for example, a compound of Formula (Ia) or Formula (Ib), or a pharmaceutically acceptable salt thereof, in combination with a therapeutically effective amount of one or more (for example, one, two, three, or four; or one or two; or one to three; or one to four) additional therapeutic agents.

In one embodiment, pharmaceutical compositions comprising a compound disclosed herein (for example, a compound of Formula (Ia) or (Ib), or a pharmaceutically acceptable salt thereof) in combination with one or more (for example, one, two, three, or four; or one to three; or one to four) additional therapeutic agents, and a pharmaceutically acceptable excipient are provided.

In some embodiments, pharmaceutical compositions comprising a compound disclosed herein (for example, a compound of Formula (Ia) or Formula (Ib), or a pharmaceutically acceptable salt thereof) in combination with one or more (for example, one, two, three, or four; or one or two; or one to three; or one to four) additional therapeutic agents, and a pharmaceutically acceptable excipient are provided.

In certain embodiments, the present disclosure provides a method for treating an HIV infection, comprising administering to a patient in need thereof a therapeutically effective amount of a compound disclosed herein (for example, a compound of Formula (Ia) or Formula (Ib), or a pharmaceutically acceptable salt thereof) in combination with a therapeutically effective amount of one or more additional therapeutic agents which are suitable for treating an HIV infection.

In certain embodiments, the present disclosure provides a method for treating an HIV infection, comprising administering to a heavily treatment-experienced patient in need thereof a therapeutically effective amount of a compound disclosed herein (for example, a compound of Formula (Ia) or Formula (Ib), or a pharmaceutically acceptable salt thereof) in combination with a therapeutically effective amount of one or more additional therapeutic agents which are suitable for treating an HIV infection in a heavily treatment-experienced patient. In some embodiments, the heavily treatment-experienced patients are patients with multidrug resistant HIV infection.

In certain embodiments, the present disclosure provides a method for treating an HIV infection in a heavily treatment-experienced patient, comprising administering to a patient in need thereof a therapeutically effective amount of a compound disclosed herein (for example, a compound of Formula (Ia) or Formula (Ib), or a pharmaceutically acceptable salt thereof).

In certain embodiments, a compound disclosed herein (for example, a compound of Formula (Ia) or Formula (Ib), or a pharmaceutically acceptable salt thereof, is combined with one, two, three, four, or more additional therapeutic agents. In certain embodiments, a compound disclosed herein (for example, a compound of Formula (Ia) or (Ib), or a pharmaceutically acceptable salt thereof), is combined with one additional therapeutic agent. In certain embodiments, a compound disclosed herein (for example, a compound of Formula (Ia) or (Ib), or a pharmaceutically acceptable salt thereof), is combined with two additional therapeutic agents. In other embodiments, a compound disclosed herein (for example, a compound of Formula (Ia) or (Ib), or a pharmaceutically acceptable salt thereof), is combined with three additional therapeutic agents. In further embodiments, a compound disclosed herein (for example, a compound of Formula (Ia) or (Ib), or a pharmaceutically acceptable salt thereof), is combined with four additional therapeutic agents. The one, two, three, four, or more additional therapeutic agents can be different therapeutic agents selected from the same class of therapeutic agents, and/or they can be selected from different classes of therapeutic agents.

In some embodiments, a compound disclosed herein (for example, a compound of Formula (Ia) or Formula (Ib), or a pharmaceutically acceptable salt thereof, is combined with one, two, three, four, or more additional therapeutic agents. In certain embodiments, a compound disclosed herein (for example, a compound of Formula (Ia) or Formula (Ib), or a pharmaceutically acceptable salt thereof, is combined with one additional therapeutic agent. In certain embodiments, a compound disclosed herein (for example, a compound of Formula (Ia) or Formula (Ib), or a pharmaceutically acceptable salt thereof, is combined with two additional therapeutic agents. In other embodiments, a compound disclosed herein (for example, a compound of Formula (Ia) or Formula (Ib), or a pharmaceutically acceptable salt thereof, is combined with three additional therapeutic agents. In further embodiments, a compound disclosed herein (for example, a compound of Formula (Ia) or Formula (Ib), or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein (for example, a compound of Formula (Ia) or (Ib), or a pharmaceutically acceptable salt thereof), is administered with one or more additional therapeutic agents. Co-administration of a compound disclosed herein (for example, a compound of Formula (Ia) or (Ib), or a pharmaceutically acceptable salt thereof), with one or more additional therapeutic agents generally refers to simultaneous or sequential administration of a compound disclosed herein (for example, a compound of Formula (Ia) or (Ib), or a pharmaceutically acceptable salt thereof) and one or more additional therapeutic agents, such that therapeutically effective amounts of the compound disclosed herein (for example, a compound of Formula (Ia) or (Ib), or a pharmaceutically acceptable salt thereof), and the one or more additional therapeutic agents are both present in the body of the patient. When administered sequentially, the combination may be administered in two or more administrations.

In some embodiments, a compound disclosed herein (for example, a compound of Formula (Ia) or Formula (Ib), or a pharmaceutically acceptable salt thereof, is administered with one or more additional therapeutic agents. Co-administration of a compound disclosed herein (for example, a compound of Formula (Ia) or Formula (Ib), or a pharmaceutically acceptable salt thereof), with one or more additional therapeutic agents generally refers to simultaneous or sequential administration of a compound disclosed herein (for example, a compound of Formula (Ia) or Formula (Ib), or a pharmaceutically acceptable salt thereof, and one or more additional therapeutic agents, such that therapeutically effective amounts of the compound disclosed herein (for example, a compound of Formula (Ia) or Formula (Ib), or a pharmaceutically acceptable salt thereof), and the one or more additional therapeutic agents are both present in the body of the patient. When administered sequentially, the combination may be administered in two or more administrations.

Co-administration includes administration of unit dosages of the compounds disclosed herein (for example, a compound of Formula (Ia) or (Ib), or pharmaceutically acceptable salts thereof), before or after administration of unit dosages of one or more additional therapeutic agents. For example, the compound disclosed herein (for example, a compound of Formula (Ia) or (Ib), or a pharmaceutically acceptable salt thereof), may be administered within seconds, minutes, or hours of the administration of the one or more additional therapeutic agents. In some embodiments, a unit dose of a compound disclosed herein (for example, a compound of Formula (Ia) or (Ib), or a pharmaceutically acceptable salt thereof), is administered first, followed within seconds or minutes by administration of a unit dose of one or more additional therapeutic agents. Alternatively, a unit dose of one or more additional therapeutic agents is administered first, followed by administration of a unit dose of a compound disclosed herein (for example, a compound of Formula (Ia) or (Ib), or a pharmaceutically acceptable salt thereof) within seconds or minutes. In other embodiments, a unit dose of a compound disclosed herein (for example, a compound of Formula (Ia) or (Ib), or a pharmaceutically acceptable salt thereof) is administered first, followed, after a period of hours (for example, 1-12 hours), by administration of a unit dose of one or more additional therapeutic agents. In yet other embodiments, a unit dose of one or more additional therapeutic agents is administered first, followed, after a period of hours (for example, 1-12 hours), by administration of a unit dose of a compound disclosed herein (for example, a compound of Formula (Ia) or (Ib), or a pharmaceutically acceptable salt thereof).

In some embodiments, co-administration includes administration of unit dosages of the compounds disclosed herein (for example, a compound of Formula (Ia) or Formula (Ib), or a pharmaceutically acceptable salt thereof), before or after administration of unit dosages of one or more additional therapeutic agents. For example, the compound disclosed herein (for example, a compound of Formula (Ia) or Formula (Ib), or a pharmaceutically acceptable salt thereof), may be administered within seconds, minutes, or hours of the administration of the one or more additional therapeutic agents. In some embodiments, a unit dose of a compound disclosed herein (for example, a compound of Formula (Ia) or Formula (Ib), or a pharmaceutically acceptable salt thereof, is administered first, followed within seconds or minutes by administration of a unit dose of one or more additional therapeutic agents. Alternatively, a unit dose of one or more additional therapeutic agents is administered first, followed by administration of a unit dose of a compound disclosed herein (for example, a compound of Formula (Ia) or Formula (Ib), or a pharmaceutically acceptable salt thereof) within seconds or minutes. In other embodiments, a unit dose of a compound disclosed herein (for example, a compound of Formula (Ia) or Formula (Ib), or a pharmaceutically acceptable salt thereof) is administered first, followed, after a period of hours (for example, 1-12 hours), by administration of a unit dose of one or more additional therapeutic agents. In yet other embodiments, a unit dose of one or more additional therapeutic agents is administered first, followed, after a period of hours (for example, 1-12 hours), by administration of a unit dose of a compound disclosed herein (for example, a compound of Formula (Ia) or Formula (Ib), or a pharmaceutically acceptable salt thereof).

For the avoidance of doubt, co-administration of a compound disclosed herein (for example, a compound of Formula (Ia) or Formula (Ib), or a pharmaceutically acceptable salt thereof, with one or more additional therapeutic agents, may refer to co-administration with one or more of the therapeutic agents described herein.

In certain embodiments, a compound disclosed herein (for example, a compound of Formula (Ia) or (Ib), or a pharmaceutically acceptable salt thereof), is combined with one or more additional therapeutic agents in a unitary dosage form for simultaneous administration to a patient. In certain embodiments, such a unitary dosage form can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the unitary dosage form can be dosed intravenous, subcutaneous, or intramuscular. In certain embodiments, the unitary dosage form is orally bioavailable and can be dosed orally. In certain embodiments, the unitary dosage form can be a solid dosage form for oral administration.

In some embodiments, a compound disclosed herein (for example, a compound of Formula (Ia) or Formula (Ib), or a pharmaceutically acceptable salt thereof, is combined with one or more additional therapeutic agents in a unitary dosage form for simultaneous administration to a patient. In certain embodiments, such a unitary dosage form can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the unitary dosage form can be dosed intravenous, subcutaneous, or intramuscular. In certain embodiments, the unitary dosage form is orally bioavailable and can be dosed orally. In certain embodiments, the unitary dosage form can be a solid dosage form for oral administration.

The compound disclosed herein (for example, a compound of Formula (Ia) or (Ib), or a pharmaceutically acceptable salt thereof), in combination with one or more additional therapeutic agents can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the compounds disclosed can be dosed intravenous, subcutaneous, or intramuscular. In certain embodiments, the compounds disclosed are orally bioavailable and can be dosed orally.

The compound disclosed herein (for example, a compound of Formula (Ia) or Formula (Ib), or a pharmaceutically acceptable salt thereof), in combination with one or more additional therapeutic agents can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the compounds disclosed can be dosed intravenous, subcutaneous, or intramuscular. In certain embodiments, the compounds disclosed are orally bioavailable and can be dosed orally.

In certain embodiments, a compound of Formula (Ia) or (Ib), or a pharmaceutically acceptable salt thereof, is formulated as a tablet, which may optionally contain one or more other compounds useful for treating HIV. In certain embodiments, the tablet can contain one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV nucleoside reverse transcriptase translocation inhibitors, pharmacokinetic enhancers, and combinations thereof.

In certain embodiments, a compound of Formula (Ia) or Formula (Ib), or a pharmaceutically acceptable salt thereof, is formulated as a solution formulation, which may optionally contain one or more other compounds useful for treating HIV. In certain embodiments, the solution can contain one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV nucleoside reverse transcriptase translocation inhibitors, pharmacokinetic enhancers, and combinations thereof.

In certain embodiments, a compound of Formula (Ia) or Formula (Ib), or a pharmaceutically acceptable salt thereof, is formulated as a suspension, which may optionally contain one or more other compounds useful for treating HIV. In certain embodiments, the suspension can contain one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV nucleoside reverse transcriptase translocation inhibitors, pharmacokinetic enhancers, and combinations thereof.

In certain embodiments, such tablets are suitable for once daily dosing.

HIV Combination Therapy

In some embodiments, a compound of Formula (Ia) or Formula (Ib), or a pharmaceutically acceptable salt thereof, is administered with a therapeutically effective amount of at least one additional therapeutic agent.

In the above embodiments, the additional therapeutic agent can be an anti-HIV agent selected from the group consisting of combination drugs for treating HIV, other drugs for treating HIV, HIV nucleoside reverse transcriptase translocation inhibitors, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies such as chimeric antigen receptor T-cell, CAR-T (e.g., YESCARTA® (axicabtagene ciloleucel)), and engineered T cell receptors, TCR-T.

In some embodiments, the additional therapeutic agent is selected from the group consisting of combination drugs for HIV, other drugs for treating HIV, HIV nucleoside reverse transcriptase translocation inhibitors, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine);

COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, and tenofovir alafenamide); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; cabotegravir and rilpivirine; cabotegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine; lamivudine+abacavir+zidovudine; lamivudine+abacavir; lamivudine+tenofovir disoproxil fumarate; lamivudine+zidovudine+nevirapine; lopinavir+ritonavir; lopinavir+ritonavir+abacavir+lamivudine; lopinavir+ritonavir+zidovudine+lamivudine; tenofovir+lamivudine; and tenofovir disoproxil fumarate+emtricitabine+rilpivirine hydrochloride; lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Nucleoside Reverse Transcriptase Translocation Inhibitors

Examples of HIV nucleoside reverse transcriptase translocation inhibitors ("NRTTIs") include 4'-ethynyl-2-fluoro-2'-deoxyadenosine triphosphate (also known as MK-8591 and EFdA).

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500. Further examples of non-nucleoside reverse transcriptase inhibitors are disclosed in U.S. Patent Publication No. US 2016/0250215.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

In some embodiments, examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, KP-1461, and 4'-ethynyl-2-fluoro-2'-deoxyadenosine (EFdA).

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs

Examples of gp120 inhibitors include Radha-108 (receptol) 3B3-PE38, BanLec, bentonite-based nanomedicine, fostemsavir tromethamine, IQP-0831, and BMS-663068

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66

Examples of those targeting HIV in such a manner include bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8, VRC-07-523, VRC-HIVMAB080-00-AB, MGD-014 and VRC07.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-05, VAC-3 S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICH-vac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine.

HIV Combination Therapy

In a particular embodiment, a compound disclosed herein (for example, a compound of Formula (Ia) or (Ib), or a pharmaceutically acceptable salt thereof), is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUIMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMIBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, a compound disclosed herein (for example, a compound of Formula (Ia) or Formula (Ib), or a pharmaceutically acceptable salt thereof), is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; abacavir sulfate; 4'-ethynyl-2-fluoro-2'-deoxyadenosine (EFdA); and bictegravir, or a pharmaceutically acceptable salt thereof.

It will be appreciated by one of skill in the art that the additional therapeutic agents listed above may be included in more than one of the classes listed above. The particular classes are not intended to limit the functionality of those compounds listed in those classes.

In some embodiments, a compound disclosed herein (for example, a compound of Formula (Ia) or (Ib), or a pharmaceutically acceptable salt thereof), is combined with at least one HIV nucleoside reverse transcriptase translocation inhibitor. In some embodiments, a compound disclosed herein (for example, a compound of Formula (Ia) or (Ib), or a pharmaceutically acceptable salt thereof), is combined with at least one HIV nucleoside or nucleotide inhibitor of reverse transcriptase. In a specific embodiment, a compound disclosed herein (for example, a compound of Formula (Ia) or (Ib), or a pharmaceutically acceptable salt thereof), is combined with at least one HIV nucleoside or nucleotide inhibitor of reverse transcriptase and at least one HIV non-nucleoside inhibitor of reverse transcriptase. In another specific embodiment, a compound disclosed herein (for example, a compound of Formula (Ia) or (Ib), or a pharmaceutically acceptable salt thereof) is combined with an HIV nucleoside or nucleotide inhibitor of reverse transcriptase, and an HIV protease inhibiting compound. In an additional embodiment, a compound disclosed herein (for example, a compound of Formula (Ia) or (Ib), or a pharmaceutically acceptable salt thereof) is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein (for example, a compound of Formula (Ia) or (Ib), or a pharmaceutically acceptable salt thereof) is combined with at least one HIV nucleoside inhibitor of reverse transcriptase, an integrase inhibitor, and a pharmacokinetic enhancer. In another embodiment, a compound disclosed herein (for example, a compound of Formula (Ia) or (Ib), or a pharmaceutically acceptable salt thereof) is combined with two HIV nucleoside or nucleotide inhibitors of reverse transcriptase.

In some embodiments, a compound disclosed herein (for example, a compound of Formula (Ia) or Formula (Ib), or a pharmaceutically acceptable salt thereof) is combined with one or two HIV nucleoside or nucleotide inhibitors of reverse transcriptase. In a specific embodiment, a compound disclosed herein (for example, a compound of Formula (Ia) or Formula (Ib), or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein (for example, a compound of Formula (Ia) or Formula (Ib), or a pharmaceutically acceptable salt thereof, is combined with an HIV nucleoside or nucleotide inhibitor of reverse transcriptase, and an HIV protease inhibiting compound. In an additional embodiment, a compound disclosed herein (for example, a compound of Formula (Ia) or Formula (Ib), or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein (for example, a compound of Formula (Ia) or Formula (Ib), or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein (for example, a compound of Formula (Ia) or Formula (Ib), or a pharmaceutically acceptable salt thereof, is combined with two HIV nucleoside or nucleotide inhibitors of reverse transcriptase.

In some embodiments, a compound disclosed herein (for example, a compound of Formula (Ia) or Formula (Ib), or a pharmaceutically acceptable salt thereof), is combined with abacavir sulfate, tenofovir, tenofovir disoproxil, tenofovir disoproxil fumarate, tenofovir disoproxil hemifumarate, tenofovir alafenamide, tenofovir alafenamide fumarate, tenofovir alafenamide hemifumarate, bictegravir (or a pharmaceutically acceptable salt thereof), or 4'-ethynyl-2-fluoro-2'-deoxyadenosine (EFdA).

In a particular embodiment, a compound disclosed herein (for example, a compound of Formula (Ia) or (Ib) or a pharmaceutically acceptable salt thereof), is combined with at least one HIV nucleoside reverse transcriptase translocation inhibitor. In some embodiments, the HIV nucleoside reverse transcriptase translocation inhibitor is 4'-ethynyl-2-fluoro-2'-deoxyadenosine triphosphate.

In some embodiments, a compound disclosed herein (for example, a compound of Formula (Ia) or Formula (Ib), or a pharmaceutically acceptable salt thereof), is combined with a HIV integrase inhibitor. In some embodiments, the HIV integrase inhibitor is bictegravir.

In a particular embodiment, a compound disclosed herein (for example, a compound of Formula (Ia) or Formula (Ib), or a pharmaceutically acceptable salt thereof, is combined with a nucleotide reverse transcriptase inhibitor. In some embodiments, the nucleotide reverse transcriptase inhibitor is selected from the group consisting of tenofovir, tenofovir disoproxil, tenofovir disoproxil fumarate, tenofovir alafenamide, tenofovir alafenamide fumarate, and tenofovir alafenamide hemifumarate.

In some embodiments, a compound disclosed herein (for example, a compound of Formula (Ia) or Formula (Ib), or a pharmaceutically acceptable salt thereof, is combined with tenofovir, tenofovir disoproxil, tenofovir disoproxil fumarate, tenofovir alafenamide, tenofovir alafenamide fumarate, tenofovir alafenamide hemifumarate, bictegravir (or a pharmaceutically acceptable salt thereof), or 4'-ethynyl-2-fluoro-2'-deoxyadenosine (EFdA).

In a particular embodiment, a compound disclosed herein (for example, a compound of Formula (Ia) or (Ib)), or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide fumarate and tenofovir alafenamide hemifumarate, and a second additional therapeutic agent selected from the group consisting of emtricitabine and lamivudine.

In some embodiments, a compound disclosed herein (for example, a compound of Formula (Ia) or Formula (Ib), or a pharmaceutically acceptable salt thereof), is combined with a first additional therapeutic agent selected from the group consisting of abacavir sulfate, tenofovir, tenofovir disoproxil, tenofovir disoproxil fumarate, tenofovir alafenamide, tenofovir alafenamide fumarate and tenofovir alafenamide hemifumarate, and a second additional therapeutic agent selected from the group consisting of emtricitabine and lamivudine.

In a particular embodiment, a compound disclosed herein (for example, a compound of Formula (Ia) or (Ib), or a pharmaceutically acceptable salt thereof), is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine. In a particular embodiment, a compound of Formula (Ia) or (Ib), or a pharmaceutically acceptable salt thereof, is combined with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine. In a particular embodiment, a compound of Formula (Ia) or (Ib), or a pharmaceutically acceptable salt thereof, is combined with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine. In some embodiments, the compound of Formula (Ia) or (Ib), or a pharmaceutically acceptable salt thereof, and the first and second additional therapeutic agents as disclosed above are administered simultaneously. Optionally, the compound of Formula (Ia) or (Ib), or a pharmaceutically acceptable salt thereof, and the first and second additional therapeutic agents as disclosed above are combined in a unitary dosage form for simultaneous administration to a patient. In other embodiments, the compound of Formula (Ia) or (Ib), or a pharmaceutically acceptable salt thereof, and the first and second additional therapeutic agents as disclosed above are administered sequentially.

In some embodiments, a compound disclosed herein (for example, a compound of Formula (Ia) or Formula (Ib), or a pharmaceutically acceptable salt thereof), is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine. In a particular embodiment, a compound of Formula (Ia) or Formula (Ib), or a pharmaceutically acceptable salt thereof, is combined with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine. In a particular embodiment, a compound of Formula (Ia) or Formula (Ib), or a pharmaceutically acceptable salt thereof, is combined with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine. In some embodiments, a compound of Formula (Ia) or Formula (Ib), or a pharmaceutically acceptable salt thereof, and the first and second additional therapeutic agents as disclosed above are administered simultaneously. Optionally, a compound of Formula (Ia) or Formula (Ib), or a pharmaceutically acceptable salt thereof, and the first and second additional therapeutic agents as disclosed above are combined in a unitary dosage form for simultaneous administration to a patient. In other embodiments, a compound of Formula (Ia) or Formula (Ib), or a pharmaceutically acceptable salt thereof, and the first and second additional therapeutic agents as disclosed above are administered sequentially.

In some embodiments, a compound disclosed herein (for example, a compound of Formula (Ia) or Formula (Ib), or a pharmaceutically acceptable salt thereof, is combined with bictegravir or a pharmaceutically acceptable salt thereof.

A compound as disclosed herein (for example, any compound of Formula (Ia) or (Ib)) may be combined with one or more additional therapeutic agents in any dosage amount of the compound of Formula (Ia) or (Ib) (for example, from about 1 mg to about 1000 mg of compound).

In some embodiments, a compound as disclosed herein (for example, a compound of Formula (Ia) or Formula (Ib), or a pharmaceutically acceptable salt thereof) may be combined with one or more additional therapeutic agents in any dosage amount of a compound of Formula (Ia) or Formula (Ib), or a pharmaceutically acceptable salt thereof (for example, from about 1 mg to about 1000 mg of compound).

In certain embodiments, a compound disclosed herein (for example, a compound of Formula (Ia) or (Ib), or a pharmaceutically acceptable salt thereof), is combined with about 5-30 mg tenofovir alafenamide fumarate, tenofovir alafenamide hemifumarate, or tenofovir alafenamide, and about 200 mg emtricitabine. In certain embodiments, a compound disclosed herein (for example, a compound of Formula (Ia) or (Ib), or a pharmaceutically acceptable salt thereof), is combined with about 5-10 mg, about 5-15 mg, about 5-20 mg, about 5-25 mg, about 25-30 mg, about 20-30 mg, about 15-30 mg, or about 10-30 mg tenofovir alafenamide fumarate, tenofovir alafenamide hemifumarate, or tenofovir alafenamide, and about 200 mg emtricitabine. In certain embodiments, a compound disclosed herein (for example, a compound of Formula (Ia) or (Ib)), or a pharmaceutically acceptable salt thereof, is combined with about 10 mg tenofovir alafenamide fumarate, tenofovir alafenamide hemifumarate, or tenofovir alafenamide, and about 200 mg emtricitabine. In certain embodiments, a compound disclosed herein, or a pharmaceutically acceptable salt thereof, is combined with about 25 mg tenofovir alafenamide fumarate, tenofovir alafenamide hemifumarate, or tenofovir alafenamide, and about 200 mg emtricitabine. A compound as disclosed herein (for example, a compound of Formula (Ia) or (Ib), or a pharmaceutically acceptable salt thereof) can be combined with the agents provided herein in any dosage amount of the compound (for example, from about 1 mg to about 1000 mg of compound), the same as if each combination of dosages were specifically and individually listed.

In some embodiments, a compound disclosed herein (for example, a compound of Formula (Ia) or Formula (Ib), or a pharmaceutically acceptable salt thereof), is combined with about 5-30 mg tenofovir alafenamide fumarate, tenofovir alafenamide hemifumarate, or tenofovir alafenamide, and about 200 mg emtricitabine. In certain embodiments, a compound disclosed herein (for example, a compound of Formula (Ia) or Formula (Ib), or a pharmaceutically acceptable salt thereof) is combined with about 5-10 mg, about 5-15 mg, about 5-20 mg, about 5-25 mg, about 25-30 mg, about 20-30 mg, about 15-30 mg, or about 10-30 mg tenofovir alafenamide fumarate, tenofovir alafenamide hemifumarate, or tenofovir alafenamide, and about 200 mg emtricitabine. In certain embodiments, a compound disclosed herein (for example, a compound of Formula (Ia) or Formula (Ib), or a pharmaceutically acceptable salt thereof) is combined with about 10 mg tenofovir alafenamide fumarate, tenofovir alafenamide hemifumarate, or tenofovir alafenamide, and about 200 mg emtricitabine. In certain embodiments, a compound disclosed herein, or a pharmaceutically acceptable salt thereof, is combined with about 25 mg tenofovir alafenamide fumarate, tenofovir alafenamide hemifumarate, or tenofovir alafenamide, and about 200 mg emtricitabine. A compound as disclosed herein (for example, a compound of Formula (Ia) or (Ib), or a pharmaceutically acceptable salt thereof) can be combined with the agents provided herein in any dosage amount of the compound (for example, from about 1 mg to about 1000 mg of compound), the same as if each combination of dosages were specifically and individually listed.

In certain embodiments, a compound disclosed herein (for example, a compound of Formula (Ia) or (Ib), or a pharmaceutically acceptable salt thereof) is combined with about 200-400 mg tenofovir disoproxil fumarate, tenofovir disoproxil hemifumarate, or tenofovir disoproxil, and about 200 mg emtricitabine. In certain embodiments, a compound disclosed herein (for example, a compound of Formula (Ia) or (Ib), or a pharmaceutically acceptable salt thereof) is combined with about 200-250 mg, about 200-300 mg, about 200-350 mg, about 250-350 mg, about 250-400 mg, about 350-400 mg, about 300-400 mg, or about 250-400 mg tenofovir disoproxil fumarate, tenofovir disoproxil hemifumarate, or tenofovir disoproxil, and about 200 mg emtricitabine. In certain embodiments, a compound disclosed herein (for example, a compound of Formula (Ia) or (Ib), or a pharmaceutically acceptable salt thereof) is combined with about 300 mg tenofovir disoproxil fumarate, tenofovir disoproxil hemifumarate, or tenofovir disoproxil, and about 200 mg emtricitabine. A compound as disclosed herein (for example, a compound of Formula (Ia) or (Ib), or a pharmaceutically acceptable salt thereof) can be combined with the agents provided herein in any dosage amount of the compound (for example, from about 1 mg to about 1000 mg of compound), the same as if each combination of dosages were specifically and individually listed.

In some embodiments, a compound disclosed herein (for example, a compound of Formula (Ia) or Formula (Ib), or a pharmaceutically acceptable salt thereof) is combined with about 200-400 mg tenofovir disoproxil fumarate, tenofovir disoproxil hemifumarate, or tenofovir disoproxil, and about 200 mg emtricitabine. In certain embodiments, a compound disclosed herein (for example, a compound of Formula (Ia) or Formula (Ib), or a pharmaceutically acceptable salt thereof), is combined with about 200-250 mg, about 200-300 mg, about 200-350 mg, about 250-350 mg, about 250-400 mg, about 350-400 mg, about 300-400 mg, or about 250-400 mg tenofovir disoproxil fumarate, tenofovir disoproxil hemifumarate, or tenofovir disoproxil, and about 200 mg emtricitabine. In certain embodiments, a compound disclosed herein (for example, a compound of Formula (Ia) or Formula (Ib), or a pharmaceutically acceptable salt thereof) is combined with about 300 mg tenofovir disoproxil fumarate, tenofovir disoproxil hemifumarate, or tenofovir disoproxil, and about 200 mg emtricitabine. A compound as disclosed herein (for example, a compound of Formula (Ia) or Formula (Ib), or a pharmaceutically acceptable salt thereof) can be combined with the agents provided herein in any dosage amount of the compound (for example, from about 1 mg to about 1000 mg of compound), the same as if each combination of dosages were specifically and individually listed.

In some embodiments, a compound disclosed herein (for example, a compound of Formula (Ia) or Formula (Ib), or a pharmaceutically acceptable salt thereof) is combined with about 20-80 mg of bictegravir or a pharmaceutically acceptable salt thereof. In some embodiments, a compound disclosed herein (for example, a compound of Formula (Ia) or Formula (Ib), or a pharmaceutically acceptable salt thereof) is combined with about 50 mg of bictegravir or a pharmaceutically acceptable salt thereof. A compound as disclosed herein (for example, a compound of Formula (Ia) or Formula (Ib), or a pharmaceutically acceptable salt thereof) can be combined with the agents provided herein in any dosage amount of the compound (for example, from about 1 mg to about 1000 mg of compound), the same as if each combination of dosages were specifically and individually listed.

In some embodiments of the methods disclosed herein, the methods further comprise administering one other therapeutic agent selected from the group consisting of tenofovir alafenamide, tenofovir alafenamide hemifumarate, and bictegravir, wherein the one other therapeutic agent is simultaneously administerd or co-administered with the compound of Formula (Ia) or (Ib), or a pharmaceutically acceptable salt thereof. In some embodiments, the methods disclosed herein further comprise administering one other therapeutic agent selected from the group consisting of tenofovir alafenamide hemifumarate and bictegravir, wherein the one other therapeutic agent is simultaneously administerd or co-administered with the compound of Formula (Ia) or (Ib), or a pharmaceutically acceptable salt thereof. In some embodiments, the methods disclosed herein further comprise simultaneously administering or co-administering tenofovir alafenamide with the compound of Formula (Ia) or (Ib), or a pharmaceutically acceptable salt thereof. In some embodiments, the methods disclosed herein further comprise simultaneously administering or co-administering tenofovir alafenamide hemifumarate with the compound of Formula (Ia) or (Ib), or a pharmaceutically acceptable salt thereof. In some embodiments, the methods disclosed herein further comprise simultaneously administering or co-administering bictegravir with the compound of Formula (Ia) or (Ib), or a pharmaceutically acceptable salt thereof.

In one embodiment, kits comprising a compound disclosed herein (for example, a compound of Formula (Ia) or (Ib), or a pharmaceutically acceptable salt thereof) in combination with one or more (for example, one, two, three, one or two, or one to three) additional therapeutic agents are provided.

In some embodiments, kits comprising a compound disclosed herein (for example, a compound of Formula (Ia) or Formula (Ib), or a pharmaceutically acceptable salt thereof), or a pharmaceutically acceptable salt thereof, in combination with one or more (for example, one, two, three, one or two, or one to three) additional therapeutic agents are provided.

Kits and Articles of Manufacture

The present disclosure relates to a kit comprising a compound of Formula (Ia) or Formula (Ib), or a pharmaceutically acceptable salt thereof. In one embodiment, the kit contains one or more additional therapeutic agents as described herein. The kit can further contain instructions for use, for example, instructions for use in inhibiting an HIV reverse transcriptase, such as for use in treating an HIV infection or AIDS or as a research tool. The instructions for use are generally written instructions, although electronic storage media (for example, magnetic diskette or optical disk) containing instructions are also acceptable.

The present disclosure also relates to a pharmaceutical kit containing one or more containers that contain a compound of Formula (Ia) or Formula (Ib), or a pharmaceutically acceptable salt thereof. Optionally associated with such container(s) can be a notice in the form prescribed by a governmental agency regulating the manufacture, use or sale of pharmaceuticals. In some embodiments, the notice reflects approval by the agency for the manufacture, use, or sale for human administration. Each component (if there is more than one component) can be packaged in separate containers or some components can be combined in one container where cross-reactivity and shelf life permit. The kits can be in unit dosage forms, bulk packages (for example, multi-dose packages) or sub-unit doses. Kits can also include multiple unit doses of the compounds and instructions for use and be packaged in quantities sufficient for storage and use in pharmacies (for example, hospital pharmacies and compounding pharmacies).

Also disclosed are articles of manufacture comprising a unit dosage of a compound of Formula (Ia) or Formula (Ib), or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture can further be sterilized and/or sealed.

EXAMPLES

Example 1: Synthesis of the Compound of Formula (Ia)

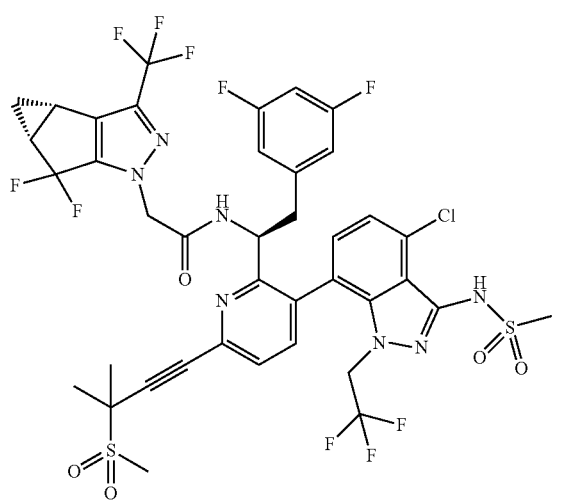

(Ia)

N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Ia), was synthesized according the methods described below and is also described in WO 2018/035359, which is incorporated by reference in its entirety herein. The compound structure for the compound of Formula (Ia) provided above may also be named or identified as 1H-Cyclopropa[3,4]cyclopenta[1,2]pyrazole-1-acetamide, N-[(1S)-1-[3-[4-chloro-3-[(methylsulfonyl)amino]-1-(2,2,2-trifluoroethyl)-1H-indazol-7-yl]-6-[3-methyl-3-(methylsulfonyl)-1-butyn-1-yl]-2-pyridinyl]-2-(3, 5-difluorophenyl)ethyl]-5,5-difluoro-3b,4,4a,5-tetrahydro-3-(trifluoromethyl)-, (3bS,4aR)-under CAS; CAS Registry Number 2189684-44-2.

A. Preparation of Compounds (8a) and (8b)

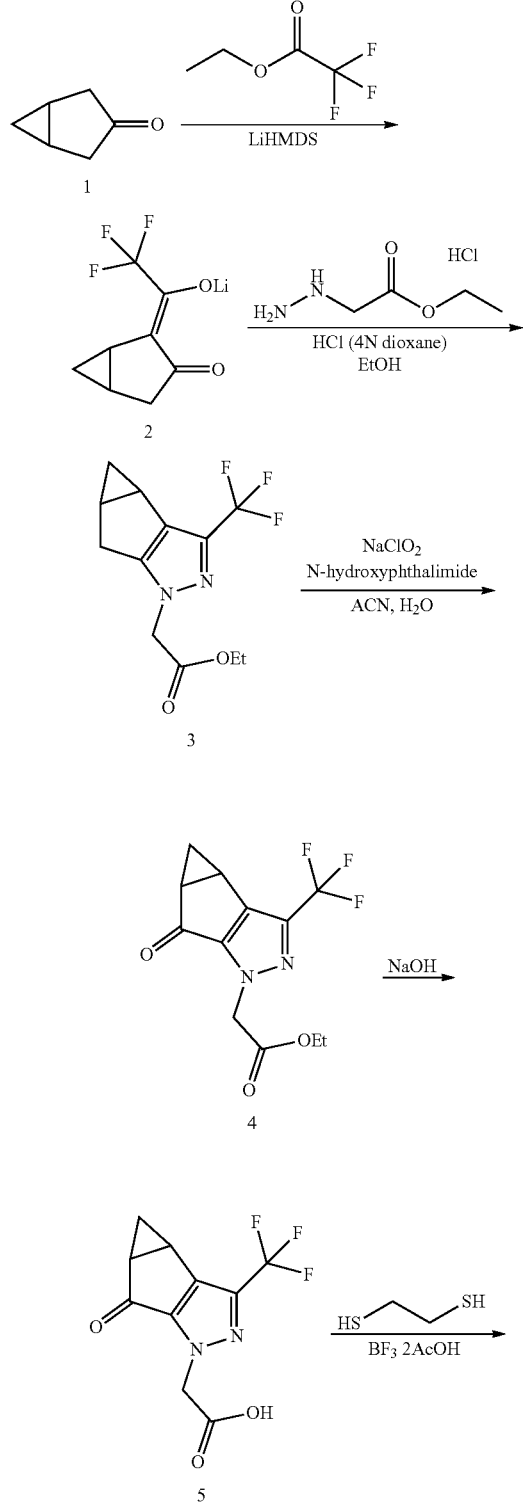

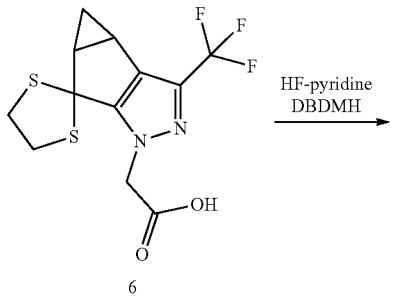

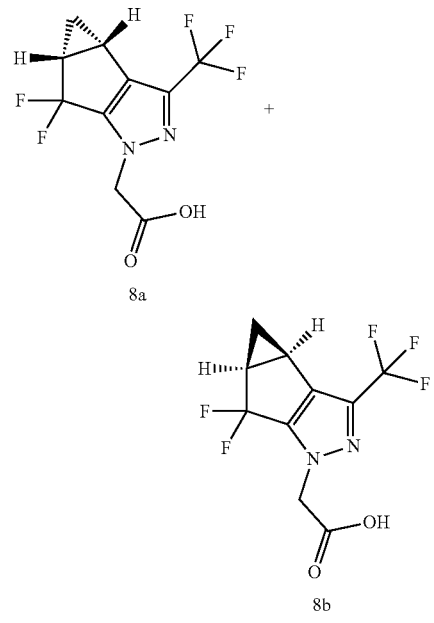

Synthesis of lithium 2,2,2-trifluoro-1-(3-oxobicyclo[3.1.0]hexan-2-ylidene)ethan-1-olate (2)

A reactor was charged with bicyclo[3.1.0]hexan-3-one (1) (95.6 g, 0.99 mol), ethyl 2,2,2-trifluoroacetate (113.2 mL, 0.95 mol), and THF (50 mL). The reaction mixture was cooled to 0° C. LiHMDS (lithium bis(trimethylsilyl)amide) (1 L of 1.0 M solution in THF, 1 mol) was added via an addition funnel at a rate to maintain an internal temperature of ≤1° C. After the addition was complete, hexanes (235 mL) was added in a steady stream via an addition funnel and stirred for 15 min. The resultant solids were collected by filtration, washed with hexanes (3×400 mL), and dried to provide the title compound.

Synthesis of ethyl 2-(3-(trifluoromethyl)-3b,4,4a,5-tetrahydro-1H-cyclopropa[3,4]cyclopenta[1,2-c]pyrazol-1-yl)acetate (3)

A reactor was charged with lithium 2,2,2-trifluoro-1-(3-oxobicyclo[3.1.0]hexan-2-ylidene)ethan-1-olate (2) (177.2 g, 0.89 mol) and EtOH (ethanol) (779 mL). The temperature was brought to and maintained at 0° C. HCl in dioxane (4.0 N, 443 mL) was added via an addition funnel followed by the addition of solid ethyl hydrazinoacetate HCl salt (138.4 g, 0.90 mol). The reaction temperature was adjusted to 35° C. After 1 h, the reaction volume was reduced by ~40% by distillation at reduced pressure. Water (1.3 L) was added with vigorous agitation and the temperature was adjusted to 15° C. The resultant solids were collected by filtration, washed with water (3×500 mL), then hexanes (3×400 mL), and dried to provide the title compound. MS (m/z) 275.1 [M+H]$^+$.

Synthesis of ethyl 2-(5-oxo-3-(trifluoromethyl)-3b,4,4a,5-tetrahydro-1H-cyclopropa[3,4]cyclopenta[1,2-c]pyrazol-1-yl)acetate (4)

A reactor was charged with ethyl 2-(3-(trifluoromethyl)-3b,4,4a,5-tetrahydro-1H-cyclopropa[3,4]cyclopenta[1,2-c]pyrazol-1-yl)acetate (3) (291.2 g, 1.06 mol), acetonitrile (1.65 L) and water (825 mL) to which N-hydroxyphthalimide (17.4 g, 0.103 mol) and NaClO$_2$ (41.0 g, 0.45 mol, ~20% of total amount to be added) were added. The reaction mixture was heated to 50° C. and the remaining NaClO$_2$ (163.0 g, 1.80 mol) was added in five portions over 2 h. After consumption of starting material, the temperature was adjusted to 20° C. and aqueous sodium bisulfite (40% w/w, 350 mL) was added via an addition funnel. Ethyl acetate (1.75 L) was added and the layers were separated. The aqueous layer was back extracted with EtOAc (ethyl acetate) (500 mL). The organic layers were combined and washed with saturated aqueous NaHCO$_3$ (500 mL) and 1:1 water/brine (500 mL). The organic layer was concentrated under reduced pressure and co-evaporated with IPAc (isopropyl acetate) (300 mL). The crude solid was crystallized from a mixture of IPAc/heptane. The resultant solids were collected by filtration, washed with heptane, and dried to provide the title compound. MS (m/z) 289.0 [M+H]$^+$.

Synthesis of 2-(5-oxo-3-(trifluoromethyl)-3b,4,4a,5-tetrahydro-1H-cyclopropa[3,4]cyclopenta[1,2-c]pyrazol-1-yl)acetic acid (5)

To a solution of ethyl 2-(5-oxo-3-(trifluoromethyl)-3b,4,4a,5-tetrahydro-1H-cyclopropa[3,4]cyclopenta[1,2-c]pyrazol-1-yl)acetate (4) (80.40 g, 278.95 mmol) in 2-MeTHF (2-methyltetrahydrofuran) (167 mL) was added 2M aqueous sodium hydroxide (167 mL). After 25 minutes of stirring at room temperature, the reaction mixture was diluted with 2-MeTHF and was slowly acidified by the dropwise addition of concentrated HCl. The organic layer was isolated and the aqueous layer was extracted with an additional portion of 2-MeTHF. The combined organic layers were washed with saturated aqueous sodium chloride, then dried over sodium sulfate, filtered, and concentrated. The resulting oil was taken in ethyl acetate. Hexanes was added with vigorous stirring until solid formation was observed. The solid was isolated by filtration and dried to provide the title compound. MS (m/z) 259.00 [M−H]$^-$.

Synthesis of 2-(3-(trifluoromethyl)-4,4a-dihydrospiro[cyclopropa[3,4]cyclopenta[1,2-c]pyrazole-5,2'-[1,3]dithiolane]-1(3bH)-yl)acetic acid (6)

To a solution of 2-(5-oxo-3-(trifluoromethyl)-3b,4,4a,5-tetrahydro-1H-cyclopropa[3,4]cyclopenta[1,2-c]pyrazol-1-yl)acetic acid (5) (3.0 g, 11.5 mmol) in DCM (dichloromethane) (25 mL) was added 1,2-ethanedithiol (1.07 mL, 12.68 mmol) followed by boron trifluoride-acetic acid complex (4.0 mL, 28.8 mmol). The reaction mixture was stirred at room temperature overnight. To the reaction mixture was added water (60 mL) and 2-MeTHF (60 mL). The organic layer was isolated, dried over sodium sulfate, filtered, and concentrated. The crude material was dissolved in ethyl acetate (2 mL) and the solution diluted with hexanes (12 mL) with vigorous stirring to provide a solid. The solid was isolated by filtration and dried to provide the title compound. MS (m/z) 337.12 [M+H]$^+$.

Synthesis of 2-(5,5-difluoro-3-(trifluoromethyl)-3b,4,4a,5-tetrahydro-1H-cyclopropa[3,4]cyclopenta[1,2-c]pyrazol-1-yl)acetic acid (7)

To a suspension of 1,3-dibromo-5,5-dimethylhydantoin (12.75 g, 44.6 mmol) in DCM (35 mL) was added pyridine hydrofluoride (5.0 mL) at 0° C. The suspension was stirred at 0° C. for 10 minutes. To the suspension was added a solution of 2-(3-(trifluoromethyl)-4,4a-dihydrospiro[cyclopropa[3,4]cyclopenta[1,2-c]pyrazole-5,2'-[1,3]dithiolane]-1(3bH)-yl)acetic acid (6) (5.00 g, 14.9 mmol) dropwise. After addition was complete, the reaction mixture was stirred at 0° C. for an additional 15 minutes. The reaction mixture was poured into a saturated aqueous sodium bicarbonate solution (300 mL) with vigorous stirring. The organic layer was removed and the aqueous layer was acidified to pH ~1 with concentrated HCl. The aqueous phase was extracted with three portions of MTBE (methyl tert-butyl ether). The combined organic layers were dried over sodium sulfate, filtered, and concentrated. The resulting solid was taken in MTBE (16 mL) and filtered to remove any resulting solid. The solution was then extracted with 2N NaOH (16 mL). The aqueous layer was diluted with water (16 mL) with vigorous stirring and continued stirring at room temperature for 15 minutes. The resulting solid was removed by filtration. The aqueous layer was acidified by slow, dropwise addition of concentrated HCl to pH ~1 with vigorous stirring to provide a solid precipitate. The solid was isolated by filtration to provide the title compound. MS (m/z) 281.12 [M+H]$^+$.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (8a) and 2-((3bR,4aS)-5,5-difluoro-3-(trifluoromethyl)-3b,4,4a,5-tetrahydro-1H-cyclopropa[3,4]cyclopenta[1,2-c]pyrazol-1-yl)acetic acid (8b)

2-(5,5-Difluoro-3-(trifluoromethyl)-3b,4,4a,5-tetrahydro-1H-cyclopropa[3,4]cyclopenta[1,2-c]pyrazol-1-yl)acetic acid was separated to its constituent enantiomers, the title compounds, by chiral SFC under the following conditions: Instrument: Thar 350 preparative SFC; Column: ChiralPak IC-10 u, 300×50 mmI.D; Mobile phase: 35% Isopropanol (0.1% NH$_3$·H$_2$O) and CO$_2$; Flow rate: 200 mL/min; Column temperature: 38° C.; UV detection: 220 nm; Sample preparation: Compound was dissolved in isopropanol to ~45 mg/mL; Injection: 6.5 mL per injection. Analytical SFC

[mobile phase: A for $CO_2$ and B for Isopropanol (0.05% DEA); Gradient: B 20%; A; Flow rate: 2.35 mL/min; Column: Chiralpak IC-3, 150×4.6 mm, 3 um; Wavelength: 254 nm] (8a): t=3.39 min, (8b): t=2.17 min.

Compound (8a): $^1$H NMR (400 MHz, chloroform-d) δ 4.93 (s, 2H), 2.52-2.43 (m, 2H), 1.44-1.38 (m, 1H), 1.15 (m, 1H).

B. Preparation of Compound (12)

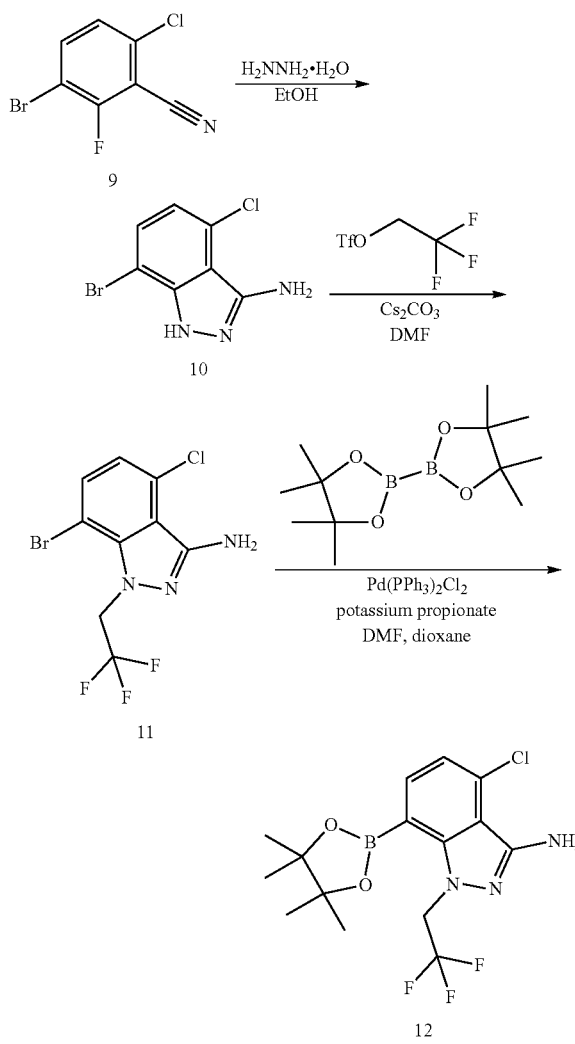

Synthesis of 7-bromo-4-chloro-1H-indazol-3-amine (10)

To 3-bromo-6-chloro-2-fluorobenzonitrile (9) (13.9 g, 59.3 mmol) in EtOH (ethanol) (60 mL) was added hydrazine monohydrate (5.77 mL). The reaction mixture was heated to 80° C. for 3 h. After cooling to ambient temperature, EtOH (20 mL) was added to allow for stirring. The solids were isolated by filtration, washed with cold EtOH, and dried to provide the title compound. MS (m/z) 247.9 [M+H]$^+$.

Synthesis of 7-bromo-4-chloro-1-(2,2,2-trifluoroethyl)-1H-indazol-3-amine (11)

A reactor was charged with 7-bromo-4-chloro-1H-indazol-3-amine (10) (397.2 g, 1.6 mol) and $Cs_2CO_3$ (1052 g, 3.2 mol) then diluted with DMF (dimethylformamide) (4000 mL). To this was slowly added 2,2,2-trifluoroethyl trifluoromethanesulfonate (463.2 g, 1.9 mol) via addition funnel. Upon completion of the addition, the reaction mixture was allowed to stir for 1 hour, at which time, $H_2O$ (16 L) was added slowly. Upon completion of the addition, the mixture was allowed to stir for 12 hours at 15° C. The slurry was filtered and the collected solids were suspended in DMF (800 mL). To this was added $H_2O$ (4800 mL) and the resulting solids were collected by filtration and dried to provide the title compound. MS (m/z) 330.1 [M+H]$^+$.

Synthesis of 4-chloro-7-(4,4,5,5-tetramethyl-1,3,2-dioxaborolan-2-yl)-1-(2,2,2-trifluoroethyl)-1H-indazol-3-amine (12)

A reaction vessel was charged with 7-bromo-4-chloro-1-(2,2,2-trifluoroethyl)-1H-indazol-3-amine (11) (15.00 g, 45.66 mmol), bis(pinacolato)diboron (17.39 g, 68.49 mmol), potassium propionate (15.36 g, 136.98 mmol), dioxane (90 mL), and DMF (dimethylformamide) (30 mL). Bis(triphenylphosphine)palladium(II) dichloride (0.64 g, 0.91 mmol) was added and the reaction solution degassed by bubbling argon for 2 min. The reaction mixture was heated to 105° C. for 4 hrs. After cooling to ambient temperature, the reaction mixture was filtered through a pad of Celite and silica gel while washing with EtOAc. The filtrate was washed with a 5% LiCl solution and brine. The organic layers were separated, dried, and concentrated under reduced pressure. The residue was treated with IPAc/heptane (1/10) at 60° C. then cooled to ambient temperature and stirred for 15 h. The solids were collected by filtration and dried to afford the title compound. MS (m/z) 376.7 [M+H]$^+$ $^1$H NMR (400 MHz, DMSO-d$_6$) δ 7.69 (d, 1H), 7.06 (d, 1H), 5.55 (s, 2H), 5.45 (q, 2H), 1.32 (s, 12H).

C. Preparation of Compound (14)

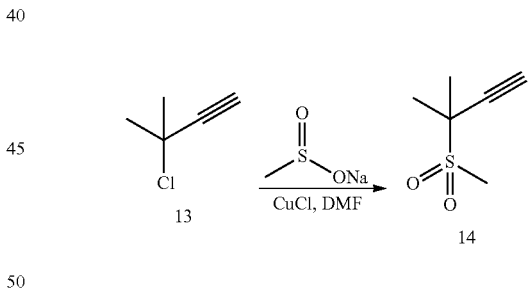

Synthesis of 3-methyl-3-(methylsulfonyl)but-1-yne (14)

To a stirred suspension of sodium methanesulfinate (18.47 g, 175.5 mmol) and copper(I) chloride (1.45 g, 14.6 mmol) in DMF (dimethylformamide) (50 mL) was added 3-chloro-3-methylbut-1-yne (13) (15.00 g, 146.3 mmol, 16.4 mL) dropwise. The resulting reaction mixture was heated to 40° C. and stirred for 16 h. The reaction mixture was cooled to room temperature and diluted with EtOAc. The solution was washed with water and brine. The organic layer was collected and dried over sodium sulfate, then filtered. The solution was concentrated under vacuum and purified by silica gel chromatography to provide the title compound. Mp: 114.8-115.5° C. $^1$H NMR (400 MHz, chloroform-d) δ 3.04 (s, 3H), 2.58 (s, 1H), 1.67 (s, 6H).

D. Preparation of Compound (19)

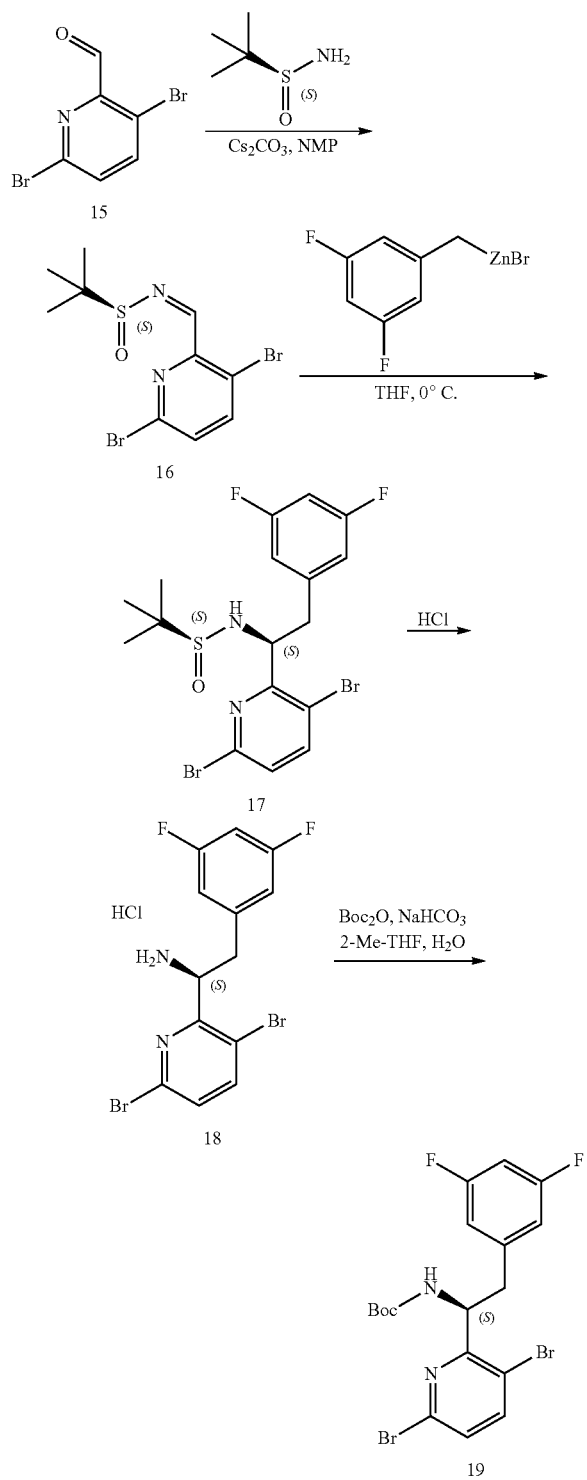

Synthesis of (S)—N-((3,6-dibromopyridin-2-yl)methylene)-2-methylpropane-2-sulfinamide (16)

3,6-Dibromopicolinaldehyde (15) (76.0 g, 0.287 mol) and (S)-2-methylpropane-2-sulfinamide (36.51 g, 0.301 mol) were combined in NMP (N-methyl-2-pyrrolidone) (200 mL). To the reaction mixture was added $Cs_2CO_3$ (41.94 g, 0.316 mol) as a solid in one portion. The reaction mixture was stirred for 2 h then cooled to 5° C. Water (1.3 L) was added to the reaction mixture. The resulting suspension was stirred for 1 h, the solids were isolated by filtration, then washed with water (5×100 mL) and dried to provide the title compound. MS (m/z) 368.9 $[M+H]^+$.

Synthesis of (S)—N—((S)-1-(3,6-dibromopyridin-2-yl)-2-(3,5-difluorophenyl)ethyl)-2-methylpropane-2-sulfinamide (17)

A reaction vessel was charged with (S)—N-((3,6-dibromopyridin-2-yl)methylene)-2-methylpropane-2-sulfinamide (16) (65.5 g, 177.95 mmol) followed by DMF (dimethylformamide) (260 mL). The mixture was stirred for 5 min until homogeneous and the solution was cooled to 8° C. To the reaction mixture was added (3,5-difluorobenzyl)zinc bromide (0.5 M in THF (tetrahydrofuran), 516.04 mL) dropwise over 90 mins. The mixture was stirred for an additional 2.5 h. To the reaction mixture, 5% AcOH (acetic acid) in water (640 mL) was added over 10 mins followed by CPME (cyclopentyl methyl ether) (320 mL) in one portion. The mixture was stirred for 5 mins, warmed to room temperature, and the layers were separated. The organic layer was washed with 5% AcOH (320 mL) then treated with 0.5 M NaOH (330 mL) and washed with brine. The organic layer was collected, dried with $Na_2SO_4$, and filtered. To the crude mixture was added MeOH (methanol) (33 mL). To the stirring mixture was added dropwise 3M HCl in CPME (128 mL) over 15 mins. After stirring for 1 h, the precipitate was removed by filtration. The filtrate was diluted with hexane (300 mL) and the product was extracted with water (450 mL). The aqueous layer was basified with 8 M NaOH and extracted with CPME (375 mL). The organic layer was washed with brine, dried over $Na_2SO_4$, and filtered to provide the title compound in solution which was used directly in the next reaction. MS (m/z) 497.0 $[M+H]^+$.

Synthesis of (S)-1-(3,6-dibromopyridin-2-yl)-2-(3,5-difluorophenyl)ethan-1-amine (18)

The resulting solution of (S)—N—((S)-1-(3,6-dibromopyridin-2-yl)-2-(3,5-difluorophenyl)ethyl)-2-methylpropane-2-sulfinamide (17) was diluted with CPME to a volume of 700 mL to which acetonitrile (350 mL) was added. To the stirring mixture, concentrated HCl (37%, 16.4 mL) was added dropwise over 10 mins at room temperature. The thick slurry was vigorously stirred for 4 h. The solids were filtered and washed with 2:1 CPME:ACN to provide the title compound. MS (m/z) 393.3 $[M+H]^+$.

Synthesis of tert-butyl (S)-(1-(3,6-dibromopyridin-2-yl)-2-(3,5-difluorophenyl)ethyl)carbamate (19)

A reaction vessel was charged with 2-MeTHF (190 mL), water (190 mL), and (S)-1-(3,6-dibromopyridin-2-yl)-2-(3,5-difluorophenyl)ethan-1-amine (18) (46.9 g, 0.11 mol) followed by portionwise addition of $NaHCO_3$ (30.34 g, 0.36 mol). The reaction mixture was cooled to 5° C. and di-tert-butyl dicarbonate (27.47 g, 0.13 mol) was added. The reaction mixture was stirred at 0° C. for 2 h and ambient temperature for 2 h. The reaction mixture was diluted with water and extracted with MTBE (methyl tert-butyl ether). The organic layers were washed with brine, dried, and concentrated. Crude compound was purified by column chromatography on silica to provide the title compound. MS (m/z) 492.8 $[M+H]^+$. $^1$H NMR (400 MHz, methanol-$d_4$) δ 7.85 (d, 1H), 7.42 (d, 1H), 6.90-6.72 (m, 3H), 5.33 (dd, 1H), 3.10 (dd, 1H), 2.92 (dd, 1H), 1.36 (s, 9H).

E. Preparation of the Compound of Formula (Ia)
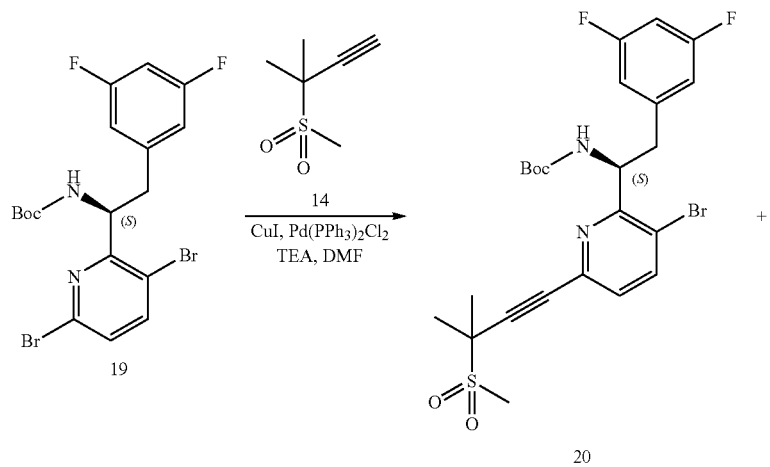
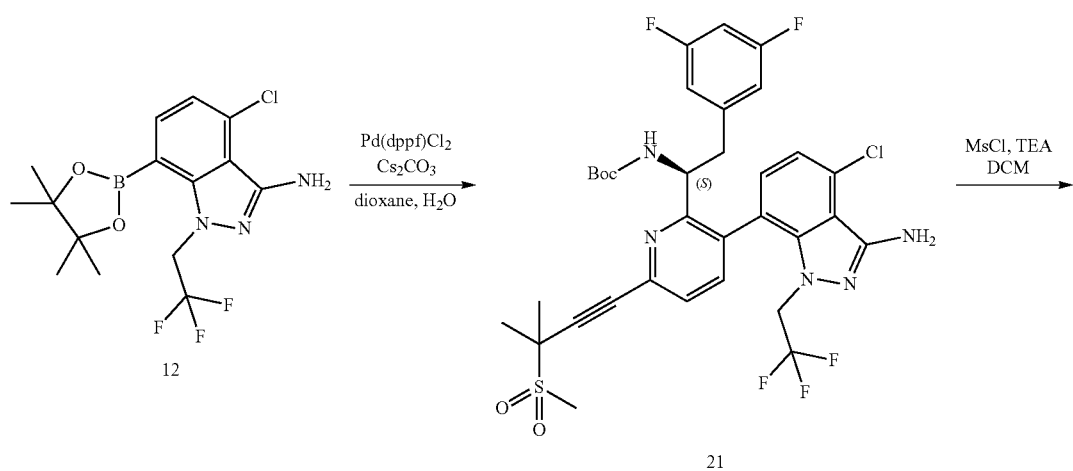
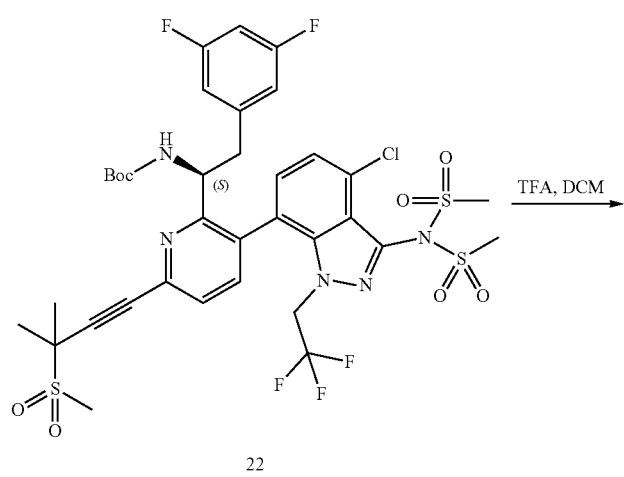

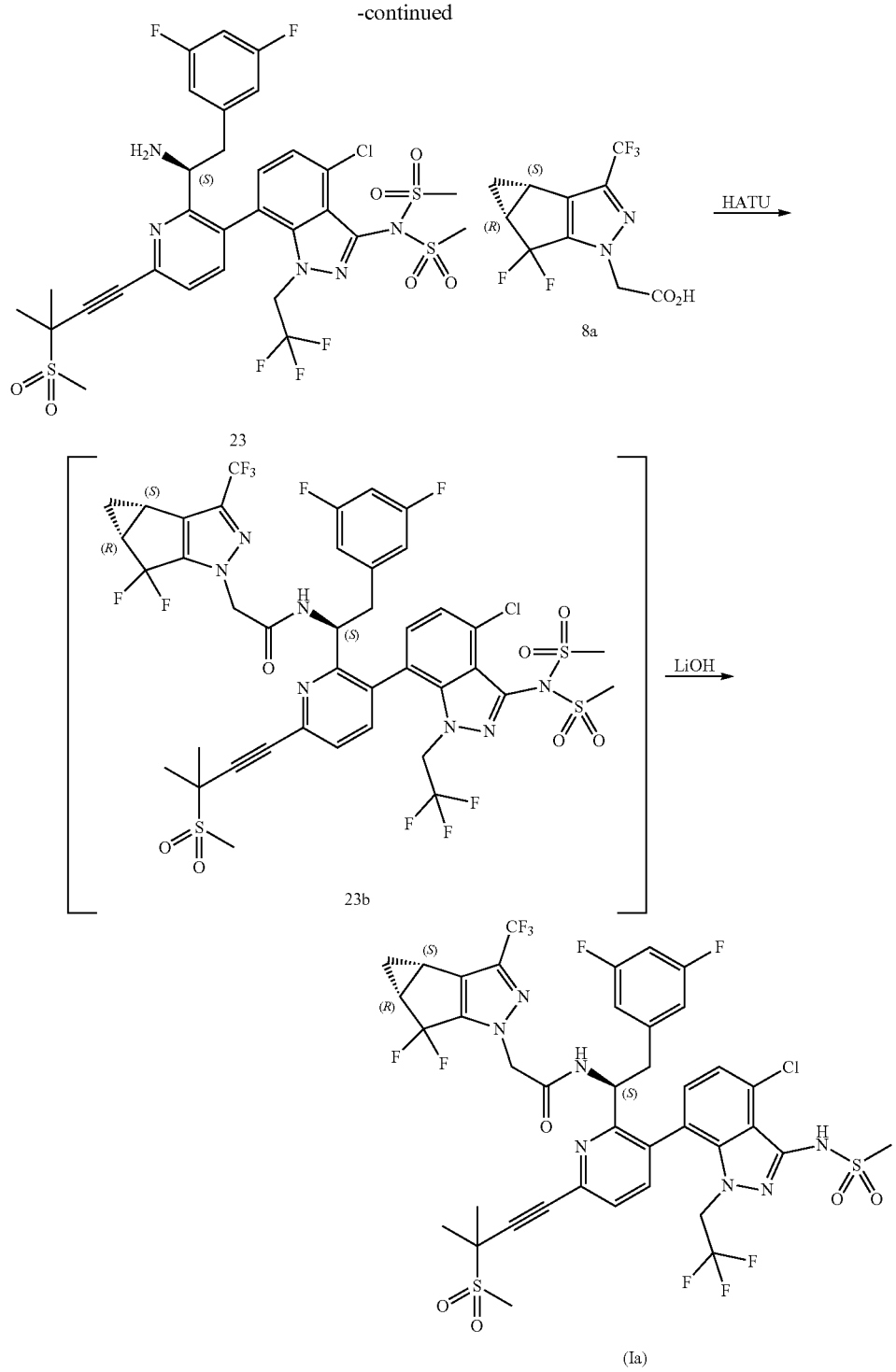

Synthesis of tert-butyl (S)-(1-(3-bromo-6-(3-methyl-3-(methylsulfonyl)but-1-yn-1-yl)pyridin-2-yl)-2-(3,5-difluorophenyl)ethyl)carbamate (20)

A reactor was charged with tert-butyl (S)-(1-(3,6-dibromopyridin-2-yl)-2-(3,5-difluorophenyl)ethyl)carbamate (19) (50.00 g, 101.8 mmol), 3-methyl-3-methylsulfonyl-but-1-yne (14) (17.86 g, 122.2 mmol), DMF (dimethylformamide) (90 mL), and Et$_3$N (trimethylamine) (42.5 mL, 305.4 mmol). The reaction mixture was heated to 50° C. Bis(triphenylphosphine)palladium(II) dichloride (2.14 g, 3.1 mmol) and copper(I) iodide (0.58 g, 3.1 mmol) were added. After 30 min, the reaction mixture was diluted with MeCN (acetonitrile) (200 mL) and then 7% aq. NH$_4$Cl (200 mL) was added dropwise. A slurry was formed and adjusted to ambient temperature. After 3 h, the solids were collected by filtration. The cake was washed with MeCN/water twice (1:1, 75 mL) and MTBE (methyl tert-butyl ether) (75 mL).

The solid was dried to provide the title compound. MS (m/z) 556 [M+H]⁺. ¹H NMR (400 MHz, chloroform-d) δ 7.84 (d, J=8.2 Hz, 1H), 7.29-7.15 (m, 1H), 6.70-6.55 (m, 2H), 5.79 (d, J=9.0 Hz, 1H), 5.57-5.45 (m, 1H), 3.21-3.05 (m, 4H), 2.99-2.88 (m, 1H), 1.80 (s, 6H), 1.40* (s, 7H), 1.30* (s, 2H).
* denotes presence of atropisomers in 4.6:1 ratio.

Synthesis of tert-butyl (S)-(1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (21)

tert-Butyl (S)-(1-(3-bromo-6-(3-methyl-3-(methylsulfonyl)but-1-yn-1-yl)pyridin-2-yl)-2-(3,5-difluorophenyl)ethyl)carbamate (20) (1000.0 mg, 1.79 mmol), 4-chloro-7-(4,4,5,5-tetramethyl-1,3,2-dioxaborolan-2-yl)-1-(2,2,2-trifluoroethyl)-1H-indazol-3-amine (12) (808.5 mg, 2.15 mmol), [1,1'-bis(diphenylphosphino)ferrocene]dichloropalladium (II) (65.6 mg, 0.09 mmol), and cesium carbonate (876.7 mg, 2.69 mmol) were charged in a round bottom flask and placed under argon. Dioxane (10 mL) and water (2 mL) were added, and the suspension was degassed by bubbling argon for 60 seconds. After degassing, the reaction flask was fitted with a reflux condenser and heated to 80° C. overnight. The reaction mixture was cooled to room temperature, and the aqueous layer was removed. The organic layer was concentrated under vacuum, and the resulting residue was purified by silica gel column chromatography to provide the title compound. MS (m/z) 726.1 [M+H]⁺. ¹H NMR (400 MHz, chloroform-d) δ 7.69-7.55 (m), 7.55-7.42 (m), 7.16-7.06 (m), 7.07-6.96 (m), 6.89 (d), 6.60 (tt), 6.44 (dd), 6.20 (d), 6.16 (d), 6.08 (s), 5.69-5.53 (m), 5.29 (s), 5.26 (d), 4.95-4.85 (m), 4.64 (q), 4.59-4.46 (m), 4.36-4.19 (m), 3.94-3.76 (m), 3.64-3.54 (m), 3.18 (s), 3.17 (s), 3.01-2.84 (m), 2.78-2.68 (m), 1.86-1.82 (m), 1.38 (s), 1.34 (s), 1.26 (s), 1.23 (s), 1.15 (s).

Synthesis of tert-butyl (S)-(1-(3-(4-chloro-3-(N-(methylsulfonyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (22)

tert-Butyl (S)-(1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (21) (37.89 g, 52.18 mmol) was dissolved in methylene chloride (380 mL) with stirring at ambient temperature. Triethylamine (21.82 mL, 156.54 mmol) was added, followed by slow addition of methanesulfonyl chloride (8.08 mL, 104.36 mmol). When the reaction was complete, water (200 mL) was added and stirred for 0.5 hours. The organic layer was separated and the aqueous layer was extracted with methylene chloride once. The combined organic layers were washed with water and brine, dried over MgSO₄, filtered, and concentrated to a small volume. Hexanes was added. The liquid suspension was decanted. The remaining solid was dried under reduced pressure to afford the title compound. MS (m/z): 882.69 [M+H]⁺. ¹H NMR (400 MHz, methanol-d₄) δ 7.87 (d), 7.83 (d), 7.76 (s), 7.74 (s), 7.69 (s), 7.67 (s), 7.65 (s), 7.52-7.47 (m), 7.46 (s), 7.37 (d), 7.33 (d), 7.11-7.03 (m), 4.79-4.55 (m), 4.51 (t), 4.36 (dt), 4.20-4.05 (m), 3.64 (s), 3.62 (s), 3.60 (s), 3.59 (s), 3.23 (s), 3.04 (d), 3.01 (d), 2.95-2.83 (m), 1.81 (s), 1.34 (s), 1.29 (s), 0.98 (s).

Synthesis of (S)—N-(7-(2-(1-amino-2-(3,5-difluorophenyl)ethyl)-6-(3-methyl-3-(methylsulfonyl)but-1-yn-1-yl)pyridin-3-yl)-4-chloro-1-(2,2,2-trifluoroethyl)-1H-indazol-3-yl)-N-(methylsulfonyl)methanesulfonamide (23)

To tert-butyl (S)-(1-(3-(4-chloro-3-(N-(methylsulfonyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (22) (39 g, 44 mmol) dissolved in methylene chloride (120 mL) was added trifluoroacetic acid (80 mL). The reaction mixture was stirred at ambient temperature for 50 minutes. The reaction mixture was diluted with methylene chloride and slowly poured into ice cold saturated aqueous NaHCO₃. The organic layer was separated, washed with water and brine, dried over MgSO₄, filtered, and concentrated to dryness to afford the title compound. MS (m/z): 782.84 [M+H]⁺. ¹H NMR (400 MHz, chloroform-d) δ 7.61 (d), 7.54-7.44 (m), 7.40 (d), 7.33 (d), 7.20 (d), 6.66-6.57 (m), 6.44 (d), 6.33 (d), 6.17 (d), 4.64 (s), 3.68 (s), 3.64 (s), 3.61 (s), 3.55 (s), 3.19 (s), 3.05 (dd), 2.85-2.72 (m), 1.86 (s), 1.62 (s).

Synthesis of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Ia)

(S)—N-(7-(2-(1-Amino-2-(3,5-difluorophenyl)ethyl)-6-(3-methyl-3-(methylsulfonyl)but-1-yn-1-yl)pyridin-3-yl)-4-chloro-1-(2,2,2-trifluoroethyl)-1H-indazol-3-yl)-N-(methylsulfonyl)methanesulfonamide (23) (1757 mg, 2.25 mmol), 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (8a) (666 mg, 2.36 mmol), and HATU (1-[bis(dimethylamino)methylene]-1H-1,2,3-triazolo[4,5-b]pyridinium 3-oxide hexafluorophosphate) (854 mg, 2.25 mmol) were charged in a round bottom flask and dissolved in DMF (dimethylformamide) (10.0 mL). To the solution was added N,N-diisopropylethylamine (0.80 mL, 4.49 mmol) at a rapid dropwise rate. After addition was complete, the reaction mixture was stirred at room temperature for 15 minutes to provide the intermediate (23b) which was not isolated (MS (m/z) 1046.65 [M+H]⁺). To the solution was added a 2 N aq. sodium hydroxide solution (5.0 mL). The mixture was stirred at room temperature for 30 minutes. The reaction mixture was partitioned between water and ethyl acetate. The organic layer was collected and washed with two portions of 5% lithium chloride solution followed by brine. The organic layer was isolated, dried over sodium sulfate, filtered, and concentrated under vacuum. The resulting residue was purified by silica gel column chromatography to yield the title compound (Ia) as an amorphous solid. MS (m/z) 968.24 [M+H]⁺. ¹H NMR (400 MHz, methanol-d₄) δ 7.87-7.57 (m), 7.33-7.09 (m), 6.80-6.70 (m), 6.54 (d), 6.47 (d), 6.37-6.19 (m), 5.02-4.94 (m), 4.90-4.70 (m), 4.70-4.51 (m), 3.94 (dq), 3.32-3.28 (m), 3.23 (d), 3.07 (dd, J=13.1, 7.6 Hz), 2.93 (dd), 2.68-2.35 (m), 1.81 (s), 1.41 (q), 1.12-1.00 (m). ¹⁹F NMR (377 MHz, methanol-d₄) δ −63.65, −71.78 (t), −72.35 (t), −82.75 (dd), −105.70 (ddd), −111.73-−113.10 (m).

Compound (23b) was isolated and characterized. ¹H NMR (400 MHz, DMSO-d6) δ 9.20 (d), 8.99 (d), 7.96 (d), 7.83 (d), 7.80 (d), 7.76 (d), 7.45 (d), 7.41 (d), 7.31 (d), 7.02

(tt), 6.92 (m), 6.91 (d), 6.48 (m), 4.92 (m) 4.88 (d), 4.79 (d), 4.73 (d), 4.71 (m), 4.69 (m), 4.62 (m), 4.60 (m), 4.38 (dq), 4.12 (dq), 3.68 (s), 3.66 (s), 3.63 (s), 3.58 (s), 3.26 (s), 3.12 (dd), 3.05 (dd), 2.97 (dd), 2.78 (dd), 2.59 (m), 2.53 (m), 1.75 (s), 1.39 (m), 0.98 (m).

Example 2: Synthesis of the Compound of Formula (Ib)

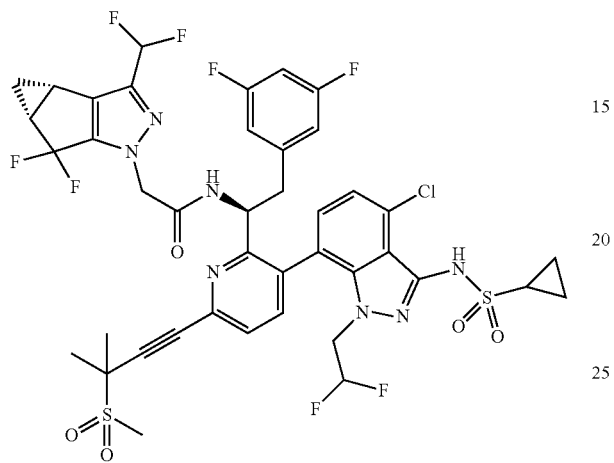

N—((S)-1-(3-(4-chloro-3-(cyclopropanesulfonamido)-1-(2,2-difluoroethyl)-1H-indazol-7-yl)-6-(3-methyl-3-(methyl sulfonyl)but-1-yn-1-yl)pyridin-2-yl)-2-(3,5-difluorophenyl)ethyl)-2-((3b S,4aR)-3-(difluoromethyl)-5,5-difluoro-3b,4,4a,5-tetrahydro-1H-cyclopropa[3,4]cyclopenta[1,2-c]pyrazol-1-yl)acetamide (Ib), was synthesized according to the methods described below and is also described in WO 2018/035359, which is incorporated by reference in its entirety herein. The compound structure for the compound of Formula (Ib) provided above may also be named or identified as 1H-cyclopropa[3,4]cyclopenta[1,2-c]pyrazole-1-acetamide, N-[(1S)-1-[3-[4-chloro-3-[(cyclopropylsulfonyl)amino]-1-(2,2-difluoroethyl)-1H-indazol-7-yl]-6-[3-methyl-3-(methylsulfonyl)-1-butyn-1-yl]-2-pyridinyl]-2-(3,5-difluorophenyl)ethyl]-3-(difluoromethyl)-5,5-difluoro-3b,4,4a,5-tetrahydro-, (3bS,4aR)-under CAS; CAS Registry Number 2189684-45-3.

A. Preparation of Compound (32)

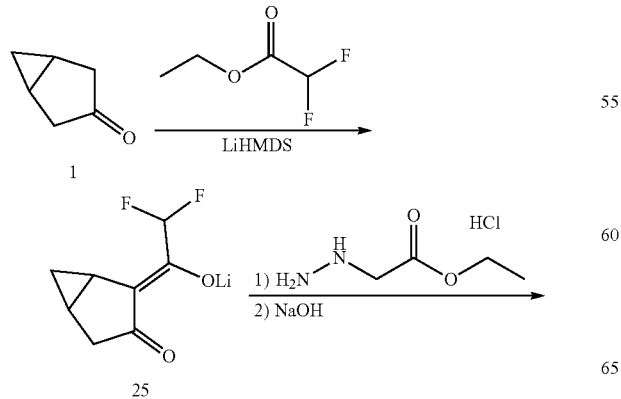

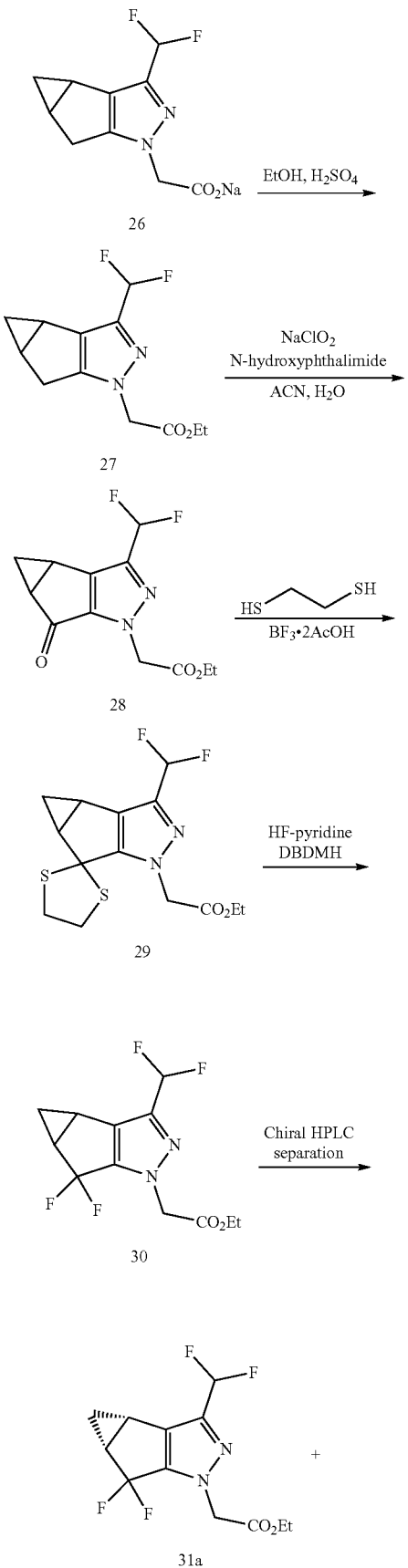

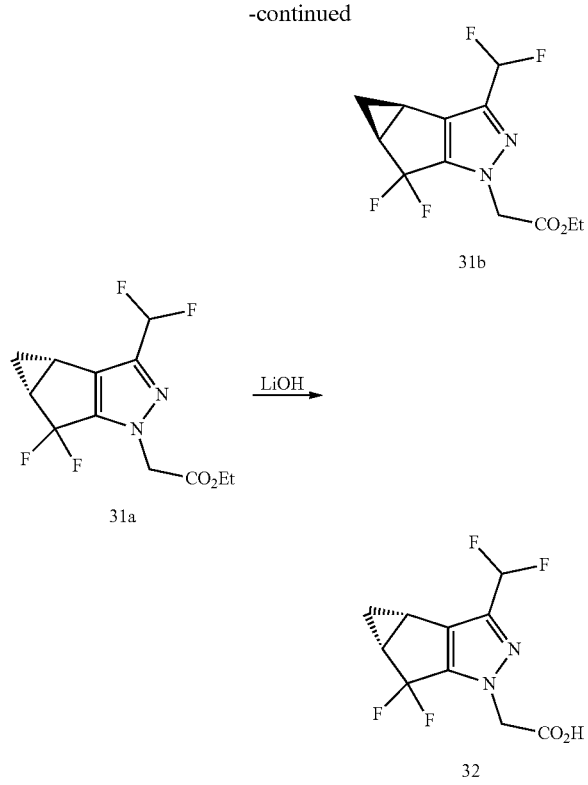

Synthesis of lithium 2,2-difluoro-1-(3-oxobicyclo[3.1.0]hexan-2-ylidene)ethan-1-olate (25)

The title compound (25) was prepared according to the method described for the synthesis of compound (2), utilizing ethyl 2,2-difluoroacetate. $^1$H NMR (400 MHz, chloroform-d) δ 6.17 (t, J=53.6 Hz, 1H), 2.78-2.73 (m, 1H), 2.44-2.39 (m, 1H), 2.25-2.24 (m, 1H), 1.70-1.69 (m, 1H), 1.22-1.14 (m, 1H), 0.31-0.27 (m, 1H).

Synthesis of sodium 2-(3-(difluoromethyl)-3b,4,4a,5-tetrahydro-1H-cyclopropa[3,4]cyclopenta[1,2-c]pyrazol-1-yl)acetate (26)

Me-THF (1.32 L) was added to a 4 L reactor, followed by lithium 2,2-difluoro-1-(3-oxobicyclo[3.1.0]hexan-2-ylidene)ethan-1-olate (25) (247 g, 1.32 mol). HCl (4 N in dioxane) (0.685 L, 2.74 mol) was slowly added to the mixture maintaining an internal temperature around 20° C. Following addition of ethyl hydrazinoacetate hydrochloride (212.05 g, 1.372 mol), the resulting mixture was stirred at 20° C. for 4 hours. The reaction mixture was heated to 50° C. for overnight. 10 N aqueous NaOH (0.548 L, 5.48 mol) was slowly added to the reaction mixture and the internal temperature was maintained at 20° C. After addition, 300 mL MeTHF was added, and the resultant suspension was stirred at 20° C. for 3 hours. The suspension was drained and filtered. The filter cake was washed with hexane (1 L) and dried in a vacuum oven at 56° C. to obtain the title compound which was used directly in the next step. MS (m/z) 229.1 [M-Na+H]$^+$.

Synthesis of ethyl 2-(3-(difluoromethyl)-3b,4,4a,5-tetrahydro-1H-cyclopropa[3,4]cyclopenta[1,2-c]pyrazol-1-yl)acetate (27)

Ethyl 2-(3-(difluoromethyl)-3b,4,4a,5-tetrahydro-1H-cyclopropa[3,4]cyclopenta[1,2-c]pyrazol-1-yl)acetate (26) from the previous step was charged in a 4 L reactor, followed by the addition of EtOH (3.5 L) and concentrated H$_2$SO$_4$ (152 mL, 2.74 mol). The resulting mixture was stirred under reflux for 2 hours. The EtOH was reduced under vacuo to 150 mL. H$_2$O (500 mL) was then added slowly. Solids were collected and washed with H$_2$O and NaHCO$_3$, followed by hexane (500 mL). The solid was dried in the oven at 45° C. to obtain the title compound. MS (m/z) 257.1 [M+H]$^+$.

Synthesis of ethyl 2-(3-(difluoromethyl)-5-oxo-3b,4,4a,5-tetrahydro-1H-cyclopropa[3,4]cyclopenta[1,2-c]pyrazol-1-yl)acetate (28)

The title compound (28) was prepared according to the method presented for the synthesis of compound (4) utilizing ethyl 2-(3-(difluoromethyl)-3b,4,4a,5-tetrahydro-1H-cyclopropa[3,4]cyclopenta[1,2-c]pyrazol-1-yl)acetate (27). MS (m/z) 271.1 [M+H]$^+$.

Synthesis of ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate (29)

To ethyl 2-(3-(difluoromethyl)-5-oxo-3b,4,4a,5-tetrahydro-1H-cyclopropa[3,4]cyclopenta[1,2-c]pyrazol-1-yl)acetate (28) (148.5 g, 0.55 mol) in DCM (2.0 L) was added ethane-1,2-dithiol (88.0 g, 0.94 mol) in one portion followed by BF$_3$·2AcOH (175.8 g, 0.94 mol). The reaction was stirred at room temperature for 12 h. The system was cooled to 0° C. and quenched with saturated aqueous NaHCO$_3$ (1000 mL). The organic layer was separated, washed with brine (500 mL), and dried over Na$_2$SO$_4$. Solvents were removed in vacuo and the residue was purified by silica gel column chromatography to provide the title compound. MS (m/z): 347.1 [M+H]$^+$.

Synthesis of ethyl 2-(3-(difluoromethyl)-5,5-difluoro-3b,4,4a,5-tetrahydro-1H-cyclopropa[3,4]cyclopenta[1,2-c]pyrazol-1-yl)acetate (30)

A solution of DBDMH (99 g, 0.35 mol) in DCM (120 mL) was cooled to −8° C. in a teflon bottle. HF/Py (120 mL) was added drop-wise over a period of 30 min. The reaction was stirred at −78° C. for 30 min. A solution of ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate (29) (40 g, 0.12 mol) in DCM (80 mL) was added drop-wise over a period of 15 min at −78° C. The resulting mixture was stirred for 30 min, then slowly warmed to −30° C. and stirred for 1.5 h. The reaction mixture was slowly poured into aq. NaHCO$_3$ (500 mL) and extracted with ethyl acetate (3×500 mL). The combined organic layer was washed with 10% aq. Na$_2$S$_2$O$_3$ (500 mL), brine (500 mL), and dried over Na$_2$SO$_4$. Solvents were removed in vacuo to afford the crude product, which was further purified by column chromatography to provide the title compound. MS (m/z): 293.2 [M+H]$^+$.

Separation of ethyl 2-((3b S,4aR)-3-(difluoromethyl)-5,5-difluoro-3b,4,4a,5-tetrahydro-1H-cyclopropa[3,4]cyclopenta[1,2-c]pyrazol-1-yl)acetate (31a) and ethyl 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetate (31b)

Ethyl 2-(3-(difluoromethyl)-5,5-difluoro-3b,4,4a,5-tetrahydro-1H-cyclopropa[3,4]cyclopenta[1,2-c]pyrazol-1-yl)

acetate was separated to its constituent enantiomers, the title compounds (31a) and (31b), by chiral HPLC under the following conditions: Column: ChiralPak AD; Mobile phase: Hex/3C EtOH=95/5; Room temperature; UV detection: 250 nm. Analytical HPLC [mobile phase: Hex/3C EtOH=95/5; Flow rate: 0.75 mL/min; Column: Chiralpak AD-H, 150×4.6 mm, 5um; Wavelength: 220 nm] (31a): t=5.30 min, (31b): t=7.00 min.

Compound (31a): $^1$H NMR (400 MHz, chloroform-d) δ 6.63 (t, J=54.8 Hz, 1H), 4.83 (s, 2H), 4.24 (q, J=7.2 Hz, 2H), 2.48-2.45 (m, 2H), 1.38-1.36 (m, 1H), 1.28 (t, J=7.2 Hz, 3H), 1.13-1.12 (m, 1H).

Synthesis of 2-((3b S,4aR)-3-(difluoromethyl)-5,5-difluoro-3b,4,4a,5-tetrahydro-1H-cyclopropa[3,4]cyclopenta[1,2-c]pyrazol-1-yl)acetic acid (32)

To a solution of ethyl 2-((3b S,4aR)-3-(difluoromethyl)-5,5-difluoro-3b,4,4a,5-tetrahydro-1H-cyclopropa[3,4]cyclopenta[1,2-c]pyrazol-1-yl)acetate (31a) (26 g, 89.0 mmol) in THF (180 mL), MeOH (90 mL), and water (90 mL) was added LiOH (5.13 g, 213.5 mmol). The mixture was stirred for 4 h. The mixture was concentrated to remove most of the THF and MeOH, and the aqueous layer was acidified by 1N HCl to adjust the pH to 2-3, then extracted with ethyl acetate (2×600 mL). The organic phase was separated and combined, dried over Na$_2$SO$_4$, filtered, and concentrated in vacuum to provide the title compound. MS (m/z) 265.0 [M+H]$^+$.

B. Preparation of Compound (34)

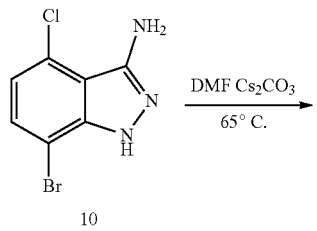

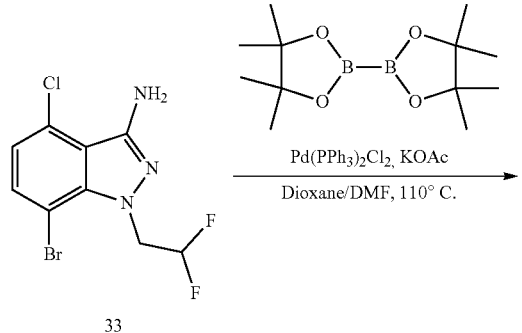

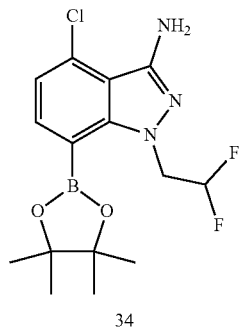

Synthesis of 7-bromo-4-chloro-1-(2,2-difluoroethyl)-1H-indazol-3-amine (33)

To a 2000 mL 4-necked round-bottom flask was placed 7-bromo-4-chloro-1H-indazol-3-amine (10) (130 g, 527.40 mmol, 1.00 equiv), N,N-dimethylformamide (1300 mL), and Cs$_2$CO$_3$ (260 g, 797.99 mmol, 1.50 equiv) with stirring for 20 min, followed by the addition of 1,1-difluoro-2-iodoethane (122 g, 635.59 mmol, 1.20 equiv). The resulting mixture was stirred overnight at 65° C., then cooled to room temperature, quenched by the addition of 3 L of water/ice, and extracted with 3×1.5 L of ethyl acetate. The combined organic layer was washed with 1×1.5 L of H$_2$O, 1×1.5 L of brine, dried over anhydrous sodium sulfate, concentrated under vacuum, and recrystallized from ethanol to afford the title compound. MS (m/z) 312.1 [M+H]$^+$.

Synthesis of 4-chloro-1-(2,2-difluoroethyl)-7-(4,4,5,5-tetramethyl-1,3,2-dioxaborolan-2-yl)-1H-indazol-3-amine (34)

To a 3000-mL 4-necked round-bottom flask that was purged and maintained with an inert atmosphere of nitrogen was placed 7-bromo-4-chloro-1-(2,2-difluoroethyl)-1H-indazol-3-amine (33) (80 g, 257.63 mmol, 1.00 equiv), 1,4-dioxane (800 mL), N,N-dimethylformamide (800 mL), KOAc (76 g, 774.40 mmol, 3.00 equiv), 4,4,5,5-tetramethyl-2-(tetramethyl-1,3,2-dioxaborolan-2-yl)-1,3,2-dioxaborolane (197 g, 775.78 mmol, 3.00 equiv) and Pd(PPh$_3$)$_2$Cl$_2$ (8 g, 11.40 mmol, 0.04 equiv). The mixture was stirred for 4 h at 110° C., then cooled to room temperature, quenched by the addition of 5 L of water/ice, and extracted with 2×2 L of ethyl acetate. The combined organic layer was washed with 1×1 L of H$_2$O, 1×1 L of brine, dried over anhydrous sodium sulfate, and concentrated under vacuum. The residue was applied onto a silica gel column and eluted with ethyl acetate/petroleum ether (1:10) to afford the title compound. MS (m/z): 358 [M+H]$^+$. $^1$H-NMR: (DMSO-d$_6$, 300 MHz, ppm): δ7.63-7.66 (1H, d), 7.00-7.03 (1H, d), 6.06-6.43 (1H, t), 5.46 (2H, s), 4.90-5.01 (2H, t), 1.34 (12H, s).

C. Preparation of the Compound of Formula (Ib)

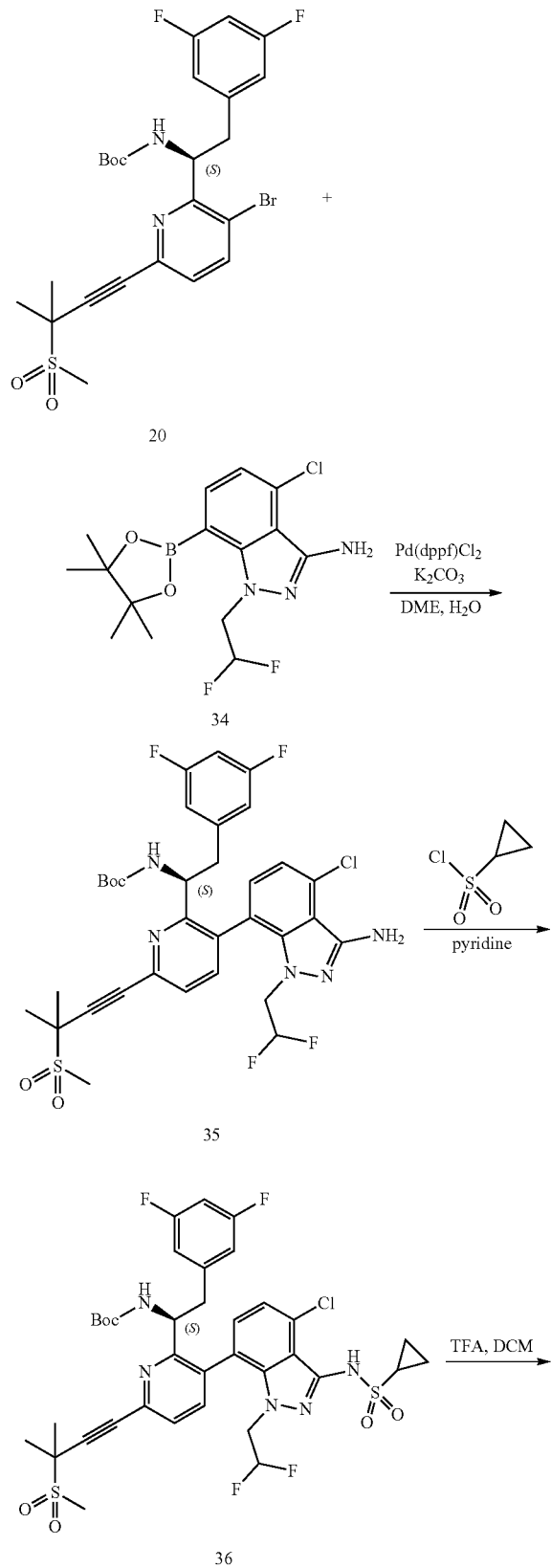

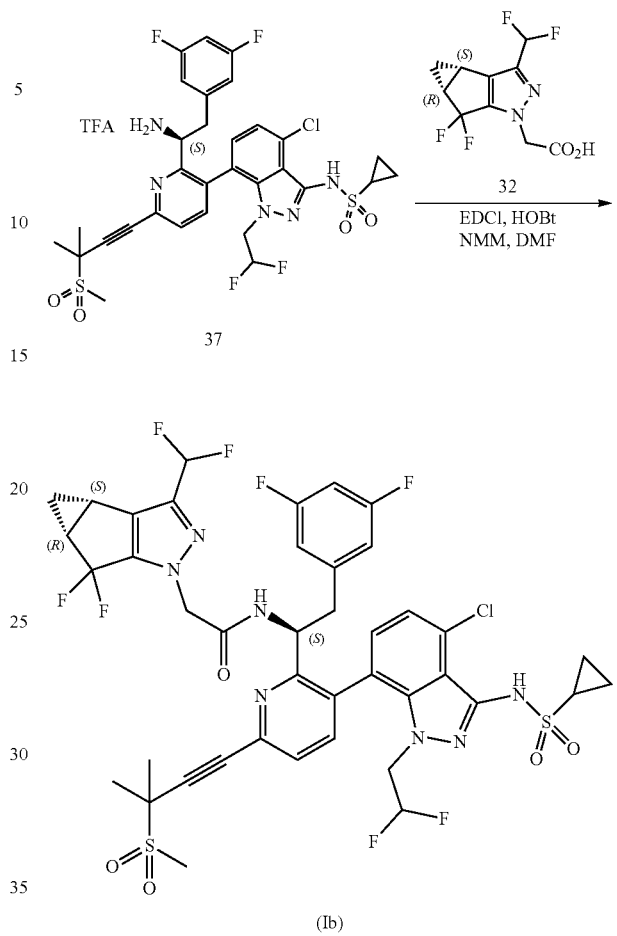

Synthesis of tert-butyl (S)-(1-(3-(3-amino-4-chloro-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (35)

tert-Butyl (S)-(1-(3-bromo-6-(3-methyl-3-(methylsulfonyl)but-1-yn-1-yl)pyridin-2-yl)-2-(3,5-difluorophenyl)ethyl)carbamate (20) (300 mg, 0.53 mmol), 4-chloro-1-(2,2-difluoroethyl)-7-(4,4,5,5-tetramethyl-1,3,2-dioxaborolan-2-yl)-1H-indazol-3-amine (34) (250 mg, 0.7 mmol), [1,1'-bis(diphenylphosphino)ferrocene]dichloropalladium(II) (14 mg, 0.016 mmol), and potassium carbonate (186 mg, 1.35 mmol) were charged in a microwave tube and placed under argon. Dimethoxyethane (2.5 mL) and water (0.3 mL) were added, and the reaction mixture was heated to 130° C. in a microwave reactor (Biotage® Initiator+) for 7 minutes. The reaction mixture was cooled to room temperature, and partitioned between EtOAc and 0.1 N HCl. The aqueous layer was removed and the organic layer was concentrated under vacuum. The resulting residue was purified by silica gel column chromatography to provide the title compound. MS (m/z) 708.20 [M+H]$^+$). $^1$H NMR (400 MHz, methanol-d$_4$) δ 7.91-7.50 (m), 7.28-6.89 (m), 6.88-6.65 (m), 6.56 (dd), 6.46-6.17 (m), 6.08-5.60 (m), 4.76-4.47 (m), 4.04-3.73 (m), 3.73-3.41 (m), 3.22 (s), 3.17-2.69 (m), 1.80 (s), 1.29 (d), 0.98 (d).

Synthesis of tert-butyl (S)-(1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (36)

tert-Butyl (S)-(1-(3-(3-amino-4-chloro-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (35) (700 mg, 0.99 mmol) and 4-dimethylaminopyridine (24 mg, 0.2 mmol) were dissolved in pyridine (2 mL) with stirring at ambient temperature. Cyclopropane-1-sulfonyl chloride (222 μL, 2.2 mmol) was then added. The reaction mixture was stirred at 70° C. until the reaction was complete. Water was added and stirred for 1 hour, and the resulting precipitate was collected by vacuum filtration and then dissolved in methylene chloride, dried over $MgSO_4$, filtered, and concentrated. The residue was purified by silica chromatography to afford the title compound. MS (m/z): 812.44 $[M+H]^+$. $^1$H NMR (400 MHz, methanol-$d_4$) δ 7.93-7.58 (m), 7.50-7.15 (m), 7.00 (dd), 6.82-6.51 (m), 6.47-6.29 (m), 6.18-5.65 (m), 4.77-4.43 (m), 4.31-4.08 (m), 3.99-3.63 (m), 3.22 (s), 3.18-2.71 (m), 1.80 (s), 1.28 (s), 1.20-0.76 (m).

Synthesis of (S)—N-(7-(2-(1-amino-2-(3,5-difluorophenyl)ethyl)-6-(3-methyl-3-(methylsulfonyl)but-1-yn-1-yl)pyridin-3-yl)-4-chloro-1-(2,2-difluoroethyl)-1H-indazol-3-yl)cyclopropanesulfonamide (37)

To a solution of tert-butyl (S)-(1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (36) (705 mg, 0.87 mmol) in methylene chloride (5 mL) was added trifluoroacetic acid (3 mL). The reaction mixture was stirred for 1 hour, then slowly poured into a saturated sodium bicarbonate solution and extracted with EtOAc. The organic layer was separated, washed with brine, dried over $MgSO_4$, filtered, and concentrated to afford the title compound. MS (m/z): 712.34 [M+H]+. $^1$H NMR (400 MHz, methanol-$d_4$) δ 7.93-7.58 (m), 7.50-7.15 (m), 7.00 (dd), 6.82-6.51 (m), 6.47-6.29 (m), 6.18-5.65 (m), 4.77-4.43 (m), 4.31-4.08 (m), 3.99-3.63 (m), 3.22 (d), 3.18-2.71 (m), 1.80 (d), 1.28 (s), 1.20-0.76 (m).

Synthesis of N—((S)-1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)-2-43bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Ib)

(S)—N-(7-(2-(1-amino-2-(3,5-difluorophenyl)ethyl)-6-(3-methyl-3-(methylsulfonyl)but-1-yn-1-yl)pyridin-3-yl)-4-chloro-1-(2,2-difluoroethyl)-1H-indazol-3-yl)cyclopropanesulfonamide (37) (514 mg, 0.72 mmol), 2-((3b S,4aR)-3-(difluoromethyl)-5,5-difluoro-3b,4,4a,5-tetrahydro-1H-cyclopropa[3,4]cyclopenta[1,2-c]pyrazol-1-yl)acetic acid (32) (191 mg, 0.72 mmol), 1-hydroxybenzotriazole (49 mg, 0.36 mmol), and 1-(3-dimethylaminopropyl)-3-ethylcarbodiimide hydrochloride (180 mg, 0.94 mmol) were charged in a round bottom flask and dissolved in DMF (10 mL). n-Methylmorpholine (0.20 mL, 1.8 mmol) was then added. The reaction mixture was stirred at ambient temperature for 30 minutes. Water was added and stirred for 1 hour. The resulting precipitate was collected by vacuum filtration, then dissolved in methylene chloride, dried over $MgSO_4$, filtered, and concentrated. The residue was purified by RP-HPLC to yield the title compound (Ib) as a TFA salt. MS (m/z) 958.88 $[M+H]^+$. $^1$H NMR (400 MHz, methanol-$d_4$) δ 7.90-7.56 (m), 7.30-7.07 (m), 6.91-6.54 (m), 6.54-6.39 (m), 6.37-6.21 (m), 6.16-5.70 (m), 4.85-4.57 (m), 4.34-4.12 (m), 3.87-3.41 (m), 3.23 (s), 3.17-3.02 (m), 3.00-2.77 (m), 2.57-2.37 (m), 1.81 (s), 1.50-0.84 (m).

Example 3: Formulations

Formulations containing the compound of Formula (Ia) were prepared as aqueous solutions or oral formulations and administered subcutaneously to rats, dogs, cynomolgus monkey, and/or rhesus monkey.

A. 10% Ethanol/13% Water/77% PEG 200 Solution (400 mg/mL Formula (Ia))

Figure 3:
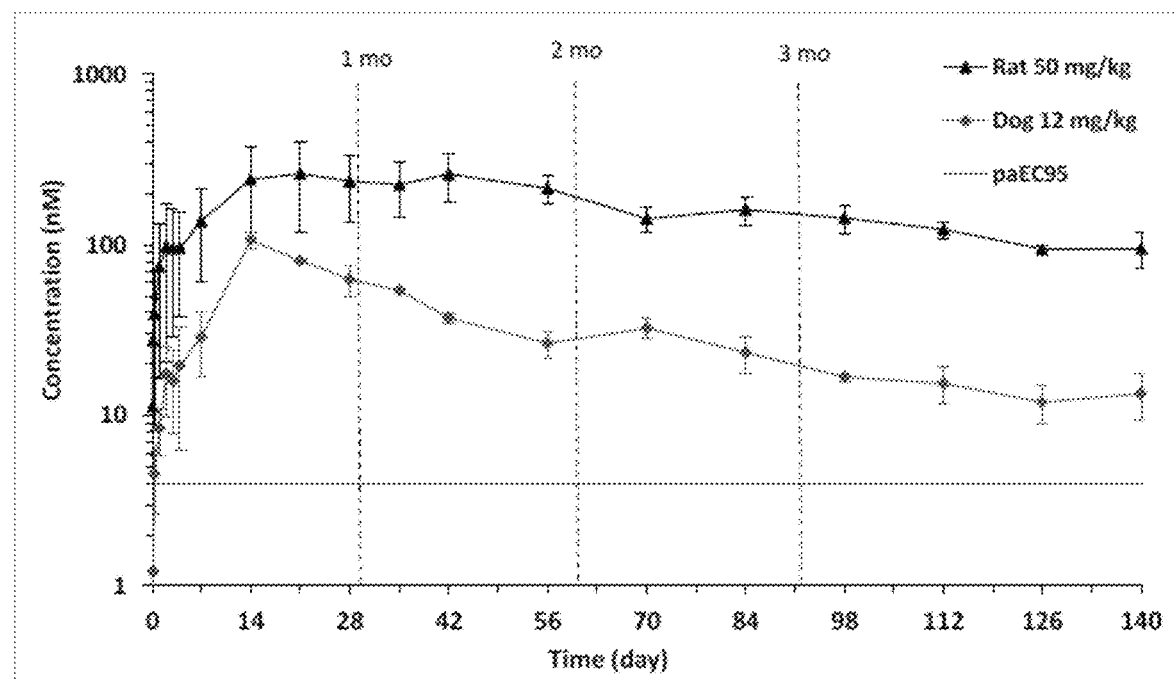
FIG. 3 shows a plot of plasma concentration over time of 400 mg/mL of the compound of Formula (Ia) in 10% ethanol, 13% water, and 77% PEG 200 when dosed subcutaneously in dogs at 12 mg/kg and rats at 50 mg/kg.

A solution of the compound of Formula (Ia) in 10% ethanol, 13% water, and 77% PEG 200 (400 mg/mL) was prepared. The solution was administered subcutaneously to dogs at a dose of 12 mg/kg and rats at a dose of 50 mg/kg and the pharmacokinetic (PK) profile was determined. FIG. 3 shows a plot of the plasma concentration of the compound of Formula (Ia) as a function of time. In both species, plasma concentrations of the compound of Formula (Ia) were maintained above the target trough concentration of 20 nM (corresponding to an IQ of 5) for at least 84 days (12 weeks). The results are summarized in Table 1 below.

TABLE 1

PK parameters of the compound of Formula (Ia) following SC administration in solution

| Species | Dose (mg/kg) | Dose Concentration (mg/mL) | Dose Volume (mL/kg) | $AUC_{0-84\,d}$ (μM · h) | $AUC_{0-140\,d}$ (μM · h) | $C_{max}$ (μM) | $T_{max}$ (h) | $C_{84\,d}$ (μM) |
|---|---|---|---|---|---|---|---|---|
| Wistar Han Rat | 50 | 400 | 0.125 | 404 ± 139 | 569 ± 157 | 0.283 ± 0.119 | 840 ± 291 | 0.162 ± 0.030 |
| Beagle Dog | 12 | 400 | 0.030 | 89.6 ± 10.1 | 111 ± 14 | 0.107 ± 0.013 | 336 ± 0 | 0.0234 ± 0.0057 |

Formula (Ia): 1 nM = 0.968 ng/mL;
d = day
Values are the mean ± SD from 3 animals

B. 15% Water/85% PEG 300 Solution (300 mg/mL Formula (Ia))

Figure 4:
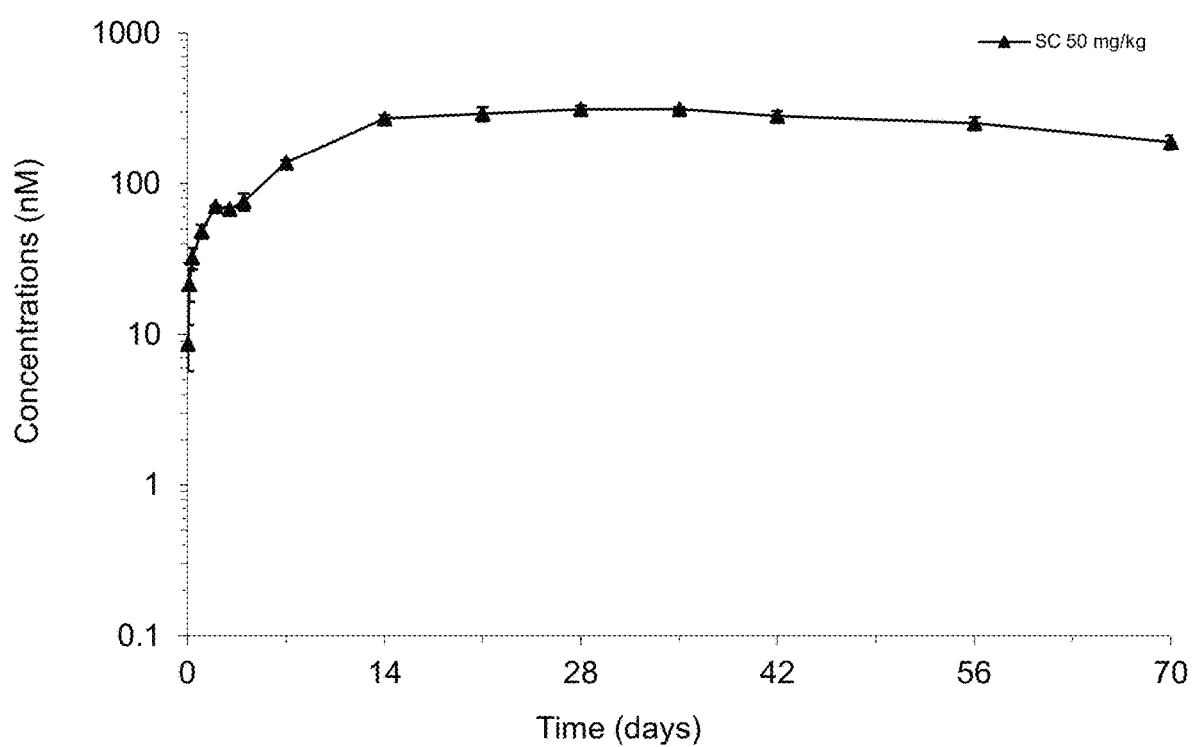
FIG. 4 shows a plot of plasma concentration over time of 300 mg/mL of the compound of Formula (Ia) in 15% water and 85% PEG 300 when dosed subcutaneously in rats at 50 mg/kg.

A solution of the free acid of the compound of Formula (Ia) in 15% water and 85% PEG 300 (300 mg/mL) was prepared. The solution was administered subcutaneously to male Wistar Han rats at a dose level of 50 mg/kg and dose volume of 0.167 mL/kg and the pharmacokinetic (PK) profile was determined. FIG. 4 shows a plot of the plasma concentration of the compound of Formula (Ia) as a function of time. The results are summarized in Tables 2 and 3 below.

TABLE 2

PK parameters of the compound of Formula (Ia) following single SC dose in rats (mean ± SD, n = 3)

| | |
|---|---|
| Dosing Concentration (mg/mL) | 300 |
| Dosing Volume (mL/kg) | 0.167 |
| Dose (mg/kg) | 50 |
| Formulation | 85:15 w/w PEG 300:water |
| $AUC_{0-168h}$ (µM · h) | 13.3 ± 0.3 |
| $AUC_{0-336h}$ (µM · h) | 47.6 ± 1.2 |
| $AUC_{0-672h}$ (µM · h) | 146 ± 6 |
| $AUC_{0-1344h}$ (µM · h) | 338 ± 15 |
| $AUC_{0-1680h}$ (µM · h) | 412 ± 21 |
| $AUC_{inf}$ (µM · h) | NA |
| $t_{1/2}$ (days) | NA |
| $C_{max}$ (µM) | NA |
| $T_{max}$ (h) | NA |

TABLE 3

Plasma concentration-time data of the compound of Formula (Ia) in rats after subcutaneous administration (mean ± SD, n = 3)

| | Plasma concentration (nM) | | | | |
|---|---|---|---|---|---|
| Time (h) | #1 | #2 | #3 | Mean | SD |
| 0 | BLQ | BLQ | BLQ | NC | NC |
| 1 | 8.9 | 11.4 | 5.6 | 8.6 | 2.9 |
| 3 | 27.0 | 17.3 | 20.1 | 21.5 | 5.0 |
| 8 | 37.0 | 32.8 | 26.8 | 32.2 | 5.1 |
| 24 | 52.6 | 49.2 | 42.8 | 48.2 | 5.0 |
| 48 | 69.8 | 71.1 | 70.8 | 70.6 | 0.7 |
| 72 | 65.6 | 66.9 | 70.1 | 67.5 | 2.3 |
| 96 | 65.5 | 76.8 | 85.2 | 75.8 | 9.9 |
| 168 | 143 | 132 | 137 | 137 | 5.5 |
| 336 | 258 | 273 | 284 | 272 | 13.1 |
| 504 | 327 | 267 | 281 | 292 | 31.4 |
| 672 | 333 | 299 | 304 | 312 | 18.4 |
| 840 | 322 | 316 | 302 | 313 | 10.3 |
| 1008 | 300 | 258 | 289 | 282 | 21.8 |
| 1344 | 251 | 229 | 278 | 253 | 24.5 |
| 1680 | 202 | 166 | 200 | 189 | 20.2 |

C. 15% Water/85% PEG 300 Solution (400 mg/mL Formula (Ia))

Figure 5:
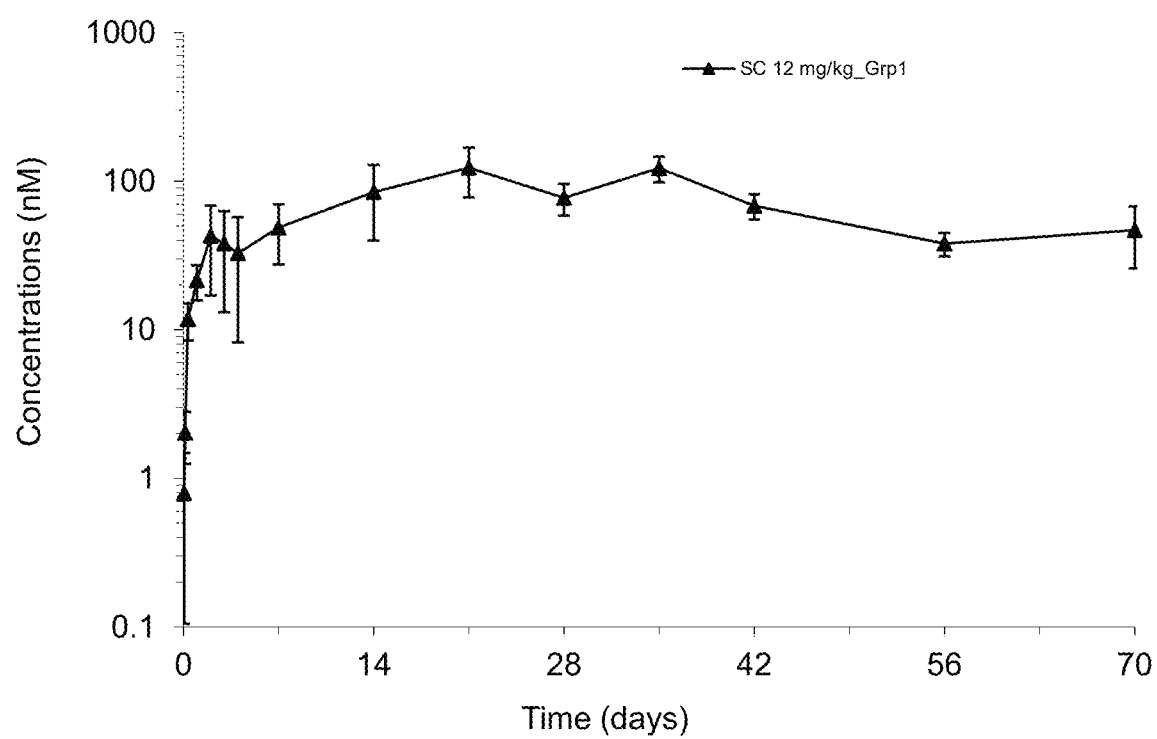
FIG. 5 shows a plot of plasma concentration over time of 400 mg/mL of the compound of Formula (Ia) in 15% water and 85% PEG 300 when dosed subcutaneously in dogs at 12 mg/kg.

A solution of the compound of Formula (Ia) in 15% water and 85% PEG 300 (400 mg/mL) was prepared. The solution was administered subcutaneously to male beagle dogs at a dose level of 12 mg/kg and dose volume of 0.04 mL/kg and the pharmacokinetic (PK) profile was determined. FIG. 5 shows a plot of the plasma concentration of the compound of Formula (Ia) as a function of time. The results are summarized in Tables 4 and 5 below.

TABLE 4

PK parameters of the compound of Formula (Ia) following single SC dose in male beagle dogs (mean ± SD, n = 3)

| | |
|---|---|
| Dosing Concentration (mg/mL) | 400 |
| Dosing Volume (mL/kg) | 0.03 |
| Dose (mg/kg) | 12 |
| Formulation | 85% PEG300 and 15% water |
| $AUC_{0-24h}$ (µM · h) | 0.304 ± 0.082 |
| $AUC_{0-48h}$ (µM · h) | 1.08 ± 0.44 |
| $AUC_{0-72h}$ (µM · h) | 2.04 ± 0.98 |
| $AUC_{0-168h}$ (µM · h) | 5.82 ± 3.04 |
| $AUC_{0-672h}$ (µM · h) | 51.2 ± 21.0 |
| $AUC_{0-1344h}$ (µM · h) | 102 ± 30 |
| $AUC_{0-1680h}$ (µM · h) | 116 ± 35 |
| $t_{1/2}$ (days) | NA |
| $C_{max}$ (µM) | NA |
| $T_{max}$ (h) | NA |

TABLE 5

Plasma concentration-time data of the compound of Formula (Ia) in beagle dogs after subcutaneous administration (mean ± SD, n = 3)

| | Plasma concentration (nM) | | | | |
|---|---|---|---|---|---|
| Time (h) | #1 | #2 | #3 | Mean | SD |
| 0 | BLQ | BLQ | BLQ | NC | NC |
| 1.0 | BLQ | 1.2 | 1.2 | 1.2 | NC |
| 3.0 | 1.2 | 2.6 | 2.3 | 2.0 | 0.8 |
| 8.0 | 10.6 | 15.5 | 9.2 | 11.8 | 3.3 |
| 24.0 | 19.8 | 27.8 | 16.8 | 21.5 | 5.7 |
| 48.0 | 54.6 | 60.6 | 13.2 | 42.8 | 25.8 |
| 72.0 | 62.8 | 37.8 | 13.2 | 37.9 | 24.8 |
| 96.0 | 58.9 | 28.8 | 10.4 | 32.7 | 24.5 |
| 168 | 71.9 | 43.1 | 30.8 | 48.6 | 21.1 |
| 336 | 135 | 64.7 | 53.0 | 84.2 | 44.4 |
| 504 | 172 | 114 | 82.9 | 123 | 45.2 |
| 672 | 93.1 | 81.5 | 56.9 | 77.2 | 18.5 |
| 840 | 150 | 110 | 107 | 122.3 | 24.0 |
| 1008 | 80.2 | 70.7 | 54.1 | 68.3 | 13.2 |
| 1344 | 42.7 | 41.2 | 30.2 | 38.0 | 6.8 |
| 1680 | 69.5 | 42.2 | 28.5 | 46.7 | 20.9 |

D. 22.6% Water/50% PEG 300/1.1% NaOH/26.3% Formula (Ia) Solution

Figure 6:
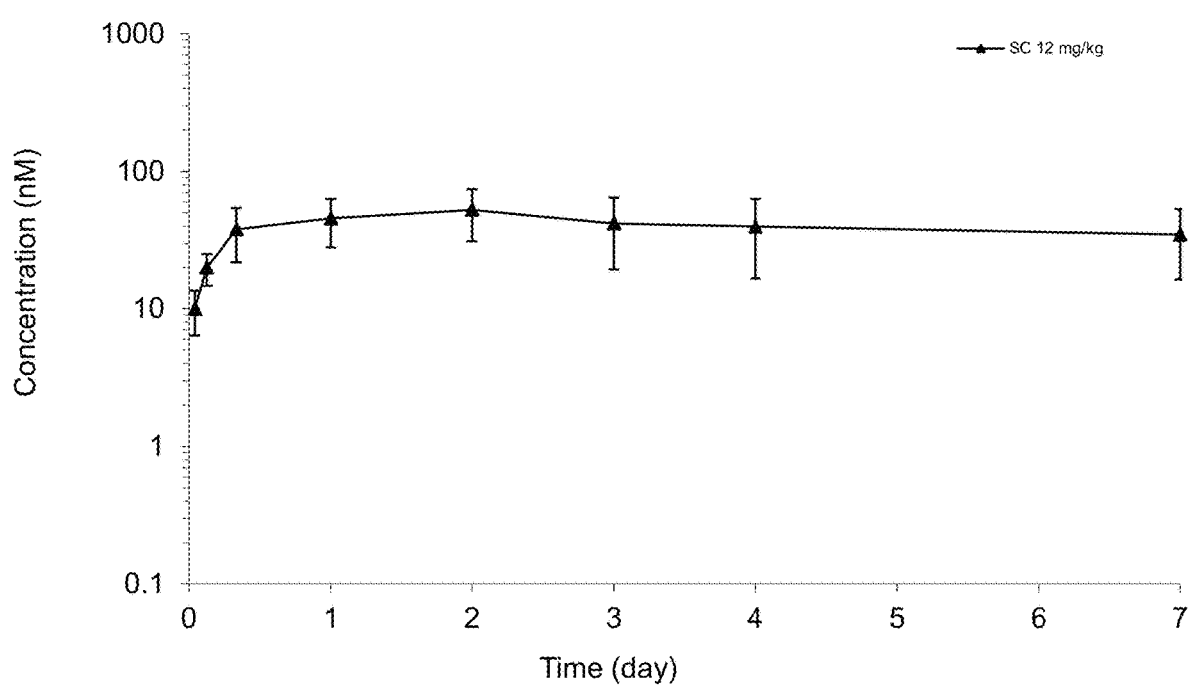
FIG. 6 shows a plot of plasma concentration over time of 300 mg/mL of the compound of Formula (Ia) sodium salt in a formulation of 22.6% water/50% PEG 300/1.1% NaOH/26.3% Formula (Ia) when dosed subcutaneously in dogs at 12 mg/kg.

A solution of the compound of Formula (Ia) sodium salt in water and 300 (300 mg/mL) was prepared that contained 22.6% water/50% PEG 300/1.1% NaOH/26.3% Formula (Ia). The solution was administered subcutaneously to male beagle dogs at a dose level of 12 mg/kg and dose volume of 0.04 mL/kg and the pharmacokinetic (PK) profile was determined. FIG. 6 shows a plot of the plasma concentration of the compound of Formula (Ia) as a function of time. The results are summarized in Tables 6 and 7 below. The results for the male beagle dogs is also shown in Table 6a.

TABLE 6

PK parameters of the compound of Formula (Ia) sodium salt following single SC dose in male beagle dogs (mean ± SD, n = 3)

| | |
|---|---|
| Dosing Concentration (mg/mL) | 300 |
| Dosing Volume (mL/kg) | 0.04 |
| Dose (mg/kg) | 12 |
| Formulation | 50, 22.6, 1.1, 26.3/ PEG300:Water:NaOH:GS-6207 w/w/w/w % |
| $AUC_{0-24h}$ (µM · h) | 0.85 ± 0.31 |
| $AUC_{0-48h}$ (µM · h) | 2.03 ± 0.76 |
| $AUC_{0-72h}$ (µM · h) | 3.16 ± 1.27 |
| $AUC_{0-168h}$ (µM · h) | 6.83 ± 3.24 |
| $t_{1/2}$ (days) | NA |
| $C_{max}$ (µM) | NA |
| $T_{max}$ (h) | NA |

TABLE 6a

PK parameters of the compound of Formula (Ia) sodium salt following single SC dose in male beagle dogs (mean ± SD, n = 3)

| | |
|---|---|
| Dosing Concentration (mg/mL) | 300 |
| Dosing Volume (mL/kg) | 0.04 |
| Dose (mg/kg) | 12 |
| Formulation | 50, 22.6, 1.1, 26.3/ PEG300:Water:NaOH:compound of Formula (Ia) w/w/w/w % |
| $AUC_{0-24h}$ (µM · h) | 0.85 ± 0.31 |
| $AUC_{0-48h}$ (µM · h) | 2.03 ± 0.76 |
| $AUC_{0-72h}$ (µM · h) | 3.16 ± 1.27 |
| $AUC_{0-168h}$ (µM · h) | 6.83 ± 3.24 |
| $t_{1/2}$ (days) | NA |
| $C_{max}$ (µM) | NA |
| $T_{max}$ (h) | NA |

TABLE 7

Plasma concentration-time data of the compound of Formula (Ia) sodium salt in beagle dogs after subcutaneous administration (mean ± SD, n = 3)

| | Plasma concentration (nM) | | | | |
|---|---|---|---|---|---|
| Time (h) | #1 | #2 | #3 | Mean | SD |
| 0 | BLQ | BLQ | BLQ | NC | NC |
| 1.0 | 14.0 | 7.2 | 8.6 | 10.0 | 3.6 |
| 3.0 | 26.0 | 17.0 | 16.8 | 19.9 | 5.3 |
| 8.0 | 56.3 | 25.8 | 32.1 | 38.1 | 16.1 |
| 24 | 57.1 | 25.4 | 54.5 | 45.7 | 17.6 |
| 48 | 71.1 | 29.0 | 57.8 | 52.6 | 21.5 |
| 72 | 51.5 | 16.2 | 58.0 | 41.9 | 22.5 |
| 96 | 46.4 | 14.0 | 59.2 | 39.9 | 23.3 |
| 168 | 47.7 | 13.6 | 43.1 | 34.8 | 18.5 |

E. 5% Ethanol/20% Propylene Glycol/45% PEG 300/30% 0.01 N HCl Oral Formulation An oral formulation containing a compound of Formula (Ia) in 5% ethanol, 20% propylene glycol, 45% PEG 300, and 30% 0.01 N HCl was prepared. The formulation was orally administered to male rat, dog, cynomolgus monkey, and rhesus monkey according to the doses shown in Table 8 below. The plasma PK parameters are also summarized in Table 8. The compound of Formula (Ia) demonstrated moderate F % (bioavailability) in rats and dogs and low F % in cynomolgus monkey and rhesus monkey. The compound of Formula (Ia) was slowly absorbed with an average $T_{max}$ range from 8.7 to 18.7 hours.

TABLE 8

Plasma PK parameters following a single oral administration of the compound of Formula (Ia) in solution to rat, dog, cynomolgus monkey, and rhesus monkey

| Species | Dose (mg/kg) | $AUC_{0-24\,h}$ (µM · h) | $AUC_{0-72\,h}$ (µM · h) | $AUC_{inf}$ (µM · h) | $C_{max}$ (µM) | $T_{max}$ (h) | F (%) |
|---|---|---|---|---|---|---|---|
| Sprague-Dawley Rat | 5.0 | ND | 13467 ± 3927 | 25200 ± 10221 | 336 ± 116 | 10.0 ± 3.5 | 21.7 ± 8.9[a] |
| Beagle Dog | 4.0 | ND | 11410 ± 4324 | 16533 ± 10366 | 471 ± 203 | 10.7 ± 11.5 | 22.1 ± 8.4[a] |
| Cynomolgus Monkey | 4.0 | 298 ± 85 | ND | ND | 17.7 ± 5.6 | 8.7 ± 3.1 | 2.2 ± 0.6[b] |
| Rhesus Monkey | 4.0 | ND | 972 ± 367 | 1133 ± 446 | 29.4 ± 7.5 | 18.7 ± 9.2 | 4.4 ± 1.7[a] |

$AUC_{0-24\,h}$ = area under the plasma concentration-time curve from 0 to 24 h;

$AUC_{0-72\,h}$ = area under the plasma concentration-time curve from 0 to 72 h;

$AUC_{inf}$ = area under the plasma concentration-time curve extrapolated to time infinity;

$C_{max}$ = maximum plasma concentration;

F = oral bioavailability;

ND = not determined;

$T_{max}$ = time to reach the maximum plasma concentration

[a]Calculated based on $AUC_{0-72\,h}$

[b]Calculated based on $AUC_{0-24\,h}$

Values are the mean ± standard deviation from 3 animals

F. Liquid-Filled Capsules

A single dose of the compound of Formula (Ia), formulated as liquid-filled capsules (LFC) containing either 100% glycerol monocaprylocaprate or 20% caprylocaproyl polyoxyl-8 glycerides and 80% glycerol monocaprylocaprate was administered orally at 7.5 mg fixed dose to 6 male beagle dogs (Table 9). At 100 mg/mL of the compound of Formula (Ia), the $AUC_{inf}$ increased with increasing glycerol monocaprylocaprate content. For the formulation with 100% glycerol monocaprylocaprate, the $AUC_{inf}$ at 50 mg/mL was higher than that at 100 mg/mL.

TABLE 9

Pharmacokinetics of the compound of Formula (Ia) following oral administration in liquid-filled capsules at 7.5 mg fixed dose to fasted male beagle dogs pretreated with pentagastrin[a,b]

| Formulation | (Ia) Dose Concentration (mg/mL) | $AUC_{0-72\,h}$ ($\mu M \cdot h$) | $AUC_{inf}$ ($\mu M \cdot h$) | $C_{max}$ (nM) | $T_{max}$ (h) | F %[c] |
|---|---|---|---|---|---|---|
| 20% caprylocaproyl polyoxyl-8 glycerides and 80% glycerol monocaprylocaprate | 100 | 1181 ± 575 | 1303 ± 634 | 53.2 ± 16.7 | 7.7 ± 8.0 | 11 ± 4 |
| 100% glycerol monocaprylocaprate | 100 | 1667 ± 1045 | 1867 ± 1188 | 71.2 ± 25.8 | 5.0 ± 1.1 | 16 ± 9 |
|  | 50 | 2178 ± 1243 | 2329 ± 1348 | 82.7 ± 32.1 | 4.0 ± 0.0 | 22 ± 10 |

[a]Animals were fasted at least 12 hours prior to dosing and fed 4 hours post dose

[b]Pentagastrin (6 µg/kg) was administered intramuscularly ~30 minutes prior to dosing to ensure an acidic pH in the gastrointestinal tract

[c]% F calculated based on $AUC_{0-72\,h}$ with average IV $AUC_{0-72\,h}$ = 13,467 nM · h at 1 mg/kg Values are the mean ± standard deviation from 6 animals

G. 9.8 w/w % Water, 65.0 w/w % PEG 300, and 25.2 w/w % of a Compound of Formula (Ia) Solution (300 mg/mL of Compound of Formula (Ia))

Figure 7A:
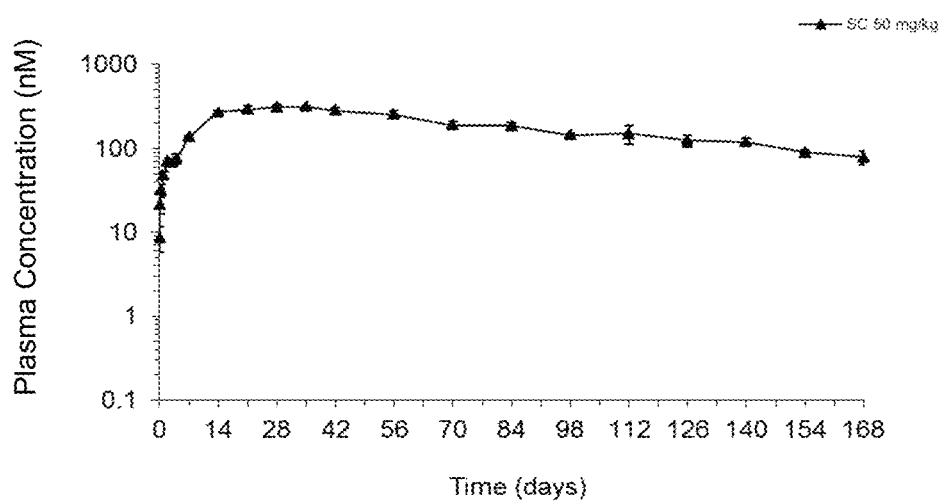
FIGS. 7A and 7B show plots of the plasma concentration over time of 300 mg/ml of the compound of Formula (Ia) in a solution of 9.8 w/w % water, 65.0 w/w % PEG 300, and 25.2 w/w % of a compound of Formula (Ia) when dosed subcutaneously in rats at 50 mg/kg (FIG. 7A) and in dogs at 12 mg/kg (FIG. 7B).
Figure 7B:
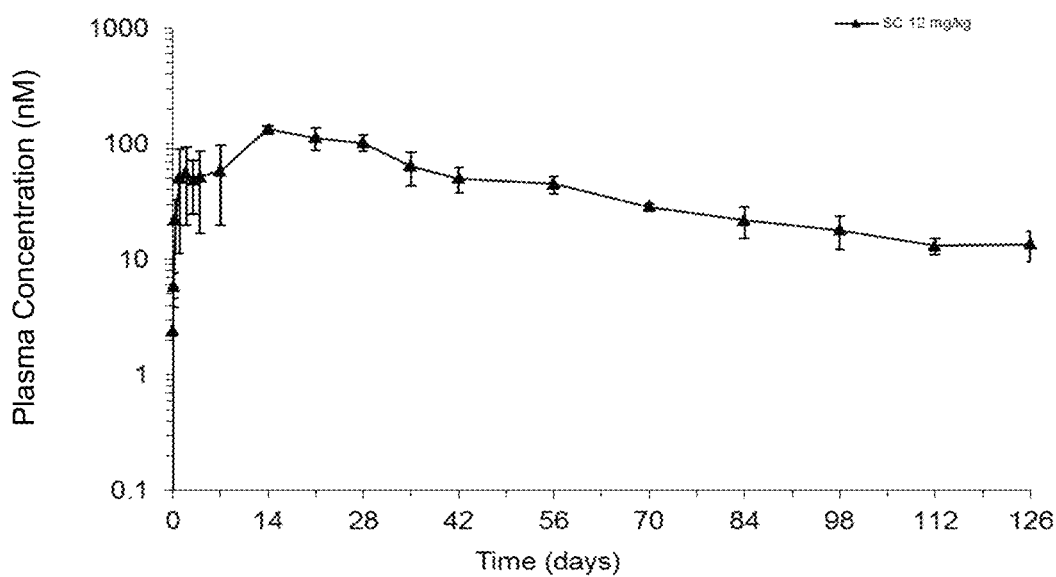

A 300 mg/ml solution of a compound of Formula (Ia) having 9.8 w/w % water, 65.0 w/w % PEG 300, and 25.2 w/w % of the compound of Formula (Ia) was prepared. The solution was administered subcutaneously to rats at a dose of 50 mg/kg and to dogs at a dose of 12 mg/kg and the pharmacokinetic (PK) profile was determined. FIG. 7A shows a plot of the plasma concentration of the compound of Formula (Ia) as a function of time in the rat and FIG. 7B shows a plot of the plasma concentration of the compound of Formula (Ia) as a function of time in the dog. In the rat, plasma concentrations of the compound of Formula (Ia) were maintained above the target trough concentration of 20 nM for at least 168 days (24 weeks). In the dog, plasma concentrations of the compound of Formula (Ia) were maintained above the target trough concentration of 20 nM for at least 84 days (12 weeks). The results are summarized in Tables A and B below.

TABLE A

PK parameters of the compound of Formula (Ia) following subcutaneous (SC) administration in solution in rats

| Species | Dose (mg/kg) | Dose Concentration (mg/mL) | Dose Volume (mL/kg) | $AUC_{0-98\,d}$ ($\mu M \cdot h$) | $AUC_{0-168\,d}$ ($\mu M \cdot h$) | $C_{max}$ ($\mu M$) | $T_{max}$ (h) | $C_{d168}$ ($\mu M$) |
|---|---|---|---|---|---|---|---|---|
| Wistar Han Rat | 50 | 300 | 0.167 | 531 ± 30 | 730 ± 55 | 0.318 ± 0.146 | 728 ± 97 | 0.0784 ± 0.0138 |

Formula (Ia): 1 nM = 0.968 ng/mL;

d = day;

h = hour

Values are the mean ± SD from 3 animals

TABLE B

PK parameters of the compound of Formula (Ia) following SC administration in solution in dogs

| Species | Dose (mg/kg) | Dose Concentration (mg/mL) | Dose Volume (mL/kg) | $AUC_{0-98\,d}$ ($\mu M \cdot h$) | $AUC_{0-126\,d}$ ($\mu M \cdot h$) | $C_{max}$ ($\mu M$) | $T_{max}$ (h) | $C_{84\,d}$ ($\mu M$) |
|---|---|---|---|---|---|---|---|---|
| Beagle Dog | 12 | 300 | 0.04 | 130.0 ± 9.1 | 139 ± 8 | 0.133 ± 0.010 | 336 ± 0 | 0.0217 ± 0.0065 |

Formula (Ia): 1 nM = 0.968 ng/mL;
d = day;
h = hour
Values are the mean ± SD from 3 animals

H. 27.92 w/w % Water, 58.04 w/w % PEG 300, 13.47 w/w % of a Compound of Formula (Ia), and 1.1 w/w % NaOH Solution (150 mg/mL of Compound of Formula (Ia))

Figure 8A:
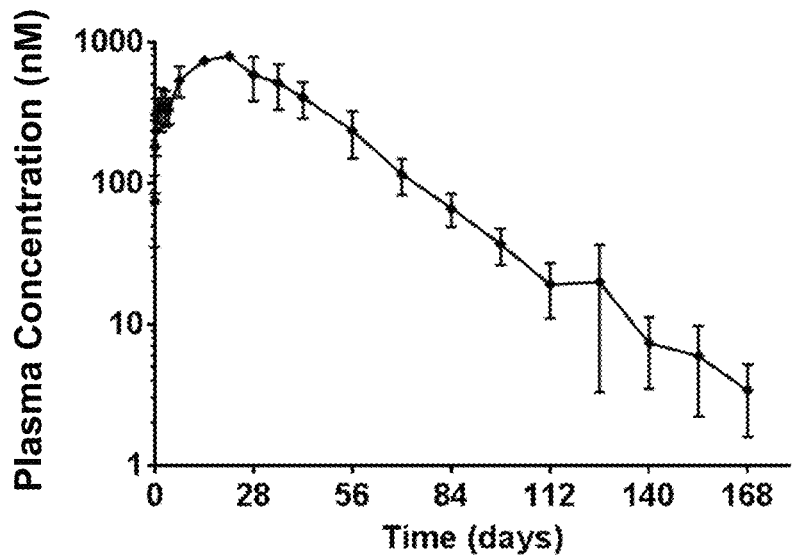
FIGS. 8A and 8B show plots of the plasma concentration over time of 150 mg/ml of the compound of Formula (Ia) in a solution of 27.92 w/w % water, 58.04 w/w % PEG 300, 13.47 w/w % of a compound of Formula (Ia), and 0.58 w/w % NaOH when dosed subcutaneously in rats at 50 mg/kg (FIG. 8A) and in dogs at 12 mg/kg (FIG. 8B).
Figure 8B:
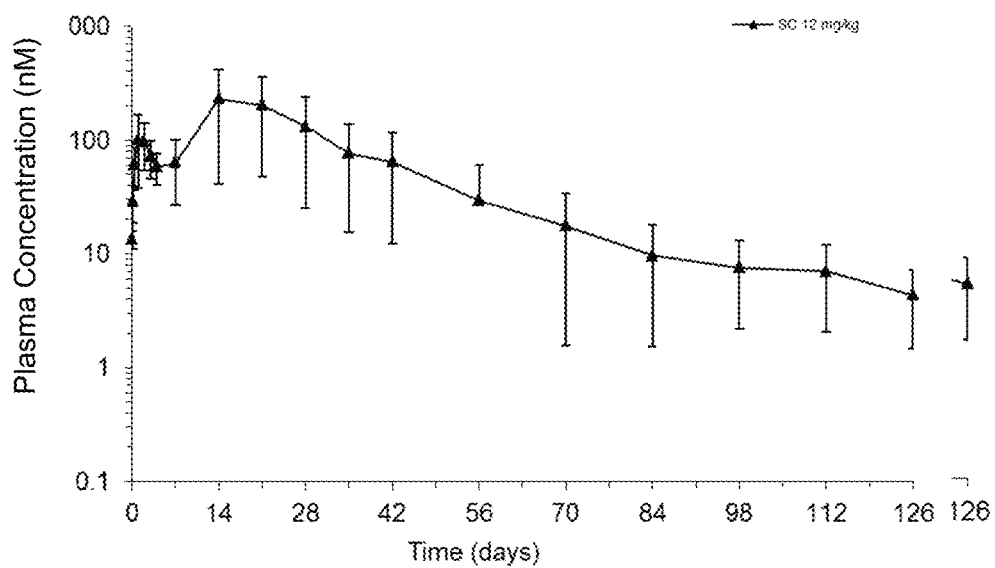

A 150 mg/ml solution of a compound of Formula (Ia) having 27.92 w/w % water, 58.04 w/w % PEG 300, 13.47 w/w % of a compound of Formula (Ia), and 1.1 w/w % NaOH was prepared. The solution was administered subcutaneously to rats at a dose of 50 mg/kg and to dogs at a dose of 12 mg/kg and the pharmacokinetic (PK) profile was determined. FIG. 8A shows a plot of the plasma concentration of the compound of Formula (Ia) as a function of time in the rat and FIG. 8B shows a plot of the plasma concentration of the compound of Formula (Ia) as a function of time in the dog. In the rat, plasma concentrations of the compound of Formula (Ia) were maintained above the target trough concentration of 20 nM for at least 126 days (18 weeks). In the dog, plasma concentrations of the compound of Formula (Ia) were maintained above the target trough concentration of 20 nM for at least 56 days (8 weeks). The results are summarized in Tables C and D below.

TABLE C

PK parameters of the compound of Formula (Ia) following SC administration in solution in rats

| Species | Dose (mg/kg) | Dose Concentration (mg/mL) | Dose Volume (mL/kg) | $AUC_{0-98\,d}$ ($\mu M \cdot h$) | $C_{max}$ ($\mu M$) | $T_{max}$ (h) | $C_{d98}$ ($\mu M$) |
|---|---|---|---|---|---|---|---|
| Wistar Han Rat | 50 | 150 | 0.333 | 801 ± 119 | 0.809 ± 0.021 | 448 ± 97 | 0.0370 ± 0.0107 |

Formula (Ia): 1 nM = 0.968 ng/mL;
d = day;
h = hour
Values are the mean ± SD from 3 animals

TABLE D

PK parameters of the compound of Formula (Ia) following SC administration in solution in dogs

| Species | Dose (mg/kg) | Dose Concentration (mg/mL) | Dose Volume (mL/kg) | $AUC_{0-28\,d}$ ($\mu M \cdot h$) | $AUC_{0-126\,d}$ ($\mu M \cdot h$) | $C_{max}$ ($\mu M$) | $T_{max}$ (h) | $C_{56\,d}$ ($\mu M$) |
|---|---|---|---|---|---|---|---|---|
| Beagle Dog | 12 | 150 | 0.08 | 137.0 ± 38 | 196 ± 31 | 0.312 ± 0.093 | 392 ± 97 | 0.0229 ± 0.0056 |

Formula (Ia): 1 nM = 0.968 ng/mL;
d = day;
h = hour
Values are the mean ± SD from 3 animals I. 23.2 w/w % Water, 50.0 w/w % PEG 300, 25.7 w/w % of a Compound of Formula (Ia), and 1.1 w/w % NaOH Solution (300 mg/mL of Compound of Formula (Ia))

Figure 9A:
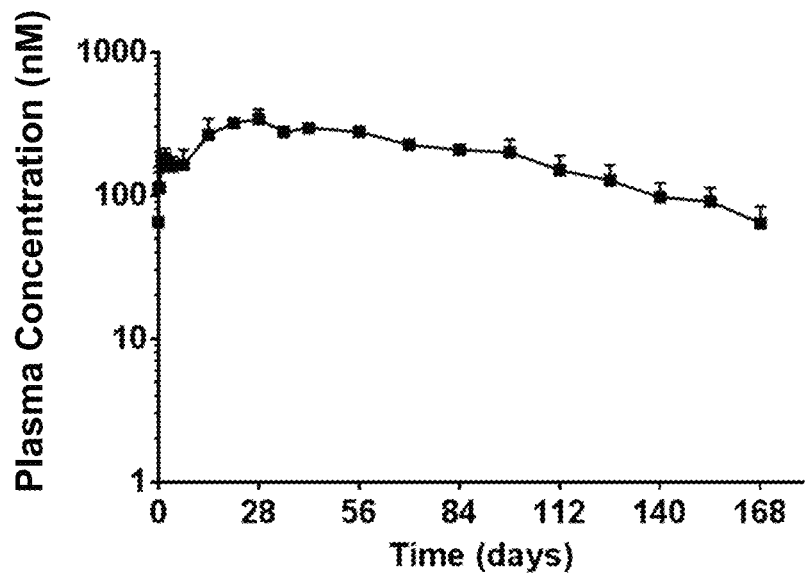
FIGS. 9A and 9B show plots of the plasma concentration over time of 300 mg/ml of a compound of Formula (Ia) in a solution of 23.2 w/w % water, 50.0 w/w % PEG 300, 25.7 w/w % of a compound of Formula (Ia), and 1.1 w/w % NaOH when dosed subcutaneously in rats at 50 mg/kg (FIG. 9A) and in dogs at 12 mg/kg (FIG. 9B).
Figure 9B:
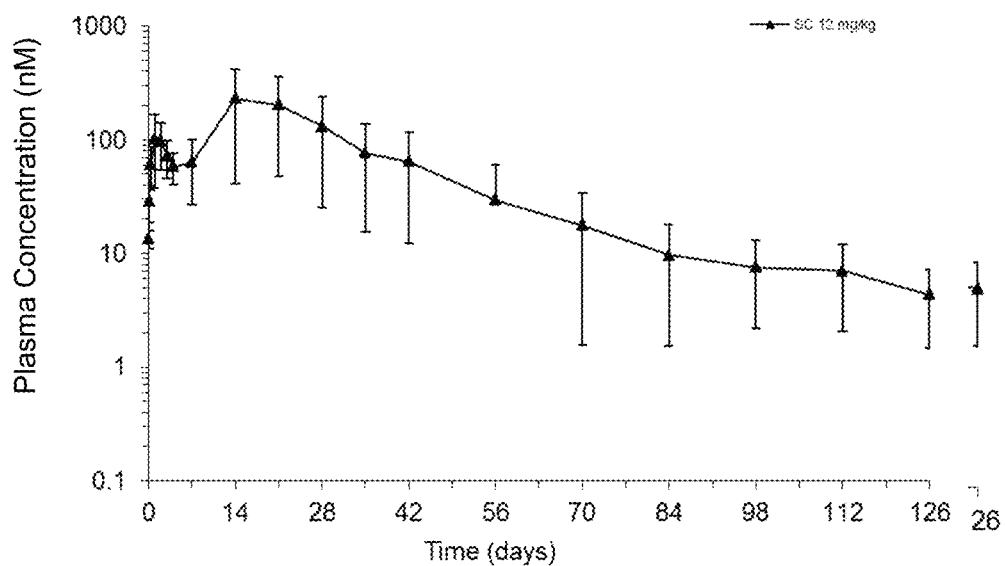

A 300 mg/ml solution of a compound of Formula (Ia) having 23.2 w/w % water, 50.0 w/w % PEG 300, 25.7 w/w % of a compound of Formula (Ia), and 1.1 w/w % NaOH was prepared. The solution was administered subcutaneously to rats at a dose of 50 mg/kg and to dogs at a dose of 12 mg/kg and the pharmacokinetic (PK) profile was determined. FIG. 9A shows a plot of the plasma concentration of the compound of Formula (Ia) as a function of time in the rat and FIG. 9B shows a plot of the plasma concentration of the compound of Formula (Ia) as a function of time in the dog. In the rat, plasma concentrations of the compound of Formula (Ia) were maintained above the target trough concentration of 20 nM for at least 126 days (18 weeks). In the dog, plasma concentrations of the compound of Formula (Ia) were maintained above the target trough concentration of 20 nM for at least 56 days (8 weeks). The results are summarized in Tables E and F below.

J. 30.07 w/w % Water, 64.40 w/w % PEG 300, 4.68 w/w % of a Sodium Salt of the Compound of Formula (Ia), and 0.85 w/w % Poloxamer 188 Solution (50 mg/mL of Compound of Formula (Ia))

Figure 10A:
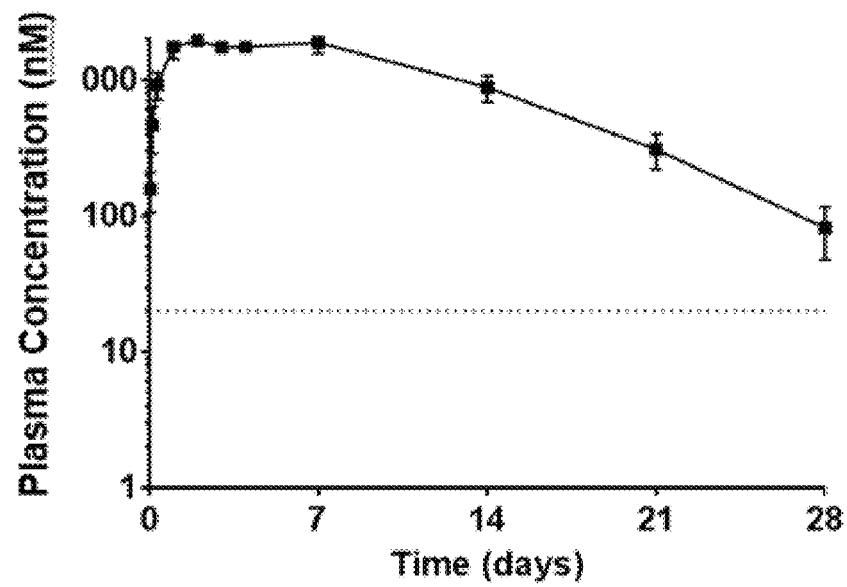
FIGS. 10A and 10B show plots of the plasma concentration over time of 50 mg/ml of a compound of Formula (Ia) in a solution of 30.07 w/w % water, 64.40 w/w % PEG 300, 4.68 w/w % of a sodium salt of the compound of Formula (Ia), and 0.85 w/w % poloxamer 188 when dosed subcutaneously in rats at 50 mg/kg (FIG. 10A) and in dogs at 6 mg/kg (FIG. 10B).
Figure 10B:
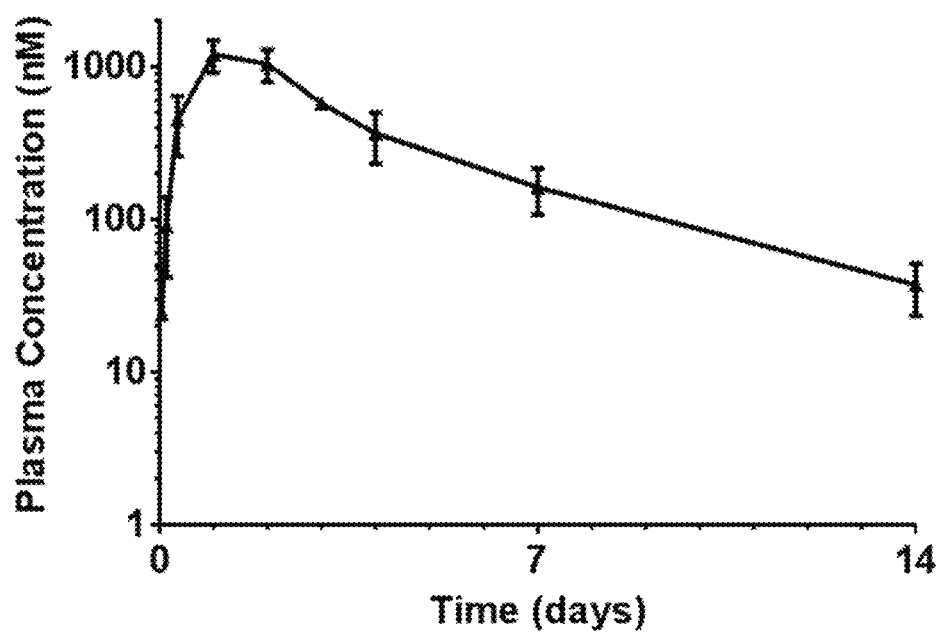

A 50 mg/ml solution of a compound of Formula (Ia) having 30.07 w/w % water, 64.40 w/w % PEG 300, 4.68 w/w % of a sodium salt of the compound of Formula (Ia), and 0.85 w/w % poloxamer 188 was prepared. The solution was administered subcutaneously to rats at a dose of 50 mg/kg and to dogs at a dose of 6 mg/kg and the pharmacokinetic (PK) profile was determined. FIG. 10A shows a plot of the plasma concentration of the compound of Formula (Ia) as a function of time in the rat and FIG. 10B shows a plot of the plasma concentration of the compound of Formula (Ia) as a function of time in the dog. In the rat, plasma concentrations of the compound of Formula (Ia) were maintained above the target trough concentration of 20 nM for at least 28 days (4 weeks). In the dog, plasma concentrations of the compound of Formula (Ia) were maintained above the target trough concentration of 20 nM for at least 14 days (2 weeks). The results are summarized in Tables G and H below.

TABLE E

PK parameters of the compound of Formula (Ia) following SC administration in solution in rats

| Species | Dose (mg/kg) | Dose Concentration (mg/mL) | Dose Volume (mL/kg) | $AUC_{0-126\,d}$ ($\mu M \cdot h$) | $C_{max}$ ($\mu M$) | $T_{max}$ (h) | $C_{d168}$ ($\mu M$) |
|---|---|---|---|---|---|---|---|
| Wistar Han Rat | 50 | 300 | 0.167 | 698 ± 13 | 0.355 ± 0.036 | 616 ± 96 | 0.0128 ± 0.0035 |

Formula (Ia): 1 nM = 0.968 ng/mL;

d = day;

h = hour

Values are the mean ± SD from 3 animals

TABLE F

PK parameters of the compound of Formula (Ia) following SC administration in solution in dogs

| Species | Dose (mg/kg) | Dose Concentration (mg/mL) | Dose Volume (mL/kg) | $AUC_{0-56\,d}$ ($\mu M \cdot h$) | $C_{max}$ ($\mu M$) | $T_{max}$ (h) | $C_{56\,d}$ ($\mu M$) |
|---|---|---|---|---|---|---|---|
| Beagle Dog | 12 | 300 | 0.04 | 166 ± 110 | 0.267 ± 0.176 | 296 ± 231 | 0.0296 ± 0.0308 |

Formula (Ia): 1 nM = 0.968 ng/mL;

d = day;

h = hour

Values are the mean ± SD from 3 animals

TABLE G

PK parameters of the compound of Formula (Ia) following SC administration in solution in rats

| Species | Dose (mg/kg) | Dose Concentration (mg/mL) | Dose Volume (mL/kg) | $AUC_{0\text{-}7\,d}$ ($\mu M \cdot h$) | $AUC_{0\text{-}28\,d}$ ($\mu M \cdot h$) | $C_{max}$ ($\mu M$) | $T_{max}$ (h) | $C_{d28}$ ($\mu M$) |
|---|---|---|---|---|---|---|---|---|
| Wistar Han Rat | 50 | 50 | 1.0 | 156 ± 48 | 643 ± 75 | N/A | N/A | 0.082 ± 0.035 |

Formula (Ia): 1 nM = 0.968 ng/mL;
d = day;
h = hour
Values are the mean ± SD from 3 animals

TABLE H

PK parameters of the compound of Formula (Ia) following SC administration in solution in dogs

| Species | Dose (mg/kg) | Dose Concentration (mg/mL) | Dose Volume (mL/kg) | $AUC_{0\text{-}24\,h}$ ($\mu M \cdot h$) | $AUC_{0\text{-}14\,d}$ ($\mu M \cdot h$) | $C_{max}$ ($\mu M$) | $T_{max}$ (h) | $C_{14\,d}$ ($\mu M$) |
|---|---|---|---|---|---|---|---|---|
| Beagle Dog | 6 | 50 | 0.12 | 14.7 ± 4.4 | 108 ± 16 | N/A | N/A | 0.0372 ± 0.0139 |

Formula (Ia): 1 nM = 0.968 ng/mL;
d = day;
h = hour
Values are the mean ± SD from 3 animals K. 29.21 w/w % Water, 62.55 w/w % PEG 300, 6.97 w/w % of a Sodium Salt of the Compound of Formula (Ia), and 1.68 w/w % Poloxamer 188 Solution (75 mg/mL of Compound of Formula (Ia))

Figure 11A:
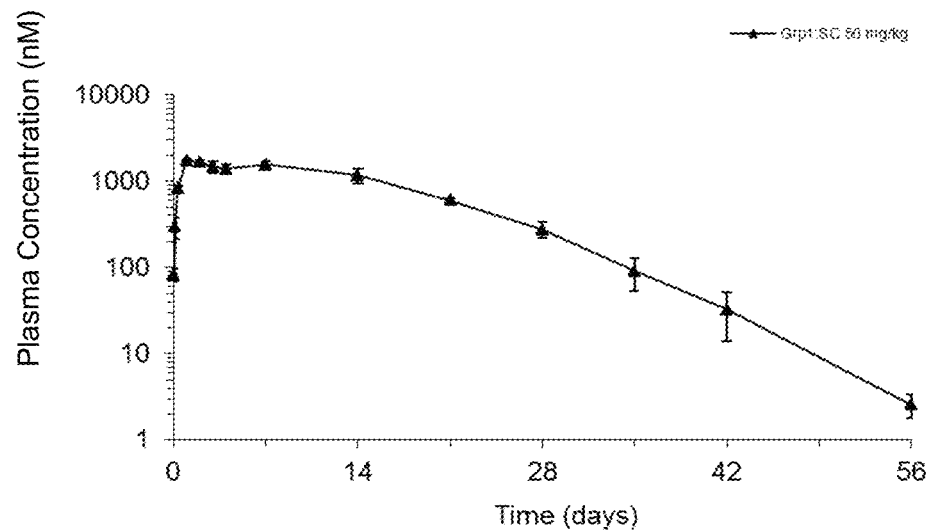
FIGS. 11A and 11B show plots of the plasma concentration over time of 75 mg/ml of a compound of Formula (Ia) in a solution of 29.21 w/w % water, 62.55 w/w % PEG 300, 6.97 w/w % of a sodium salt of the compound of Formula (Ia), and 1.68 w/w % poloxamer 188 when dosed subcutaneously in rats at 50 mg/kg (FIG. 11A) and in dogs at 6 mg/kg (FIG. 11B).
Figure 11B:
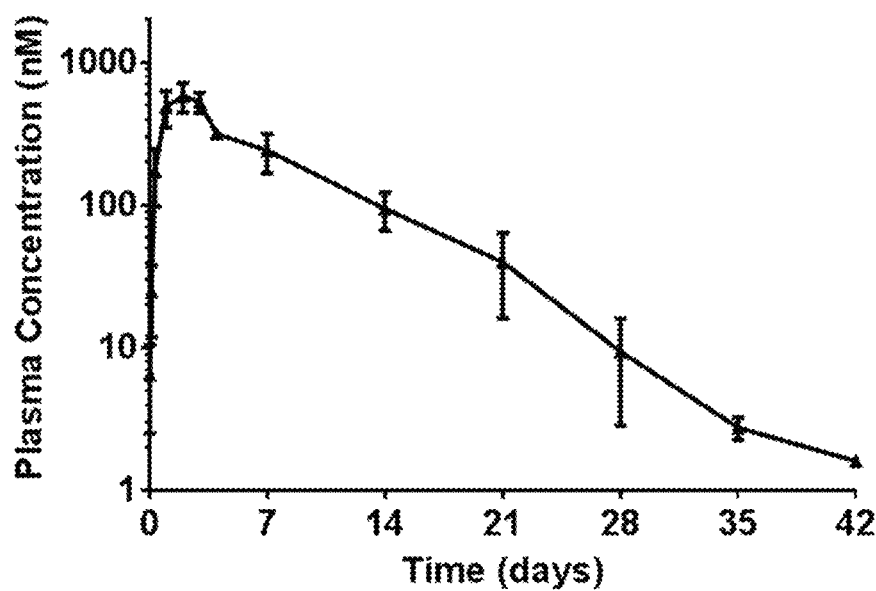

A 75 mg/ml solution of a compound of Formula (Ia) having 29.21 w/w % water, 62.55 w/w % PEG 300, 6.97 w/w % of a sodium salt of the compound of Formula (Ia), and 1.68 w/w % poloxamer 188 was prepared. The solution was administered subcutaneously to rats at a dose of 50 mg/kg and to dogs at a dose of 6 mg/kg and the pharmacokinetic (PK) profile was determined. FIG. 11A shows a plot of the plasma concentration of the compound of Formula (Ia) as a function of time in the rat and FIG. 11B shows a plot of the plasma concentration of the compound of Formula (Ia) as a function of time in the dog. In the rat, plasma concentrations of the compound of Formula (Ia) were maintained above the target trough concentration of 20 nM for at least 42 days (6 weeks). In the dog, plasma concentrations of the compound of Formula (Ia) were maintained above the target trough concentration of 20 nM for at least 21 days (3 weeks). The results are summarized in Tables I and J below.

TABLE I

PK parameters of the compound of Formula (Ia) following SC administration in solution in rats

| Species | Dose (mg/kg) | Dose Concentration (mg/mL) | Dose Volume (mL/kg) | $AUC_{0\text{-}7\,d}$ ($\mu M \cdot h$) | $AUC_{0\text{-}28\,d}$ ($\mu M \cdot h$) | $C_{max}$ ($\mu M$) | $T_{max}$ (h) | $C_{d28}$ ($\mu M$) |
|---|---|---|---|---|---|---|---|---|
| Wistar Han Rat | 50 | 75 | 0.667 | 241 ± 22 | 690 ± 32 | N/A | N/A | 0.0325 ± 0.0185 |

Formula (Ia): 1 nM = 0.968 ng/mL;
d = day;
h = hour
Values are the mean ± SD from 3 animals

TABLE J

PK parameters of the compound of Formula (Ia) following SC administration in solution in dogs

| Species | Dose (mg/kg) | Dose Concentration (mg/mL) | Dose Volume (mL/kg) | $AUC_{0-24\,h}$ ($\mu M \cdot h$) | $AUC_{0-28\,d}$ ($\mu M \cdot h$) | $C_{max}$ ($\mu M$) | $T_{max}$ (h) | $C_{21\,d}$ ($\mu M$) |
|---|---|---|---|---|---|---|---|---|
| Beagle Dog | 6 | 75 | 0.06 | 5.88 ± 1.95 | 101 ± 11 | N/A | N/A | 0.040 ± 0.024 |

Formula (Ia): 1 nM = 0.968 ng/mL;

d = day;

h = hour

Values are the mean ± SD from 3 animals

L. 28.36 w/w % Water, 60.73 w/w % PEG 300, 9.23 w/w % of a Sodium Salt of a Compound of Formula (Ia), and 1.68 w/w % Poloxamer 188 Solution (100 mg/mL of Compound of Formula (Ia))

Figure 12A:
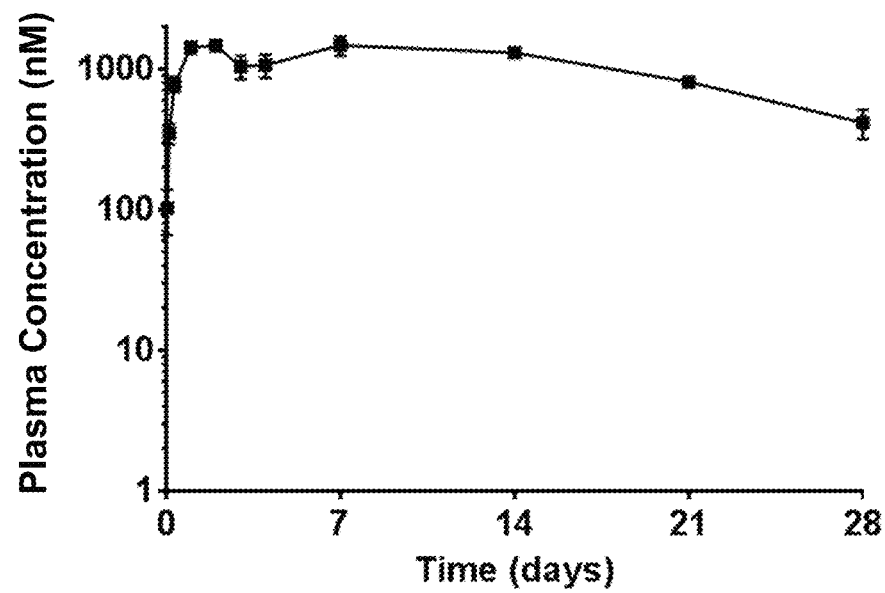
FIGS. 12A and 12B show plots of the plasma concentration over time of 100 mg/ml of a compound of Formula (Ia) in a solution of 28.36 w/w % water, 60.73 w/w % PEG 300, 9.23 w/w % of a sodium salt of a compound of Formula (Ia), and 1.68 w/w % poloxamer 188 when dosed subcutaneously in rats at 50 mg/kg (FIG. 12A) and in dogs at 6 mg/kg (FIG. 12B).

A 100 mg/ml solution of a compound of Formula (Ia) having 28.36 w/w % water, 60.73 w/w % PEG 300, 9.23 w/w % of a sodium salt of a compound of Formula (Ia), and 1.68 w/w % poloxamer 188 was prepared. The solution was administered subcutaneously to rats at a dose of 50 mg/kg and the pharmacokinetic (PK) profile was determined. FIG. 12A shows a plot of the plasma concentration of the compound of Formula (Ia) as a function of time. Plasma concentrations of the compound of Formula (Ia) were maintained above the target trough concentration of 20 nM for at least 28 days (4 weeks). The results are summarized in Table K below.

TABLE K

PK parameters of the compound of Formula (Ia) following SC administration in solution in rats

| Species | Dose (mg/kg) | Dose Concentration (mg/mL) | Dose Volume (mL/kg) | $AUC_{0-7\,d}$ ($\mu M \cdot h$) | $AUC_{0-28\,d}$ ($\mu M \cdot h$) | $C_{max}$ ($\mu M$) | $T_{max}$ (h) | $C_{d28}$ ($\mu M$) |
|---|---|---|---|---|---|---|---|---|
| Wistar Han Rat | 50 | 100 | 0.5 | 202 ± 27 | 716 ± 62 | N/A | N/A | 0.415 ± 0.098 |

Formula (Ia): 1 nM = 0.968 ng/mL;

d = day;

h = hour

Values are the mean ± SD from 3 animals

M. 28.36 w/w % Water, 60.73 w/w % PEG 300, 9.23 w/w % of a Sodium Salt of a Compound of Formula (Ia), and 1.68 w/w % Poloxamer 188 Solution (100 mg/mL of Compound of Formula (Ia))

Figure 12B:
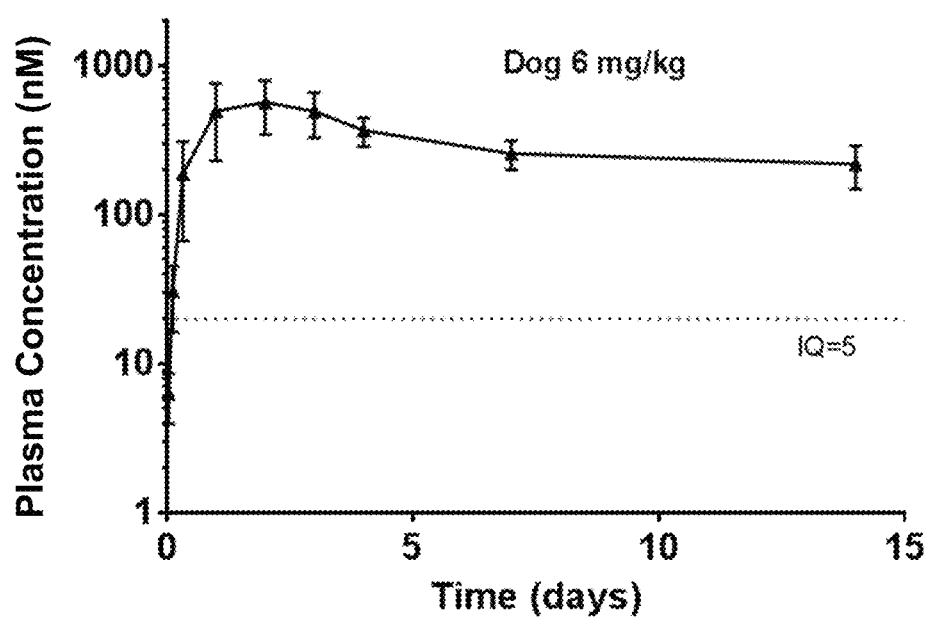

A 100 mg/ml solution of a compound of Formula (Ia) having 28.36 w/w % water, 60.73 w/w % PEG 300, 9.23 w/w % of a sodium salt of a compound of Formula (Ia), and 1.68 w/w % poloxamer 188 was prepared. The solution was administered subcutaneously to dogs at a dose of 6 mg/kg and the pharmacokinetic (PK) profile was determined. FIG. 12B shows a plot of the plasma concentration of the compound of Formula (Ia) as a function of time. Plasma concentrations of the compound of Formula (Ia) were maintained above the target trough concentration of 20 nM for at least 14 days (2 weeks). The results are summarized in Table L below.

TABLE L

PK parameters of the compound of Formula (Ia) following SC administration in solution in dogs

| Species | Dose (mg/kg) | Dose Concentration (mg/mL) | Dose Volume (mL/kg) | $AUC_{0-24\,h}$ (µM · h) | $AUC_{0-14\,d}$ (µM · h) | $C_{max}$ (µM) | $T_{max}$ (h) | $C_{14\,d}$ (µM) |
|---|---|---|---|---|---|---|---|---|
| Beagle Dog | 6 | 100 | 0.06 | 6.05 ± 3.43 | 104 ± 26 | N/A | N/A | 219 ± 70 |

Formula (Ia): 1 nM = 0.968 ng/mL;
d = day;
h = hour
Values are the mean ± SD from 3 animals

N. 27.51 w/w % Water, 58.92 w/w % PEG 300, 11.48 w/w % of a Sodium Salt of the Compound of Formula (Ia), and 2.09 w/w % Poloxamer 188 Solution (125 mg/mL of Compound of Formula (Ia))

Figure 13A:
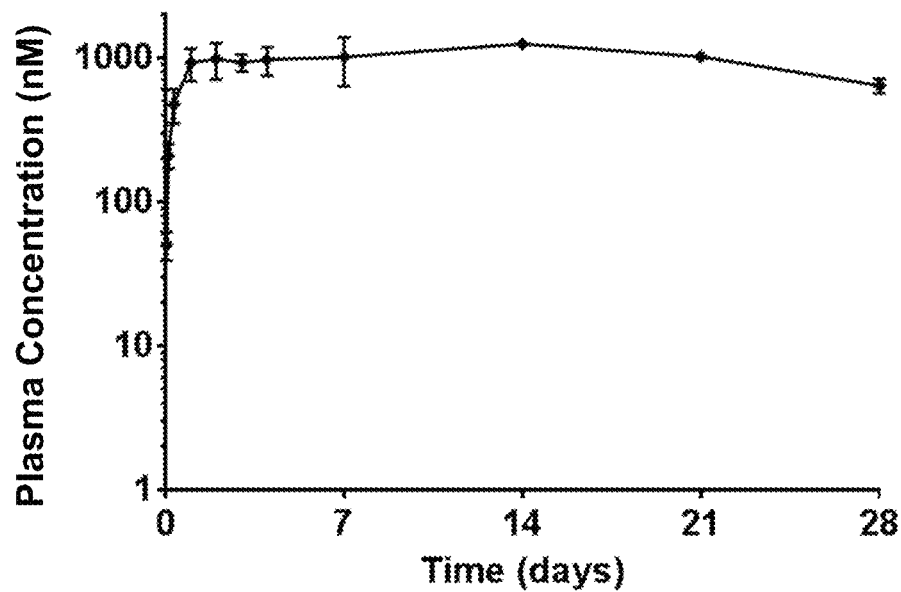
FIGS. 13A and 13B show plots of the plasma concentration over time of 125 mg/ml of a compound of Formula (Ia) in a solution of 27.51 w/w % water, 58.92 w/w % PEG 300, 11.48 w/w % of a sodium salt of the compound of Formula (Ia), and 2.09 w/w % poloxamer 188 when dosed subcutaneously in rats at 50 mg/kg (FIG. 13A) and in dogs at 6 mg/kg (FIG. 13B).
Figure 13B:
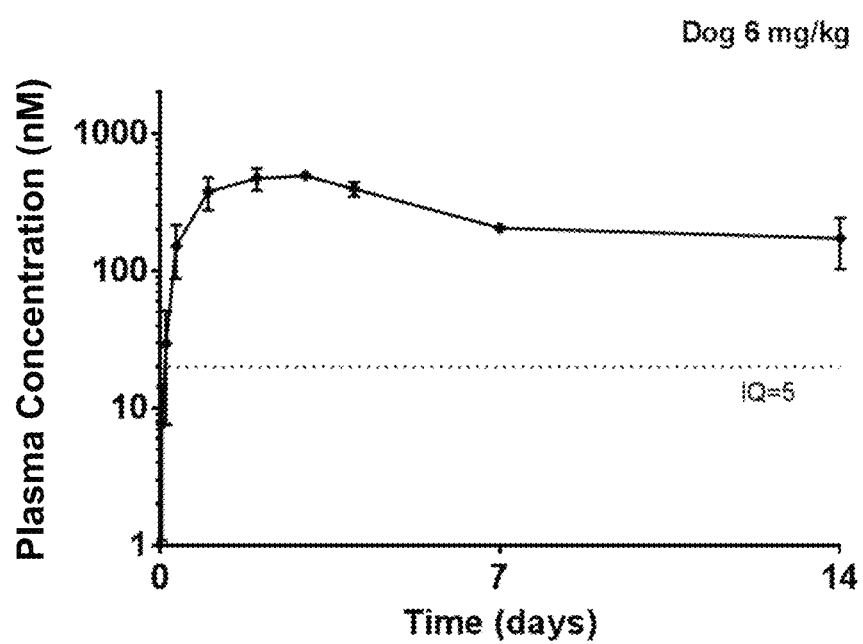

A 125 mg/ml solution of a compound of Formula (Ia) having 27.51 w/w % water, 58.92 w/w % PEG 300, 11.48 w/w % of a sodium salt of the compound of Formula (Ia), and 2.09 w/w % poloxamer 188 was prepared. The solution was administered subcutaneously to rats at a dose of 50 mg/kg and to dogs at a dose of 6 mg/kg and the pharmacokinetic (PK) profile was determined. FIG. 13A shows a plot of the plasma concentration of the compound of Formula (Ia) as a function of time in the rat and FIG. 13B shows a plot of the plasma concentration of the compound of Formula (Ia) as a function of time in the dog. In the rat, plasma concentrations of the compound of Formula (Ia) were maintained above the target trough concentration of 20 nM for at least 28 days (4 weeks). In the dog, plasma concentrations of the compound of Formula (Ia) were maintained above the target trough concentration of 20 nM for at least 14 days (2 weeks). The results are summarized in Tables M and N below.

TABLE M

PK parameters of the compound of Formula (Ia) following SC administration in solution in rats

| Species | Dose (mg/kg) | Dose Concentration (mg/mL) | Dose Volume (mL/kg) | $AUC_{0-7\,d}$ (µM · h) | $AUC_{0-28\,d}$ (µM · h) | $C_{max}$ (µM) | $T_{max}$ (h) | $C_{d28}$ (µM) |
|---|---|---|---|---|---|---|---|---|
| Wistar Han Rat | 50 | 125 | 0.4 | 153 ± 38 | 673 ± 67 | N/A | N/A | 0.0279 ± 0.0262 |

Formula (Ia): 1 nM = 0.968 ng/mL;
d = day;
h = hour
Values are the mean ± SD from 3 animals

TABLE N

PK parameters of the compound of Formula (Ia) following SC administration in solution in dogs

| Species | Dose (mg/kg) | Dose Concentration (mg/mL) | Dose Volume (mL/kg) | $AUC_{0-24\,h}$ (µM · h) | $AUC_{0-14\,d}$ (µM · h) | $C_{max}$ (µM) | $T_{max}$ (h) | $C_{14\,d}$ (µM) |
|---|---|---|---|---|---|---|---|---|
| Beagle Dog | 6 | 125 | 0.048 | 4.71 ± 1.51 | 90.3 ± 3.5 | N/A | N/A | 173 ± 70 |

Formula (Ia): 1 nM = 0.968 ng/mL;
d = day;
h = hour
Values are the mean ± SD from 3 animals O. 26.6 w/w % Water, 56.97 w/w % PEG 300, 13.39 w/w % of a Compound of Formula (Ia), 0.57 w/w % NaOH, and 2.49 w/w % Poloxamer 188 Solution (150 mg/mL of Compound of Formula (Ia))

Figure 14A:
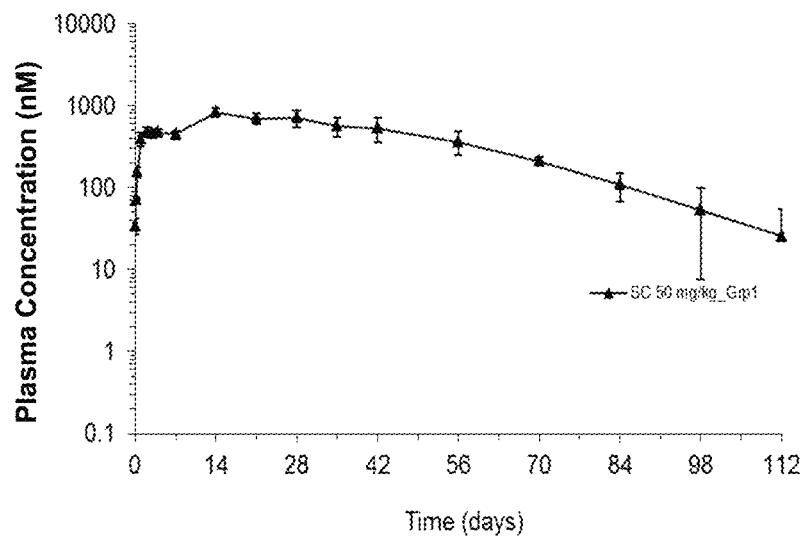
FIG. 14A shows a plot of the plasma concentration over time of 150 mg/ml of the compound of Formula (Ia) in a solution of 26.6 w/w % water, 56.97 w/w % PEG 300, 13.39 w/w % of a compound of Formula (Ia), 0.57 w/w % NaOH, and 2.49 w/w % poloxamer 188 when dosed subcutaneously in rats at 50 mg/kg.

A 150 mg/ml solution of a compound of Formula (Ia) having 26.6 w/w % water, 56.97 w/w % PEG 300, 13.39 w/w % of a compound of Formula (Ia), 0.57 w/w % NaOH, and 2.49 w/w % poloxamer 188 was prepared. The solution was administered subcutaneously to rats at a dose of 50 mg/kg and the pharmacokinetic (PK) profile was determined. FIG. 14A shows a plot of the plasma concentration of the compound of Formula (Ia) as a function of time. Plasma concentrations of the compound of Formula (Ia) were maintained above the target trough concentration of 20 nM for at least 98 days (14 weeks). The results are summarized in Table 0 below.

TABLE O

PK parameters of the compound of Formula (Ia) following SC administration in solution in rats

| Species | Dose (mg/kg) | Dose Concentration (mg/mL) | Dose Volume (mL/kg) | $AUC_{0\text{-}98\,d}$ ($\mu M \cdot h$) | $AUC_{0\text{-}112\,d}$ ($\mu M \cdot h$) | $C_{max}$ ($\mu M$) | $T_{max}$ (h) | $C_{d84}$ ($\mu M$) |
|---|---|---|---|---|---|---|---|---|
| Wistar Han Rat | 50 | 150 | 0.330 | 949 ± 114 | 963 ± 102 | N/A | N/A | 0.0533 ± 0.0457 |

Formula (Ia): 1 nM = 0.968 ng/mL;
d = day;
h = hour
Values are the mean ± SD from 3 animals P. 26.6 w/w % Water, 56.97 w/w % PEG 300, 13.39 w/w % of a Compound of Formula (Ia), 0.57 w/w % NaOH, and 2.49 w/w % Poloxamer 188 Solution (150 mg/mL of Compound of Formula (Ia))

Figure 14B:
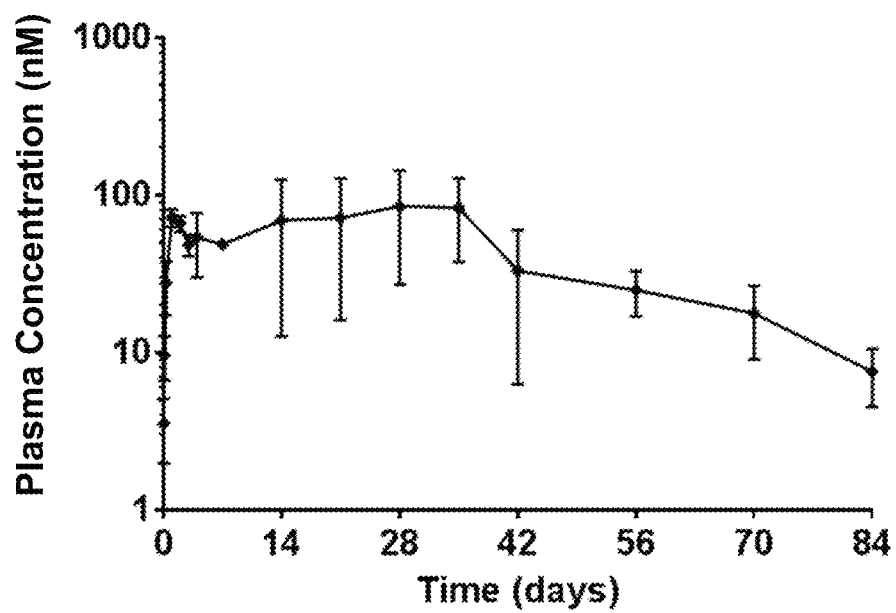
FIG. 14B shows a plot of the plasma concentration over time of 150 mg/ml of the compound of Formula (Ia) in a solution of 26.6 w/w % water, 56.97 w/w % PEG 300, 13.39 w/w % of a compound of Formula (Ia), 0.57 w/w % NaOH, and 2.49 w/w % poloxamer 188 when dosed subcutaneously in dogs at 6 mg/kg.

A 150 mg/ml solution of a compound of Formula (Ia) having 26.6 w/w % water, 56.97 w/w % PEG 300, 13.39 w/w % of a compound of Formula (Ia), 0.57 w/w % NaOH, and 2.49 w/w % poloxamer 188 was prepared. The solution was administered subcutaneously to dogs at a dose of 6 mg/kg and the pharmacokinetic (PK) profile was determined. FIG. 14B shows a plot of the plasma concentration of the compound of Formula (Ia) as a function of time. Plasma concentrations of the compound of Formula (Ia) were maintained above the target trough concentration of 20 nM for at least 56 days (8 weeks). The results are summarized in Table P below.

Q. 21.97 w/w % Water, 47.05 w/w % PEG 300, 25.21 w/w % of a Compound of Formula (Ia), 1.08 w/w % of NaOH, and 4.69 w/w % Poloxamer 188 Solution (300 mg/mL of Compound of Formula (Ia))

Figure 15A:
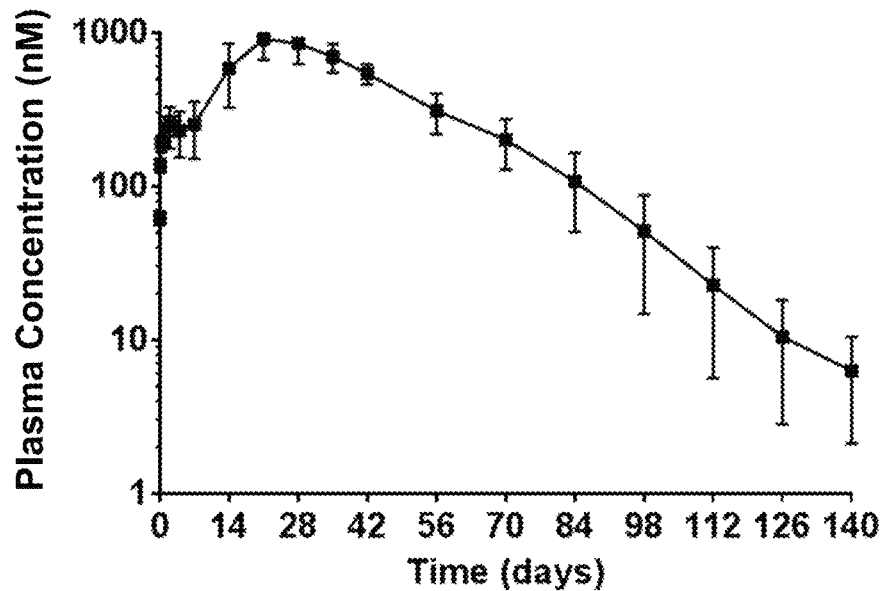
FIGS. 15A and 15B show plots of the plasma concentration over time of 300 mg/ml of the compound of Formula (Ia) in a solution of 21.97 w/w % water, 47.05 w/w % PEG 300, 25.21 w/w % of a compound of Formula (Ia), 1.08 w/w % of NaOH, and 4.69 w/w % poloxamer 188 when dosed subcutaneously in rats at 50 mg/kg (FIG. 15A) and in dogs at 6 mg/kg (FIG. 15B).
Figure 15B:
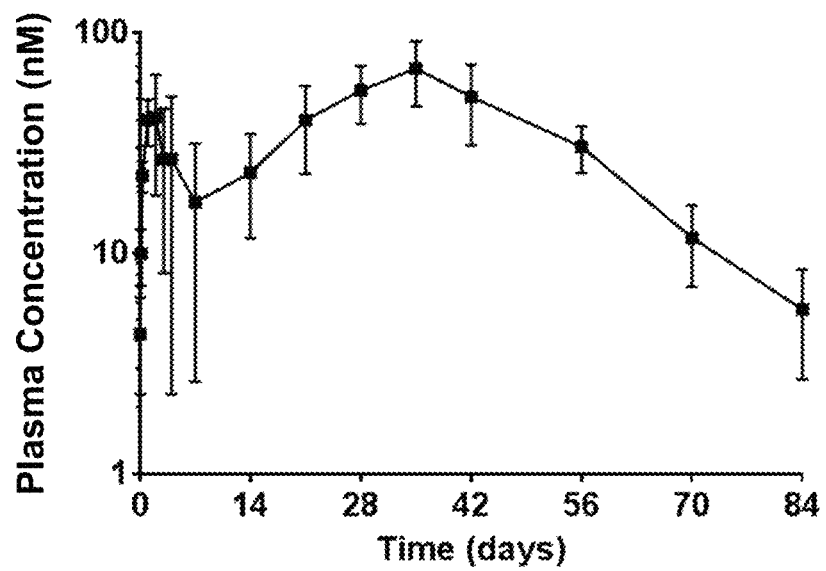

A 300 mg/ml solution of a compound of Formula (Ia) having 21.97 w/w % water, 47.05 w/w % PEG 300, 25.21 w/w % of a compound of Formula (Ia), 1.08 w/w % of NaOH, and 4.69 w/w % poloxamer 188 was prepared. The solution was administered subcutaneously to rats at a dose of 50 mg/kg and to dogs at a dose of 6 mg/kg and the pharmacokinetic (PK) profile was determined. FIG. 15A shows a plot of the plasma concentration of the compound of Formula (Ia) as a function of time in the rat and FIG. 15B shows a plot of the plasma concentration of the compound of Formula (Ia) as a function of time in the dog. In the rat, plasma concentrations of the compound of Formula (Ia) were maintained above the target trough concentration of 20 nM for at least 98 days (14 weeks). In the dog, plasma concentrations of the compound of Formula (Ia) were maintained above the target trough concentration of 20 nM for at least 56 days (8 weeks). The results are summarized in Tables Q and R below.

TABLE P

PK parameters of the compound of Formula (Ia) following SC administration in solution in dogs

| Species | Dose (mg/kg) | Dose Concentration (mg/mL) | Dose Volume (mL/kg) | $AUC_{0\text{-}56\,d}$ ($\mu M \cdot h$) | $AUC_{0\text{-}84\,d}$ ($\mu M \cdot h$) | $C_{max}$ ($\mu M$) | $T_{max}$ (h) | $C_{56\,d}$ ($\mu M$) |
|---|---|---|---|---|---|---|---|---|
| Beagle Dog | 6 | 150 | 0.04 | 69.0 ± 13.9 | 76.6 ± 8.5 | 0.101 ± 0.044 | 240 ± 374 | 0.0249 ± 0 |

Formula (Ia): 1 nM = 0.968 ng/mL;
d = day;
h = hour
Values are the mean ± SD from 3 animals

TABLE Q

PK parameters of the compound of Formula (Ia) following SC administration in solution in rats

| Species | Dose (mg/kg) | Dose Concentration (mg/mL) | Dose Volume (mL/kg) | $AUC_{0-98\,d}$ ($\mu M \cdot h$) | $AUC_{0-140\,d}$ ($\mu M \cdot h$) | $C_{max}$ ($\mu M$) | $T_{max}$ (h) | $C_{d98}$ ($\mu M$) |
|---|---|---|---|---|---|---|---|---|
| Wistar Han Rat | 50 | 300 | 0.170 | 928 ± 175 | 948 ± 169 | 0.915 ± 0.248 | 504 ± 0 | 0.0513 ± 0.0365 |

Formula (Ia): 1 nM = 0.968 ng/mL;

d = day;

h = hour

Values are the mean ± SD from 3 animals

TABLE R

PK parameters of the compound of Formula (Ia) following SC administration in solution in dogs

| Species | Dose (mg/kg) | Dose Concentration (mg/mL) | Dose Volume (mL/kg) | $AUC_{0-56\,d}$ ($\mu M \cdot h$) | $AUC_{0-84\,d}$ ($\mu M \cdot h$) | $C_{max}$ ($\mu M$) | $T_{max}$ (h) | $C_{56\,d}$ ($\mu M$) |
|---|---|---|---|---|---|---|---|---|
| Beagle Dog | 6 | 300 | 0.02 | 55.4 ± 20.8 | 65.4 ± 21.5 | 0.069 ± 0.022 | 840 ± 0 | 0.0304 ± 0.0072 |

Formula (Ia): 1 nM = 0.968 ng/mL;

d = day;

h = hour

Values are the mean ± SD from 3 animals

R. Liquid-Filled Capsules

Figure 16:
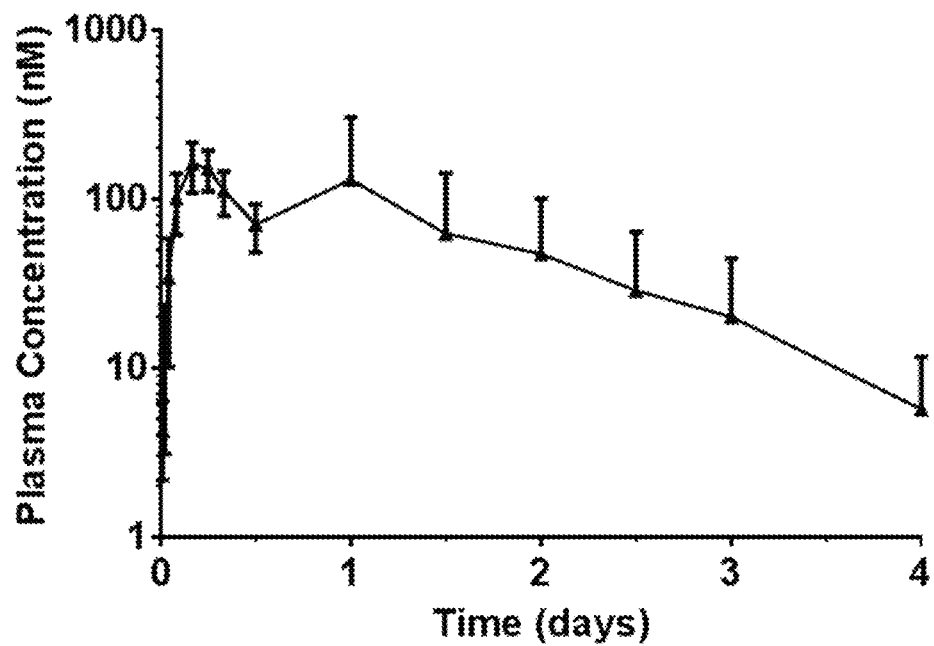
FIG. 16 shows a plot of the plasma concentration over time of a compound of Formula (Ia) in 100% glycerol monocaprylocaprate when orally administered in dogs as liquid-filled capsules at 7.5 mg fixed dose.

A single dose of the compound of Formula (Ia), formulated as liquid-filled capsules (LFC) containing 100% glycerol monocaprylocaprate, was administered orally at 7.5 mg fixed dose to 6 beagle dogs (Table S) and the pharmacokinetic (PK) profile was determined. FIG. 16 shows a plot of the plasma concentration of the compound of Formula (Ia) as a function of time. Plasma concentrations of the compound of Formula (Ia) were maintained above the target trough concentration of 20 nM for at least 72 hours (3 days).

TABLE S

PK parameters of the compound of Formula (Ia) following oral administration in liquid-filled capsules at 7.5 mg fixed dose to dogs

| Species | Dose (mg/kg) | Dose Concentration (mg/mL) | Dose Volume (mL/kg) | $AUC_{0-72\,h}$ ($\mu M \cdot h$) | $AUC_{0-14\,d}$ ($\mu M \cdot h$) | $C_{max}$ ($\mu M$) | $T_{max}$ (h) | $C_{72\,h}$ ($\mu M$) |
|---|---|---|---|---|---|---|---|---|
| Beagle Dog | 6 | 50 | 0.12 | 5.070 ± 4.649 | 108 ± 16 | 201 ± 129 | 11.0 ± 10.1 | 0.0201 ± 0.0244 |

Formula (Ia): 1 nM = 0.968 ng/mL;

d = day;

h = hour

Values are the mean ± SD from 6 animals

S. Spray-Dried Dispersion (SDD) Tablets

Figure 17:
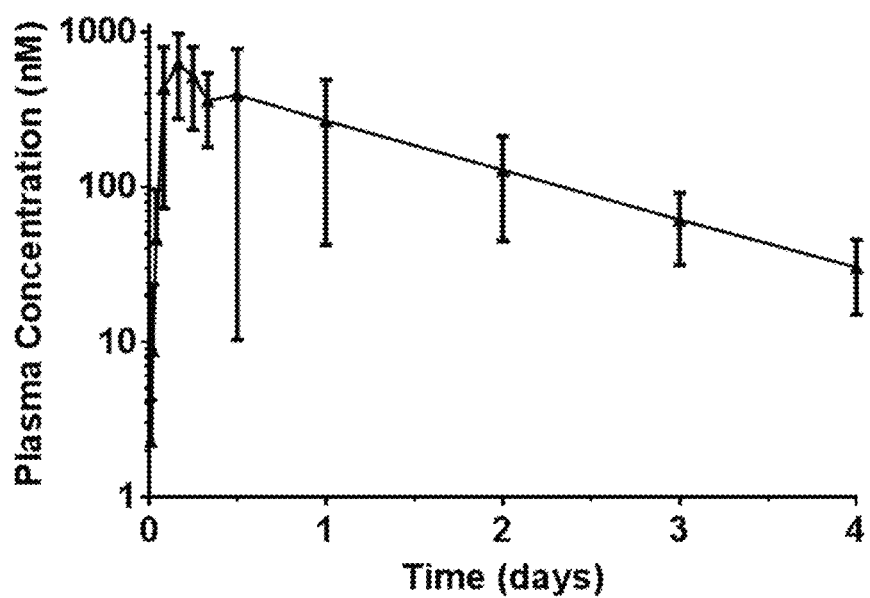
FIG. 17 shows a plot of the plasma concentration over time of a tablet prepared from a spray-dried dispersion of a sodium salt of the compound of Formula (Ia) (composition described in Table T with an outer film coating made of Opadry® II White 85F18422, wherein the outer film coating provides a 3% weight gain based on the uncoated tablet) when orally administered in dogs at 300 mg fixed dose.

A tablet, prepared from a spray-dried disperstion of a sodium salt of the compound of Formula (Ia), was prepared in a composition shown in Table T below (with an outer film coating made of Opadry® II White 85F18422, wherein the outer film coating provides a 3% weight gain based on the uncoated tablet) and was administered orally at 300 mg fixed dose to 6 beagle dogs (Table U) and the pharmacokinetic (PK) profile was determined. FIG. 17 shows a plot of the plasma concentration of the compound of Formula (Ia) as a function of time. Plasma concentrations of the compound of Formula (Ia) were maintained above the target trough concentration of 20 nM for at least 14 days (2 weeks).

TABLE T

Composition of SDD tablets at 300 mg fixed dose

| Ingredient | Amount (w/w %) |
|---|---|
| Sodium salt of compound of Formula (Ia) | 20.46 |
| Copovidone | 4.88 |
| Poloxamer 407 | 1.33 |
| Microcrystalline Cellulose | 21.28 |
| Mannitol | 42.55 |
| Croscarmellose Sodium | 8.00 |
| Magnesium Stearate | 1.50 |

TABLE U

PK parameters of the compound of Formula (Ia) following oral administration in SDD tablets at 300 mg fixed dose to dogs

| Species | Dose | $AUC_{0-72\,h}$ ($\mu M \cdot h$) | $AUC_{inf}$ ($\mu M \cdot h$) | $C_{max}$ ($\mu M$) | $T_{max}$ (h) | $C_{72\,h}$ ($\mu M$) |
|---|---|---|---|---|---|---|
| Beagle Dog | 300 mg fixed | 15.8 ± 10.0 | 18.5 ± 11.1 | 0.718 ± 0.409 | 5.3 ± 3.3 | 0.0614 ± 0.0300 |

Formula (Ia): 1 nM = 0.968 ng/mL;
h = hour
Values are the mean ± SD from 6 animals

Example 4: Pharmacology

A. Activity Against HIV Clinical Isolates

The antiretroviral activity of the compound of Formula (Ia) was tested against a panel of 22 HIV-1 clinical isolates of HIV-1 and two HIV-2 isolates in freshly isolated, PHA-stimulated human peripheral blood mononuclear cells (PBMCs). The HIV-1 isolates included representative strains from subtypes A, B, C, D, E, F, G, N, O, AE, and AG. Following a 7-day infection, virus production was determined by measuring reverse transcriptase activity in cell-free culture supernatants. The compound of Formula (Ia) displayed potent antiviral activity against all HIV-1 clinical isolates tested, with a mean $EC_{50}$ value of 0.05±0.03 nM (range of 0.02 to 0.16 nM) (Table 4). When tested in parallel against the same panel of viruses, DTG and AZT exhibited mean $EC_{50}$ values of 0.70±0.26 nM and 19.0±13.5 nM, respectively. The compound of Formula (Ia) was 11- to 20-fold less active against HIV-2 relative to HIV-1 as evidenced by its higher $EC_{50}$ value of 0.57 nM and 1.02 nM against HIV-2 strains CBL-20 and CDC310319, respectively (Table 10). Both of these HIV-2 isolates were susceptible to dolutegravir (DTG) and atazanavir (AZT).

TABLE 10

Antiviral activity against HIV clinical isolates

| Sub-type | HIV Isolate | Genbank Accession # | $EC_{50}$ in human PBMCs (nM)[a] (Ia) | DTG | AZT |
|---|---|---|---|---|---|
| A | 92UG031 | L34667 | 0.04 | 0.63 | 51.6 |
| A | 92UG037 | AB253428 | 0.07 | 0.47 | 21.7 |
| B | 89BZ_167 | AY173956 | 0.08 | 1.18 | 10.1 |
| B | 90US_873 | AY713412 | 0.04 | 0.82 | 13.2 |
| B | 91US001 | AY173952 | 0.03 | 0.53 | 20.3 |
| B | 91US004 | AY173955 | 0.04 | 0.40 | 19.7 |
| B | 96TH_NP1538 | AY713408 | 0.05 | 0.40 | 4.10 |
| B | Ba-L | AY713409 | 0.04 | 0.40 | 43.2 |
| B | JR-CSF | M38429 | 0.04 | 0.41 | 4.53 |
| C | 92BR025 | U52953 | 0.05 | 0.91 | 16.9 |
| C | 98US_MSC5016 | AY444801 | 0.10 | 0.77 | 37.8 |
| D | 92UG001 | AJ320484 | 0.02 | 1.09 | 7.29 |
| D | 98UG_57128 | AF484502 | 0.03 | 0.70 | 6.61 |
| E | CMU02 | AY494967 | 0.05 | 0.81 | 8.13 |
| E | CMU08 | U48268 | 0.05 | 0.96 | 34.1 |
| F | 93BR020 | AF005494 | 0.05 | 0.38 | 25.1 |
| G | JV1083 | U88826 | 0.16 | 0.93 | 20.5 |
| Group N | YBF30 | AJ006022 | 0.02 | 0.54 | 8.96 |
| Group O | BCF01 | AF458283 | 0.04 | 0.64 | 10.5 |
| CRF01_AE | 90TH_CM235 | AF259954 | 0.04 | 1.02 | 10.7 |
| CRF02_AG | 01CM0008BBY | AY371124 | 0.05 | 1.04 | 8.21 |
| CRF02_AG | 91DJ263 | AF063223 | 0.04 | 0.45 | 34.9 |
| HIV-1 | | Mean ± s.d. | 0.05 ± 0.03 | 0.70 ± 0.26 | 19.0 ± 13.5 |
| | $EC_{50}$ (nM) | Median | 0.04 | 0.67 | 15.1 |
| | | Range | 0.02-0.16 | 0.38-1.18 | 4.1-51.6 |
| HIV-2 | CBL-20 | AY965906 | 0.57 | 0.36 | 14.3 |
| HIV-2 | CDC310319 | AT965902 | 1.02 | 1.81 | 28.8 |

[a]$EC_{50}$ values represented the mean of triplicate measurements in human PBMCs

B. Activity Against Viruses Resistant to Other Antiretroviral Classes

The antiviral activity of the compound of Formula (Ia) was tested against a panel of known HIV-1 mutants resistant to HIV PIs (ATV and DRV), NRTIs (TFV and FTC), NNRTIs (RPV and EFV) or INSTIs (RAL, EVG and DTG) using a cytopathic antiviral assay in MT-2 cells. The compound of Formula (Ia) was fully active against all tested mutants resistant to PIs (Table 11), NRTIs (Table 12), NNRTIs (Table 13) or INSTIs (Table 14). These results support the use of the compound of Formula (Ia) in the treatment of infection with HIV-1 variants resistant to these four approved classes of antiretrovirals.

TABLE 11

Activity of the compound of Formula (Ia) against PI-resistant viruses

| Compound[a] | WT HXB2D EC$_{50}$ (nM)[b] | EC$_{50}$ Fold-Change[b,c] | | | |
|---|---|---|---|---|---|
| | | I50V | I84V/ L90M | G48V/ V82A/L90M | G48V/ V82S |
| (Ia) | 0.24 ± 0.14 | 0.6 ± 0.2 | 0.3 ± 0.1 | 0.4 ± 0.2 | 0.4 ± 0.1 |
| ATV | 4.18 ± 0.46 | 3.5 ± 0.4 | 33.1 ± 7.8 | 32.5 ± 11.9 | 15.4 ± 3.1 |
| DRV | 2.82 ± 0.47 | 31.6 ± 22.8 | 1.9 ± 0.9 | 0.5 ± 0.2 | 0.3 ± 0.1 |
| EFV | 1.64 ± 0.55 | 3.0 ± 0.9 | 0.4 ± 0.1 | 0.9 ± 0.4 | 0.7 ± 0.1 |
| EVG | 2.02 ± 0.88 | 1.7 ± 1.0 | 1.0 ± 0.7 | 0.8 ± 0.4 | 0.7 ± 0.3 |

[a]ATV = atazanavir (PI),
DRV = darunavir (DRV);
EFV = efavirenz (NNRTI);
EVG = elvitegravir (INSTI)
[b]The data represent the mean (± s.d) of three independent experiments performed in triplicate
[c]Mutant/WT EC$_{50}$ ratio

TABLE 12

Activity of the compound of Formula (Ia) against NRTI-resistant viruses

| Compound[a] | WT LAI EC$_{50}$ (nM)[b] | EC$_{50}$ Fold-Change[b,c] | | |
|---|---|---|---|---|
| | | K65R | M184V | 6TAMs |
| (Ia) | 0.14 ± 0.03 | 0.7 ± 0.2 | 0.5 ± 0.3 | 0.4 ± 0.2 |
| TFV | 4.458 ± 1.872 | 2.4 ± 1.0 | 0.9 ± 1.0 | 3.0 ± 1.1 |
| FTC | 2.406 ± 1.156 | 12.8 ± 2.4 | >20.8 | 4.1 ± 2.5 |
| EVG | 2.64 ± 0.90 | 0.8 ± 0.2 | 1.1 ± 0.7 | 0.6 ± 0.4 |
| ATV | 4.78 ± 1.26 | 0.9 ± 0.3 | 0.6 ± 0.2 | 0.5 ± 0.2 |

[a]TFV = tenofovir (NRTI);
FTC = emtracitabine (NRTI);
EVG = elvitegravir (INSTI);
ATV = atazanavir (PI)
[b]The data represent the mean (± s.d.) of three independent experiments performed in triplicate
[c]Mutant/WT EC$_{50}$ ratio

TABLE 13

Activity of the compound of Formula (Ia) against NNRTI-resistant viruses

| Compound[a] | WT HXB2D EC$_{50}$ (nM)[b] | EC$_{50}$ Fold-Change[b,c] | | | | |
|---|---|---|---|---|---|---|
| | | K103N | Y181C | Y188L | L100I/ K103N | K103N/ Y181C |
| (Ia) | 0.18 ± 0.02 | 0.3 ± 0.1 | 1.6 ± 1.0 | 0.5 ± 0.1 | 0.5 ± 0.2 | 0.5 ± 0.2 |
| RPV | 0.93 ± 0.23 | 0.7 ± 0.3 | 5.9 ± 4.3 | 6.9 ± 1.3 | 7.8 ± 2.6 | 3.2 ± 1.4 |
| EFV | 2.23 ± 0.18 | 14.2 ± 2.7 | 3.3 ± 2.5 | >22.4 | >22.4 | >22.4 |
| ATV | 4.60 ± 1.48 | 0.6 ± 0.3 | 1.8 ± 1.0 | 0.6 ± 0.3 | 0.6 ± 0.3 | 0.6 ± 0.3 |

[a]RPV = rilpivirine (NNRTI); EFV = efavirenz (NNRTI); ATV = atazanavir (PI)
[b]The data represent the mean (±s.d.) of three independent experiments performed in triplicate
[c]Mutant/WT EC$_{50}$ ratio

TABLE 14

Activity of the compound of Formula (Ia) against INSTI-resistant viruses

| Compound[a] | WT HXB2D EC$_{50}$ (nM)[b] | EC$_{50}$ Fold-Change[b,c] | | | | | |
|---|---|---|---|---|---|---|---|
| | | Y143R | E138K/ Q148K | G140S/ Q148R | E92Q/ N155H | N155H/ Q148R | R263K/ M50I |
| (Ia) | 0.13 ± 0.03 | 0.5 ± 0.1 | 0.7 ± 0.3 | 0.8 ± 0.3 | 0.9 ± 0.4 | 1.3 ± 0.7 | 0.9 ± 0.5 |
| RAL | 6.41 ± 2.15 | 10.1 ± 1.2 | >15.6 | >15.6 | >15.6 | 13.9 ± 2.2 | 1.6 ± 1.2 |
| EVG | 1.87 ± 0.19 | 2.1 ± 0.2 | >53.5 | >53.5 | >53.5 | 51.0 ± 2.5 | 5.1 ± 3.7 |

TABLE 14-continued

Activity of the compound of Formula (Ia) against INSTI-resistant viruses

| Compound[a] | WT HXB2D EC$_{50}$ (nM)[b] | EC$_{50}$ Fold-Change[b,c] | | | | | |
|---|---|---|---|---|---|---|---|
| | | Y143R | E138K/ Q148K | G140S/ Q148R | E92Q/ N155H | N155H/ Q148R | R263K/ M50I |
| DTG | 2.24 ± 0.46 | 0.8 ± 0.3 | 7.3 ± 4.1 | 6.9 ± 3.1 | 3.0 ± 1.1 | 1.5 ± 0.6 | 2.8 ± 2.1 |
| EFV | 1.37 ± 0.51 | 0.9 ± 0.6 | 0.7 ± 0.3 | 1.0 ± 0.3 | 1.2 ± 0.6 | 1.1 ± 0.5 | 1.3 ± 0.9 |
| ATV | 3.7 ± 1.07 | 0.8 ± 0.2 | 0.8 ± 0.3 | 1.1 ± 0.5 | 1.0 ± 0.4 | 0.9 ± 0.4 | 1.1 ± 0.6 |

[a]RAL = raltegravir (INSTI); EVG = elvitegravir (INSTI); DTG = dolutegravir (INSTI); EFV = efavirenz (NNRTI); ATV = atazanavir (PI)
[b]The data represent the mean (±s.d.) of three independent experiments performed in triplicate
[c]Mutant/WT EC$_{50}$ ratio

C. Activity in Combination with Other Antiretrovirals

The antiviral activity of the compound of Formula (Ia) was evaluated in MT-2 cells infected with HIV-1 IIIb in combination with selected approved anti-HIV drugs: tenofovir alafenamide (TAF), efavirenz (EFV), dolutegravir (DTG), and darunavir (DRV). The combinatorial effects of the compound of Formula (Ia) were analyzed by the Prichard and Shipman method using MacSynergy II software. The results of the combination assays were expressed as the mean combination volumes (µM$^2$%) that were calculated at the 95% confidence level from three independent experiments performed in triplicate (Table 15). The combination effects were defined as:

Highly synergistic: >100 µM2%

Moderate synergy: >50 and <100 µM2%

Additive: <50 and >−50 µM2%

Moderate antagonism: <−50 and >−100 µM12%

Highly antagonistic: <−100 µM2%

Combinations of the compound of Formula (Ia) with EFV, DTG or DRV showed highly synergistic anti-HIV activity. The compound of Formula (Ia) was slightly synergistic when combined with TAF. The compound of Formula (Ia), combined with itself, TAF combined with EVG, and ribavirin combined with d4T were used as additivity, synergy and antagonism controls, respectively.

TABLE 15

Antiviral activity of the compound of Formula (Ia) in combination with other antiretrovirals

| Drug Combination[a] | Combination Volume (µM$^2$ %)[b] | | Combination Effect |
|---|---|---|---|
| | Type | Mean | |
| (Ia) + TAF | Synergy | 87 ± 32 | Moderate Synergy |
| | Antagonism | −8 ± 7 | |
| (Ia) + EFV | Synergy | 101 ± 40 | Highly Synergistic |
| | Antagonism | −8 ± 8 | |
| (Ia) + DTG | Synergy | 116 ± 13 | Highly Synergistic |
| | Antagonism | −8 ± 7 | |
| (Ia) + DRV | Synergy | 119 ± 39 | Highly Synergistic |
| | Antagonism | −3 ± 3 | |
| (Ia) + (Ia) | Synergy | 18 ± 8 | Additive |
| | Antagonism | −16 ± 6 | |

TABLE 15-continued

Antiviral activity of the compound of Formula (Ia) in combination with other antiretrovirals

| Drug Combination[a] | Combination Volume (µM$^2$ %)[b] | | Combination Effect |
|---|---|---|---|
| | Type | Mean | |
| TAF + EVG | Synergy | 164 ± 24 | Highly Synergistic |
| | Antagonism | −3 ± 3 | |
| RBV + d4T | Synergy | 0 ± 0 | Highly Antagonistic |
| | Antagonism | −398 ± 23 | |

[a]TAF = tenofovir alafenamide (NRTI);
EFV = efavirenz (NNRTI);
DTG = dolutegravir (INSTI);
DRV = darunavir (PI);
EVG = elvitegravir (INSTI);
RBV = ribavirine;
d4T = stavudine
[b]The synergy/antagonism volumes represent the mean (± s.d.) of three independent experiments performed in triplicate

What is claimed is:

1. A method of treating human immunodeficiency virus (HIV) infection in a heavily treatment-experienced patient, the method comprising administering to the patient a therapeutically effective amount of a pharmaceutical composition comprising a sodium salt of the compound of Formula (Ia):

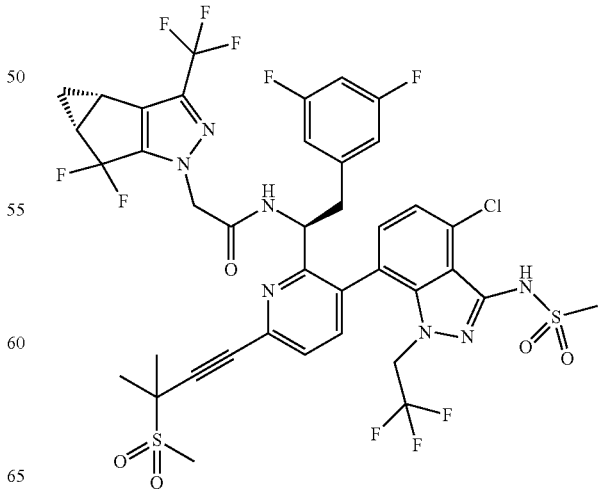

(Ia)

one or more pharmaceutically acceptable excipients, wherein the pharmaceutical composition is in the form of a solution comprising about 10 w/w % to about 40 w/w % water, about 35 w/w % to about 75 w/w % polyethylene glycol 300 (PEG 300), and about 5 w/w % to about 35 w/w % of the sodium salt of the compound of Formula (Ia);
wherein the HIV infection is an HIV-1 infection characterized by HIV-1 mutant resistance to one or more antiretroviral medications.

2. The method of claim 1, wherein the HIV-1 mutant is resistant to a protease inhibitor (PI), a nucleoside or nucleotide reverse transcriptase inhibitor (NRTI), a non-nucleoside or non-nucleotide reverse transcriptase inhibitor (NNRTI), or an integrase strand transfer inhibitor (INSTI).

3. The method of claim 1, wherein the patient is infected with HIV-1 resistant to at least one antiretroviral medication.

4. The method of claim 1, wherein the patient is infected with multidrug resistant HIV-1 which is resistant to at least one antiretroviral medication from each of two different classes of antiretroviral medications, wherein the different classes of antiretroviral medications are selected from a nucleoside or nucleotide reverse transcriptase inhibitor (NRTI), a non-nucleoside or non-nucleotide reverse transcriptase inhibitor (NNRTI), a protease inhibitor (PI), and an integrase strand transfer inhibitor (INSTI).

5. The method of claim 1, wherein the pharmaceutical composition comprising the sodium salt of the compound of Formula (Ia) further comprises one or more other compounds selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV nucleoside reverse transcriptase translocation inhibitors, and pharmacokinetic enhancers.

6. The method of claim 1, wherein the patient has a viral load of greater than about 200 copies of HIV-1 RNA/mL at the time of beginning administration of the compound of Formula (Ia), or a pharmaceutically acceptable salt thereof.

7. The method of claim 6, wherein administration of the pharmaceutical composition comprising the sodium salt of the compound of Formula (Ia) results in a decrease in the viral load in the patient.

8. The method of claim 1, wherein the amount of water in the solution comprising the sodium salt of the compound of Formula (Ia), PEG 300, and water is about 21 w/w % to about 29 w/w %.

9. The method of claim 1, wherein the amount of PEG 300 in the solution comprising the sodium salt of the compound of Formula (Ia), PEG 300, and water is about 50 w/w % to about 59 w/w %.

10. The method of claim 1, wherein the amount of the sodium salt of the compound of Formula (Ia) in the solution comprising the sodium salt of the compound of Formula (Ia), PEG 300, and water is about 13 w/w % to about 27 w/w %.

11. The method of claim 1, wherein the solution comprises about 21 w/w % to about 29 w/w % water, about 50 w/w % to about 59 w/w % PEG 300, and about 13 w/w % to about 27 w/w % of the sodium salt of the compound of Formula (Ia).

12. The method of claim 1, wherein the solution comprises about 23.41 w/w % to about 27.47 w/w % water, about 50.13 w/w % to about 58.84 w/w % PEG 300, and about 13.69 w/w % to about 26.46 w/w % of the sodium salt of the compound of Formula (Ia).

13. The method of claim 1, wherein the solution comprises about 27.47 w/w % water, about 58.84 w/w % PEG 300, and about 13.69 w/w % of the sodium salt of the compound of Formula (Ia).

14. The method of claim 1, wherein the solution comprises about 23.41 w/w % water, about 50.13 w/w % PEG 300; and about 26.46 w/w % of the sodium salt of the compound of Formula (Ia).

15. A method of treating human immunodeficiency virus (HIV) infection in a heavily treatment-experienced patient, the method comprising administering to the patient a therapeutically effective amount of pharmaceutical composition comprising a sodium salt of the compound of Formula (Ia):

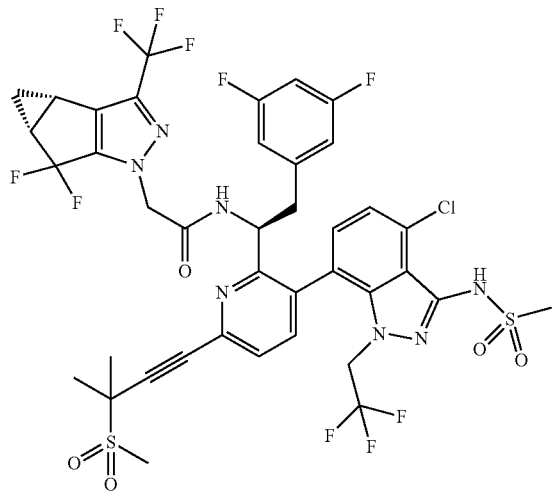

(Ia)

and one or more pharmaceutically acceptable excipients, wherein the pharmaceutical composition is in the form of a tablet comprising about 5 w/w % to about 45 w/w % of the sodium salt of the compound of Formula (Ia), about 1 w/w % to about 10 w/w % of copovidone, about 0.01 w/w % to about 10 w/w % of poloxamer 407, about 5 w/w % to about 45 w/w % of microcrystalline cellulose, about 15 w/w % to about 70 w/w % of mannitol, about 1 w/w % to about 30 w/w % of croscarmellose sodium, and about 0.01 w/w % to about 10 w/w % of magnesium stearate;
wherein the HIV infection is an HIV-1 infection characterized by HIV-1 mutant resistance to one or more antiretroviral medications.

16. The method of claim 15, wherein the tablet is prepared from a spray-dried dispersion technology.

17. The method of claim 15, wherein the amount of the sodium salt of the compound of Formula (Ia) is about 5 mg to about 500 mg.

18. The method of claim 15, wherein the amount of the sodium salt of the compound of Formula (Ia) is about 300 mg.

19. The method of claim 15, wherein the amount of the sodium salt of the compound of Formula (Ia) in the tablet comprising the sodium salt of the compound of Formula (Ia), copovidone, poloxamer 407, microcrystalline cellulose, mannitol, croscarmellose sodium, and magnesium stearate is about 15 w/w % to about 25 w/w %.

20. The method of claim 15, wherein the amount of copovidone in the tablet comprising the sodium salt of the compound of Formula (Ia), copovidone, poloxamer 407, microcrystalline cellulose, mannitol, croscarmellose sodium, and magnesium stearate is about 3 w/w % to about 6 w/w %.

21. The method of claim 15, wherein the amount of poloxamer 407 in the tablet comprising the sodium salt of the compound of Formula (Ia), copovidone, poloxamer 407, microcrystalline cellulose, mannitol, croscarmellose sodium, and magnesium stearate is about 0.5 w/w % to about 3.0 w/w %.

22. The method of claim 15, wherein the amount of microcrystalline cellulose in the tablet comprising the sodium salt of the compound of Formula (Ia), copovidone, poloxamer 407, microcrystalline cellulose, mannitol, croscarmellose sodium, and magnesium stearate is about 18 w/w % to about 30 w/w %.

23. The method of claim 15, wherein the amount of mannitol in the tablet comprising the sodium salt of the compound of Formula (Ia), copovidone, poloxamer 407, microcrystalline cellulose, mannitol, croscarmellose sodium, and magnesium stearate is about 40 w/w % to about 50 w/w %.

24. The method of claim 15, wherein the amount of croscarmellose sodium in the tablet comprising the sodium salt of the compound of Formula (Ia), copovidone, poloxamer 407, microcrystalline cellulose, mannitol, croscarmellose sodium, and magnesium stearate is about 6 w/w % to about 10 w/w %.

25. The method of claim 15, wherein the amount of magnesium stearate in the tablet comprising the sodium salt of the compound of Formula (Ia), copovidone, poloxamer 407, microcrystalline cellulose, mannitol, croscarmellose sodium, and magnesium stearate is about 1.0 w/w % to about 3.0 w/w %.

26. The method of claim 15, wherein the tablet further comprises an outer film coat.

27. The method of claim 15, wherein the outer film coat provides from about 1% to about 8% weight gain based on the uncoated tablet.

28. The method of claim 15, wherein the outer film coat provides about 4% weight gain based on the uncoated tablet.

29. The method of claim 28, wherein the HIV-1 mutant is resistant to a protease inhibitor (PI), a nucleoside or nucleotide reverse transcriptase inhibitor (NRTI), a non-nucleoside or non-nucleotide reverse transcriptase inhibitor (NNRTI), or an integrase strand transfer inhibitor (INSTI).

30. The method of claim 15, wherein the patient is infected with HIV-1 resistant to at least one antiretroviral medication.

31. The method of claim 15, wherein the patient is infected with multidrug resistant HIV-1 which is resistant to at least one antiretroviral medication from each of two different classes of antiretroviral medications, wherein the different classes of antiretroviral medications are selected from a nucleoside or nucleotide reverse transcriptase inhibitor (NRTI), a non-nucleoside or non-nucleotide reverse transcriptase inhibitor (NNRTI), a protease inhibitor (PI), and an integrase strand transfer inhibitor (INSTI).

32. The method of claim 15, wherein the composition further comprises one or more other compounds selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV nucleoside reverse transcriptase translocation inhibitors, and pharmacokinetic enhancers.

33. The method of claim 15, wherein the patient has a viral load of greater than about 200 copies of HIV-1 RNA/mL at the time of beginning administration of the pharmaceutical composition comprising the compound of Formula (Ia), or a pharmaceutically acceptable salt thereof.

34. The method of claim 33, wherein administration of the pharmaceutical composition the sodium salt of the compound of Formula (Ia) results in a decrease in the viral load in the patient.

* * * * *

UNITED STATES PATENT AND TRADEMARK OFFICE
CERTIFICATE OF CORRECTION

| | | |
|---|---|---|
| PATENT NO. | : 11,944,611 B2 | Page 1 of 1 |
| APPLICATION NO. | : 16/512166 | |
| DATED | : April 2, 2024 | |
| INVENTOR(S) | : Bauer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 775 days.

Signed and Sealed this
Eighth Day of October, 2024

Katherine Kelly Vidal
*Director of the United States Patent and Trademark Office*